United States Patent
Ng et al.

(10) Patent No.: US 10,239,951 B2
(45) Date of Patent: Mar. 26, 2019

(54) BISPECIFIC HER2 AND HER3 ANTIGEN BINDING CONSTRUCTS

(71) Applicant: Zymeworks Inc., Vancouver (CA)

(72) Inventors: Gordon Yiu Kon Ng, Vancouver (CA); Peter Wing Yiu Chan, Richmond (CA); Grant Raymond Wickman, Vancouver (CA)

(73) Assignee: Zymeworks Inc., Vancouver (CA)

( * ) Notice: Subject to any disclaimer, the term of this patent is extended or adjusted under 35 U.S.C. 154(b) by 0 days.

(21) Appl. No.: 14/888,580

(22) PCT Filed: May 8, 2014

(86) PCT No.: PCT/US2014/037401
§ 371 (c)(1),
(2) Date: Nov. 2, 2015

(87) PCT Pub. No.: WO2014/182970
PCT Pub. Date: Nov. 13, 2014

(65) Prior Publication Data
US 2016/0083480 A1 Mar. 24, 2016

Related U.S. Application Data

(60) Provisional application No. 61/821,197, filed on May 8, 2013.

(51) Int. Cl.
| | | |
|---|---|---|
| *C07K 16/32* | (2006.01) | |
| *C07K 16/46* | (2006.01) | |
| *A61K 45/06* | (2006.01) | |
| *A61K 47/68* | (2017.01) | |
| *A61K 39/00* | (2006.01) | |

(52) U.S. Cl.
CPC .............. *C07K 16/32* (2013.01); *A61K 45/06* (2013.01); *A61K 47/6803* (2017.08); *A61K 47/6871* (2017.08); *A61K 47/6879* (2017.08); *A61K 2039/505* (2013.01); *C07K 2317/31* (2013.01); *C07K 2317/41* (2013.01); *C07K 2317/52* (2013.01); *C07K 2317/526* (2013.01); *C07K 2317/55* (2013.01); *C07K 2317/622* (2013.01); *C07K 2317/64* (2013.01); *C07K 2317/73* (2013.01); *C07K 2317/732* (2013.01); *C07K 2317/76* (2013.01); *C07K 2317/77* (2013.01); *C07K 2317/94* (2013.01)

(58) Field of Classification Search
CPC ....... C07K 16/32; C07K 16/00–16/468; C07K 2317/31
See application file for complete search history.

(56) References Cited

U.S. PATENT DOCUMENTS

| | | | |
|---|---|---|---|
| 5,821,337 A * | 10/1998 | Carter | C07K 16/28 530/387.3 |
| 6,737,056 B1 | 5/2004 | Presta | |
| 7,642,228 B2 | 1/2010 | Carter et al. | |
| 7,951,917 B1 | 5/2011 | Arathoon et al. | |
| 8,329,873 B2 | 12/2012 | Adams et al. | |
| 8,383,122 B2 * | 2/2013 | Dai | A61K 47/48407 424/145.1 |
| 8,592,562 B2 | 11/2013 | Kannan et al. | |
| 8,937,158 B2 | 1/2015 | Lazar et al. | |
| 9,079,965 B2 * | 7/2015 | Zhou | C07K 16/32 |
| 9,499,634 B2 | 11/2016 | Dixit et al. | |
| 2003/0228663 A1 * | 12/2003 | Lowman | C07K 16/32 435/69.1 |
| 2004/0071696 A1 | 4/2004 | Adams et al. | |
| 2004/0110226 A1 | 6/2004 | Lazar et al. | |
| 2006/0074225 A1 | 4/2006 | Chamberlain et al. | |
| 2010/0196265 A1 | 8/2010 | Adams et al. | |
| 2010/0266584 A1 * | 10/2010 | Schoeberl | A61K 31/337 424/133.1 |
| 2011/0059076 A1 | 3/2011 | McDonagh et al. | |
| 2011/0059090 A1 * | 3/2011 | Revets | C07K 16/2863 424/138.1 |

(Continued)

FOREIGN PATENT DOCUMENTS

| | | |
|---|---|---|
| WO | WO 03/031464 A2 | 4/2003 |
| WO | WO 2009/126920 A2 | 10/2009 |
| WO | WO 2012/143523 A1 | 10/2012 |

OTHER PUBLICATIONS

Robinson et al., Br. J. Cancer 2008; 99:1415-1425.*
Haryadi et al., Bioengineered; published on line Mar. 1, 2012; 4:2, 90-94, DOI: 10.4161/bioe.22262.*
WE Paul, "Fundamental Immunology, Fourth Edition", Lippincott-Raven Publishers, pp. 112-118 (Year: 1999).*
Finlay & Alnnagro, Front. Immunol., 3:342, doi: 10.3389/finnnnu. 2012.00342 (Year: 2012).*
Bostrom et al., Science 323:1610-1614 (Year: 2009).*
European Extended Search Report, European Application No. 14794897. 0, dated Dec. 7, 2016, 10 pages.
Vitetta, E.S. et al., "Considering Therapeutic Antibodies," Science, 2006, pp. 38-309, vol. 313.

(Continued)

*Primary Examiner* — Jessica H Roark
(74) *Attorney, Agent, or Firm* — Fenwick & West LLP

(57) ABSTRACT

Described herein are isolated bi-specific antigen binding constructs, e.g., antibodies. The bi-specific antigen binding constructs include two antigen binding polypeptide constructs, e.g., a Fab and an scFv. The first antigen-binding polypeptide construct monovalently and specifically binds to extracellular domain 4 (ECD4) of HER2 (human epidermal growth factor receptor 2); the second antigen-binding polypeptide construct monovalently and specifically binds to an extracellular domain (ECD) of HER3 (human epidermal growth factor receptor 3). One antigen binding polypeptide construct is a Fab format and the other antigen binding polypeptide construct is an scFv format. The bi-specific antigen binding constructs includes an Fc having two Fc polypeptides each having a CH3 domain for dimerization. Each Fc polypeptide is linked to the C-terminus of one of the antigen binding polypeptide constructs with or without a linker.

20 Claims, 33 Drawing Sheets
Specification includes a Sequence Listing.

(56) References Cited

U.S. PATENT DOCUMENTS

2012/0149876 A1   6/2012   Von Kreudenstein et al.
2012/0244578 A1   9/2012   Kannan et al.
2018/0016347 A1   1/2018   Von Kreudenstein et al.

OTHER PUBLICATIONS

United States Office Action, U.S. Appl. No. 13/289,934, dated Nov. 16, 2015, 19 pages.
United States Office Action, U.S. Appl. No. 13/289,934, dated May 13, 2015, 19 pages.
United States Office Action, U.S. Appl. No. 13/289,934, dated Feb. 27, 2015, 15 pages.
United States Notice of Allowance, U.S. Appl. No. 13/289,934, dated Sep. 29, 2016, 9 pages.
United States Advisory Action, U.S. Appl. No. 13/289,934, dated Feb. 5, 2016, 8 pages.
United States Office Action, U.S. Appl. No. 13/668,098, dated Nov. 17, 2015, 16 pages.
United States Office Action, U.S. Appl. No. 13/668,098, dated Apr. 3, 2015, 18 pages.
United States Notice of Allowance, U.S. Appl. No. 13/668,098, dated Sep. 23, 2016, 12 pages.
Janeway, C.A. et al., "Chapter 3: Structure of the Antibody Molecule and Immunoglobulin Genes," Immuno Biology Third Edition, Garland Publishing Inc., 1997, pp. 3:1-3:11.
Rudikoff, S. et al., "Single Amino Acid Substitution Altering Antigen-Binding Specifity," PNAS, 1982, pp. 1979-1983, vol. 79.
Berzofsky, J.A. et al., Chapter 8: Immunogenicity and Antigen Structure Fundamental Immunology, $3^{rd}$ Edition, Paul, W.E., ed., 1993, p. 242.
Portolano, S. et al., "Lack of Promiscuity in Autoantigen-Specific H and L Chain Combinations as Revealed by Human H and L Chain "Roulette"," Journal of Immunology, 1993, pp. 880-887, vol. 150.
Omidfar, K. et al., "Studies of Thermostability in *Camelus bactrianus* (Bactrian Camel) Single-Domain Antibody Specific for the Mutant Epidermal-Growth-Factor Receptor Expressed by Pichia," Biotechnol . . . Appl. Biochem., 2007, pp. 41-49, vol. 46.
United States Office Action, U.S. Appl. No. 13/892,198, dated Oct. 6, 2015, 23 pages.
United States Notice of Abandonment, U.S. Appl. No. 13/892,198, dated May 20, 2016, 3 pages.
United States Office Action, U.S. Appl. No. 13/927,065, dated Feb. 22, 2016, 6 pages.
United States Office Action, U.S. Appl. No. 13/927,065, dated Oct. 7, 2015, 10 pages.
United States Notice of Allowance, U.S. Appl. No. 13/927,065, dated Aug. 26, 2016, 7 pages.
United States Office Action, U.S. Appl. No. 13/638,362, dated May 26, 2015, 12 pages.
United States Notice of Allowance, U.S. Appl. No. 13/638,362, dated Dec. 18, 2015, 9 pages.
Gunasekaran, K., et al., "Enhancing Antibody Fc Heterodimer Formation through Electrostatic Steering Effects," The Journal of Biological Chemistry, vol. 285, No. 25, pp. 19637-19646, Jun. 18, 2010.
Kang, J.C., et al., "Engineering multivalent antibodies to target heregulin-induced HER3 signaling in breast cancer cells," MAbs, vol. 6, No. 2, pp. 340-353, Dec. 26, 2013.
Lu, D., et al., "Fab-scFv fusion protein: an efficient approach to production of bispecific antibody fragments," Journal of Immunological Methods, vol. 267, pp. 213-226, 2002.
McDonagh, C.F., et al., "Antitumor Activity of a Novel Bispecific Antibody That Targets the ErbB2/ErbB3 Oncogenic Unit and Inhibits Heregulin-Induced Activation of ErbB3," Molecular Cancer Therapeutics, vol. 11, pp. 582-593, Jan. 16, 2012.
Patent Cooperation Treaty, International Search Report and Written Opinion of the International Searching Authority, International Patent Application No. PCT/US2014/037401, dated Oct. 7, 2014, 14 Pages.
Robinson, M.K., et al., "Targeting ErbB2 and ErbB3 with a bispecific single-chain Fv enhances targeting selectivity and induces a therapeutic effect in vitro," British Journal of Cancer, vol. 99, pp. 1415-1425, 2008.
Dong, J. et al., "Stable IgG-Like Bispecific Antibodies Directed Toward the Type I Insulin-Like Growth Factor Receptor Demonstrate Enhanced Ligand Blockade and Anti-Tumor Activity," The Journal of Biological Chemistry, Feb. 11, 2011, pp. 4703-4717, vol. 286, No. 6.
Scheer, J.M. et al., "Reorienting the Fab Domains of Trastuzumab Results in Potent HER2 Activators," PLOS One, Dec. 2012, pp. 1-13, vol. 7, Issue 12, e51817.
U.S. Appl. No. 13,289,934—Restriction Requirement dated Sep. 16, 2014, 6 pages.
U.S. Appl. No. 13/289,934—Notice of Allowance dated Apr. 25, 2016, 9 pages.
U.S. Appl. No. 13/927,065—Restriction Requirement dated Apr. 15, 2015, 9 pages.
U.S. Appl. No. 15/355,019—Non-Final Office Action dated Jul. 21, 2017, 7 pages.
U.S. Appl. No. 15/355,019—Notice of Allowance dated May 22, 2018, 6 pages.
Vu, T. et al., "Trastuzumab: Updated Mechanisms of Action and Resistance in Breast Cancer," Frontiers in Oncology, Jun. 18, 2012, pp. 1-6, vol. 2, Article 62.
Gershoni, J.M. et al., "Epitope Mapping—The First Step in Developing Epitope-Based Vaccines," Biodrugs, Adis Data International Ltd., Jan. 2007, pp. 145-156, vol. 21, No. 3.
Winkler, K et al., "Changing the Antigen Binding Specificity by Single Point Mutations of an Anti-P24 (HIV-1) Antibody," The Journal of Immunology, Oct. 15, 2000, pp. 4505-4514, vol. 165, No. 8.
Brown, M. et al., "Tolerance to Single but Not Multiple, Amino Acid Replacements in Antibody $V_H$ CDR2: A Means of Minimizing B Cell Wastage from Somatic Hypermutation?" The Journal of Immunology, Jan. 1996, pp. 3285-3291, vol. 156, No. 9.
Maynard, J. et al., "Protection Against Anthrax Toxin by Recombinant Antibody Fragments Correlates with Antigen Affinity," Nature Biotechnology, Jun. 2002, pp. 597-601, vol. 20, No. 6.
Barderas, R. et al., "Affinity Maturation of Antibodies Assisted by in Silicon Modeling," Proceedings National Academy of Sciences PNAS, Jul. 1, 2008, pp. 9029-9034, vol. 105, No. 26.

* cited by examiner

A
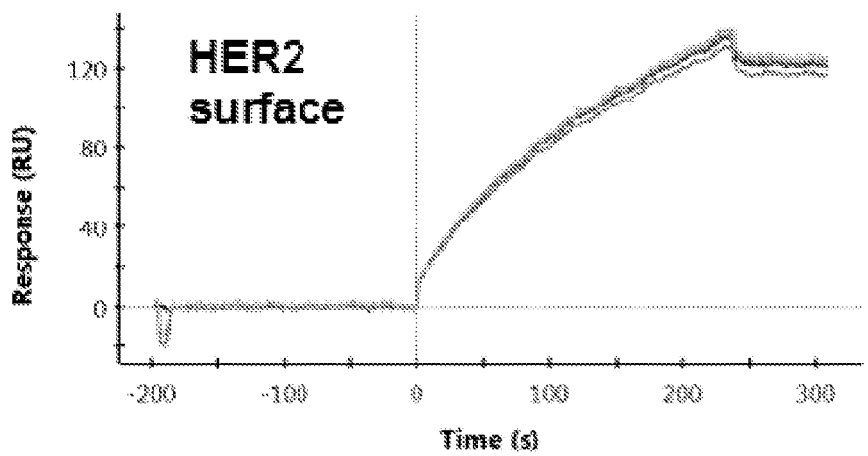
B
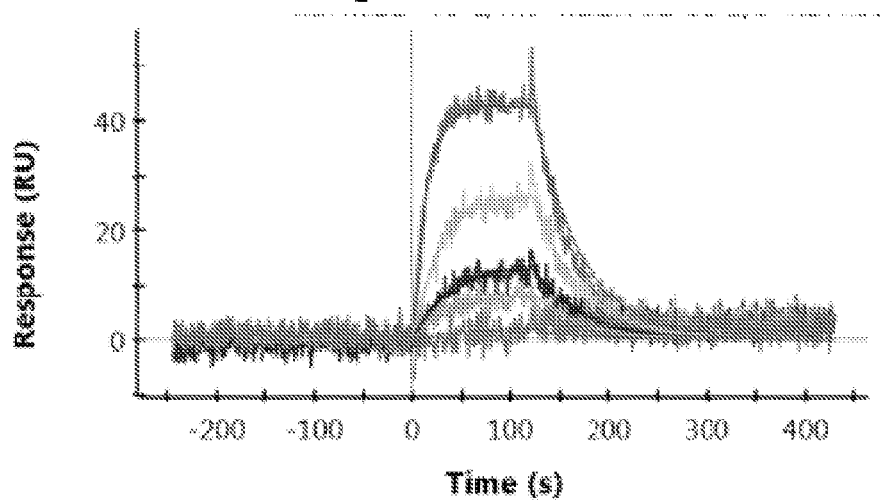
FIG. 3

|  | v792 | v506 | v1040 | v880 |
|---|---|---|---|---|
| Span (% lysis) | 47.76 | 39.72 | 52.77 | 63.06 |
| Span 95% Confidence Intervals | 24.28 to 71.24 | 33.21 to 46.24 | 49.01 to 56.54 | 56.65 to 69.48 |
| EC50 (nM) | 0.1677 | 0.1318 | 0.6944 | 0.5982 |
| EC50 95% Confidence Intervals | 0.02865 to 0.9814 | 0.06567 to 0.2645 | 0.5090 to 0.9473 | 0.3864 to 0.9262 |

|  | v792 | v506 | v880 |
|---|---|---|---|
| Span (% lysis) | 33.5 | 27.63 | 47.71 |
| Span 95% Confidence Intervals | 24.49 to 42.50 | 21.69 to 33.57 | 39.82 to 55.60 |
| EC50 (nM) | 0.03878 | 0.01262 | 0.1168 |
| EC50 95% Confidence Intervals | 0.01166 to 0.1290 | 0.003385 to 0.04704 | 0.04414 to 0.3091 |

| | v880 | v876 | v877 | v878 | v879 |
|---|---|---|---|---|---|
| Span (% lysis) | 45.85 | ~ 7.879 | 9.179 | 7.373 | 6.509 |
| Span 95% Confidence Intervals | 40.61 to 51.10 | n/a | -73.75 to 92.11 | 3.179 to 11.57 | 3.249 to 9.769 |
| EC50 (nM) | 1.87 | 19.08 | 275.6 | 2.291 | ~ 6.792 |
| EC50 95% Confidence Intervals | 1.140 to 3.067 | 0.0 to 4.314e+018 | 0.0 to 1.690e+024 | 0.1934 to 27.14 | (Very wide) |

|  | v792 | v506 | v880 |
|---|---|---|---|
| Span (% lysis) | 37.08 | 34.91 | 38.6 |
| Span 95% Confidence Intervals | 34.49 to 39.66 | 33.41 to 36.41 | 36.28 to 40.92 |
| EC50 (nM) | 0.03497 | 0.03869 | 0.1173 |
| EC50 95% Confidence Intervals | 0.02695 to 0.04538 | 0.03310 to 0.04523 | 0.09032 to 0.1523 |

| "Name" | Variant name | Clone name HC-A* | Clone name HC-B* | Clone name LC** | description |
|---|---|---|---|---|---|
| hIgG1 | v6908 | NA | NA | NA | polyclonal human IgG1 |
| hIgG1-DM1 | v6249 | NA | NA | NA | polyclonal human IgG1 ADC |
| FSA-tras | v506 | CL #642 | NA | CL #-2 | full sized trastuzumab |
| FSA-tras-HET | v792 | CL #1011 | CL #1015 | CL #-2 | full sized trastuzumab on Asymmetric Fc |
| FSA-tras-DM1 | v6246 | NA | NA | NA | full sized trastuzumab ADC |
| OA-tras | v1040 | CL #4553 | CL #4560 | CL #4561 | one armed trastuzumab |
| OA-tras-afuco | v7188 | CL #4553 | CL #4560 | CL #4561 | afucosylated one armed trastuzumab |
| FSA-pert | v4184 | CL #3057 | CL #3041 | CL #1811 | full sized pertuzumab |
| OA-pert | v4182 | CL #3057 | CL #4560 | CL #1811 | one armed pertuzumab |
| FSA-H3 | v877 | CL #1069 | NA | NA | full sized H3 scFv |
| OA-H3 | v879 | CL #1059 | CL #1071 |  | one armed H3 scFv |
| B1D2-H3 | v880 | CL #1070 | CL #1071 |  | anti-HER2-HER3 bsAb |
| MM111 | v1087 | CL #1102 | NA | NA | HSA fused to scFvs B1D2 and H3 |
| tras-H3 | v4248 | CL #1011 | CL #1071 | CL #4561 | anti-HER2-HER3 bsAb |
| tras-H3-afuco | v7186 | CL #1011 | CL #1071 | CL #4561 | afucosylated anti-HER2-HER3 bsAb |
| tras-H3-DM1 | v6362 | NA | NA | NA | anti-HER2-HER3 bsADC |
| tras-H3-SS | v9918 | CL #4371 | CL #5454 | CL #785 | disulphide stabilized anti-HER2-HER3 bsAb |
| tras-H3-SS 190T | v9919 | CL #4371 | CL #5466 | CL #785 | disulphide/190T stabilized anti-HER2-HER3 bsAb |
| tras-scFv-H3-Fab lambda CL | v9920 | CL #6577 | CL #5244 | CL #5474 | lambda domain swapped anti-HER2-HER3 bsAb |
| tras-scFv-SS-H3-Fab lambda CL | v9921 | CL #6577 | CL #5259 | CL #5474 | lambda domain swapped anti-HER2-HER3 bsAb |
| tras-scFv-H3-Fab kappa CL | v9922 | CL #6577 | CL #5244 | CL #5476 | kappa domain swapped anti-HER2-HER3 bsAb |
| tras-scFv-SS-H3-Fab kappa CL | v9923 | CL #6577 | CL #5259 | CL #5476 | kappa domain swapped anti-HER2-HER3 bsAb |

| Variant | DNA ratio: HC-A/HC-B/LC | Conc after protein A mg/ml | Amount mg after protein A | Conc after SEC mg/ml | Amount mg after SEC |
|---|---|---|---|---|---|
| 4248 | 30%/30%/40% | 1.1 | 4.4 | 0.8 | 0.4 |
| 4248 | 20%/40%/40% | 0.75 | 3 | 0.84 | 0.378 |
| 4248 | 40%/20%/40% | 1.13 | 4.52 | 0.52 | 0.234 |

B)

| Variant | DNA ratio: HC-A:B:LC | Titre (mg/L) in supernatant |
|---|---|---|
| v9918 | 40:20:40 | 3.7 |
| v9918 | 30:30:40 | 2.28 |
| v9918 | 20:40:40 | 1.36 |
| v9919 | 40:20:40 | 4.33 |
| v9919 | 30:30:40 | 2.3 |
| v9919 | 20:40:40 | 1.71 |
| v9920 | 40:20:40 | 21.13 |
| v9920 | 30:30:40 | 19.32 |
| v9920 | 20:40:40 | 14.36 |
| v9921 | 40:20:40 | 24.14 |
| v9921 | 30:30:40 | 23.76 |
| v9921 | 20:40:40 | 16.74 |
| v9922 | 40:20:40 | 19 |
| v9922 | 30:30:40 | 17.4 |
| v9922 | 20:40:40 | 17.66 |
| v9923 | 40:20:40 | 16.31 |
| v9923 | 30:30:40 | 15.38 |
| v9923 | 20:40:40 | 12.81 |

| | 3aF | | 3aV | | | 2aH | | | 2aR | | | 2bY | | | 1A | | |
|---|---|---|---|---|---|---|---|---|---|---|---|---|---|---|---|---|---|
| | FMCO | AMCO | Ratio | FMCO | AMCO | Ratio | FMCO | AMCO | Ratio | FMCO | AMCO | Ratio | FMCO | AMCO | Ratio | FMCO | AMCO | Ratio |
| 1040 | 3.1E-07 | 3.5E-08 | 8.7 | 1.1E-07 | 1.2E-08 | 9.7 | n/d | 1.03E-07 | - | n/d | 1.42E-07 | - | n/d | 1.81E-07 | - | n/d | 1.72E-08 | - |
| 4249 | 3.2E-07 | 3.9E-08 | 8.3 | 1.3E-07 | 1.2E-08 | 10.5 | 1.21E-07 | 1.29E-07 | 0.9 | 2.51E-07 | 1.65E-07 | 1.5 | 3.06E-07 | 2.16E-07 | 1.4 | 1.29E-07 | 1.93E-08 | 0.7 |
| 506 | 6.7E-07 | 6.0E-08 | 11.2 | 2.3E-07 | 1.5E-08 | 14.8 | n/d | 2.53E-07 | - | n/d | 2.63E-07 | - | n/d | 3.48E-07 | - | n/d | 1.87E-08 | - |
| Average | | | 8.9 | | | 11.0 | | | 0.9 | | | 1.5 | | | 1.5 | | | 1.1 |

BISPECIFIC HER2 AND HER3 ANTIGEN BINDING CONSTRUCTS

CROSS REFERENCE TO RELATED APPLICATIONS

This application claims the benefit of U.S. Provisional Application No. 61/821,197, filed May 8, 2013, which is hereby incorporated in its entirety by reference.

SEQUENCE LISTING

The instant application contains and is filed with a Sequence Listing which has been submitted via EFS-Web and is hereby incorporated by reference in its entirety. Said ASCII copy, created on May 8, 2014, is named 24689PCT_sequencelisting.txt, and is 137,000 bytes in size.

BACKGROUND OF THE INVENTION

Field of Invention

The field of the invention is bispecific HER2 and HER3 antigen binding constructs useful for, e.g., biotherapeutics.

Description of Related Art

The human epidermal growth factor receptor (HER, erbB) family includes EGFR (HER1), HER2 (erbB2), HER3 (erbB3), and HER4 (erbB4) and the activity of this receptor family regulates the development and maintenance of normal tissue. However, overexpression of and/or aberrant regulation of the activity of this receptor family have been implicated in the development and growth of human tumor cells, and thus the members of this family have become targets for the development of therapeutic antibodies for the treatment of cancers. For example, trastuzumab (Herceptin™) and pertuzumab (Perjeta™) are anti-HER2 antibodies that have been developed for the treatment of breast cancers expressing high levels of HER2 (HER2 3+), as measured by the Herceptest™), while T-DM1 (Kadcycla™), a maytansine conjugate of trastuzumab has also been developed for the treatment of these types of breast cancers.

As indicated on their respective labels, trastuzumab, pertuzumab, and T-DM1 are only indicated for patients with breast tumors characterized as HER2 3+. Unfortunately, not all patients with these HER2 3+ breast cancers are responsive to trastuzumab, alone or in combination with pertuzumab, and in fact, the majority of patients who are treated with trastuzumab become resistant to the antibody (Wilken and Maihle (2010) ann. N.Y. Acad. Sci. 1210: 53-65).

More recently, other members of the erbB family or combinations of erbB family members have been identified as potential targets for therapeutic antibodies. For example, HER2 and HER3 are cognate receptor pairs and the HER2-HER3 heterodimer is the most mitogenic. Mono-specific, bivalent antibodies that bind to HER2 and HER3 have been identified, but because these target biologies involving HER2-HER3 heterodimerization, monospecific targeting may be insufficiently efficacious. In addition, because mono-specific, bivalent antibodies that bind to HER2 and HER3 are also expressed on normal tissues, at lower levels, administration of these antibodies to a patient can potentially result in toxicity or other adverse events.

Antibody-based bi-specific polypeptide therapeutics that bind HER2 and HER3 have been identified, and are in various stages of development. Specifically, MM-111 is a bi-specific HER2-HER3 binding polypeptide that comprises an anti-HER2 binding domain in scFv format and an anti-HER3 binding domain in scFv format linked to a human serum albumin (HSA) scaffold (McDonagh et al. (2012) Mol Cancer Ther 11:582-593, and International Patent Publication No. WO 2009/126920). MM-111 is currently in early stage clinical trials for the treatment of HER2 positive (gene amplified) cancers, in combination with Herceptin™ or chemotherapeutics. ALM is a bi-specific single chain scFv that binds to HER2 and HER3 (Robinson et al, (2008) British Journal of Cancer 99:1415-1425 and U.S. Pat. No. 8,329,873). Both of these antibody-based polypeptides lack the Fc portion of a naturally occurring antibody and thus cannot mediate antibody-induced immune cytotoxicity. In addition, the lack of an Fc portion for ALM results in a polypeptide with a relatively short half-life in the body, limiting therapeutic utility.

A multivalent, bi-specific antibody targeting heregulin-induce HER3 signaling in breast cancer cells has been described (Kang et al (2014) mAbs 6:2, 340353). For example, a tetravalent antibody is described that includes a dimeric Fc with two ant HER2 scFv at one end of the Fc and two anti HER3 scFv at the second end of the Fc.

SUMMARY OF THE INVENTION

Described herein are isolated bi-specific antigen binding constructs, e.g., antibodies. The bi-specific antigen binding constructs include two antigen binding polypeptide constructs, e.g., a Fab and an scFv. The first antigen-binding polypeptide construct monovalently and specifically binds to extracellular domain 4 (ECD4) of HER2 (human epidermal growth factor receptor 2); the second antigen-binding polypeptide construct monovalently and specifically binds to an extracellular domain (ECD) of HER3 (human epidermal growth factor receptor 3). One antigen binding polypeptide construct is a Fab format and the other antigen binding polypeptide construct is an scFv format. The bi-specific antigen binding constructs includes an Fc having two Fc polypeptides each having a CH3 domain for dimerization. Each Fc polypeptide is linked to the C-terminus of one of the antigen binding polypeptide constructs with or without a linker. The isolated bi-specific antigen binding construct displays greater maximum binding (Bmax) in cells expressing HER2 and HER3, compared to a reference bivalent monospecific antibody comprising two first antigen-binding polypeptide constructs or two second antigen-binding polypeptide constructs.

In some embodiments the first antigen binding polypeptide construct is the antigen binding polypeptide construct of anti-HER2 antibody trastuzumab, or a variant thereof, e.g., includes the CDRs of trasmuzutab or variants thereof. In some embodiments the second antigen binding polypeptide construct is the scFv of anti-HER3 antibody H3, e.g., includes the CDRs of H3 or variants thereof.

In some embodiments the Fc includes modifications, e.g., mutations, to enhance heterodimerization and/or effector functions such as ADCC, ADCP, and CDC. In some embodiments the bi-specific antigen binding constructs is afucosylated.

In some embodiments, the bi-specific antigen binding constructs is conjugated to a molecular label. In other embodiments, the bi-specific antigen binding constructs is conjugated to a drug, e.g., conjugated to maytansine, e.g., DM1 and DM4.

Also described are polynucleotides encoding the bi-specific antigen binding constructs; isolated cells including the bi-specific antigen binding constructs; and methods of production of bi-specific antigen binding constructs.

Also described are pharmaceutical compositions having the bi-specific antigen binding constructs described herein and methods of treatment of, e.g., cancer, e.g., breast cancer using the bi-specific antigen binding constructs described herein.

BRIEF DESCRIPTION OF THE DRAWINGS

FIG. 1 (left) depicts SDS-PAGE analysis of v878, FIG. 1 (middle) depicts SDS-PAGE analysis of v879, and FIG. 1 (right) depicts SDS-PAGE analysis of v880.

FIG. 3A depicts SPR data examining the ability of variant 880 to bind to HER2, and FIG. 3B depicts the ability of HER3 to bind to HER2-bound variant 880.

FIG. 10 provides a summary of exemplary anti-HER2-HER3 bispecific antibodies (bsAbs) and controls described herein. The sequences of the polypetides "_protein") and encoding polynucleotides ("_DNA") are found in the sequence listing with SEQ ID NOS as follows:
>CL#-2_DNA, (SEQ ID NO: 1), >CL#-2_protein, (SEQ ID NO: 2), >CL#642_DNA, (SEQ ID NO: 3), >CL#642_protein, (SEQ ID NO: 4), >CL#1011_DNA, (SEQ ID NO: 5), >CL#1011_protein, SEQ ID NO: 6), >CL#1015_DNA, (SEQ ID NO: 7), >CL#1015_protein, (SEQ ID NO: 8), >CL#1059_DNA, (SEQ ID NO: 9), >CL#1059_protein, (SEQ ID NO: 10), >CL#1069_DNA, (SEQ ID NO: 11), >CL#1069_protein, (SEQ ID NO: 12), >CL#1070_DNA, (SEQ ID NO: 13), >CL#1070_protein, (SEQ ID NO: 14), >CL#1071_DNA, (SEQ ID NO: 15), >CL#1071_protein, (SEQ ID NO: 16), >CL#1102_DNA, (SEQ ID NO: 17), >CL#1102_protein, (SEQ ID NO: 18), >CL#1811_DNA, (SEQ ID NO: 19), >CL#1811_protein, (SEQ ID NO: 20), >CL#3041_DNA, (SEQ ID NO: 21), >CL#3041_protein, (SEQ ID NO: 22), >CL#3057_DNA, (SEQ ID NO: 23), >CL#3057_protein, (SEQ ID NO: 24), >CL#4553_DNA, (SEQ ID NO: 25), >CL#4553_protein, (SEQ ID NO: 26), >CL#4560_DNA, (SEQ ID NO: 27), >CL#4560_protein, (SEQ ID NO: 28), >CL#4561_DNA, (SEQ ID NO: 29), >CL#4561_protein, (SEQ ID NO: 30), >CL_#785_DNA, (SEQ ID NO: 31), >CL #785, (SEQ ID NO: 32), >CL_#4371_DNA, (SEQ ID NO: 33), >CL_#4371_protein, (SEQ ID NO: 34), >CL#5244_DNA, (SEQ ID NO: 35), >CL_#5244_protein, (SEQ ID NO: 36), >CL_#5259_DNA, (SEQ ID NO: 37), >CL_#5259_protein, (SEQ ID NO: 38), >CL_#5454_DNA, (SEQ ID NO: 39), >CL_#5454_protein, (SEQ ID NO: 40), >CL_#5466_DNA, (SEQ ID NO: 41), >CL_#5466_protein, (SEQ ID NO: 42), >CL_#5474_DNA, (SEQ ID NO: 43), >CL_#5474_protein, (SEQ ID NO: 44), >CL_#5476_DNA, (SEQ ID NO: 45), >CL_#5476_protein, (SEQ ID NO: 46), >CL_#6577_DNA, GC (SEQ ID NO: 47), >CL_#6577_protein, (SEQ ID NO: 48).

FIG. 11A depicts selected ratio and step yield of 50 ml productions of v4248.

FIG. 11B depicts the supernatant titre for 10 mL expressions of derivatives of v4248.

FIG. 12 depicts purification results of representative exemplary molecules.

FIG. 13A shows the SEC profiles of v4248 and v6362 before and after conjugation to DM1. FIG. 13B shows UPLC-SEC of v6362 purified by SEC.

FIG. 14A depicts bsAb v7186, and FIG. 14B depicts bsAb v4248 and v6362.

FIG. 15 provides the dissociation constants ($K_D$) for binding of exemplary fucosylated/afucosylated antigen binding constructs with FcγRs.

FIG. 19A depicts viability in the absence of heregulin, while FIG. 19B depicts viability in the presence of heregulin.

FIG. 20A shows the ability of selected bsAbs to internalize and bind to the surface of BT-474 cells; FIG. 20B shows the ability of selected bsAbs to internalize and bind to the surface of JIMT1 cells; FIG. 20C shows the ability of selected bsAbs to internalize and bind to the surface of SKOV cells.

DETAILED DESCRIPTION OF THE INVENTION

Figure 1:
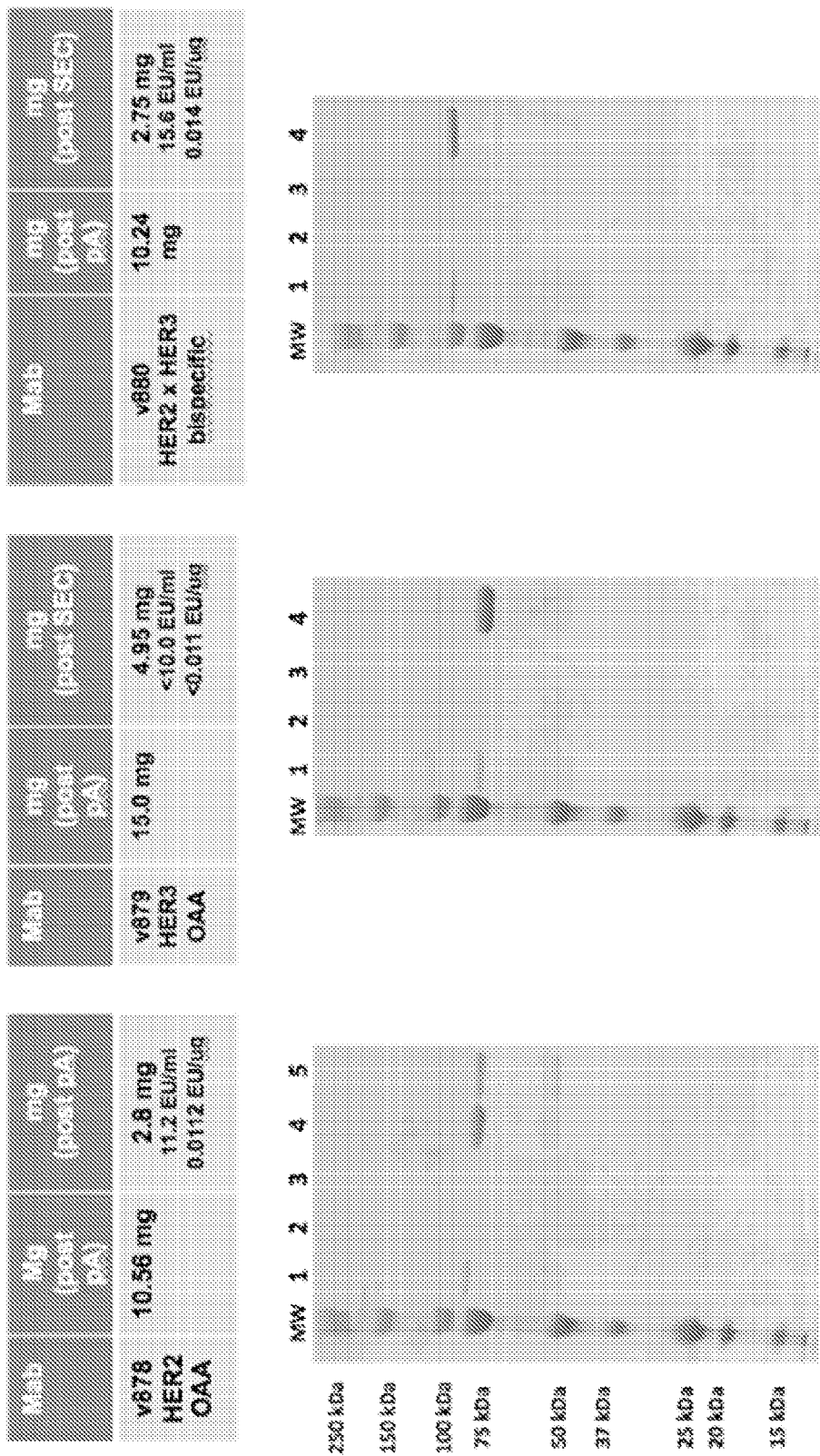
FIG. 1 depicts the SDS-PAGE analysis of an exemplary bsAbs after Protein A purification.

As described in further detail below, described herein are bi-specific antigen binding constructs, e.g., bi-specific antibodies. The bi-specific antigen binding constructs includes a first antigen binding polypeptide construct that binds to ECD4 of HER2 and a second antigen binding polypeptide construct that specifically binds to an ECD of HER3. One of the antigen binding constructs is in an Fc format; the other is in a Fab format. The bi-specific antigen binding constructs includes an Fc having two Fc polypeptides each having a CH3 domain for dimerization. Each Fc polypeptide is linked to the C-terminus of one of the antigen binding polypeptide constructs with or without a linker. The isolated bi-specific antigen binding construct displays greater maximum binding (Bmax) in cells expressing HER2 and HER3, compared to a reference bivalent monospecific antibody comprising two first antigen-binding polypeptide constructs or two second antigen-binding polypeptide constructs.

Definitions

Terms used in the claims and specification are defined as set forth below unless otherwise specified.

As used herein, "isolated" means an agent, e.g., a bispecific antigen binding construct, that has been identified and separated and/or recovered from a component of its natural cell culture environment. Contaminant components of its natural environment are materials that would interfere with diagnostic or therapeutic uses for the construct, and may include enzymes, hormones, and other proteinaceous or non-proteinaceous solutes.

Bi-specific refers to a construct which binds to two different antigens.

Antigen binding polypeptide construct refers to that part of the bi-specific antigen binding construct that binds to an antigen. A antigen binding polypeptide construct can be in any number of formats, e.g., scFv or Fab (both single and double chain).

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell.

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen.

"Antibody-dependent cellular phagocytosis and "ADCP" refer to the destruction of target cells via monocyte or macrophage-mediated phagocytosis.

"Cancer" refers to the physiological condition in mammals that is typically characterized by unregulated cell growth/proliferation, e.g., breast cancer. Additional examples are described herein.

"Treatment" refers to clinical intervention in an attempt to alter the natural course of the individual or cell being treated, and can be performed either for prophylaxis or during the course of clinical pathology.

The term "subject" refers to an animal, in some embodiments a mammal, who is the object of treatment, observation or experiment. An animal may be a human, a companion animal (e.g., dogs, cats, and the like), farm animal (e.g., cows, sheep, pigs, horses, and the like) or a laboratory animal (e.g., rats, mice, guinea pigs, and the like).

The term "mammal" as used herein includes both humans and non-humans and include but is not limited to humans, non-human primates, canines, felines, murines, bovines, equines, and porcines.

The term "effective amount" as used herein refers to that amount of construct being administered, which will accomplish the goal of the recited method, e.g., relieve to some extent one or more of the symptoms of the disease, condition or disorder being treated.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Examples include HER2 antigens and HER3 antigens.

"Specifically binds", "specific binding" or "selective binding" means that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al, Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of <1 μM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M).

An antibody "which binds" an antigen of interest, e.g., a HER2 (ErbB2) antigen, is one capable of binding that antigen with sufficient affinity such that the antibody is useful as a diagnostic and/or therapeutic agent in targeting a cell expressing the antigen and/or for targeted delivery of a cytotoxic or other chemotherapeutic agent, such as a maytansinoid. Where the antibody is one which binds ErbB2, it will usually preferentially bind ErbB2 as opposed to other ErbB receptors, and may be one which does not significantly cross-react with other proteins such as EGFR, ErbB3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (RIA). Sometimes, the anti-ErbB2 antibody will not significantly cross-react with the rat neu protein, e.g., as described in Schecter et al. *Nature* 312:513 (1984) and Drebin et al., *Nature* 312:545-548 (1984).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$, which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

A "HER receptor" is a receptor protein tyrosine kinase which belongs to the human epidermal growth factor receptor (HER) family and includes EGFR, HER2, HER3 and HER4 receptors. The HER receptor will generally comprise an extracellular domain, which may bind an HER ligand; a lipophilic transmembrane domain; a conserved intracellular tyrosine kinase domain; and a carboxyl-terminal signaling domain harboring several tyrosine residues which can be phosphorylated.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" and "neu" refers to the gene encoding human ErbB2 protein. p185 or p185neu refers to the protein product of the neu gene. Preferred HER2 is native sequence human HER2.

HER2 ECD4 refers to an extracellular domain of HER2. The extracellular (ecto) domain of HER2 comprises four domains, Domain I (ECD1, amino acid residues from about 1-195), Domain II (ECD2, amino acid residues from about 196-319), Domain III (ECD3, amino acid residues from about 320-488), and Domain IV (ECD4, amino acid residues from about 489-630) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), Tse et al. Cancer Treat Rev. 2012 April; 38(2):133-42 (2012), or Plowman et al. *Proc. Natl. Acad. Sci.* 90:1746-1750 (1993).

"ErbB3" and "HER3" refer to the receptor polypeptide as disclosed, for example, in U.S. Pat. Nos. 5,183,884 and 5,480,968 as well as Kraus et al. PNAS (USA) 86:9193-9197 (1989), and functional derivatives, including amino acid sequence variants thereof. Examples of antibodies which bind HER3 are described in U.S. Pat. No. 5,968,511 (Akita and Sliwkowski), e.g. the 8B8 antibody (ATCC HB 12070) or a humanized variant thereof.

"HER3 extracellular domain" or "HER3ECD" refers to a domain of HER3 that is outside of a cell, either anchored to a cell membrane, or in circulation, including fragments thereof. In one embodiment, the extracellular domain of HER3 may comprise four domains: Domain I, Domain II, Domain III, and Domain IV. In one embodiment, the HER3ECD comprises amino acids 1-636 (numbering including signal peptide). In one embodiment, HER3 domain III comprises amino acids 328-532 (numbering including signal peptide).

"HER ligand" or "ErbB ligand" means a polypeptide which binds to and/or activates an HER receptor. The HER ligand of particular interest herein is a native sequence human HER ligand such as epidermal growth factor (EGF) (Savage et al., *J. Biol. Chem.* 247:7612-7621 (1972)); transforming growth factor alpha (TGF-α) (Marquardt et al., *Science* 223:1079-1082 (1984)); amphiregulin also known as schwanoma or keratinocyte autocrine growth factor (Shoyab et al. *Science* 243:1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251: 936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Harari et al. *Oncogene* 18:2681-89 (1999)) or cripto (CR-1) (Kannan et al. *J. Biol. Chem.* 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4 and heregulins.

"Heregulin" (HRG) when used herein refers to a polypeptide encoded by the heregulin gene product as disclosed in U.S. Pat. No. 5,641,869 or Marchionni et al., *Nature*, 362:312-318 (1993). Examples of heregulins include heregulin-α, heregulin-β1, heregulin-β2 and heregulin-β3 (Holmes et al., *Science*, 256:1205-1210 (1992); and U.S. Pat. No. 5,641,869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature*, 362:312-318 (1993)); sensory and motor neuron derived factor (SMDF) (Ho et al. *J. Biol. Chem.* 270:14523-14532 (1995)); γ-heregulin (Schaefer et al. *Oncogene* 15:1385-1394 (1997)). The term includes biologically active fragments and/or amino acid sequence variants of a native sequence HRG polypeptide, such as an EGF-like domain fragment thereof (e.g. HRGβ1177-244). Heregulin refers to a polypeptide which activates the ErbB2-ErbB3 and ErbB2-ErbB4 protein complexes (i.e. induces phosphorylation of tyrosine residues in the complex upon binding thereto).

"HER activation" or "HER2 activation" refers to activation, or phosphorylation, of any one or more HER receptors, or HER2 receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

Bispecific Antigen Binding Constructs, Antibody and Related Terms

Disclosed herein are bi-specific antigen binding constructs, e.g., antibodies that selectively bind both HER2 and HER3.

As used herein, an "antibody" or "immunoglobulin" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

An exemplary immunoglobulin (antibody) structural unit is composed of two pairs of polypeptide chains, each pair having one "light" (about 25 kD) and one "heavy" chain (about 50-70 kD). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain comprised in an immunoglobulin construct provided herein, is from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

A "Fab molecule" refers to a protein consisting of the VH and CH1 domain of the heavy chain (the "Fab heavy chain") and the VL and CL domain of the light chain (the "Fab light chain") of an immunoglobulin. In certain embodiments the Fab light chain and Fab heavy chain in the Fab construct are linked by a polypeptide sequence to yield a single chain Fab (scFab).

The "Fab fragment" of an antibody (also referred to as fragment antigen binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen binding. Fab' fragments differ from Fab fragments by the addition of a few residues at the carboxy terminus of the heavy chain CH1 domain including one or more cysteines from the antibody hinge region.

The term "Fc" or "Fc domain" or "Fc region" or "Fc construct" herein is used to define a C-terminal region of an immunoglobulin heavy chain. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, Md., 1991.

"Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. The Fc sequence of an immunoglobulin generally comprises two constant domains, a CH2 domain and a CH3 domain, and optionally comprises a CH4 domain. By "Fc polypeptide" herein is meant one of the polypeptides that make up an Fc region. An Fc polypeptide may be obtained from any suitable immunoglobulin, such as IgG1, IgG2, IgG3, or IgG4 subtypes, IgA, IgE, IgD or IgM. In some embodiments, an Fc polypeptide comprises part or all of a wild type hinge sequence (generally at its N terminus). In some embodiments, an Fc polypeptide does not comprise a functional or wild type hinge sequence.

Fused or linked means that the components (e.g. a Fab molecule and an Fc domain subunit) are linked by peptide bonds, either directly or via one or more peptide linkers.

As used herein, the term "single-chain" refers to a molecule comprising amino acid monomers linearly linked by peptide bonds. In certain embodiments, one of the antigen binding moieties, e.g., antigen binding polypeptide construct, is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule. In certain other embodiments, one of the antigen binding moieties is a single-chain Fv molecule (scFv).

"Single-chain Fv" or "scFv" antibody fragments comprise the VH and VL domains of an antibody, wherein these domains are present in a single polypeptide chain. In one embodiment, the Fv polypeptide further comprises a polypeptide linker between the VH and VL domains which enables the scFv to form the desired structure for antigen binding. For a review of scFv see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "modification promoting the association of the first and the second subunit of the Fc domain" is a manipulation of the peptide sequence or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein they promote association of the two Fc domain subunits and the formation of heterodimers. For example in certain embodiments, a modification promoting association may alter the structure or charge of one or both of the Fc domain subunits so as to make their association favorable.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD 16a), FcγRI (CD64), and FcγRIIa (CD32).

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain (reviewed in Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

Fc and Fc Modifications

The bi-specific antigen binding constructs described herein includes an Fc. The Fc includes two Fc polypeptides each having a CH3 domain for dimerization. The N-terminal end of each Fc polypeptide is linked to the C-terminus of one of the antigen binding polypeptide constructs with or without a linker.

In one embodiment, the Fc is an IgG1 Fc construct, and IgG2 Fc construct, an IgG3 Fc construct, or an IgG4 Fc construct.

In some embodiments, at least one CH3 domain has at least one amino acid modification that promotes the formation of a heterodimeric Fc with stability comparable to a wild-type homodimeric Fc. Exemplary modifications are described below. In some embodiments, the dimerized CH3 domains of the heterodimeric Fc have a melting temperature (Tm) as measured by differential scanning calorimetry (DSC) of about 68, 69, 70, 71, 72, 73, 74, 75, 76, 77, 77.5, 78, 79, 80, 81, 82, 83, 84, or 85° C. or higher. In some embodiments, the dimeric Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when produced; or wherein the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed or when expressed via a single cell.

In some aspects, the Fc comprises one or more modifications in at least one of the $C_{H3}$ sequences. In some aspects, the Fc comprises one or more modifications in at least one of the $C_{H2}$ sequences.

In some aspects, Fc is an Fc described in patent applications PCT/CA2011/001238, filed Nov. 4, 2011 or PCT/CA2012/050780, filed Nov. 2, 2012, the entire disclosure of each of which is hereby incorporated by reference in its entirety for all purposes.

In some aspects, a construct described herein comprises a heterodimeric Fc comprising a modified CH3 domain that has been asymmetrically modified. The heterodimeric Fc can comprise two heavy chain constant domain polypeptides: a first heavy chain polypeptide and a second heavy chain polypeptide, which can be used interchangeably provided that Fc comprises one first heavy chain polypeptide and one second heavy chain polypeptide. Generally, the first heavy chain polypeptide comprises a first CH3 sequence and the second heavy chain polypeptide comprises a second CH3 sequence.

Two CH3 sequences that comprise one or more amino acid modifications introduced in an asymmetric fashion generally results in a heterodimeric Fc, rather than a homodimer, when the two CH3 sequences dimerize. As used herein, "asymmetric amino acid modifications" refers to any modification where an amino acid at a specific position on a first CH3 sequence is different from the amino acid on a second CH3 sequence at the same position, and the first and second CH3 sequence preferentially pair to form a heterodimer, rather than a homodimer. This heterodimerization can be a result of modification of only one of the two amino acids at the same respective amino acid position on each sequence; or modification of both amino acids on each sequence at the same respective position on each of the first and second CH3 sequences. The first and second CH3 sequence of a heterodimeric Fc can comprise one or more than one asymmetric amino acid modification.

Table X1 provides the amino acid sequence of a human IgG1 Fc sequence, corresponding to amino acids 231 to 447 of a full-length human IgG1 heavy chain. The CH3 sequence comprises amino acid 341-447 of the full-length human IgG1 heavy chain.

Typically an Fc can include two contiguous heavy chain sequences (A and B) that are capable of dimerizing. In some aspects, one or both sequences of an Fc include one or more mutations or modifications at the following locations: L351, F405, Y407, T366, K392, T394, T350, S400, and/or N390, using EU numbering. In some aspects, an Fc includes a mutant sequence shown in Table X. In some aspects, an Fc includes the mutations of Variant 1 A-B. In some aspects, an Fc includes the mutations of Variant 2 A-B. In some aspects, an Fc includes the mutations of Variant 3 A-B. In some aspects, an Fc includes the mutations of Variant 4 A-B. In some aspects, an Fc includes the mutations of Variant 5 A-B.

acid modifications at positions F405 and Y407, and a second CH3 sequence having amino acid modifications at position T394. In one embodiment, the heterodimeric Fc comprises a modified CH3 domain with a first CH3 sequence having one or more amino acid modifications selected from L351Y, F405A, and Y407V, and the second CH3 sequence having one or more amino acid modifications selected from T366L, T366I, K392L, K392M, and T394W.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, and one of the first or second CH3 sequences further comprising amino acid modifications at position Q347, and the other CH3 sequence further comprising amino acid modification at position K360. In another embodiment, a heterodimeric Fc comprises a modified CH3 domain with a first CH3 sequence having amino acid modifications at positions L351, F405 and Y407, and a second CH3 sequence having amino acid modifications at position T366, K392, and T394, one of the first or second CH3 sequences further comprising amino acid modifications at position Q347, and the other CH3 sequence further comprising amino acid modification at position K360, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394 and one of said first and second CH3 sequences further comprising amino acid modification of D399R or D399K and the other CH3 sequence comprising one or more of T411E, T411D, K409E,

TABLE X

Exemplary Fc sequence and CH3 modifications

| Human IgG1 Fc sequence 231-447 (EU-numbering) Variant IgG1 Fc sequence (231-447) | Chain | APELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDI AVEWESNGQPENNYKTTPPVLDSDGSFFLYSKLTVDKSRWQQGNVFSCS VMHEALHNHYTQKSLSLSPGK (SEQ ID NO: 69) Mutations |
|---|---|---|
| 1 | A | L351Y_F405A_Y407V |
| 1 | B | T366L_K392M_T394W |
| 2 | A | L351Y_F405A_Y407V |
| 2 | B | T366L_K392L_T394W |
| 3 | A | T350V_L351Y_F405A_Y407V |
| 3 | B | T350V_T366L_K392L_T394W |
| 4 | A | T350V_L351Y_F405A_Y407V |
| 4 | B | T350V_T366L_K392M_T394W |
| 5 | A | T350V_L351Y_S400E_F405A_Y407V |
| 5 | B | T350V_T366L_N390R_K392M_T394W |

The first and second CH3 sequences can comprise amino acid mutations as described herein, with reference to amino acids 231 to 447 of the full-length human IgG1 heavy chain. In one embodiment, the heterodimeric Fc comprises a modified CH3 domain with a first CH3 sequence having amino K409D, K392E and K392D. In another embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, one of said first and second CH3 sequences further comprises amino acid modification of D399R or D399K and the other CH3 sequence comprising one or more of T411E, T411D, K409E, K409D, K392E and K392D, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, wherein one or both of said CH3 sequences further comprise the amino acid modification of T350V.

In one embodiment, a heterodimeric Fc comprises a modified CH3 domain comprising the following amino acid modifications, where "A" represents the amino acid modifications to the first CH3 sequence, and "B" represents the amino acid modifications to the second CH3 sequence:
A:L351Y_F405A_Y407V, B:T366L_K392M_T394W,
A:L351Y_F405A_Y407V, B:T366L_K392L_T394W,
A:T350V_L351Y_F405A_Y407V,
B:T350V_T366L_K392L_T394W,
A:T350V_L351Y_F405A_Y407V.
B:T350V_T366L_K392M_T394W,
A:T350V_L351Y_S400E_F405A_Y407V, and/or
B:T350V_T366L_N390R_K392M_T394W.

The one or more asymmetric amino acid modifications can promote the formation of a heterodimeric Fc in which the heterodimeric CH3 domain has a stability that is comparable to a wild-type homodimeric CH3 domain. In an embodiment, the one or more asymmetric amino acid modifications promote the formation of a heterodimeric Fc domain in which the heterodimeric Fc domain has a stability that is comparable to a wild-type homodimeric Fc domain. In an embodiment, the one or more asymmetric amino acid modifications promote the formation of a heterodimeric Fc domain in which the heterodimeric Fc domain has a stability observed via the melting temperature (Tm) in a differential scanning calorimetry study, and where the melting temperature is within 4° C. of that observed for the corresponding symmetric wild-type homodimeric Fc domain. In some aspects, the Fc comprises one or more modifications in at least one of the $C_{H3}$ sequences that promote the formation of a heterodimeric Fc with stability comparable to a wild-type homodimeric Fc.

In one embodiment, the stability of the CH3 domain can be assessed by measuring the melting temperature of the CH3 domain, for example by differential scanning calorimetry (DSC). Thus, in a further embodiment, the CH3 domain has a melting temperature of about 68° C. or higher. In another embodiment, the CH3 domain has a melting temperature of about 70° C. or higher. In another embodiment, the CH3 domain has a melting temperature of about 72° C. or higher. In another embodiment, the CH3 domain has a melting temperature of about 73° C. or higher. In another embodiment, the CH3 domain has a melting temperature of about 75° C. or higher. In another embodiment, the CH3 domain has a melting temperature of about 78° C. or higher. In some aspects, the dimerized $C_{H3}$ sequences have a melting temperature (Tm) of about 68, 69, 70, 71, 72, 73, 74, 75, 76, 77, 77.5, 78, 79, 80, 81, 82, 83, 84, or 85° C. or higher.

In some embodiments, a heterodimeric Fc comprising modified CH3 sequences can be formed with a purity of at least about 75% as compared to homodimeric Fc in the expressed product. In another embodiment, the heterodimeric Fc is formed with a purity greater than about 80%. In another embodiment, the heterodimeric Fc is formed with a purity greater than about 85%. In another embodiment, the heterodimeric Fc is formed with a purity greater than about 90%. In another embodiment, the heterodimeric Fc is formed with a purity greater than about 95%. In another embodiment, the heterodimeric Fc is formed with a purity greater than about 97%. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed via a single cell.

Additional methods for modifying monomeric Fc polypeptides to promote heterodimeric Fc formation are described in International Patent Publication No. WO 96/027011 (knobs into holes), in Gunasekaran et al. (Gunasekaran K. et al. (2010) J Biol Chem. 285, 19637-46, electrostatic design to achieve selective heterodimerization), in Davis et al. (Davis, J H. et al. (2010) Prot Eng Des Sel; 23(4): 195-202, strand exchange engineered domain (SEED) technology), and in Labrijn et al [Efficient generation of stable bi-specific IgG1 by controlled Fab-arm exchange. Labrijn A F, Meesters J I, de Goeij B E, van den Bremer E T, Neijssen J, van Kampen M D, Strumane K, Verploegen S, Kundu A, Gramer M J, van Berkel P H, van de Winkel J G, Schuurman J, Parren P W. Proc Natl Acad Sci USA. 2013 Mar. 26; 110(13):5145-50.

In some embodiments an isolated construct described herein comprises an antibody construct which binds an antigen; and a dimeric Fc polypeptide construct that has superior biophysical properties like stability and ease of manufacture relative to an antibody construct which does not include the same Fc polypeptide. A number of mutations in the heavy chain sequence of the Fc are known in the art for selectively altering the affinity of the antibody Fc for the different Fcgamma receptors. In some aspects, the Fc comprises one or more modifications to promote selective binding of Fc-gamma receptors.

Additional Fc Modifications to Improve Effector Function.

In some embodiments the bi-specific antigen binding construct may be modified to improve effector function. Such modifications are known in the art and include afucosylation, and engineering of the affinity of the Fc portion of antibodies towards the activating receptors, mainly FCGR3a and FCGRb for ADCC, and towards C1q, for CDC. In one embodiment the effector function is one or more function selected from the group consisting of CDC, ADCC, ADCP, and cytokine secretion. In a particular embodiment the effector function is ADCC.

CH2 Modifications and Selective Binding of FcγR

In some embodiments the bi-specific antigen binding construct includes a variant CH2 domain having asymmetric amino acid modifications to promote selective binding of a FcγR. In some embodiments the variant CH2 domain allows for separation and purification of the isolated monovalent antibody described herein.

In some embodiments, the bi-specific antigen binding constructs includes an Fc with amino acid modifications of at least one CH2 domain. The CH2 domain is amino acid 231-340 of the sequence shown in Table X.

The following table summarizes the different designs reported in the literature for effector function engineering.

TABLE Y

Effector function engineering

| Reference | Mutations | Effect |
| --- | --- | --- |
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

S298A/E333A/K334A, S298A/E333A/K334A/K326A (Lu Y, Vernes J M, Chiang N, et al. J Immunol Methods. 2011 Feb. 28; 365 (1-2):132-41);

F243L/R292P/Y300L/V305I/P396L, F243 J/R292P/Y300L/L235V/P396L (Stavenhagen J B, Gorlatov S, Tuaillon N, et al. Cancer Res. 2007 Sep. 15; 67 (18):8882-90; Nordstrom J L, Gorlatov S, Zhang W, et al. Breast Cancer Res. 2011 Nov. 30; 13 (6):R123);

F243L (Stewart R. Thom G. Levens M, et al. Protein Eng Des Sel. 2011 September; 24(9):671-8), S298A/E333A/K334A (Shields R L, Namenuk A K, Hong K, et al. J Biol Chem. 2001 Mar. 2; 276(9):6591-604);

S239D/I332E/A330L, S239D/I332E (Lazar G A, Dang W, Karki S, et al. Proc Natl Acad Sci USA. 2006 Mar. 14; 103(11):4005-10);

S239D/S267E, S267E/L328F (Chu S Y, Vostiar I, Karki S, et al. Mol Immunol. 2008 September; 45 (15):3926-33);

S239D/D265S/S298A/I332E, S239E/S298A/K326A/A327H, G237F/S298A/A330L/I332E, S239D/I332E/S298A, S239D/K326E/A330L/I332E/S298A. G236A/S239D/D270L/I332E, S239E/S267E/H268D, L234F/S267E/N325L, G237F/V266L/S267D and other mutations listed in WO2011/120134 and WO2011/120135, herein incorporated by reference. *Therapeutic Antibody Engineering* (by William R. Strohl and Lila M. Strohl, Woodhead Publishing series in Biomedicine No 11, ISBN 1 907568 37 9, October 2012) lists mutations on page 283.

Fc Modifications and Neonatal Fc Receptor

In one embodiment the Fc region exhibits binding affinity to neonatal Fc receptor (FcRn). In certain embodiments, the FcRn binding affinity is substantially similar to that of a native IgG1 Fc. In some embodiments, substantially similar binding to FcRn is achieved when the Fc region of a construct described herein exhibits greater than about 70%, or in some embodiments greater than about 80%, and in some particular embodiments greater than about 90% of the binding affinity of a native IgG1 Fc domain to FcRn.

As is known in the art, binding to FcRn recycles endocytosed antibody from the endosome back to the bloodstream (Raghavan et al., 1996, Annu Rev Cell Dev Biol 12:181-220; Ghetie et al., 2000, Annu Rev Immunol 18:739-766). This process, coupled with preclusion of kidney filtration due to the large size of the full-length molecule, results in favorable antibody serum half-lives ranging from one to three weeks. Binding of Fc to FcRn also plays a key role in antibody transport.

Fc Modifications and Reduced Fc Receptor Affinity

In certain embodiments the Fc regions of the constructs described herein exhibit reduced binding affinity to an Fc receptor and/or reduced effector function, as compared to a native IgG1 Fc region. In one such embodiment the Fc region exhibits less than 50%, alternatively less than 20%, alternatively less than 10% and in some embodiments, less than 5% of the binding affinity to an Fc receptor, as compared to a native IgG1 Fc region, and/or less than 50%, alternatively less than 20%, alternatively less than 10% and in some embodiments less than 5% of the effector function, as compared to a native IgG1 Fc region.

In one embodiment, the Fc region of a construct described herein does not substantially bind to an Fc receptor or induce appreciable effector function. In a certain embodiment the Fc receptor is an Fcγ receptor. In one embodiment the Fc receptor is a mammalian Fc receptor. In certain embodiments, the mammalian Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa.

Fc Linkers

The bi-specific antigen binding constructs described herein include two antigen binding polypeptide constructs described herein operatively coupled to an Fc described herein. In some aspects, Fc is coupled with or without one or more linkers. In some aspects, Fc is directly coupled to the antigen binding polypeptide constructs. In some aspects, Fc is coupled to the antigen binding polypeptide constructs by one or more linkers.

In some aspects, the one or more linkers are one or more polypeptide linkers. In some aspects, the one or more linkers comprise one or more antibody hinge regions. In some aspects, the one or more linkers comprise one or more IgG1 hinge regions.

HER2 and HER3 Binding Antigen-Binding Polypeptide Constructs

The bi-specific antigen binding constructs described include a first antigen binding polypeptide construct that specifically binds an ECD4 of HER2 and a second antigen binding polypeptide construct that specifically binds an ECD of HER3. One of the antigen binding polypeptide construct is in a Fab format; the other antigen binding polypeptide construct is in an scFv format.

The sequences of the antigen binding polypeptide constructs can be based using known FFab and/or scFv sequences of antibodies that bind HER2 or HER3. Examples include trastuzumab (binding HER2) and H3 (binding HER3).

In some embodiments, an scFv, either known or novel, can be converted to a Fab format for use as an antigen binding polypeptide construct in the invention. Methods for converting an scFv to a Fab format are described at, e.g., Zhou et al (2012) Mol Cancer Ther 11:1167-1476. The methods described therein are incorporated by reference.

In some embodiments, the first antigen binding polypeptide construct has a sequence wherein the construct binds to the 4D5 epitope of HER2. In some embodiments, the first antigen binding polypeptide construct has a sequence wherein the construct blocks by 50% or greater binding of trastuzumab to HER2 ECD4.

In some embodiments, the first antigen binding polypeptide construct has six CDRs having amino acid sequences at least 95% identical to the six CDRs of trastuzumab. In other embodiments, the CDRs have an amino acid sequence that is at least 80, 81, 82, 83, 84, 85, 86, 87, 88, 89, 90, 91, 92, 93, 94, 95, 96, 97, 98, or at least 99% identical to the six CDRs of trastuzumab. In some embodiments, the first antigen binding polypeptide construct has six CDRs comprising amino acid sequences 100% identical to the six CDRs of trastuzumab. In other embodiments, the first antigen binding polypeptide construct has an amino acid sequence that is at least 95% identical to the VH sequence of trastuzumab and a second polypeptide comprising an amino acid sequence that is at least 95% identical to the VL sequence of trastuzumab. In some embodiments, the first antigen binding polypeptide construct has a first polypeptide with an amino acid sequence that is at least 80, 81, 82, 83, 84, 85, 86, 87, 88, 89, 90, 91, 92, 93, 94, 95, 96, 97, 98, or at least 99% identical to the VH sequence of trastuzumab and a second polypeptide with an amino acid sequence that is at least 80, 81, 82, 83, 84, 85, 86, 87, 88, 89, 90, 91, 92, 93, 94, 95, 96, 97, 98, or at least 99% identical to the VL sequence of trastuzumab. In other embodiments, the first antigen binding polypeptide construct has a first polypeptide with an amino acid sequence that is 100% identical to the VH sequence of trastuzumab and a second polypeptide with an amino acid sequence that is 100% identical to the VL sequence of trastuzumab.

Table A1 provides the amino acid sequence of trastuzumab CDRs.

TABLE A1

Amino acid sequence of Trastuzumab CDRs:

| SEQ ID NO: | Sequence | Description |
| --- | --- | --- |
| 49 | GFNIKDT | Trastuzumab heavy chain CDR1 |
| 50 | YPTNG | Trastuzumab heavy chain CDR2 |
| 51 | WGGDGFYAMDY | Trastuzumab heavy chain CDR3 |
| 52 | RASQDVNTAVA | Trastuzumab light chain CDR1 |
| 53 | SASFLYS | Trastuzumab light chain CDR2 |
| 54 | QQHYTTPPT | Trastuzumab light chain CDR3 |

WO2012/143523 describes additional antibodies that bind to the same epitope as trastuzumab (i.e. they compete with trastuzumab for binding to ECD4); specifically group I as described in Example 14. In some embodiments, the first antigen binding polypeptide construct of the invention includes sequences of the Fab/scFv described therein.

In some embodiments, the second antigen binding polypeptide construct is a variant of the scFv H3 as described in U.S. Pat. No. 7,332,580. In some embodiments, the second antigen binding polypeptide construct has six CDRs having amino acid sequences at least 95% identical to the six CDRs of H3. In other embodiments, the CDRs have an amino acid sequence that is at least 80, 81, 82, 83, 84, 85, 86, 87, 88, 89, 90, 91, 92, 93, 94, 95, 96, 97, 98, or at least 99% identical to the six CDRs of H3. In some embodiments, the second antigen binding polypeptide construct has six CDRs comprising amino acid sequences 100% identical to the six CDRs of H3. In other embodiments, the second antigen binding polypeptide construct has an amino acid sequence that is at least 95% identical to the VH sequence of H3 and a second polypeptide comprising an amino acid sequence that is at least 95% identical to the VL sequence of H3. In some embodiments, the second antigen binding polypeptide construct has a first polypeptide with an amino acid sequence that is at least 80, 81, 82, 83, 84, 85, 86, 87, 88, 89, 90, 91, 92, 93, 94, 95, 96, 97, 98, or at least 99% identical to the VH sequence of H3 and a second polypeptide with an amino acid sequence that is at least 80, 81, 82, 83, 84, 85, 86, 87, 88, 89, 90, 91, 92, 93, 94, 95, 96, 97, 98, or at least 99% identical to the VL sequence of H3. In other embodiments, the second antigen binding polypeptide construct has a first polypeptide with an amino acid sequence that is 100% identical to the VH sequence of H3 and a second polypeptide with an amino acid sequence that is 100% identical to the VL sequence of H3.

In some embodiments, the second antigen binding polypeptide construct has a sequence wherein the construct blocks by 50% or greater binding of anti-HER3 scFv H3 to the ECD of HER3. In other embodiments, the second antigen binding polypeptide construct has a sequence wherein the construct competes with heregulin for binding to the ECD of HER3.

TABLE A2

| scFv H3 CDR sequences: | | |
|---|---|---|
| description | Sequence | SEQ ID NO: |
| HER3.H3 VH CDR1 | SYWMS | 64 |
| HER3.H3 VH CDR2 | NINRDGSASYYVDSVKG | 65 |
| HER3.H3 VH CDR3 | DRGVGYFDL | 66 |
| HER3.H3 VL CDR1 | TGTSSDVGGYNFVS | 67 |
| HER3.H3 VL CDR2 | DVSDRPS | 68 |
| HER3.H3 VL CDR3 | SSYGSSSTHVI | 63 |

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or Trastuzumab (HERCEPTIN®) as described in Table 3 of U.S. Pat. No. 5,821,337 expressly incorporated herein by reference; and humanized 520C9 (WO93/21319).

The bispecific antigen binding constructs of the invention include at antigen binding polypeptide construct that specifically bindes to epitope 4D5 of HER2. The "epitope 4D5" is the region in the extracellular domain of HER2 to which the antibody 4D5 (ATCC CRL 10463) and Trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive, see FIG. 1 of US Patent Publication No. 2006/0018899).

In instances where it is desirable to increase the affinity of the bi-specific antigen binding construct for its cognate antigen, methods known in the art can be used to increase the affinity of the antigen-binding polypeptide construct for its antigen. Examples of such methods are described in the following references, Birtalan et al. (2008) *JMB* 377, 1518-1528; Gerstner et al. (2002) *JMB* 321, 851-862; Kelley et al. (1993) *Biochem* 32 (27), 6828-6835; Li et al. (2010) *JBC* 285(6), 3865-3871, and Vajdos et (2002) *JMB* 6320, 415-428.

One example, of such a method is affinity maturation. One exemplary method for affinity maturation of HER2 antigen-binding domains is described as follows. Structures of the trastuzumab/HER2 (PDB code 1N8Z) complex and pertuzumab/HER2 complex (PDB code 1S78) are used for modeling. Molecular dynamics (MD) can be employed to evaluate the intrinsic dynamic nature of the WT complex in an aqueous environment. Mean field and dead-end elimination methods along with flexible backbones can be used to optimize and prepare model structures for the mutants to be screened. Following packing a number of features will be scored including contact density, clash score, hydrophobicity and electrostatics. Generalized Born method will allow accurate modeling of the effect of solvent environment and compute the free energy differences following mutation of specific positions in the protein to alternate residue types. Contact density and clash score will provide a measure of complementarity, a critical aspect of effective protein packing. The screening procedure employs knowledge-based potentials as well as coupling analysis schemes relying on pair-wise residue interaction energy and entropy computations. Literature mutations known to enhance HER2 binding, and combinations of thereof are summarized in the following tables:

TABLE A3

| Trastuzumab mutations known to increase binding to HER2 for the Trastuzumab-HER2 system | |
|---|---|
| Mutation | Reported Improvement |
| H_D102W (H_D98W) | 3.2X |
| H_D102Y | 3.1X |
| H_D102K | 2.3X |
| H_D102T | 2.2X |
| H_N55K | 2.0X |
| H_N55T | 1.9X |
| L_H91F | 2.1X |
| L_D28R | 1.9X |

Antigen Binding Polypeptide Constructs in a Single Chain Fab Format

In some embodiments, the bispecific antigen binding construct includes a Fab that is in a single chain Fab format, or scFab. Descriptions of this format are well known to one of skill in the art and can be found in, e.g., International Patent Publication No. WO 2014/018572; US2010/0256338; and US20110293613. Description of design, expression and use of scFab from these references is incorporated by reference.

In one embodiment the antigen binding polypeptide construct in the Fab format is in the scFab format and includes the sequences found in Table A4. The table includes the CH3, CH2, CH1, VH, CL and VL domains.

TABLE A4

| Sequences of exemplary scFab | | |
|---|---|---|
| SEQ ID NO | DESCRIPTION | Sequence (polypeptide) |
| 70 | Tras-HH41-scmab-HetFc001a(trastuzumab scmab with HH41 linker) | DIQMTQSPSSLSASVGDRVTITCRASQDVNTAVAWYQQKPGKAPKLLIYSASFLYSGVPS RFSGSRSGTDFTLTISSLQPEDFATYYCQQHYTTPPTFGQGTKVEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNAGECGGSGGGSGSSADDAKKDAAKKDDAKK DDAKKDGGGSGGGSGEVQLVESGGGLVQPGGSLRLSCAASGFNIKDTYIHWVRQAPGKGL EWVARIYPTNGYTRYADSVKGRFTISADTSKNTAYLQMNSLRAEDTAVYYCSRWGGDGFY AMDYWGQGTLVTVSSASTKGPSVFPLAPSSKSTSGGTAALGCLVKDYFPEPVTVSWNSGA LTSGVHTFPAVLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKAKGQ |

TABLE A4-continued

Sequences of exemplary scFab

| SEQ ID NO | DESCRIPTION | Sequence (polypeptide) |
|---|---|---|
| | | PREPQVYVYPPSRDELTKNQVSLTCLVKGFYPSDIAVEWESNGQPENNYKTTPPVLDSDG SFALVSKLTVDKSRWQQGNVFSCSVMHEALHNHYTQKSLSLSPG |
| 71 | Tras-GSE34-scmab-HetFc001a (trastuzumab scmab with GSE34 linker) | DIQMTQSPSSLSASVGDRVTITCRASQDVNTAVAWYQQKPGKAPKLLIYSASFLYSGVPS RFSGSRSGTDFTLTISSLQPEDFATYYCQQHYTTPPTFGQGTKVEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNAGECSGGGSGGGSEGGGSEGGGSEGGGSEG GGSGGGSGEVQLVESGGGLVQPGGSLRLSCAASGFNIKDTYIHWVRQAPGKGLEWVARIY PTNGYTRYADSVKGRFTISADTSKNTAYLQMNSLRAEDTAVYYCSRWGGDGFYAMDYWGQ GTLVTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVY VYPPSRDELTKNQVSLTCLVKGFYPSDIAVEWESNGQPENNYKTTPPVLDSDGSFALVSK LTVDKSRWQQGNVFSCSVMHEALHNHYTQKSLSLSPG |
| 72 | H3-HH41-scmab-HetFc001b (H3 scmab with HH41 linker) | QSALTQPASVSGSPGQSITISCTGTSSDVGGYNFVSWYQQHPGKAPKLMIYDVSDRPSGV SDRFSGSKSGNTASLIISGLQADDEADYYCSSYGSSSTHVIFGGGTKVTVLGQPKAAPSV TLFPPSSEELQANKATLVCLISDFYPGAVTVAWKADSSPVKAGVETTTPSKQSNNKYAAS SYLSLTPEQWKSHRSYSCQVTHEGSTVEKTVAPTECSGGSGGGSGSSADDAKKDAAKKDD AKKDDAKKDGGGSGGGSGGQVQLQESGGGLVKPGGSLRLCAASGFTFSSYWMSWVRQAPG KGLEWVANINRDGSASYYVDSVKGRFTISRDDAKNSLYLQMNSLRAEDTAVYYCARDRGV GYFDLWGRGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTISKAKG QPREPQVYVLPPSRDELTKNQVSLLCLVKGFYPSDIAVEWESNGQPENNYLTWPPVLDSD GSFFLYSKLTVDKSRWQQGNVFSCSVMHEALHNHYTQKSLSLSPG |
| 73 | H3-GSE34-scmab-HetFc001b (H3 scmab with GSE34 linker) | QSALTQPASVSGSPGQSITISCTGTSSDVGGYNFVSWYQQHPGKAPKLMIYDVSDRPSGV SDRFSGSKSGNTASLIISGLQADDEADYYCSSYGSSSTHVIFGGGTKVTVLGQPKAAPSV TLFPPSSEELQANKATLVCLISDFYPGAVTVAWKADSSPVKAGVETTTPSKQSNNKYAAS SYLSLTPEQWKSHRSYSCQVTHEGSTVEKTVAPTECSSGGGSGGGSEGGGSEGGGSEGGG SEGGGSGGGSGGQVQLQESGGGLVKPGGSLRLSCAASGFTFSSYWMSWVRQAPGKGLEWVA NINRDGSASYYVDSVKGRFTISRDDAKNSLYLQMNSLRAEDTAVYYCARDRGVGYFDLWG RGTLVTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKKVEPKSCDKTHTCPP CPAPELLGGPSVFLEPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQV YVLPPSRDELTKNQVSLLCLVKGFYPSDIAVEWESNGQPENNYLTWPPVLDSDGSFFLYS KLTVDKSRWQQGNVFSCSVMHEALHNHYTQKSLSLSPG |
| 74 | Tras-HH41-scmab-HetFc001a (trastuzumab scmab with HH41 linker) | GATATTCAGATGACCCAGAGCCCTTCTTCCCTGTCCGCTTCCGTGGGAGATCGCGTGACTA TTACTTGTCGAGCCTCTCAGGATGTGAACACCGCCGTGGCTTGGTACCAGCAGAAGCCTGG AAAAGCTCCAAAGCTGCTGATCTACAGTGCATCATTCCTGTATTCAGGAGTCCCAAGCCGG TTTAGCGGCAGCCGGTCTGGCACAGACTTCACTCTGACCATTAGCTCCCTGCAGCCCGAGG ATTTTGCCACTTACTATTGCCAGCAGCACTATACCACACCCCCTACATTCGGGCAGGGAAC TAAAGTGGAGATCAAGCGCACCGTGGCCGCTCCTTCTGTCTTCATTTTTCCACCCAGTGAC GAACAGCTGAAGTCCGGCACAGCCTCTGTGGTCTGTCTGCTGAACAATTTTTACCCACGAG AAGCCAAAGTCAGTGGAAGGTCGATAACGCTCTGCAGAGTGGCAACAGCCAGGAGAGCGT GACCGAACAGGACTCCAAAGATTCTACATATAGTCTGTCTAGTACACTGACTCTGAGCAAG GCAGACTACGAGAAGCACAAAGTGTATGCTTGCGAAGTCACTCATCAGGGCCTGTCAAGCC CCGTGACCAAGTCCTTCAATAGGGGAGAGTGTGGAGGGAGTGGAGGAGGGTCAGGCAGCTC TGCAGACGATGCCAAGAAAGACGCAGCCAAGAAAGATGACGCCAAGAAAGACGATGCTAAG AAAGATGGAGGAGGGAGCGGAGGAGGGTCCGGAGAGGTGCAGCTGGTCGAAAGCGGAGGAG GACTGGTGCAGCCTGGAGGCTCTCTGCGGCTGAGTTGCGCTGCATCAGGCTTCAACATCAA AGACACCTACATTCATTGGGTGAGACAGGCCCCCGGCAAGGGACTGGAGTGGGTCGCCAGG ATCTATCCTACCAATGGCTACACAAGATATGCCGACAGCGTGAAAGGGCGCTTCACTATTA GCGCAGATACTTCCAAGAACACCGCCTACCTGCAGATGAACAGCCTGCGAGCTGAAGATAC AGCAGTGTACTATTGTAGCCGGTGGGCGGCGATGGATTCTACGCAATGGACTACTGGGGA CAGGGAACCCTGGTCACCGTCTCAAGCGCTAGCACTAAGGGGCCTTCCGTGTTTCCACTGG CTCCCTCTAGTAAATCCACCTCTGGAGGCACAGCTGCACTGGGATGTCTGGTGAAGGATTA CTTCCCTGAACCAGTCACAGTGAGTTGGAACTCAGGGGCTCTGACAAGTGGAGTCCATACT TTTCCCGCAGTGCTGCAGTCAAGCGGACTGTACTCCCTGTCCTCTGTGGTCACCGTGCCTA GTTCAAGCCTGGGCACCCAGACATATATCTGCAACGTGAATCACAAGCCATCAAATACAAA AGTCGACAAGAAAGTGGAGCCCAAGAGCTGTGATAAAACTCATACCTGCCCACCTTGTCCG GCGCCAGAACTGCTGGGAGGACCAAGCGTGTTCCTGTTTCCACCCAAGCCTAAAGACACCC TGATGATTTCCCGGACTCCTGAGGTCACCTGCGTGGTCGTGGACGTGTCTCACGAGGACCC CGAAGTCAAGTTCAACTGGTACGTGGATGGCGTCGAAGTGCATAATGCCAAGACCAAACCA CGGGAGGAACAGTACAACTCTACCTATAGAGTCGTGAGTGTCCTGACAGTGCTGCACCAGG ACTGGCTGAATGGGAAGGAGTATAAGTGTAAAGTGAGCAACAAAGCCCTGCCCGCCCCAAT CGAAAAAACAATCTCTAAAGCAAAAGGACAGCCTCGCGAACCACAGGTCTACGTCTACCCC CCATCAAGAGATGAACTGACAAAAAATCAGGTCTCTCTGACATGCCTGGTCAAAGGATTCT ACCCTTCCGACATCGCCGTGGAGTGGGAAAGTAACGGCCAGCCCGAGAACAATTACAAGAC |

TABLE A4-continued

Sequences of exemplary scFab

| SEQ ID NO | DESCRIPTION | Sequence (polypeptide) |
|---|---|---|
| | | CACACCCCCTGTCCTGGACTCTGATGGGAGTTTCGCTCTGGTGTCAAAGCTGACCGTCGAT<br>AAAAGCCGGTGGCAGCAGGGCAATGTGTTTAGCTGCTCCGTCATGCACGAAGCCCTGCACA<br>ATCACTACACACAGAAGTCCCTGAGCCTGAGCCCTGGC |
| 75 | Tras-GSE34-scmab-HetFc001a (trastuzumab scmab with GSE34 linker) | GATATTCAGATGACTCAGAGCCCCTCAAGCCTGTCCGCCTCCGTGGGAGATAGAGTGACTA<br>TTACTTGTAGAGCCTCACAGGATGTCAACACCGCTGTGGCATGGTACCAGCAGAAGCCTGG<br>CAAAGCTCCAAAGCTGCTGATCTACTCCGCATCTTTCCTGTATTCTGGGGTCCCAAGTCGG<br>TTTAGTGGCTCAAGAAGCGGGACAGACTTCACTCTGACCATTAGCTCCCTGCAGCCCGAGG<br>ATTTTGCCACTTACTATTGCCAGCAGCACTATACCACACCCCTACATTCGGACAGGGCAC<br>TAAAGTGGAGATCAAGCGCACCGTGGCCGCTCCTTCTGTCTTCATTTTTCCACCCAGCGAC<br>GAACAGCTGAAATCAGGCACAGCCAGCGTGGTCTGTCTGCTGAACAATTTTTACCCACGAG<br>AAGCCAAAGTGCAGTGGAAGGTCGATAACGCTCTGCAGTCCGGCAATTCTCAGGAGAGTGT<br>GACCGAACAGGACTCAAAAGATAGCACATATTCCCTGTCTAGTACACTGACTCTGTCTAAG<br>GCAGACTACGAGAAGCACAAAGTGTATGCCTGCGAAGTCACTCATCAGGGGCTGTCAAGCC<br>CCGTGACCAAGAGCTTCAATAGGGGAGAGTGTTCCGGAGGAGGATCTGGAGGAGGAAGTGA<br>GGGAGGAGGCAGCGAAGGCGGGGGATCTGAGGGAGGCGGAAGTGAGGGCGGAGGATCAGGC<br>GGAGGAAGCGGAGAGGTGCAGCTGGTCGAATCCGGAGGAGGACTGGTGCAGCCTGGAGGGT<br>CCCTGCGACTGTCTTGCGCAGCCAGTGGCTTTAACATCAAAGACACCTACATTCATTGGGT<br>GAGACAGGCTCCCGGGAAGGGACTGGAGTGGGTCGCAAGGATCTATCCTACCAATGGATAC<br>ACAAGATATGCCGACAGCGTGAAAGGCCGCTTCACTATTTCAGCAGATACTAGCAAGAACA<br>CCGCCTACCTGCAGATGAATAGCCTGCGAGCCGAAGATACAGCTGTGTACTATTGTTCCCG<br>GTGGGGCGGAGATGGATTCTACGCAATGGATTATTGGGGACAGGGAACCCTGGTCACCGTC<br>TCAAGCGCTAGCACTAAGGGGCCTTCCGTGTTTCCACTGGCTCCCTCTAGTAAATCCACCT<br>CTGGAGGCACAGCTGCACTGGGATGTCTGGTGAAGGATTACTTCCCTGAACCAGTCACAGT<br>GAGTTGGAACTCAGGGGCTCTGACAAGTGGAGTCCATACTTTTCCCGCAGTGCTGCAGTCA<br>AGCGGACTGTACTCCCTGTCCTCTGTGGTCACCGTGCCTAGTTCAAGCCTGGGCACCCAGA<br>CATATATCTGCAACGTGAATCACAAGCCATCAAATACAAAAGTCGACAAGAAAGTGGAGCC<br>CAAGAGCTGTGATAAAACTCATACCTGCCCACCTTGTCCGGCGCCAGAACTGCTGGGAGGA<br>CCAAGCCGTGTTCCTGTTTCCACCCAAGCCTAAAGACACCCTGATGATTTCCCGGACTCCTG<br>AGGTCACCTGCGTGGTCGTGGACGTGTCTCACGAGGACCCCGAAGTCAAGTTCAACTGGTA<br>CGTGGATGGCGTCAAGTGCATAATGCCAAGACCAAACCCCGGGAGGAACAGTACAACTCT<br>ACCTATAGAGTCGTGAGTGTCCTGACAGTGCTGCACCAGGACTGGCTGAATGGGAAGGAGT<br>ATAAGTGTAAAGTGAGCAACAAAGCCCTGCCCGCCCCAATCGAAAAAACAATCTCTAAAGC<br>AAAAGGACAGCCTCGCGAACCACAGGTCTACGTCTACCCCCCATCAAGAGATGAACTGACA<br>AAAAATCAGGTCTCTCTGACATGCCTGGTCAAAGGATTCTACCCTTCCGACATCGCCGTGG<br>AGTGGGAAAGTAACGGCCAGCCCGAGAACAATTACAAGACCACACCCCCTGTCCTGGACTC<br>TGATGGGAGTTTCGCTCTGGTGTCAAAGCTGACCGTCGATAAAAGCCGGTGGCAGCAGGGC<br>AATGTGTTTAGCTGCTCCGTCATGCACGAAGCCCTGCACAATCACTACACACAGAAGTCCC<br>TGAGCCTGAGCCCTGGC |
| 76 | H3-HH41-scmab-HetFc001b (H3 scmab with HH41 linker) | CAGAGCGCACTGACTCAGCCCGCCTCCGTGTCTGGGTCCCCTGGGCAGAGCATTACTATTT<br>CATGTACTGGAACAAGCTCCGATGTCGGCGGGTACAACTTTGTGAGCTGGTATCAGCAGCA<br>CCCAGGAAAGGCCCCCAAACTGATGATCTACGACGTGTCCGATAGGCCCTCTGGCGTCAGT<br>GACCGCTTCAGCGGCAGCAAGTCTGGCAATACCGCCAGTCTGATCATTTCAGGCCTGCAGG<br>CAGACGATGAGGCCGATTACTATTGCAGCTCCTAGTTCAACTCATGTGATCTT<br>CGGAGGCGGGACCAAGGTGACAGTCCTGGGCCAGCCTAAAGCCGCTCCAAGCGTGACACTG<br>TTTCCCCCTAGCTCCGAGGAACTGCAGGCAAACAAGGCCACTCTGGTGTGTCTGATTTCCG<br>ACTTCTACCCTGGGGCTGTGACCGTCGCTTGGAAGGCAGATTCTAGTCCCGTGAAAGCAGG<br>AGTCGAGACCACAACTCCTTCAAAGCAGAGCAACAACAAGTACGCAGCCTCAAGCTATCTG<br>AGTCTGACACCAGAACAGTGGAAGAGCCACCGCAGTTACTCATGCCAAGTGACTCATGAGG<br>GCTCTACTGTGAAAAAACCGTCGCCCCCACAGAATGTTCCGGAGGCTCGGAGGAGGCAG<br>CGGGTCCTCTGCCGACGATGCTAAGAAAGACGCTGCAAAGAAAGACGATGCCAAGAAAGAC<br>GATGCTAAGAAAGATGGAGGAGGCAGCGGAGGAGGCTCCGGACAGGTGCAGCTGCAGGAGT<br>CTGGAGGAGGACTGGTCAAGCCTGGAGGATCTCTGCGACTGAGTTGCGCCGCTTCAGGCTT<br>CACCTTTAGTTCATACTGGATGAGCTGGGTGAGACAGGCCCCAGGCAAAGGGCTGGAATGG<br>GTCGCAAACATCAATAGGGACGGGAGCGCCTCCTACTATGTGGATAGCGTCAAGGGACGGT<br>TTACCATTAGCAGAGACGATGCCAAAAACTCCCTGTATCTGCAGATGAACAGCCTGCGAGC<br>TGAGGACACAGCAGTGTACTATTGTGCTCGGGATAGAGGCGTCGGATATTTCGATCTGTGG<br>GGACGAGGAACCCTGGTCACCGTCTCAAGCGCTAGCACTAAGGGGCCTTCCGTGTTTCCAC<br>TGGCTCCCTCTAGTAAATCCACCTCTGGAGGCACAGCTGCACTGGGATGTCTGGTGAAGGA<br>TTACTTCCCTGAACCAGTCACAGTGAGTTGGAACTCAGGGGCTCTGACAAGTGGAGTCCAT<br>ACTTTTCCCGCAGTGCTGCAGTCAAGCGGACTGTACTCCCTGTCCTCTGTGGTCACCGTGC<br>CTAGTTCAAGCCTGGGCACCCAGACATATATCTGCAACGTGAATCACAAGCCATCAAATAC<br>AAAAGTCGACAAGAAAGTGGAGCCCAAGAGCTGTGATAAAACTCATACCTGCCCACCTTGT<br>CCGGCGCCAGAACTGCTGGGAGGACCAAGCCGTGTTCCTGTTTCCACCCAAGCCTAAAGACA<br>CCCTGATGATTTCCCGGACTCCTGAGGTCACCTGCGTGGTCGTGGACGTGTCTCACGAGGA<br>CCCCGAAGTCAAGTTCAACTGGTACGTGGATGGCGTCAAGTGCATAATGCCAAGACCAAA<br>CCCCGGGAGGAACAGTACAACTCTACCTATAGAGTCGTGAGTGTCCTGACAGTGCTGCACC<br>AGGACTGGCTGAATGGGAAGGAGTATAAGTGTAAAGTGAGCAACAAAGCCCTGCCCGCCCC<br>AATCGAAAAAACAATCTCTAAAGCAAAAGGACAGCCTCGCGAACCACAGGTCTACGTGCTG<br>CCCCCTAGCCGCGACGAACTGACTAAAAATCAGGTCTCTCTGACATGTCTGGTCAAAGGAT |

TABLE A4-continued

Sequences of exemplary scFab

| SEQ ID NO | DESCRIPTION | Sequence (polypeptide) |
|---|---|---|
| | | TCTACCCTTCCGACATCGCCGTGGAGTGGGAAAGTAACGGCCAGCCCGAGAACAATTACCT GACCTGGCCCCCTGTGCTGGACTCTGATGGGAGTTTCTTTCTGTATTCAAAGCTGACAGTC GATAAAAGCCGGTGGCAGCAGGGCAATGTGTTCAGCTGCTCCGTCATGCACGAAGCACTGC ACAACCATTACACTCAGAAGTCCCTGTCCCTGTCACCTGGC |
| 77 | H3-GSE34-scmab-HetFc001b(H3 scmab with GSE34 linker) | CAGAGCGCACTGACTCAGCCTGCTTCCGTGTCCGGGAGCCCTGGGCAGAGCATTACAATCT CATGCACTGGAACCTCATCCGATGTCGGCGGGTACAACTTTGTGAGTTGGTATCAGCAGCA CCCAGGCAAGGCACCCAAACTGATGATCTACGACGTGTCTGATAGGCCCTCTGGGGTCAGT GACCGCTTCAGCGGCTCCAAGTCTGGGAATACCGCTTCCCTGATCATTTCTGGGCTGCAGG CTGACGATGAGGCAGATTACTATTGCAGCTCCTATGGATCTAGTTCAACTCATGTGATCTT CGGAGGCGGGACCAAGGTGACAGTCCTGGGCCAGCCTAAAGCCGCTCCATCCGTGACACTG TTTCCCCCTAGCTCCGAGGAACTGCAGGCCAACAAGGCTACTCTGGTGTGTCTGATTAGCG ACTTCTACCCTGGCGCTGTGACCGTCGCATGGAAGGCCGATTCTAGTCCCGTGAAAGCAGG CGTCGAGACCACAACTCCTTCAAAGCAGAGCAACAACAAGTACGCAGCCTCAAGCTATCTG TCCCTGACACCAGAACAGTGGAAGTCTCACCGACGTTACTCATGCCAAGTGACTCATGAGG GCAGCACTGTGGAAAAAACCGTCGCCCCCACAGAGTGTTCCTCTGGAGGAGGGAGTGGAGG AGGGTCAGAGGGAGGCGGGAGCGAAGGAGGCGGGTCCGAGGGAGGCGGGTCTGAAGGAGGA GGGAGCGGAGGAGGGTCCGGACAGGTGCAGCTGCAGGAGTCCGGAGGAGGACTGGTCAAGC CTGGAGGCTCTCTGCGACTGAGTTGCGCTGCATCAGGCTTCACCTTTAGTTCATACTGGAT GAGCTGGGTGAGACAGGCCCCAGGGAAAGGACTGGAATGGGTCGCAAACATCAATAGGGAC GGAAGCGCCTCCTACTATGTGGATTCCGTCAAGGGCCGGTTTACCATTAGTAGAGACGATG CCAAAAACTCACTGTATCTGCAGATGAATAGCCTGCGAGCCGAAGACACAGCTGTGTACTA TTGTGCTCGGGATAGAGGCGTCGGCTATTTCGATCTGTGGGGACGAGGAACCCTGGTCACC GTCTCAAGCGCTAGCACTAAGGGGCCTTCCGTGTTTCCACTGGCTCCCTCTAGTAAATCCA CCTCTGGAGGCACAGCTGCACTGGGATGTCTGGTGAAGGATTACTTCCCTGAACCAGTCAC AGTGAGTTGGAACTCAGGGGCTCTGACAAGTGGAGTCCATACTTTTCCCGCAGTGCTGCAG TCAAGCGGACTGTACTCCCTGTCCTCTGTGGTCACCGTGCCTAGTTCAAGCCTGGGCACCC AGACATATATCTGCAACGTGAATCACAAGCCATCAAATACAAAAGTCGACAAGAAAGTGGA GCCCAAGAGCTGTGATAAAACTCATACCTGCCCACCTTGTCCGGCGCCAGAACTGCTGGGA GGACCAAGCGTGTTCCTGTTTCCACCCAAGCCTAAAGACACCCTGATGATTTCCCGGACTC CTGAGGTCACCTGCGTGGTCGTGGACGTGTCTCACGAGGACCCCGAAGTCAAGTTCAACTG GTACGTGGATGGCGTCGAAGTGCATAATGCCAAGACCAAACCCCGGGAGGAACAGTACAAC TCTACCTATAGAGTCGTGAGTGTCCTGACAGTGCTGCACCAGGACTGGCTGAATGGGAAGG AGTATAAGTGTAAAGTGAGCAACAAAGCCCTGCCCGCCCCAATCGAAAAAACAATCTCTAA AGCAAAAGGACAGCCTCGCGAACCACAGGTCTACGTGCTGCCCCCTAGCCGCGACGAACTG ACTAAAAATCAGGTCTCTCTGCTGTGTCTGGTCAAAGGATTCTACCCTTCCGACATCGCCG TGGAGTGGGAAAGTAACGGCCAGCCCGAGAACAATTACCTGACCTGGCCCCCTGTGCTGGA CTCTGATGGGAGTTTCTTTCTGTATTCAAAGCTGACAGTCGATAAAAGCCGGTGGCAGCAG GGCAATGTGTTCAGCTGCTCCGTCATGCACGAAGCACTGCACAACCATTACACTCAGAAGT CCCTGTCCCTGTCACCTGGC |

In some embodiments, the isolated bi-specific antigen binding construct of the invention includes a first antigen-binding polypeptide construct that binds HER2 and is in a scFv format and a second antigen-binding polypeptide construct that binds HER3 and is in a Fab format and the second antigen-binding polypeptide construct includes a lambda constant light chain (CL) amino acid sequence.

In other embodiments, the isolated bi-specific antigen binding construct of the invention includes a first antigen-binding polypeptide construct that binds HER2 and is in a scFv format and a second antigen-binding polypeptide construct that binds HER3 and is in the Fab format and the second antigen-binding polypeptide construct comprises a kappa CL amino acid sequence.

TABLE A5

Sequences of exemplary lambda and kappa constant light chains:

| SEQ ID NO: | Description | Sequence |
|---|---|---|
| 78 | kappa constant light chain polypeptide | RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |
| 79 | kappa constant light chain polynucleotide | AGAACCGTGGCGGCGCCCAGTGTCTTCATTTTTCCCCCTAGCG ACGAACAGCTGAAGTCTGGGACAGCCAGTGTGGTCTGTCTGCT GAACAACTTCTACCCTCGCGAGGCTAAAGTGCAGTGGAAGGTC GATAACGCACTGCAGTCCGGAAATTCTCAGGAGAGTGTGACTG AACAGGACTCAAAAGATAGCACCTATTCCCTGTCAAGCACACT GACTCTGAGCAAGGCCGACTACGAGAAGCATAAAGTGTATGCT TGTGAAGTCACCCACCAGGGGCTGAGTTCACCAGTCACAAAAT CATTCAACAGAGGGGAGTGC |

TABLE A5-continued

Sequences of exemplary lambda and kappa constant light chains:

| SEQ ID NO: | Description | Sequence |
|---|---|---|
| 80 | lambda constant light chain polypeptide | GQPKAAPSVTLFPPSSEELQANKATLVCLISDFYPGAVTVAWK ADSSPVKAGVETTTPSKQSNNKYAASSYLSLTPEQWKSHRSYS CQVTHEGSTVEKTVAPTECS |
| 81 | lambda constant light chain polynucleotide | GGGCAGCCTAAAGCGGCGCCCTCTGTGACTCTGTTTCCCCCTA GCTCCGAGGAACTGCAGGCTAACAAGGCAACTCTGGTGTGTCT GATTAGCGACTTCTACCCAGGAGCTGTGACCGTCGCCTGGAAG GCTGATTCTAGTCCCGTGAAAGCAGGCGTCGAGACCACAACTC CTAGTAAGCAGTCAAACAACAAGTACGCAGCCTCAAGCTATCT GTCTCTGACACCCGAACAGTGGAAAAGTCACAGGTCATATAGC TGCCAGGTGACTCACGAGGGCTCAACTGTGGAGAAAACCGTCG CACCAACCGAATGTTCC |

Dissociation Constant ($K_D$) and Bmax

The term "dissociation constant ($K_D$)" as used herein, is intended to refer to the dissociation rate of a particular antigen-antibody interaction. The $K_D$ is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 mM indicates weak binding affinity compared to a $K_D$ of 1 nM. $K_D$ values for antibodies can be determined using methods well established in the art. One method for determining the $K_D$ of an antibody is by using surface plasmon resonance (SPR), typically using a biosensor system such as a Biacore® system.

The binding characteristics of an antibody can be determined by various techniques. One of which is the measurement of binding to target cells expressing the antigen by flow cytometry (FACS, Fluorescence-activated cell sorting). Typically, in such an experiment, the target cells are incubated with antibodies at different concentrations, washed, incubated with a secondary detection antibody, washed, and analyzed in the flow cytometer to measure the median fluorescent intensity (MFI) representing the strength of detection signal on the cells, which in turn is related to the number of antibodies bound to the cells. The antibody concentration vs MFI data is then fitted into a saturation binding equation to yield two key binding parameters, Bmax and apparent $K_D$.

Bmax, or maximal binding, refers to the maximum antibody binding level on the cells at saturating concentrations of antibody. This parameter can be reported in the arbitrary unit MFI for relative comparison, or converted into an absolute value corresponding to the number of antibodies bound to the cell with the use of a standard curve.

Apparent $K_D$, or apparent dissociation constant, represents the antibody concentration at which half maximal cell binding is observed. Evidently, the smaller the $K_D$ value, the smaller antibody concentration is required to reach maximum cell binding and thus the higher is the affinity of the antibody. The apparent $K_D$ is dependent on the conditions of the cell binding experiment, such as different receptor levels expressed on the cells and incubation conditions, and thus the apparent $K_D$ is generally different from the $K_D$ values determined from cell-free molecular experiments such as SPR and ITC. However, there is generally good agreement between the different methods.

Lytic and Internalizing Bi-Specific Antigen Binding Constructs

The bi-specific antigen binding constructs described herein can be classed into two subtypes: bi-specific lytic (BSP-L) antibodies and bi-specific internalizing (BSP-I) antibodies depending on the balance these antibodies display between the following efficacy factors: a) the ability of the bi-specific antigen binding construct to be internalized, b) the increased $B_{max}$ of the bi-specific antigen binding construct, and c) the degree of agonism/partial agonism of the bi-specific antigen binding construct.

With respect to the efficacy factors noted above, for BSP-L antibodies the most important consideration is the additive $B_{max}$ and slow off rate compared to monospecific monovalent antibodies or monospecific bivalent antibodies (thus resulting in higher decoration of the target cell with the BSP-L and antibody dependent cytotoxicity). Ideally, BSP-L antibodies bind the target cell with additive $B_{max}$ compared to OAA (one-armed antibody) or FSA (full-sized antibody), and shows no internalization thus resulting in the maximal decoration/accumulation of antibody on a cell. Ideally, BSP-L would block cognate ligand activation of target receptors. A BSP-L antibody could be fully neutralizing (blocking cognate ligand interaction at both targets) or partly neutralizing (blocking cognate ligand interaction at the more ubiquitously expressed target receptor). Such BSP-L antibodies are capable of binding to FcγR receptors and complement proteins and at high cell surface concentration are more effective at inducing immune cell-based effector activity. BSP-L antibodies thus are useful in indications where the bi-specific antigen binding construct is used to kill target cells through Fc effector functions such as ADCC, ADCP or CDC. BSP-L ideally shows no agonism in the absence of the cognate ligand for the target, may be non-neutralizing or neutralizing depending on the anticipated side-effect profile. Should some degree of agonism and internalization be observed, additive Bmax would overcome these to result in a net efficacious effect that is still superior to OAAs and FSAs.

With respect to the efficacy factors noted above, for BSP-Int antibodies the additive $B_{max}$ and specifically the degree of internalization are the key drivers for classifying bi-specific antigen binding constructs in the BSP-Int category. Ideally, BSP-Int antibodies bind the target cell with additive $B_{max}$ compared to OAA or FSA (thus resulting in higher decoration of the target cell with the BSP-Int), and are effectively internalized and would not induce any cell growth. Compared to BSP-L and OAAs and FSAs, high Bmax plus high internalization would result in higher intracellular concentrations of BSP-Int. The degree of agonism displayed with respect to the targets is less important and it is not obligatory that BSP-Int lack agonistic activity since BSP-Int antibodies can exploit this by using the partially activated receptor as a Trojan to shuttle a payload into a cell.

Such BSP-Int antibodies are suitable for use in the preparation of antibody-drug conjugates (ADCs) and can be used in the treatment of indications where delivery of a toxic drug to the target cell is desired. With this modality, the delivery of a highly toxic payload resulting in acute cell death would overcome some agonistic activity conferred in the BSP-Int.

Increased Bmax

The isolated bi-specific antigen binding constructs of the inventions display greater maximum binding (Bmax) in cells expressing HER2 and HER3, compared to a reference bivalent monospecific antibody comprising two first antigen-binding polypeptide constructs (e.g., trastuzumab) or two second antigen-binding polypeptide constructs (e.g., H3). In some embodiments, the bi-specific antigen binding constructs displays a Bmax that is 1.1, 1.2, 1.3, 1.4, 1.5, 1.6, 1.7, 1.8, 1.9, or 2.0 times the Bmax of a reference bivalent monospecific antibody.

Bmax is achieved at saturating antibody concentrations and Kd (on and off rate of an antibody) contributes to Bmax. An antibody with a slow on and fast off would have lower apparent Bmax compared to an antibody with a fast on and slow off rate of binding.

For the antigen binding constructs according to the invention, the clearest separation in Bmax versus FSA occurs at saturating concentrations and where Bmax can no longer be increased with a FSA. The significance is less at non-saturating concentrations. In one embodiment the increase in Bmax and KD/on-off rate of the antigen binding construct compared to the monospecific bivalent antigen binding construct is independent of the level of target antigen expression on the target cell. In one embodiment, where the antigen binding construct comprises an antigen-binding polypeptide construct that binds to HER2, the increase in Bmax and KD/on-off rate of the antigen binding construct compared to the monospecific bivalent antigen binding construct is independent of the level of HER2 expression on the target cell.

In some embodiments is an isolated antigen binding construct described herein, wherein said antigen binding construct displays an increase in binding density and Bmax (maximum binding) to a target cell displaying said antigen as compared to a corresponding monospecific bivalent antigen binding construct with two antigen binding regions. In some embodiments said increase in binding density and Bmax is at least about 125% of the binding density and Bmax of the corresponding bivalent antigen binding construct. In certain embodiments, the increase in binding density and Bmax is at least about 150% of the binding density and Bmax of the corresponding bivalent antigen binding construct. In some embodiments, the increase in binding density and Bmax is at least about 200% of the binding density and Bmax of the corresponding bivalent antigen binding construct. In some embodiments, the increase in binding density and Bmax is greater than about 110% of the binding density and Bmax of the corresponding bivalent antigen binding construct.

Polypeptides and Polynucleotides

The bi-specific antigen binding constructs described herein comprise at least one polypeptide. Also described are polynucleotides encoding the polypeptides described herein.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g. α-methyl alanine), D-amino acids, histidine-like amino acids (e.g., 2-amino-histidine, β-hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Also included in the invention are polynucleotides encoding polypeptides of the antigen binding constructs. The term "polynucleotide" or "nucleotide sequence" is intended to indicate a consecutive stretch of two or more nucleotide molecules. The nucleotide sequence may be of genomic, cDNA, RNA, semisynthetic or synthetic origin, or any combination thereof.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and [0139] 8) Cysteine (C), Methionine (M) (see, e.g., Creighton, Proteins: Structures and Molecular Properties (W H Freeman & Co.; 2nd edition (December 1993))

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-

3402, and Altschul et al. (1990) J. Mol. Biol. 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, or other nucleic acids, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. The engineered proteins are expressed and produced by standard molecular biology techniques.

By "isolated nucleic acid molecule or polynucleotide" is intended a nucleic acid molecule, DNA or RNA, which has been removed from its native environment. For example, a recombinant polynucleotide encoding a polypeptide contained in a vector is considered isolated. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts, as well as positive and negative strand forms, and double-stranded forms. Isolated polynucleotides or nucleic acids described herein, further include such molecules produced synthetically, e.g., via PCR or chemical synthesis. In addition, a polynucleotide or a nucleic acid, in certain embodiments, include a regulatory element such as a promoter, ribosome binding site, or a transcription terminator.

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

A derivative, or a variant of a polypeptide is said to share "homology" or be "homologous" with the peptide if the amino acid sequences of the derivative or variant has at least 50% identity with a 100 amino acid sequence from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two monomeric polypeptides which interact with each other and result in the transformation of unfolded or improperly folded polypeptides to native, properly folded polypeptides.

A "dimer" or "heterodimer" is a molecule comprising at least a first monomer polypeptide and a second monomer polypeptide. In the case of a heterodimer, one of said monomers differs from the other monomer by at least one amino acid residue. In certain embodiments, the assembly of the dimer is driven by surface area burial. In some embodiments, the monomeric polypeptides interact with each other by means of electrostatic interactions and/or salt-bridge interactions that drive dimer formation by favoring the desired dimer formation and/or disfavoring formation of other non-desired specimen. In some embodiments, the monomer polypeptides interact with each other by means of hydrophobic interactions that drive desired dimer formation by favoring desired dimer formation and/or disfavoring formation of other assembly types. In certain embodiments, the monomer polypeptides interact with each other by means of covalent bond formation. In certain embodiments, the covalent bonds are formed between naturally present or introduced cysteines that drive desired dimer formation. In certain embodiments described herein, no covalent bonds are formed between the monomers. In some embodiments, the polypeptides interact with each other by means of packing/size-complementarity/knobs-into-holes/protruberance-cavity type interactions that drive dimer formation by favoring desired dimer formation and/or disfavoring formation of other non-desired embodiments. In some embodiments, the polypeptides interact with each other by means of cation-pi interactions that drive dimer formation. In certain embodiments the individual monomer polypeptides cannot exist as isolated monomers in solution.

Expression

Also described herein are methods of producing the bi-specific antigen binding constructs via expression of the polypeptide(s) in a host cell.

As will be appreciated, bi-specific antigen binding constructs, e.g., antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive ManLAM binding properties.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bi-specific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bi-specific antigen binding molecules of the invention or fragments thereof.

"Cell", "host cell", "cell line" and "cell culture" are used interchangeably herein and all such terms should be understood to include progeny resulting from growth or culturing of a cell. "Transformation" and "transfection" are used interchangeably to refer to the process of introducing DNA into a cell.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. In certain embodiments, progeny are not completely identical in nucleic acid content to a parent cell, but may contain mutations. Mutant progeny that have the same function or biological activity as screened or selected for in the originally transformed cell are included herein. A host cell is any type of cellular system that can be used to generate the bi-specific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the protein has been secreted, including medium either before or after a proliferation step. The term also may encompass buffers or reagents that contain host cell lysates, such as in the case where a construct described herein is produced intracellularly and the host cells are lysed or disrupted to release the construct.

The term "substantially purified" refers to a construct described herein, or variant thereof that may be substantially or essentially free of components that normally accompany or interact with the protein as found in its naturally occurring environment, i.e. a native cell, or host cell in the case of recombinantly produced construct that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the construct or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the construct or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" construct produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Methods of Recombinant and Synthetic Production of Antigen Binding Constructs

In certain embodiments the described constructs are produced as recombinant molecules by secretion from yeast, a microorganism such as a bacterium, or a human or animal cell line. In embodiments, the polypeptides are secreted from the host cells.

Embodiments include a cell, such as a yeast cell transformed to express a construct protein described herein. In addition to the transformed host cells themselves, are provided culture of those cells, preferably a monoclonal (clonally homogeneous) culture, or a culture derived from a monoclonal culture, in a nutrient medium. If the polypeptide is secreted, the medium will contain the polypeptide, with the cells, or without the cells if they have been filtered or centrifuged away. Many expression systems are known and may be used, including bacteria (for example *E. coli* and *Bacillus subtilis*), yeasts (for example *Saccharomyces cerevisiae, Kluyveromyces lactis* and *Pichia pastoris*, filamentous fungi (for example *Aspergillus*), plant cells, animal cells and insect cells.

An antigen binding construct described herein is produced in conventional ways, for example from a coding sequence inserted in the host chromosome or on a free plasmid. The yeasts are transformed with a coding sequence for the desired protein in any of the usual ways, for example electroporation. Methods for transformation of yeast by electroporation are disclosed in Becker & Guarente (1990) Methods Enzymol. 194, 182.

Successfully transformed cells, i.e., cells that contain a DNA construct of the present invention, can be identified by well known techniques. For example, cells resulting from the introduction of an expression construct can be grown to produce the desired polypeptide. Cells can be harvested and lysed and their DNA content examined for the presence of the DNA using a method such as that described by Southern (1975) J. Mol. Biol. 98, 503 or Berent et al. (1985) Biotech. 3, 208. Alternatively, the presence of the protein in the supernatant can be detected using antibodies.

Useful yeast plasmid vectors include pRS403-406 and pRS413-416 and are generally available. Plasmids pRS403, pRS404, pRS405 and pRS406 are Yeast Integrating plasmids (YIps) and incorporate the yeast selectable markers HIS3, 7RP 1, LEU2 and URA3. Plasmids pRS413-416 are Yeast Centromere plasmids (Ycps).

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary honmopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or *E. coli* DNA polymerase 1, enzymes that remove protruding, _-single-stranded termini with their 3'5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources.

Exemplary genera of yeast contemplated to be useful in the practice of the present invention as hosts for expressing the albumin, fusion proteins are *Pichua* (formerly classified as *Hansenula*), *Saccharomyces, Kluyveromyces, Aspergillus, Candida, Torulopsis, Torulaspora, Schizosaccharomyces, Citeromyces, Pachysolen, Zygosaccharomyces, Debaromyces, Trichoderma, Cephalosporium, Humicola, Mucor, Neurospora, Yarrowia, Metschunikowia, Rhodosporidium, Leucosporidium, Botryoascus, Sporidiobolus, Endomycopsis*, and the like. Preferred genera are those selected from the group consisting of *Saccharomyces, Schizosaccharomyces, Kluyveromyces, Pichia* and *Torulaspora*. Examples of *Saccharomyces* spp. are *S. cerevisiae, S. italicus* and *S. rouxii*.

Examples of *Kluyveromyces* spp. are *K. fragilis, K. lactis* and *K. marxianus*. A suitable *Torulaspora* species is *T. delbrueckii*. Examples of *Pichia* (*Hansenula*) spp. are *P. angusta* (formerly *H. polymorpha*), *P. anomala* (formerly *H. anomala*) and *P. pastoris*. Methods for the transformation of *S. cerevisiae* are taught generally in EP 251 744, EP 258 067 and WO 90/01063, all of which are incorporated herein by reference.

Provided are vectors containing a polynucleotide encoding an antigen binding construct protein described herein, host cells, and the production of the construct proteins by synthetic and recombinant techniques. The vector may be, for example, a phage, plasmid, viral, or retroviral vector. Retroviral vectors may be replication competent or replication defective. In the latter case, viral propagation generally will occur only in complementing host cells.

In certain embodiments, the polynucleotides encoding antigen binding constructs described herein are joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In certain embodiments, the polynucleotide insert is operatively linked to an appropriate promoter, such as the phage lambda PL promoter, the *E. coli* lac, trp, phoA and rac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418, glutamine synthase, or neomycin resistance for eukaryotic cell culture, and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, NSO, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A; pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

In one embodiment, polynucleotides encoding antigen binding constructs described herein are fused to signal sequences that will direct the localization of a protein of the invention to particular compartments of a prokaryotic or eukaryotic cell and/or direct the secretion of a protein of the invention from a prokaryotic or eukaryotic cell. For example, in *E. coli*, one may wish to direct the expression of the protein to the periplasmic space. Examples of signal sequences or proteins (or fragments thereof) to which the antigen binding constructs are fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-.rho. series) available from New England Biolabs. In a specific embodiment, polynucleotides albumin fusion proteins of the invention may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that are fused to antigen binding constructs in order to direct its secretion in mammalian cells include, but are not limited to, the MPIF-1 signal sequence (e.g., amino acids 1-21 of GenBank Accession number AAB51134), the stanniocalcin signal sequence (MLQNSAVLLLLVISASA) (SEQ ID NO:82), and a consensus signal sequence (MPTWAWWLFLVLLLALWA-PARG) (SEQ ID NO:83). A suitable signal sequence that may be used in conjunction with baculoviral expression systems is the gp67 signal sequence (e.g., amino acids 1-19 of GenBank Accession Number AAA72759).

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g., Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/10036; WO89/10404; and WO91/06657, which are hereby incorporated in their entireties by reference herein. Additionally, glutamine synthase expression vectors can be obtained from Lonza Biologics, Inc. (Portsmouth, N.H.). Expression and production of monoclonal antibodies using a GS expression system in murine myeloma cells is described in Bebbington et al., Bio/technology 10:169 (1992) and in Biblia and Robinson Biotechnol. Prog. 11:1 (1995) which are herein incorporated by reference.

Provided herein is a host cell comprising nucleic acid encoding an isolated antigen binding construct described herein. In certain embodiments is the host cell described herein wherein the nucleic acid encoding the antigen binding polypeptide construct and the nucleic acid encoding the Fc construct are present in a single vector.

Provided herein is a method of preparing the isolated antigen binding construct described herein, the method comprising the steps of: (a) culturing a host cell comprising nucleic acid encoding the antigen binding construct; and (b) recovering the antigen binding construct from the host cell culture.

Also provided are host cells containing vector constructs described herein, and additionally host cells containing nucleotide sequences that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. A host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the nucleic acids and nucleic acid constructs of the invention into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

In addition to encompassing host cells containing the vector constructs discussed herein, the invention also encompasses primary, secondary, and immortalized host cells of vertebrate origin, particularly mammalian origin, that have been engineered to delete or replace endogenous genetic material, and/or to include genetic material. The genetic material operably associated with the endogenous polynucleotide may activate, alter, and/or amplify endogenous polynucleotides.

In addition, techniques known in the art may be used to operably associate heterologous polynucleotides and/or heterologous control regions (e.g., promoter and/or enhancer) with endogenous polynucleotide sequences encoding a Therapeutic protein via homologous recombination (see, e.g., U.S. Pat. No. 5,641,670, issued Jun. 24, 1997; International Publication Number WO 96/29411; International Publication Number WO 94/12650; Koller et al., Proc. Natl. Acad. Sci. USA 86:8932-8935 (1989); and Zijlstra et al., Nature 342:435-438 (1989), the disclosures of each of which are incorporated by reference in their entireties).

Antigen binding constructs described herein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, hydrophobic charge interaction chromatography and lectin chromatography. Most preferably, high performance liquid chromatography ("HPLC") is employed for purification.

In certain embodiments the construct proteins of the invention are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, antigen binding constructs described herein can be chemically synthesized using techniques known in the art (e.g., see Creighton, 1983, Proteins: Structures and Molecular Principles, W. H. Freeman & Co., N.Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

Post Translational Modifications:

In certain embodiments the bi-specific antigen binding constructs described herein, are differentially modified during or after translation.

In some embodiments, the modification is at least one of: glycosylation, acetylation, phosphorylation, amidation, derivatization by known protecting/blocking groups, proteolytic cleavage and linkage to an antibody molecule or other cellular ligand. In some embodiments, the bi-specific antigen binding construct is chemically modified by known techniques, including but not limited, to specific chemical cleavage by cyanogen bromide, trypsin, chymotrypsin, papain, V8 protease, $NaBH_4$; acetylation, formylation, oxidation, reduction; and metabolic synthesis in the presence of tunicamycin.

Additional post-translational modifications of bi-specific antigen binding construct described herein include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression. The bi-specific antigen binding constructs described herein are modified with a detectable label, such as an enzymatic, fluorescent, isotopic or affinity label to allow for detection and isolation of the protein. In certain embodiments, examples of suitable enzyme labels include horseradish peroxidase, alkaline phosphatase, beta-galactosidase, or acetylcholinesterase; examples of suitable prosthetic group complexes include streptavidin biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine, carbon, sulfur, tritium, indium, technetium, thallium, gallium, palladium, molybdenum, xenon, fluorine.

In specific embodiments, bi-specific antigen binding constructs described herein are attached to macrocyclic chelators that associate with radiometal ions.

In some embodiments, the bi-specific antigen binding constructs described herein are modified by either natural processes, such as post-translational processing, or by chemical modification techniques which are well known in the art. In certain embodiments, the same type of modification may be present in the same or varying degrees at several sites in a given polypeptide. In certain embodiments, polypeptides from bi-specific antigen binding described herein are branched, for example, as a result of ubiquitination, and in some embodiments are cyclic, with or without branching. Cyclic, branched, and branched cyclic polypeptides are a result from posttranslation natural processes or made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182:626-646 (1990); Rattan et al., Ann. N.Y. Acad. Sci. 663:48-62 (1992)).

In certain embodiments, bi-specific antigen binding constructs described herein are attached to solid supports, which are particularly useful for immunoassays or purification of polypeptides that are bound by, that bind to, or associate with albumin fusion proteins of the invention. Such solid supports include, but are not limited to, glass, cellulose, polyacrylamide, nylon, polystyrene, polyvinyl chloride or polypropylene.

Theantigen binding constructs can be differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed herein include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression.

The antigen binding constructs can be modified with a detectable label, such as an enzymatic, fluorescent, isotopic or affinity label to allow for detection and isolation of the protein.

Examples of suitable enzymes include horseradish peroxidase, alkaline phosphatase, beta-galactosidase, or acetylcholinesterase; examples of suitable prosthetic group complexes include streptavidin biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine, carbon, sulfur, tritium, indium, technetium, thallium, gallium, palladium, molybdenum, xenon, fluorine.

In specific embodiments, antigen binding constructs or fragments or variants thereof are attached to macrocyclic chelators that associate with radiometal ions.

As mentioned, the antigen binding constructs described herein are modified by either natural processes, such as post-translational processing, or by chemical modification techniques which are well known in the art. It will be appreciated that the same type of modification may be present in the same or varying degrees at several sites in a given polypeptide. Polypeptides of the invention may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182:626-646 (1990); Rattan et al., Ann. N.Y. Acad. Sci. 663:48-62 (1992)).

In certain embodiments, antigen binding constructs may also be attached to solid supports, which are particularly useful for immunoassays or purification of polypeptides that are bound by, that bind to, or associate with albumin fusion proteins of the invention. Such solid supports include, but are not limited to, glass, cellulose, polyacrylamide, nylon, polystyrene, polyvinyl chloride or polypropylene.

Also provided herein are chemically modified derivatives of the antigen binding constructs which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The proteins may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a Therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 105,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

Antibody Drug Conjugates

In certain embodiments the bi-specific antigen binding construct is conjugated to a drug, e.g., a toxin, a chemotherapeutic agent, an immune modulator, or a radioisotope. Several methods of preparing ADCs (antibody drug conjugates) are known in the art and are described in U.S. Pat. No. 8,624,003 (pot method), U.S. Pat. No. 8,163,888 (one-step), and U.S. Pat. No. 5,208,020 (two-step method) for example.

In some embodiments, the drug is selected from a maytansine, auristatin, calicheamicin, or derivative thereof. In other embodiments, the drug is a maytansine selected from DM1 and DM4.

In some embodiments the drug is conjugated to the isolated bi-specific antigen binding construct with an SMCC linker (DM1), or an SPDB linker (DM4). The drug-to-antibody ratio (DAR) can be, e.g., 1.0 to 6.0 or 3.0 to 5.0 or 3.5-4.2.

In some embodiments the bispecific antigen binding construct is conjugated to a cytotoxic agent. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins such as small molecule toxins or enzymatically active toxins of bacterial, fungal, plant or animal origin, including fragments and/or variants thereof.

Preparation of Antibody-Drug Conjugates

The ADC may be prepared by several routes, employing organic chemistry reactions, conditions, and reagents known to those skilled in the art, including: (1) reaction of a nucleophilic group or an electrophilic group of an antibody with a bivalent linker reagent, to form antibody-linker intermediate Ab-L, via a covalent bond, followed by reaction with an activated drug moiety D; and (2) reaction of a nucleophilic group or an electrophilic group of a drug moiety with a linker reagent, to form drug-linker intermediate D-L, via a covalent bond, followed by reaction with the nucleophilic group or an electrophilic group of an antibody. Conjugation methods (1) and (2) may be employed with a variety of antibodies, drug moieties, and linkers to prepare the antibody-drug conjugates described here.

Several specific examples of methods of preparing ADCs are known in the art and are described in U.S. Pat. No. 8,624,003 (pot method), U.S. Pat. No. 8,163,888 (one-step), and U.S. Pat. No. 5,208,020 (two-step method).

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody-drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, G. T. (1996) Bioconjugate Techniques; Academic Press: New York, p 234-242). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Maytansine may, for example, be converted to May-SSCH3, which can be reduced to the free thiol, May-SH, and reacted with a modified antibody (Chari et al (1992) Cancer Research 52:127-131) to generate a maytansinoid-antibody immunoconjugate with a disulfide linker. Antibody-maytansinoid conjugates with disulfide linkers have been reported (WO 04/016801; U.S. Pat. No. 6,884,874; US 2004/039176 A1; WO 03/068144; US 2004/001838 A1; U.S. Pat. Nos. 6,441,163; 5,208,020; 5,416,064; WO 01/024763). The disulfide linker SPP is constructed with linker reagent N-succinimidyl 4-(2-pyridylthio)pentanoate. ADC of the invention include SMCC linkers and the DM1 maytansinoid drug moiety.

In one embodiment of Ab-(SMCC-DM1)p the average p is 1, 2, 3, or 4. (WO 2005/037992). Another embodiment of an ADC is Ab-(SIAB-DM1)p.

The drug has, or is modified to include, a group reactive with a conjugation point on the antibody. For example, a drug can be attached by alkylation (e.g., at the epsilon-amino group lysines or the N-terminus of antibodies), reductive amination of oxidized carbohydrate, transesterification between hydroxyl and carboxyl groups, amidation at amino groups or carboxyl groups, and conjugation to thiols. In some embodiments, the number of drug moieties, p, conjugated per antibody molecule ranges from an average of 1 to 8; 1 to 7, 1 to 6, 1 to 5, 1 to 4, 1 to 3, or 1 to 2. In some embodiments, p ranges from an average of 2 to 8, 2 to 7, 2 to 6, 2 to 5, 2 to 4 or 2 to 3. In other embodiments, p is an average of 1, 2, 3, 4, 5, 6, 7 or 8. In some embodiments, p ranges from an average of about 1 to about 8; about 1 to about 7, about 1 to about 6, about 1 to about 5, about 1 to about 4, about 1 to about 3, or about 1 to about 2. In some embodiments, p ranges from about 2 to about 8, about 2 to about 7, about 2 to about 6, about 2 to about 5, about 2 to about 4 or about 2 to about 3. For examples of chemistries that can be used for conjugation, see, e.g., Current Protocols in Protein *Science* (John Wiley & Sons, Inc.), Chapter 15 (Chemical Modifications of Proteins) (the disclosure of which is incorporated by reference herein in its entirety.)

For example, when chemical activation of the protein results in formation of free thiol groups, the protein may be conjugated with a sulfhydryl reactive agent. In one aspect, the agent is one which is substantially specific for free thiol groups. Such agents include, for example, malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio.

Conjugate Linkers

The drug can be linked to an antibody by a linker. Attachment of a linker to a mAb can be accomplished in a variety of ways, such as through surface lysines, reductive-coupling to oxidized carbohydrates, and through cysteine residues liberated by reducing interchain disulfide linkages. A variety of ADC linkage systems are known in the art, including hydrazone-, disulfide- and peptide-based linkages.

Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimido-capronic-valine-citruline-p-aminobenzyloxycarbonyl (mc-Val-Cit-PABA) linker. Another linker is Sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Yet another linker is maleimidocaproyl (mc). Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

A linker can include a group for linkage to the antibody. For example, linker can include an amino, hydroxyl, carboxyl or sulfhydryl reactive groups (e.g., malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio). See generally Wong, Chemistry of Protein Conjugation and Cross-linking; CRC Press, Inc., Boca Raton, 1991.

In one embodiment, covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Bioconjugate Techniques, Third Edition by Greg T. Hermanson, Academic Press 2013 ISBN-13: 978-0123822390).

In another embodiment, the linker may be substituted with groups which modulated solubility or reactivity. For example, a sulfonate substituent may increase water solubility of the reagent and facilitate the coupling reaction of the linker reagent with the antibody or the drug moiety, or facilitate the coupling reaction of Ab-L with D, or D-L with Ab, depending on the synthetic route employed to prepare the ADC.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Linkers can be peptidic, comprising one or more amino acid units. Peptide linker reagents may be prepared by solid phase or liquid phase synthesis methods (E. Schroder and K. Lübke, The Peptides, volume 1, pp 76-136 (1965) Academic Press) that are well known in the field of peptide chemistry, including t-BOC chemistry (Geiser et al "Automation of solid-phase peptide synthesis" in Macromolecular Sequencing and Synthesis, Alan R. Liss, Inc., 1988, pp. 199-218) and Fmoc/HBTU chemistry (Fields, G. and Noble, R. (1990) "Solid phase peptide synthesis utilizing 9-fluoroenylmethoxycarbonyl amino acids", Int. J. Peptide Protein Res. 35:161-214), on an automated synthesizer such as the Rainin Symphony Peptide Synthesizer (Protein Technologies, Inc., Tucson, Ariz.), or Model 433 (Applied Biosystems, Foster City, Calif.).

The compounds expressly contemplate, but are not limited to, ADC prepared with cross-linker reagents: BMPEO, BMPS, EMCS, GMBS, HBVS, LC-SMCC, MBS, MPBH, SBAP, SPDB, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)2, and BM(PEO)3, which are commercially available from Pierce Biotechnology, Inc., Customer Service Department, P.O. Box 117, Rockford, Ill. 61105 U.S.A, U.S.A 1-800-874-3723, International +815-968-0747. See pages 467-498, 2003-2004 Applications Handbook and Catalog.

Bis-maleimide reagents allow the attachment of a free thiol group of a cysteine residue of an antibody to a thiol-containing drug moiety, label, or linker intermediate, in a sequential or concurrent fashion. Other functional groups besides maleimide, which are reactive with a thiol group of an antibody, maytansinoid drug moiety, or linker intermediate include iodoacetamide, bromoacetamide, vinyl pyridine, disulfide, pyridyl disulfide, isocyanate, and isothiocyanate.

Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; U.S. Pat. No. 6,214,345 to Firestone et al; WO 02/088172; US 2003130189; US2003096743; WO 03/026577; WO 03/043583; and WO 04/032828.

The Linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King et al (2002) Tetrahedron Letters 43:1987-1990). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Drugs

Examples of drugs or payloads are selected from the group consisting of DM1 (maytansine, N2'-deacetyl-N2'-(3-mercapto-1-oxopropyl)- or N2'-deacetyl-N2'-(3-mercapto-1-oxopropyl)-maytansine), mc-MMAD (6-maleimidocaproyl-monomethylauristatin-D or N-methyl-L-valyl-N-[(1S,2R)-2-methoxy-4-[(2S)-2-[(1R,2R)-1-methoxy-2-methyl-3-oxo-3-[[(1S)-2-phenyl-1-(2-thiazolyl)ethyl] amino]propyl]-1-pyrrolidinyl]-1-[(1S)-1-methylpropyl]-4-oxobutyl]-N-methyl-(9Cl)-L-valinamide), mc-MMAF (maleimidocaproyl-monomethylauristatin F or N-[6-(2,5-dihydro-2,5-dioxo-1H-pyrrol-1-yl)-1-oxohexyl]-N-methyl-L-valyl-L-valyl-(3R,4S,5S)-3-methoxy-5-methyl-4-(methylamino)heptanoyl-($\alpha$R,$\beta$R,2S)-$\beta$-methoxy-$\alpha$-methyl-2-pyrrolidinepropanoyl-L-phenylalanine) and mc-Val-Cit-PABA-MMAE (6-maleimidocaproyl-ValcCit-(p-aminobenzyloxycarbonyl)-monomethylauristatin E or N-[[[4-[[N-[6-(2,5-dihydro-2,5-dioxo-1H-pyrrol-1-yl)-1-oxohexyl]-L-valyl-N5-(aminocarbonyl)-L-ornithyl]amino] phenyl]methoxy]carbonyl]-N-meth yl-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl-L-valinamide). DM1 is a derivative of the tubulin inhibitor maytansine while MMAD, MMAE, and MMAF are auristatin derivatives.

Maytansinoid Drug Moieties

In some embodiments the drug is a maytansinoid. Maytansine compounds inhibit cell proliferation by inhibiting the formation of microtubules during mitosis through inhibition of polymerization of the microtubulin protein, tubulin (Remillard et al (1975) Science 189:1002-1005; U.S. Pat. No. 5,208,020). Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al (1978) Can. Treatment. Rev. 5:199-207.

Maytansinoid drug moieties are attractive drug moieties in antibody-drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamitocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions Exemplary maytansinoid drug moieties also include those having modifications such as: C-9-SH, prepared by the reaction of maytansinol with H2S or P2S5 (U.S. Pat. No. 4,424,219); C-14-alkoxymethyl(demethoxy/CH2OR) (U.S. Pat. No. 4,331,598); C-14-hydroxymethyl or acyloxymethyl (CH2OH or CH2OAc) prepared from *Nocardia* (U.S. Pat. No. 4,450,254); C-15-hydroxy/acyloxy, prepared by the conversion of maytansinol by *Streptomyces*(U.S. Pat. No. 4,364,866); C-15-methoxy, isolated from Trewia nudlflora (U.S. Pat. Nos. 4,313,946 and 4,315,929); C-18-N-demethyl, prepared by the demethylation of maytansinol by *Streptomyces* (U.S. Pat. Nos. 4,362,663 and 4,322,348); and 4,5-deoxy, prepared by the titanium trichloride/LAH reduction of maytansinol (U.S. Pat. No. 4,371,533).

Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

All stereoisomers of the maytansinoid drug moiety are contemplated for the compounds of the invention, i.e. any combination of R and S configurations at the chiral carbons of D. Embodiments of the ADC include DM1, DM3, DM4 (see US20090202536).

Steric hindrance conferred by alkyl groups such as the methyl groups on the carbon adjacent to the sulfur atom of DM3 and DM4 may affect the rate of intracellular cleavage of the ADC (US 2004/0235840 A1). The variable alkyl unit (CR2)m may therefore affect potency, efficacy, and safety/toxicity in vitro and in vivo.

Auristatins

In some embodiments, the Drug is an auristatin, such as auristatin E (also known in the art as a derivative of dolastatin-10) or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include AFP, MMAF, and MMAE. The synthesis and structure of exemplary auristatins are described in U.S. Pat. Nos. 6,884,869, 7,098,308, 7,256,257, 7,423,116, 7,498,298 and 7,745,394, each of which is incorporated by reference herein in its entirety and for all purposes.

Auristatins have been shown to interfere with microtubule dynamics and nuclear and cellular division and have anticancer activity. Auristatins of the present invention bind tubulin and can exert a cytotoxic or cytostatic effect on a 5T4 expressing cell or cell line. There are a number of different assays, known in the art, that can be used for determining whether an auristatin or resultant antibody-drug conjugate exerts a cytostatic or cytotoxic effect on a desired cell or cell line. Methods for determining whether a compound binds tubulin are known in the art. See, for example, Muller et al., Anal. Chem 2006, 78, 4390-4397; Hamel et al., Molecular Pharmacology, 1995 47: 965-976; and Hamel et al., The Journal of Biological Chemistry, 1990 265:28, 17141-17149.

Chemotherapeutic Agents

In some embodiments the bispecific antigen binding construct is conjugated to a chemotherapeutic agent. Examples include but are not limited to Cisplantin and Lapatinib. A "chemotherapeutic agent" is a chemical compound useful in the treatment of cancer.

Examples of chemotherapeutic agents include alkylating agents such as thiotepa and cyclosphosphamide (CY-TOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK7; razoxane; sizofiran; spirogermanium; tenuazonic acid; triaziquone; 2,2',2'-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Methods of Treatment

In certain embodiments, constructs described herein, are used in assays to test for one or more biological activities as described in further detail herein. If a construct exhibits an activity in a particular assay, it is likely that the antigen binding construct comprised by the antigen binding construct is implicated in the diseases associated with the biological activity. Thus, the construct is of use in a treatment of the associated disease.

In certain embodiments, provided is a method of treating a disease or disorder comprising administering to a patient in which such treatment, prevention or amelioration is desired, an antigen binding construct described herein, in an amount effective to treat, prevent or ameliorate the disease or disorder.

"Disorder" refers to any condition that would benefit from treatment with an antibody or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

"Treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishing of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder. In one embodiment, antibodies and methods of the invention effect tumor regression. In one embodiment, antibodies and methods of the invention effect inhibition of tumor/cancer growth.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, construct constructs described herein are used to delay development of a disease or to slow the progression of a disease. The term "instructions" is used to refer to instructions customarily included in commercial packages of therapeutic products that contain information about the indications, usage, dosage, administration, combination therapy, contraindications and/or warnings concerning the use of such therapeutic products.

The antigen binding constructs described herein, comprising at least a fragment or variant of an antibody may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in an embodiment, human antibodies, fragments derivatives, analogs, or nucleic acids, are administered to a human patient for therapy or prophylaxis.

Method of Treatment of Cancers

Provided herein is the use of a antigen binding construct described herein for the manufacture of a medicament for treating cancer. Also provided is use of a antigen binding construct described herein for the manufacture of a medicament for an immune system disorder. In certain embodiments is use of a antigen binding construct described herein for the manufacture of a medicament for inhibiting growth of a tumor. In certain embodiments is use of a antigen binding construct described herein for the manufacture of a medicament for shrinking a tumor.

In certain embodiments is use of a construct provided herein for the treatment of at least one of breast cancer, gastric cancer, brain cancer, essentially proliferative diseases (cancers) associated with HER2, HER3, IGF1R, EGFR dysfunction. In certain embodiments, a construct provided herein is used in the treatment of patients that are partially responsive to anti-Her2 or anti-Her3 bivalent antibodies. In certain embodiments, the construct is used in the treatment of patients not responsive to trastuzumab, pertuzumab, or TDM-1 or anti-Her2 or anti-Her3, alone or in combination. In some embodiments the patients are not responsive to scFv Her2/Her3. In some embodiments are provide a construct described herein in combination With Herceptin in Patients With Advanced Her2 Amplified, Heregulin Positive Breast. In some embodiments are provide a construct described herein in combination With Herceptin in patients with HER2 Expressing Carcinomas of the Distal Esophagus, Gastroesophageal (GE) Junction and Stomach. In certain embodiments, are provide a construct described herein to patients with advanced, refractory Her2 amplified, Heregulin positive cancers.

"Cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, myeloma (e.g., multiple myeloma), hepatocellular cancer, gastrointestinal cancer, pancreatic cancer, glioblastoma/glioma (e.g., anaplastic astrocytoma, glioblastoma multiforme, anaplastic oligodendroglioma, anaplastic oligodendroastrocytoma), cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

The cancer will comprise ErbB-expressing cells, such that an anti-ErbB antibody herein is able to bind to the cancer, and will be typically characterized by overexpression of the ErbB receptor. In a preferred embodiment, the cancer comprises ErbB2-expressing cells, even more preferably, cells which are characterized by overexpression of the ErbB2 receptor. To determine ErbB, e.g. ErbB2 expression in the cancer, various diagnostic/prognostic assays are available. In one embodiment, ErbB2 overexpression may be analyzed by IHC, e.g. using the HERCEPTEST® (Dako). Parrafin embedded tissue sections from a tumor biopsy may be subjected to the IHC assay and accorded a ErbB2 protein staining intensity criteria as follows: Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for ErbB2 overexpression assessment may be characterized as not overexpressing ErbB2, whereas those tumors with 2+ or 3+ scores may be characterized as overexpressing ErbB2.

Alternatively, or additionally, fluorescence in situ hybridization (FISH) assays such as the INFORM™ (sold by Ventana, Ariz.) or PATHVISION™ (Vysis, Ill.) may be carried out on formalin-fixed, paraffin-embedded tumor tissue to determine the extent (if any) of ErbB2 overexpression in the tumor. In comparison with IHC assay, the FISH assay, which measures her2 gene amplification, seems to correlate better with response of patients to treatment with HERCEPTIN®, and is currently considered to be the preferred assay to identify patients likely to benefit from HERCEPTIN® treatment or treatment with the immunoconjugates of the present invention.

Preferably, the immunoconjugates of the present invention and/or ErbB, e.g. ErbB2 or EGFR protein to which they are bound are internalized by the cell, resulting in increased therapeutic efficacy of the immunoconjugate in killing the cancer cell to which they bind. In a preferred embodiment, the cytotoxic agent (maytansinoid) targets or interferes with nucleic acid in the cancer cell.

The treatment of the present invention targets ErbB overexpressing tumors that do not respond, or respond poorly, to treatment with an unconjugated anti-ErbB antibody. Such patients might have received prior treatment with an anti-ErbB antibody not conjugated to a maytansinoid moiety, where the prior treatment either did not result in significant improvement, or resulted in transient response. Prior treatment of any particular patient with an unconjugated anti-ErbB antibody is, however, not a prerequisite of identifying patients who are candidates for treatment in accordance with the present invention. An ordinary skilled physician can readily identify patients who are expected to benefit from treatment with the immunoconjugates of the present invention based on publicly available clinical data and his or her own experience. Treatment of mammals, and in particular human patients, with or without prior treatment with an (unconjugated) anti-ErbB antibody is specifically within the scope of the present invention.

Pharmaceutical Compositions

Also included are pharmaceutical compositions comprising the antigen binding construct and a pharmaceutically acceptable carrier.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

The term "pharmaceutical composition" refers to a preparation which is in such form as to permit the biological activity of a construct contained therein to be effective, and which contains no additional components which are unacceptably toxic to a subject to which the formulation would be administered.

Also provided herein are pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the antigen binding constructs is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

As used herein, the term "modulated serum half-life" means the positive or negative change in circulating half-life of an antigen binding polypeptide that is comprised by an antigen binding construct described herein relative to its native form. Serum half-life is measured by taking blood samples at various time points after administration of the construct, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of an antigen binding polypeptide comprised by a antigen binding construct described herein, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule or an increase or decrease in receptor-mediated clearance of the molecule.

Administration

A bi-specific antigen binding construct described herein can be administered to a subject, e.g., a human.

Various delivery systems are known and can be used to administer an antigen binding construct formulation described herein, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in certain embodiments, it is desirable to introduce the antigen binding construct compositions described herein into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it is desirable to administer the antigen binding constructs, or compositions described herein locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the antigen binding constructs or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the antigen binding constructs or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, supra, vol. 2, pp. 115-138 (1984)).

In a specific embodiment comprising a nucleic acid encoding antigen binding constructs described herein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

In certain embodiments a antigen binding construct described herein is administered as a combination with other monovalent or multivalent antibodies with non-overlapping binding target epitopes.

The amount of the composition described herein which will be effective in the treatment, inhibition and prevention of a disease or disorder associated with aberrant expression and/or activity of a Therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

Testing of Antigen Binding Constructs

The antigen binding constructs or pharmaceutical compositions described herein are tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered antigen binding construct, and the effect of such antigen binding construct upon the tissue sample is observed.

Candidate bi-specific antigen binding constructs can be assayed using cells, e.g., breast cancer cell lines, expressing HER2 and HER3. The following Table A describes the expression level of HER2 and HER3 on several representative breast cancer cell lines.

TABLE A5

Relative expression levels of selected receptors in cell lines of interest.

| Cell line | HER2 | HER3 | Description |
| --- | --- | --- | --- |
| SKBR3 | high | mid | HER2 3+ breast |
| BT-474 | high | mid | HER2 3+ breast |
| SKOV3 | high | low | ovarian |
| MDA-MB-231 | low | low/mid | triple negative breast |
| MCF7 | low | mid | estrogen receptor positive breast |
| JIMT1 | mid | low | trastuzumab resistant breast |
| NCI-N87 | high | low | gastric |

McDonagh et al Mol Cancer Ther. 2012 March; 11(3):582-93

Subik et al. (2010) Breast Cancer: Basic Clinical Research: 4; 35-41

Anido et al Clin Cancer Res. 2003 April; 9(4):1274-83

Neve et al Cancer Cell 2006 10:515-527

Dragowska et al BMC Cancer 2011 11:420

Prang et a. (2005) British Journal of Cancer Research:92; 342-349

For example, to identify growth inhibitory anti-ErbB2 antibodies, one may screen for antibodies which inhibit the growth of cancer cells which overexpress ErbB2. In one embodiment, the growth inhibitory antibody of choice is able to inhibit growth of SK-BR-3 cells in cell culture by about 20-100% and preferably by about 50-100% at an antibody concentration of about 0.5 to 30 μg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 μg/ml of the anti-ErbB2 antibody is added per dish. After six days, the number of cells, compared to untreated cells are counted using an electronic COULTER™ cell counter. Those antibodies which inhibit growth of the SK-BR-3 cells by about 20-100% or about 50-100% may be selected as growth inhibitory antibodies.

To select for antibodies which induce cell death, loss of membrane integrity as indicated by, e.g., PI, trypan blue or 7AAD uptake may be assessed relative to control. The preferred assay is the PI uptake assay using BT474 cells. According to this assay, BT474 cells (which can be obtained from the American Type Culture Collection (Rockville, Md.)) are cultured in Dulbecco's Modified Eagle Medium (D-MEM):Ham's F-12 (50:50) supplemented with 10% heat-inactivated FBS (Hyclone) and 2 mM L-glutamine (Thus, the assay is performed in the absence of complement and immune effector cells). The BT474 cells are seeded at a density of 3×10⁶ per dish in 100×20 mm dishes and allowed to attach overnight. The medium is then removed and replaced with fresh medium alone or medium containing 10 μg/ml of the appropriate monoclonal antibody. The cells are incubated for a 3 day time period. Following each treatment, monolayers are washed with PBS and detached by trypsinization. Cells are then centrifuged at 1200 rpm for 5 minutes at 4° C., the pellet resuspended in 3 ml ice cold Ca2+ binding buffer (10 mM Hepes, pH 7.4, 140 mM NaCl, 2.5 mM CaCl2) and aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

In order to select for antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 μg/ml of the monoclonal antibody. Following a three day incubation period, monolayers are washed with PBS and detached by trypsinization. Cells are then centrifuged, resuspended in Ca2+ binding buffer and aliquoted into tubes as discussed above for the cell death assay. Tubes then receive labeled annexin (e.g. annexin V-FTIC) (1 μg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies.

In addition to the annexin binding assay, a DNA staining assay using BT474 cells is available. In order to perform this assay, BT474 cells which have been treated with the antibody of interest as described in the preceding two paragraphs are incubated with 9 μg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay.

To identify an antibody which blocks ligand activation of an ErbB receptor, the ability of the antibody to block ErbB ligand binding to cells expressing the ErbB receptor (e.g. in conjugation with another ErbB receptor with which the ErbB receptor of interest forms an ErbB hetero-oligomer) may be determined. For example, cells naturally expressing, or transfected to express, ErbB receptors of the ErbB hetero-oligomer may be incubated with the antibody and then exposed to labeled ErbB ligand. The ability of the anti-ErbB2 antibody to block ligand binding to the ErbB receptor in the ErbB hetero-oligomer may then be evaluated.

For example, inhibition of HRG binding to MCF7 breast tumor cell lines by anti-ErbB2 antibodies may be performed using monolayer MCF7 cultures on ice in a 24-well-plate format essentially as described in Example 1 below. Anti- ErbB2 monoclonal antibodies may be added to each well and incubated for 30 minutes. 125I-labeled rHRGβ1177-224 (25 pm) may then be added, and the incubation may be continued for 4 to 16 hours. Dose response curves may be prepared and an IC50 value may be calculated for the antibody of interest. In one embodiment, the antibody which blocks ligand activation of an ErbB receptor will have an IC50 for inhibiting HRG binding to MCF7 cells in this assay of about 50 nM or less, more preferably 10 nM or less. Where the antibody is an antibody fragment such as a Fab fragment, the IC50 for inhibiting HRG binding to MCF7 cells in this assay may, for example, be about 100 nM or less, more preferably 50 nM or less.

Alternatively, or additionally, the ability of the anti-ErbB2 antibody to block ErbB ligand-stimulated tyrosine phosphorylation of an ErbB receptor present in an ErbB hetero-oligomer may be assessed. For example, cells endogenously expressing the ErbB receptors or transfected to expressed them may be incubated with the antibody and then assayed for ErbB ligand-dependent tyrosine phosphorylation activity using an antiphosphotyrosine monoclonal (which is optionally conjugated with a detectable label). The kinase receptor activation assay described in U.S. Pat. No. 5,766,863 is also available for determining ErbB receptor activation and blocking of that activity by an antibody.

In one embodiment, one may screen for an antibody which inhibits HRG stimulation of p180 tyrosine phosphorylation in MCF7 cells. For example, the MCF7 cells may be plated in 24-well plates and monoclonal antibodies to ErbB2 may be added to each well and incubated for 30 minutes at room temperature; then rHRGβ1177-244 may be added to each well to a final concentration of 0.2 nM, and the incubation may be continued for 8 minutes. Media may be aspirated from each well, and reactions may be stopped by the addition of 100 µl of SDS sample buffer (5% SDS, 25 mM DTT, and 25 mM Tris-HCl, pH 6.8). Each sample (25 µl) may be electrophoresed on a 4-12% gradient gel (Novex) and then electrophoretically transferred to polyvinylidene difluoride membrane. Antiphosphotyrosine (at 1 µg/ml) immunoblots may be developed, and the intensity of the predominant reactive band at Mr~180,000 may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an IC50 for the antibody of interest may be calculated. In one embodiment, the antibody which blocks ligand activation of an ErbB receptor will have an IC50 for inhibiting HRG stimulation of p180 tyrosine phosphorylation in this assay of about 50 nM or less, more preferably 10 nM or less. Where the antibody is an antibody fragment such as a Fab fragment, the IC50 for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g, essentially as described in Schaefer et al. Oncogene 15:1385-1394 (1997). According to this assay, MDA-MB-175 cells may treated with an anti-ErbB2 monoclonal antibody (10 µg/mL) for 4 days and stained with crystal violet. Incubation with an anti-ErbB2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the anti-ErbB2 antibody of interest may block heregulin dependent association of ErbB2 with ErbB3 in both MCF7 and SK-BR-3 cells as determined in a co-immunoprecipitation experiment substantially more effectively than monoclonal antibody 4D5, and preferably substantially more effectively than monoclonal antibody 7F3.

To screen for antibodies which bind to an epitope on ErbB2 bound by an antibody of interest, a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art (see, e.g. FIGS. 1A and 1B herein).

The results obtained in the cell-based assays described above can then be followed by testing in animal, e.g. murine, models, and human clinical trials. In particular, the inability or limited ability of an antibody to treat ErbB2 overexpressing tumors can be demonstrated in the transgenic mouse model disclosed in the present application as described in the Examples below.

Unless defined otherwise, all technical and scientific terms used herein have the same meaning as is commonly understood by one of skill in the art to which the claimed subject matter belongs. In the event that there are a plurality of definitions for terms herein, those in this section prevail.

Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the descriptions herein are exemplary and explanatory only and are not restrictive of any subject matter claimed.

In this application, the use of the singular includes the plural unless specifically stated otherwise.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. In the present application, amino acid names and atom names (e.g. N, O, C, etc.) are used as defined by the Protein DataBank (PDB) (www.pdb.org), which is based on the IUPAC nomenclature (IUPAC Nomenclature and Symbolism for Amino Acids and Peptides (residue names, atom names etc.), Eur. J. Biochem., 138, 9-37 (1984) together with their corrections in Eur. J. Biochem., 152, 1 (1985).

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means±10% of the indicated range, value, sequence, or structure, unless otherwise indicated.

It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously. In addition, it should be understood that the individual single chain polypeptides or immunoglobulin constructs derived from various combinations of the structures and substituents described herein are disclosed by the present application to the same extent as if each single chain polypeptide or heterodimer were set forth individually. Thus, selection of particular components to form individual single chain polypeptides or heterodimers is within the scope of the present disclosure The section headings used herein are for organizational purposes only and are not to be construed as limiting the subject matter described.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All documents, or portions of documents, cited in the application including, but not limited to, patents, patent applications, articles, books, manuals, and treatises are hereby expressly incorporated by reference in their entirety for any purpose. All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

EXAMPLES

The examples below are given so as to illustrate the practice of this invention. They are not intended to limit or define the entire scope of this invention.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

All publications, patents and patent applications mentioned in this specification are herein incorporated by reference into the specification to the same extent as if each individual publication, patent or patent application was specifically and individually indicated to be incorporated herein by reference.

Example 1: Description of Exemplary Bi-Specific Antigen Binding Constructs (bsAbs) and Controls A number of exemplary bi-specific antigen binding constructs, e.g., antibody constructs and controls were designed, as described below:

1. Variant 878: a monovalent anti-HER2 antibody, where the HER2 binding domain on chain A is an scFv that binds to ECD1 (B1D2), and the Fc region is a heterodimer having the mutations L351Y_F405A_Y407V in Chain A, and T366L_K392M_T394W in Chain B. The B1D2 scFv is described in International Patent Publication Nos. WO 2009/126920, and WO2010/059315A1 and binds to an epitope on HER2 that does not overlap with trastuzumab.

2. Variant 879: a monovalent anti-HER3 antibody, where the HER3 binding domain on chain B is an scFv (H3), and the Fc region is a heterodimer having the mutations L351Y_F405A_Y407V in Chain A, and T366L_K392M_T394W in Chain B. The H3 scFv is described in U.S. Pat. No. 7,332,580.

3. Variant 880: a bi-specific anti-HER2-HER3 antibody, where the HER2 binding domain is the B1D2 scFv on chain A, the HER3 binding domain is the H3 scFv on chain B and the Fc region is a heterodimer having the mutations L351Y_F405A_Y407V in Chain A, and T366L_K392M_T394W in Chain B.

4. Variant 1040: a monovalent anti-HER2 antibody, where the HER2 binding domain on chain A is the trastuzumab Fab, and the Fc region is a heterodimer having the mutations T350V_L351Y_F405A_Y407V in Chain A, and T350V_T366L_K392L_T394W in Chain B; trastuzumab binds to extracellular domain 4 (ECD4) of HER2.

5. Variant 792: a bivalent anti-HER2 antibody, where both HER2 binding domains are Fabs from trastuzumab, and the Fc region is a heterodimer having the mutations T350V_L351Y_F405A_Y407V in Chain A, and T350V_T366L_K392L_T394W in Chain B.

6. Variant 506: trastuzumab produced in CHO (Chinese hamster ovary) cells as a control.

Example 2: Transient CHO Expression, Purification and Yield of Exemplary bsAbs

The constructs described in Example 1 were expressed in CHO cells and purified as follows. The clarified culture medium was loaded onto a MabSelect SuRe™ (GE Healthcare) protein-A column and washed with 10 column volumes of PBS buffer at pH 7.2. The antibody constructs were eluted with 10 column volumes of citrate buffer at pH 3.6 with the pooled fractions containing the antibody neutralized with TRIS at pH 11. FIG. 1 depicts the results of the SDS-PAGE analysis for the monovalent antibody controls variant 878 (FIG. 1A) and variant 879 (FIG. 1B), as well as the bsAb variant 880 (FIG. 1C), after Protein-A purification. In the three gels shown in this figure, lane 1 represents the total expressed protein, lane 2 represents the flow through fraction, lane 3 represents the wash, and lane 4 represents the purified fraction. These results show that the monovalent control antibodies and the bsAb variant 880 express well in CHO cells and purify to about ca. 80% purity post protein A purification.

The protein-A antibody eluate was further purified by gel filtration (SEC). For gel filtration, 3.5 mg of the antibody mixture was concentrated to 1.5 mL and loaded onto a Sephadex 200 HiLoad™ 16/600 200 pg column (GE Healthcare) via an AKTA Express FPLC™ at a flow-rate of 1 mL/min. PBS buffer at pH 7.4 was used at a flow-rate of 1 mL/min. Fractions corresponding to the purified antibody were collected, concentrated to ~1 mg/mL and stored at −80° C. The purified proteins were analyzed by LCMS as described below.

LCMS

The purification and yield of the bsAb variant 880 was tested by LCMS after protein A and SEC purification as described above.

LCMS Analysis of Heterodimer Purity

The purity of an exemplary bsAb, variant 880, was determined using LCMS under standard conditions. The antibody was deglycosylated with PNGasF prior to loading on the LC-MS. Liquid chromatography was carried out on an Agilent 1100 Series HPLC under the following conditions:

Flow rate: 1 mL/min split post column to 100 uL/min to MS
Solvents: A=0.1% formic acid in ddH2O, B=65% acetonitrile, 25% THF, 9.9% ddH2O, 0.1% formic acid
Column: 2.1×30 mm PorosR2
Column Temperature: 80° C.; solvent also pre-heated
Gradient: 20% B (0-3 min), 20-90% B (3-6 min), 90-20% B (6-7 min), 20% B (7-9 min)
Mass Spectrometry (MS) was subsequently carried out on an LTQ-Orbitrap XL mass spectrometer under the following conditions:
Ionization method: Ion Max Electrospray
Calibration and Tuning Method: 2 mg/mL solution of CsI is infused at a flowrate of 10 μL/min. The Orbitrap is then tuned on m/z 2211 using the Automatic Tune feature (overall CsI ion range observed: 1690 to 2800)
Cone Voltage: 40V
Tube Lens: 115V
FT Resolution: 7,500
Scan range m/z 400-4000
Scan Delay: 1.5 min A molecular weight profile of the data was generated using Thermo's Promass Deconvolution™ software.

Figure 2:
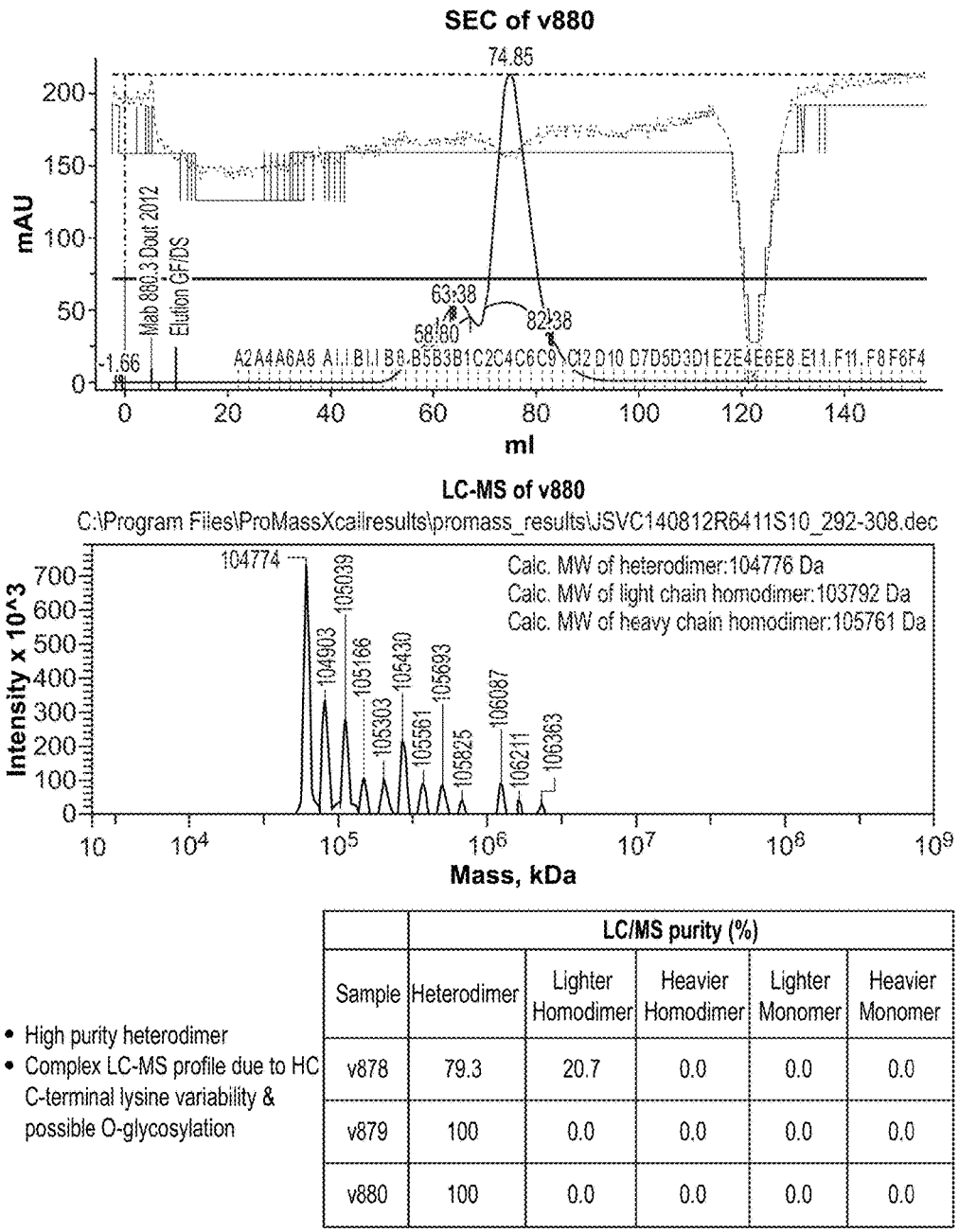
FIG. 2 depicts analysis of an exemplary bsAb by size exclusion chromatography and LCMS results.

The SEC and LC-MS results are shown in FIG. 2. LC-MS analysis shows that v879 and v880 purify to 100% heterodimer purify post protein A and SEC purification, and v878 purifies to 79% heterodimer purity and contains 20% of Chain B homodimer.

TABLE 1 shows the yield of v880 at stages of purification.

| Variant | Production scale (L) | post protein A titre (mg/L) | post SEC titre (mg/L) |
|---|---|---|---|
| v880 | 0.5 | 31.6 | 6.6 |

Example 3: BsAbs are Capable of Coengaging and Binding Both Human HER2 and HER3 as Measured by SPR The ability of an exemplary bsAb, variant 880 to bind to both targets, HER2 and HER3 was determined by SPR (Surface Plasmon Resonance) as follows using a ProteOn™ XPR36 system from BIO-RAD. HER-2 in buffer (10 mM Hepes pH 6.8) was immobilized on CMS chip through amine coupling until 3000 RU. Fc variants in an antibody format containing anti-HER2 antibodies were immobilized to the HER-2 surface to 300 RU. Running buffer and the surfactant was maintained at pH 6.8. Purified analyte Her3 was diluted in its running buffer and injected at a flow rate of 20-30 μL/min for 2 minutes, followed by dissociation for another 4 minutes. Five two-fold dilutions of each antibody beginning at 20 nM were analyzed in triplicate. Sensograms were fit globally to a 1:1 Langmuir binding model. All experiments were conducted at room temperature.

The results are shown in FIG. 3A and FIG. 3B and indicate that both antigen-binding domains of the bsAb variant 880 are able to coengage (bind) to their cognate antigen.

Example 4: BsAb Antibodies Exhibit Higher $B_{max}$ in Low her2/3-Expressing Human Tumor Cells The ability of an exemplary bsAb, variant 880, to bind to a low HER2/3-expressing cell line was determined by flow cytometry in the cell line MALME-3M. The FACS analysis was carried out as described below.

Binding of variant 880 and control monovalent variants 878 and 879, along with monospecific bivalent controls for HER2 (variant 876) and HER3 (variant 877) to the surface of MALME-3M cells was determined by flow cytometry. Cells were washed with PBS and resuspended in DMEM containing 10% FBS at 1×10$^5$ cells/100 μl. 100 μl cell suspension was added into each microcentrifuge tube, followed by 10 μl/tube of the antibody variants. The tubes were incubated for 2 hr 4° C. on a rotator. The microcentrifuge tubes were centrifuged for 2 min 2000 RPM at room temperature and the cell pellets washed with 500 μl media. Each cell pellet was resuspended 100 μl of fluorochrome-labelled secondary antibody diluted in media to 2 μg/sample. The samples were then incubated for 1 hr at 4° C. on a rotator. After incubation, the cells were centrifuged for 2 min at 2000 RPM and washed in media. The cells were resuspended in 500 μl media, filtered in tube containing 5 μl propidium iodide (PI) and analyzed on a BD™ LSRII flow cytometer according to the manufacturer's instructions.

Figure 4:
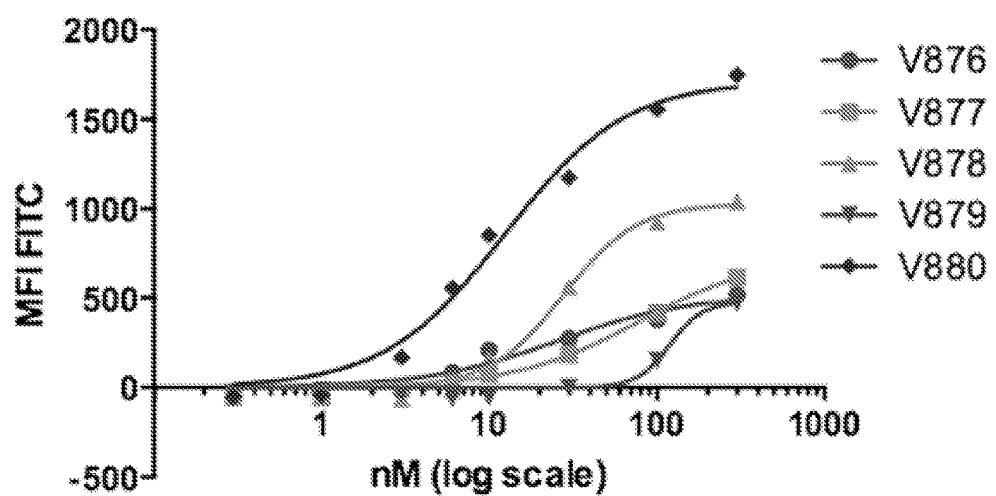
FIG. 4 demonstrates binding of variant 880 to MALME-3M cells.
Figure 5A:
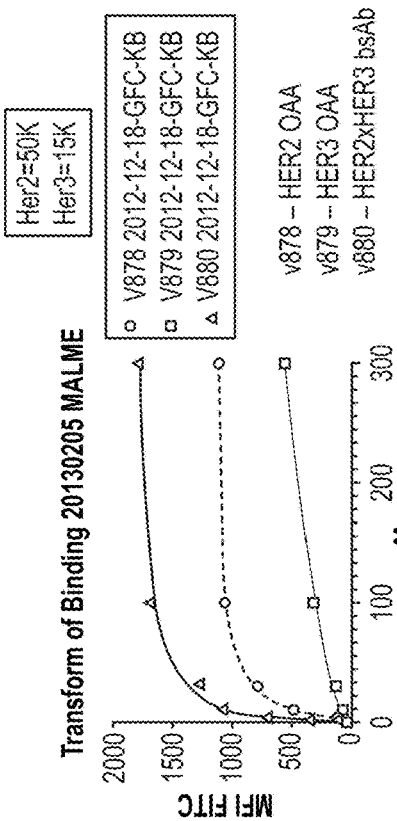
FIGS. 5A and 5B depict binding of variant 880 to SKOV-ATCC cells and FIGS. 5C and 5D depict binding of variant 880 to MALME-3M cells.
Figure 5C:
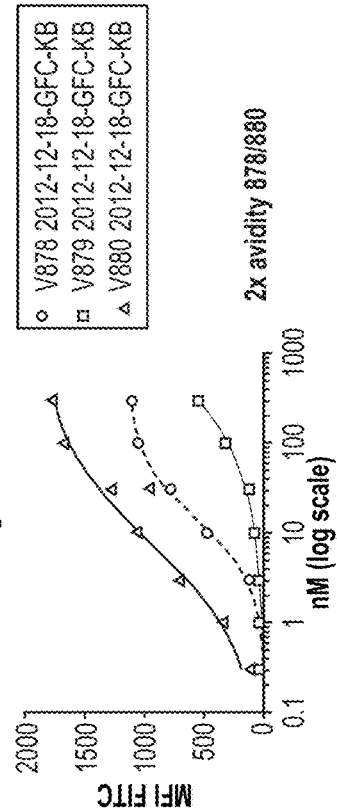
Figure 5B:
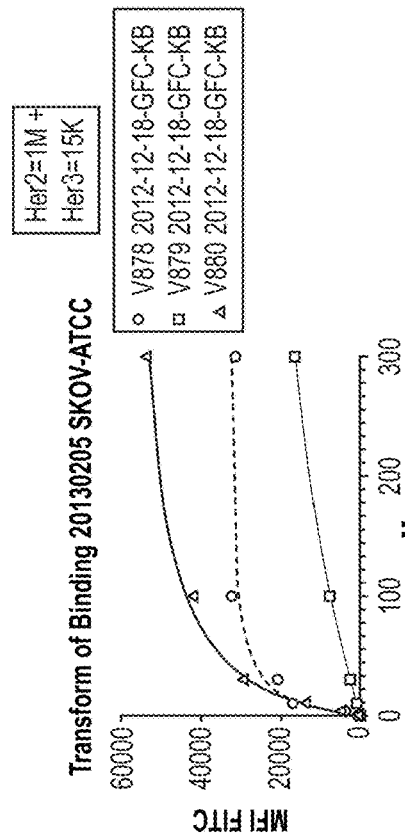
Figure 5D:
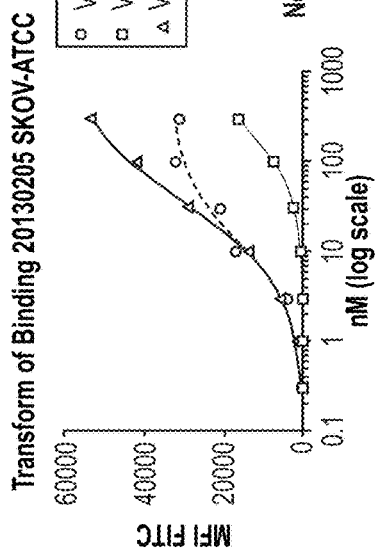

The results are shown in FIG. 4 and indicate that variant 880 bsAb exhibits the highest Bmax and increased affinity (avidity), while variant 878 (monovalent HER2) exhibits second highest $B_{max}$. The Bmax for variant 880 may be a sum of monovalent binding to HER2+HER3. The monospecific bivalent control HER2 and HER3 antibodies show lower $B_{max}$.

Example 5: BsAbs Exhibit Higher $B_{max}$ in High and Low HER2-Expressing Human Tumor Cells The ability of an exemplary bsAb, variant 880 to bind cell lines expressing variable HER2 and HER3 receptor cell densities, was determined by flow cytometry in the cell lines SKOV-ATCC and MALME-3M. Table xx identifies the relative expression levels of HER2 and HER3 in these cell lines. The FACS analysis was carried out as described in Example 4.

The results are shown in FIG. 5. FIGS. 5A and 5B show binding data in SKOV-ATCC cells. The results shown for MALME-3M cells in FIGS. 5C and 5D are a replicate data set, similar to that presented in Example 4. In FIGS. 5A and 5C the antibody concentration is plotted on a linear scale, and in FIGS. 5B and 5D the same data is plotted using a logarithmic scale for the antibody concentration. The results indicate that in SKOV-ATCC cells additive effects of the bi-specific antibody variant 880 were observed. The bsAb appeared to bind monovalently at high concentration (i.e. does not bivalently bind to Her2 and Her3). In MALME-3M cells, an avidity effect of bi-specific antibody was observed at low concentrations. The bsAb appeared to bind monovalently at high concentration. In the case of v880, these results show that relative receptor cell densities can affect the avidity of binding but do not affect the Bmax of v880 binding to the cells. In both cell lines, v880 displays superior Bmax compared to controls.

Example 6: bsAbs Elicit Higher Human NK Cell-Mediated ADCC Activity than Controls in Low HER2/3-Expressing Tumor Cells The ability of the exemplary bsAb variant 880 to direct ADCC mediated cell killing was assessed in the human triple negative breast cancer cell line MDA-MB-231 according to the method described below.

Overview: Target cells were pre-incubated with test antibodies (10 folds descending concentrations from 45 μg/mL) for 30 min followed by adding effector cells with effector/target cell ratio of 5:1 and the incubation continued for another 6 hours in 37° C./5% $CO_2$ incubators. Samples were tested with 8 concentrations, 10 fold descending from 45 ug/ml. LDH release was measured using LDH assay Kit.

Dose-response studies were performed with various concentrations of the samples with a pre-optimized Effector/Target (E/T) ratio (5:1). Half maximal effective concentration ($EC_{50}$) values were analyzed with the Sigmoidal dose-response non-linear regression fit by GraphPad Prism.

Cells were maintained in McCoy's 5A complete medium at 37° C./5% $CO_2$ and regularly sub-cultured with suitable medium supplemented with 10% FBS according to protocol from ATCC. Cells with passage number fewer than P10 were used in the assays. The samples were diluted to concentrations between 0.3-300 nM with Phenol red free MEM medium supplemented with 1% FBS and 1% Pen/strep prior to use in the assay.

ADCC Assay

MDA-MB-231 target cells were harvested by centrifugation at 800 rpm for 3 minutes. The cells were washed once with assay medium and centrifuged; the medium above the pellet was completely removed. The cells were gently suspended with assay medium to make single cell solution. The number of cells was adjusted to 4× cell stock (10,000 cells in 50 μl assay medium). The test antibodies were then diluted to the desired concentrations as noted above.

The target cells were seeded in the assay plates as follows. 50 μl of 4× target cell stock and 50 μl of 4× sample diluents was added to wells of a 96-well assay plate and the plate was incubated at room temperature for 30 min in cell culture incubator. Effector cells (NK92/FcRγ3a(158V/V), 100 μl, E/T=5:1, i.e, 50,000 effector cells per well) were added to initiate the reaction and mixed gently by cross shaking.

Triton X-100 was added to cell controls without effector cells and antibody in a final concentration of 1% to lyze the target cells and these controls served as the maximum lysis controls. ADCC assay buffer (98% Phenol red free MEM medium, 1% Pen/Strep and 1% FBS) was added in to cell controls without effector cells and antibody and it served as the minimum LDH release control. Target cells incubated with effector cells without the presence of antibodies were set as background control of non-specific LDH release when both cells were incubated together. The plate was incubated at 37° C./5% CO2 incubator for 6 hours. Cell viability was assayed with an LDH kit (Roche, cat#11644793001). The absorbance data was read at OD492 nm and OD650 nm on Flexstation 3.

Data Analysis

The percentages of cell lysis were calculated according the formula below:

Cell lysis %=100*(Experimental data−(E+T))/(Maximum release−Minimum release). Data was presented and analyzed by Graphpad (v4.0).

Figure 6:
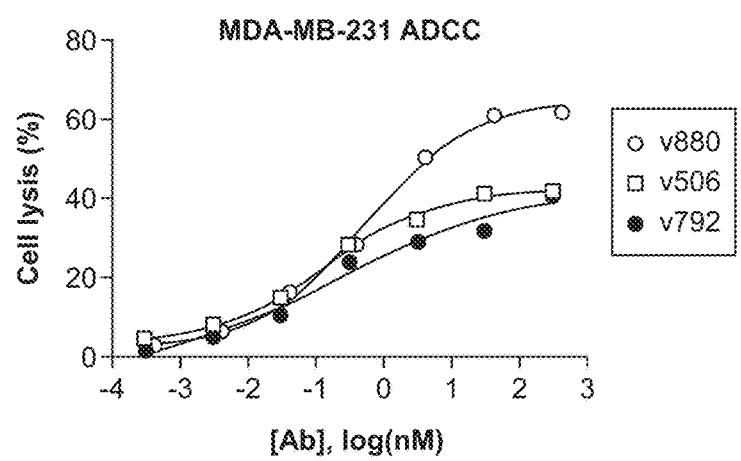
FIG. 6 depicts the ability of variant 880 and controls to mediate ADCC in MDA-MB-231 cells.

The results are shown in FIG. 6. FIG. 6 shows the results for the controls v792, v506, v1040, and the bsAb v880. These results show that in the triple negative cell line MDA-MB-231, the bi-specific variant 880 shows better efficacy than the bivalent anti-HER2 antibodies v506, and variant 792.

Example 7: bsAb Antibodies Show Higher Human NK Cell-Mediated ADCC Activity than Controls in Low HER2 ER+ Breast Tumor Cells, and in SK-BR-3 Cells The ability of the exemplary bsAb variant 880 to direct ADCC-mediated cell killing was assessed in the low HER2-expressing MCF7 cell line according to the method described in Example 6.

Figure 7:
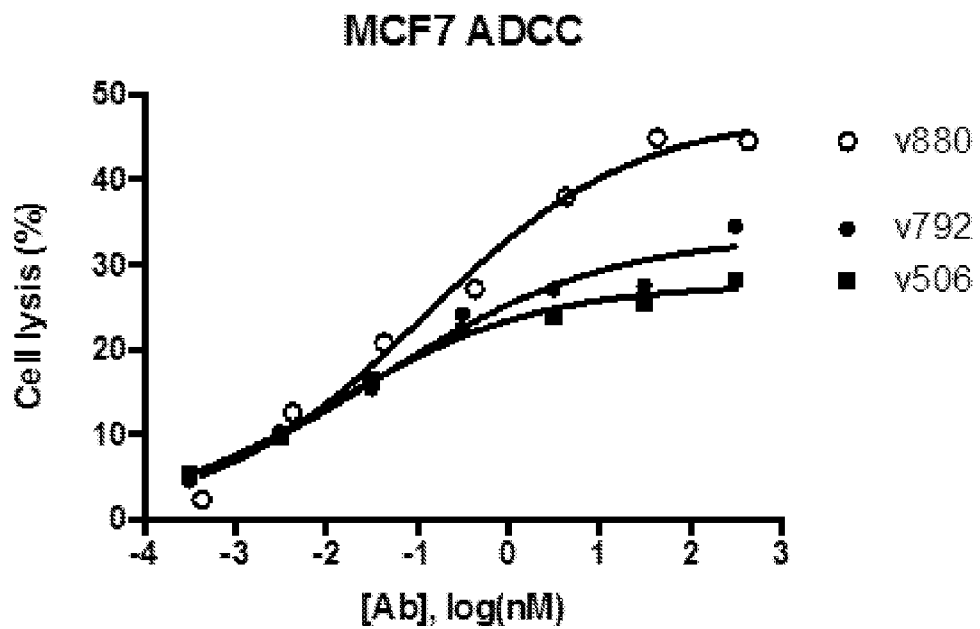
FIG. 7 depicts the ability of variant 880 and controls to mediate ADCC in MCF-7 cells.
Figure 8:
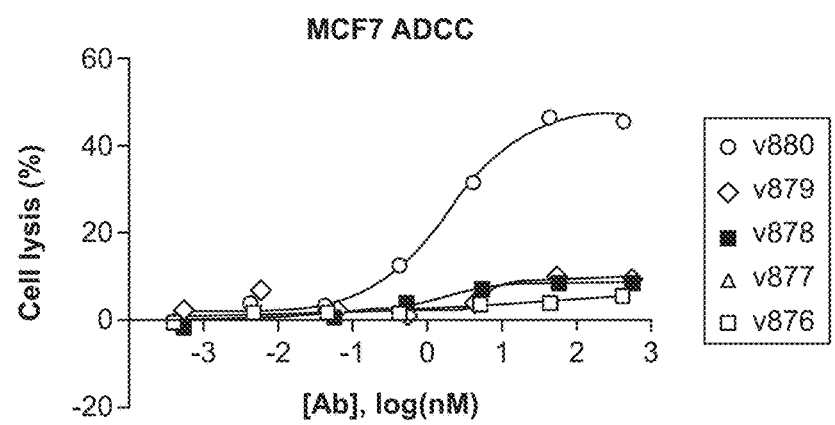
FIG. 8 depicts the ability of control variants to mediate ADCC in MCF-7 cells.
Figure 9:
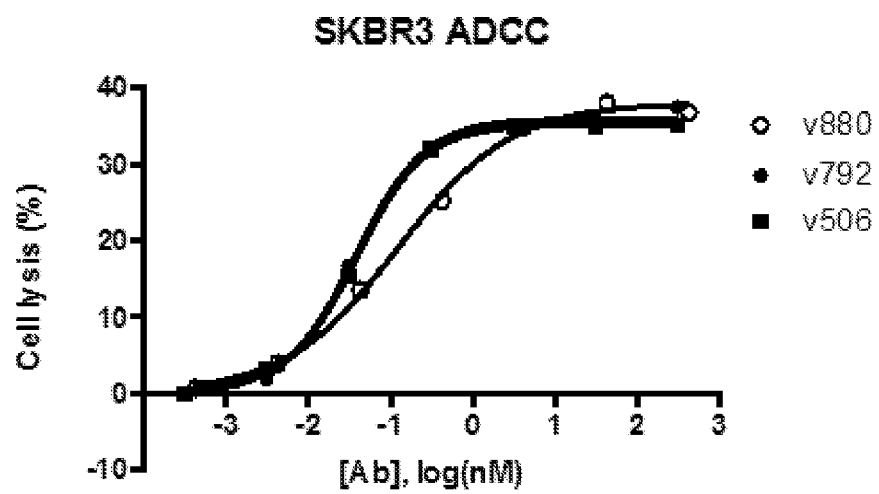
FIG. 9 depicts the ability of variant 880 and controls to mediate ADCC in SK-Br-3 cells.

The results are shown in FIGS. 7, 8 and 9. In FIG. 7, v880 is able to mediate ADCC in MCF7 cells to a greater degree than the control antibodies v792 and v506. As shown in FIG. 8, v880 is more efficacious than the bivalent control antibodies v876 and v877 in MCF-7 cells (Her2 1+). In the high density Her2 expressing cell line SK-BR-3, v880 mediates ADCC in a manner similar to the control antibodies v792 and v506, as shown in FIG. 9. These results indicate that a bi-specific antibody which displays increased decoration for binding to targets cells, may be equally or more efficacious in effector activity compared to the monospecific antibody targeting the same antigens.

Example 8: Additional Exemplary Bi-Specific Antibodies and Controls

A number of additional anti-HER2-HER3 bi-specific antibodies (bsAbs) and controls were designed and prepared. FIG. 10 lists the DNA sequence composition of the anti-HER2-HER3 bsAbs and controls tested, and Table 2 below provides epitope and reference information of tested antibodies.

TABLE 2A

| epitopes and reference information for H3 and MM111 Abs | | |
|---|---|---|
| Antibody | Antigen/Epitope | Reference |
| H3 | HER3 | US7332580B2 |
| MM111 | HER2 ECD1, HER3 | US2009060721 |

Human IgG1 was purchased from Jackson ImmunoResearch (West Grove, Pa., Cat. No. 009-000-003).

v506, v792, v1040 are as described in Example 1. v506 is a wild-type trastuzumab as produced in-house in Chinese hamster ovary (CHO) cells as a control, in which both HER2 binding domains are derived from trastuzumab in the Fab format and the Fc is a wild-type homodimer; the epitope of the antigen binding domain is domain 4 of HER2.

v792 is related to v506 but differs in the Fc region which is a heterodimer having the mutations T350V_L351Y_F405A_Y407V in Chain A, and T350V_T366L_K392L_T394W in Chain B.

v1040 is a monovalent anti-HER2 antibody, where the HER2 binding domain is a Fab derived from trastuzumab on chain A, and the Fc region is a heterodimer having the mutations T350V_L351Y_F405A_Y407V in Chain A, and T350V_T366L_K392L_T394W in Chain B; the epitope of the antigen binding domain is domain 4 of HER2.

v4184 is a wild-type pertuzumab as produced in-house in CHO cells as control, in which both HER2 binding domains are derived from pertuzumab in the Fab format and the Fc region is a heterodimer having the mutations T350V_L351Y_F405A_Y407V in Chain A, and T350V_T366L_K392L_T394W in Chain B; the epitope of the antigen binding domain is domain 2 of HER2.

v4182 is a monovalent anti-HER2 antibody, where the HER2 binding domain is a Fab derived from pertuzumab on chain A, and the Fc region is a heterodimer having the mutations T350V_L351Y_F405A_Y407V in Chain A, and T350V_T366L_K392L_T394W in Chain B; the epitope of the antigen binding domain is domain 2 of HER2.

v877 is a monospecific bivalent antibody which has two identical HER3-binding scFvs as binding arms connected to a homodimeric Fc. v879 is a monospecific monovalent one armed antibody derivative which uses the same HER3-binding scFv. The Fc region is a heterodimer having the mutations L351Y_F405A_Y407V in Chain A, and T366L_K392M_T394W in Chain B.

v1087 is a HER2 and HER3 bi-specific binding molecule, which contains an anti-HER3 scFv fused to the N-terminus, and an anti-HER2 scFv fused to the C-terminus of human serum albumin.

v4248 is an anti-HER2-HER3 bsAb, in which the HER2 binding arm is a Fab which binds domain 4 of HER2, and the HER3 binding arm is an scFv. The Fc region is a heterodimer having the mutations T350V_L351Y_F405A_Y407V in Chain A, and T366L_K392M_T394W in Chain B.

TABLE 2B sequences of v4248

| SEQ ID NO | DESCRIPTION | sequence |
|---|---|---|
| 6 | 4248 HC1 (anti HER2) | EVQLVESGGGLVQPGGSLRLSCAASGFNIKDTYIHWVRQAPGKGLEWVAR IYPTNGYTRYADSVKGRFTISADTSKNTAYLQMNSLRAEDTAVYYCSRWG GDGFYAMDYWGQGTLVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQ VYVYPPSRDELTKNQVSLTCLVKGFYPSDIAVEWESNGQPENNYKTTPPV LDSDGSFALVSKLTVDKSRWQQGNVFSCSVMHEALHNHYTQKSLSLSPGK |
| 55 | 4248 VH | EVQLVESGGGLVQPGGSLRLSCAASGFNIKDTYIHWVRQAPGKGLEWVAR IYPTNGYTRYADSVKGRFTISADTSKNTAYLQMNSLRAEDTAVYYCSRWG GDGFYAMDYWGQGTLVTVSS |
| 49 | CDR-H1 (Chothia) | GFNIKDT |
| 50 | CDR-H2 (Chothia) | YPTNG |
| 51 | CDR-H3 (Chothia) | WGGDGFYAMDY |
| 2 | 4248 LC | DIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC |
| 56 | 4248 VL (anti HER2) | DIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGQ GTKVEIK |
| 52 | CDR-L1 (Chothia) | RASQDVNTAVA |
| 53 | CDR-L2 (Chothia) | SASFLYS |
| 54 | CDR-L3 (Chothia) | QQHYTTPPT |
| 16 | 4248 HC2 (anti HER3) | QVQLQESGGGLVKPGGSLRLSCAASGFTFSSYWMSWVRQAPGKGLEWVAN INRDGSASYYVDSVKGRFTISRDDAKNSLYLQMNSLRAEDTAVYYCARDR GVGYFDLWGRGTLVTVSSASTGGGGSGGGGSGGGGSQSALTQPASVSGSP GQSITISCTGTSSDVGGYNFVSWYQQHPGKAPKLMIYDVSDRPSGVSDRF SGSKSGNTASLIISGLQADDEADYYCSSYGSSSTHVIFGGGTKVTVLGAA EPKSSDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSL LCLVKGFYPSDIAVEWESNGQPENNYMTWPPVLDSDGSFFLYSKLTVDKS RWQQGNVFSCSVMHEALHNHYTQKSLSLSPGK |
| 57 | 4248 VH | QVQLQESGGGLVKPGGSLRLSCAASGFTFSSYWMSWVRQAPGKGLEWVAN INRDGSASYYVDSVKGRFTISRDDAKNSLYLQMNSLRAEDTAVYYCARDR GVGYFDLWGRGTLVTVSS |
| 58 | CDR-H1 (IMGT) | GFTFSSYW |

TABLE 2B-continued sequences of v4248

| SEQ ID NO | DESCRIPTION | sequence |
|---|---|---|
| 59 | CDR-H2 (IMGT) | INRDGSAS |
| 60 | CDR-H3 (IMGT) | ARDRGVGYFDL |
| 61 | 4248 VL (anti HER3) | QSALTQPASVSGSPGQSITISCTGTSSDVGGYNFVSWYQQHPGKAPKLMI YDVSDRPSGVSDRFSGSKSGNTASLIISGLQADDEADYYCSSYGSSSTHV IFGGGTKVTVL |
| 62 | CDR-L1 (IMGT) | SSDVGGYNF |
|  | CDR-L2 (IMGT) | DVS |
| 63 | CDR-L3 (IMGT) | SSYGSSSTHVI | v4248 was further modified to yield v9918, v9919, v9920, v9921, v9922, v9923, v9924 and v10001 which are variants with different stabilization mutations as well as different molecular formats. v4248 was also modified to yield v9926 and v9927 which are variants with altered HER2 binding affinities.

v9918 is an anti-HER2-HER3 bsAb derived from v4248. Its HER2 binding arm is a Fab which binds domain 4 of HER2, and the HER3 binding arm is an scFv bearing a disulphide bridge between $V_H$ (residue 44) and $V_L$ (residue 100). The Fc region is a heterodimer having the mutations T350V_L351Y_F405A_Y407V in Chain A, and T350V_T366L_K392M_T394W in Chain B.

v9919 is an anti-HER2-HER3 bsAb derived from v9918. Its HER2 binding arm is a Fab which binds domain 4 of HER2, and the HER3 binding arm is an scFv bearing a disulphide bridge between $V_H$ (residue 44) and $V_L$ (residue 100), and an additional I90T mutation on $V_L$. The Fc region is a heterodimer having the mutations T350V_L351Y_F405A_Y407V in Chain A, and T350V_T366L_K392M_T394W in Chain B.

v9920 is an anti-HER2-HER3 bsAb related to v4248. Its HER2 binding arm is an scFv which binds domain 4 of HER2, and the HER3 binding arm is a Fab bearing a lambda $C_L$. The Fc region is a heterodimer having the mutations T350V_L351Y_F405A_Y407V in Chain A, and T350V_T366L_K392M_T394W in Chain B.

v9921 is an anti-HER2-HER3 bsAb derived from v9920. Its HEr2 binding arm is an scFv bearing a disulphide bridge between $V_H$ (residue 44) and $V_L$ (residue 100), which binds domain 4 of HER2, and the HER3 binding arm is a Fab bearing a lambda $C_L$. The Fc region is a heterodimer having the mutations T350V_L351Y_F405A_Y407V in Chain A, and T350V_T366L_K392M_T394W in Chain B.

v9922 is an anti-HER2-HER3 bsAb derived from v9920. Its HER2 binding arm is an scFv which binds domain 4 of HER2, and the HER3 binding arm is a Fab bearing a kappa $C_L$. The Fc region is a heterodimer having the mutations T350V_L351Y_F405A_Y407V in Chain A, and T350V_T366L_K392M_T394W in Chain B.

v9923 is an anti-HER2-HER3 bsAb derived from v9922. Its HEr2 binding arm is an scFv bearing a disulphide bridge between $V_H$ (residue 44) and $V_L$ (residue 100), which binds domain 4 of HER2, and the HER3 binding arm is a Fab bearing a kappa $C_L$. The Fc region is a heterodimer having the mutations T350V_L351Y_F405A_Y407V in Chain A, and T350V_T366L_K392M_T394W in Chain B.

v7186, v7188 and v7190 are the afucosylated derivatives of v4248, v1040 and v4182, respectively. These variants were produced the same way as the parental antibodies, with the transfection of an extra clone encoding the *Pseudomonas* GDP-6-deoxy-D-lyxo-4-hexulose reductase (see Example 9).

v6246, v6249 and v6362 are the antibody drug conjugates (ADC) derived from v506, v6908 and v4248, respectively. The naked antibodies were conjugated to the drug payload mertansine (DM1), with succinimidyl 4-(N-maleimidomethyl)-cyclohhexane-1-carboxylate (SMCC) acting as linker (see Example 11).

Example 9: Expression and Purification of Anti-HER2-HER3 bsAbs and Controls

The anti-HER2-HER3 bsAbs and controls described in Example 8 were cloned, expressed in 50 mL cultures and purified as follows. The genes encoding the antibody heavy and light chains were constructed via gene synthesis using codons optimized for human/mammalian expression. The final gene products were sub-cloned into the mammalian expression vector pTTS (NRC-BRI, Canada) and expressed in CHO cells (Durocher, Y., Perret, S. & Kamen, A. High-level and high-throughput recombinant protein production by transient transfection of suspension-growing CHO cells. *Nucleic acids research* 30, E9 (2002)).

The CHO cells were transfected in exponential growth phase ($1.5 \times 10^6$ to $2 \times 10^6$ cells/mL) with aqueous 1 mg/mL 25 kDa polyethylenimine (PEI, Polysciences) at a PEI:DNA ratio of 2.5:1 (Raymond C. et al. A simplified polyethylenimine-mediated transfection process for large-scale and high-throughput applications. Methods. 55(1):44-51 (2011)). Different ratios of heavy chain and light chain DNA, for example, 30%/30%/40%, 40%/20%/40%, or 20%/40%/40%, were first transfected in a 2 ml expression scale to optimize the formation of heterodimers. Based on the expression profiles obtained, suitable DNA ratios were selected for larger volume productions. For antibodies with an afucosylated glycosylation pattern, which is known to enhance effector mediated function, the expression was performed in the same manner, with the addition of an extra clone encoding a GDP-6-deoxy-D-lyxo-4-hexulose reductase (RMD) to 15% of the total DNA present.

Transfected cells were harvested after 5-6 days with the culture medium collected after centrifugation at 4000 rpm and clarified using a 0.45 µm filter. The clarified culture medium was loaded onto a MabSelect SuRe™ (GE Healthcare) protein-A column and washed with 10 column volumes of PBS buffer at pH 7.2. The antibody was eluted with 10 column volumes of citrate buffer at pH 3.6 with the pooled fractions containing the antibody neutralized with TRIS at pH 11. The protein was then desalted using an Econo-Pac 10DG column (Bio-Rad).

The protein was further purified by gel filtration, 3.5 mg of the antibody mixture was concentrated to 1.5 mL and loaded onto a Superdex 200 HiLoad 16/600 200 pg column (GE Healthcare) via an AKTA Express FPLC at a flow-rate of 1 mL/min. PBS buffer at pH 7.4 was used at a flow-rate of 1 mL/min. Fractions corresponding to the purified antibody were collected, concentrated to ~1 mg/mL and stored at −80° C.

For purifying human serum albumin fusion proteins, the AlbuPure™ affinity resin was used, following the manufacturer's recommendations. In brief, the harvested cell culture supernatant was adjusted to pH 6 with 0.5 M $NaH_2PO_4$. The protein sample was then allowed to bind to the AlbuPure™ resin for 60 min at room temperature in a batch binding mode. The resin was then washed with 75 mM $NaPO_4$ pH 6 followed by 75 mM $NaPO_4$ pH 7.8. Finally the protein was eluted with PBS supplemented with 20 mM sodium octanoate.

FIG. 11A) shows the selected ratio and step yield for 50 mL productions of exemplary bsAb v4248. FIG. 11B) shows the supernatant titre for 10 mL scouting expressions of v4248 derivatives.

FIG. 12 shows the purification results of exemplary bsAb v4248 as assessed by SDS-PAGE and SEC.

Figures 12A, 12B:
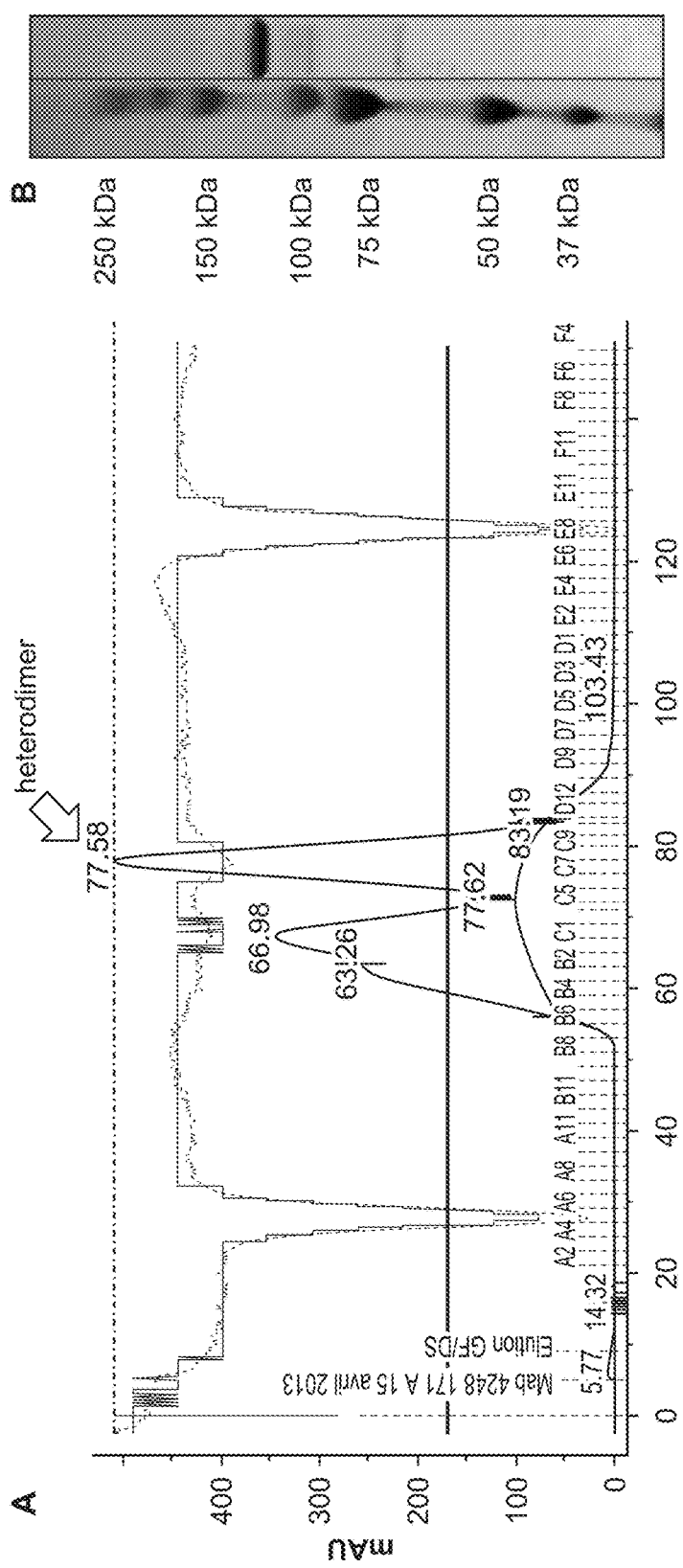
FIG. 12A SEC chromatogram of protein A-purified v4248.
FIG. 12B shows the post-protein A/post SEC sodium dodecyl sulfate polyacrylamide gel electrophoresis (SDS-PAGE) of main heterodimer peak of v4248.

When expressed using the selected DNA ratios, a number of exemplary bsAbs still showed significant amounts of homodimer contaminants or high molecular weight aggregates, as seen in the SEC chromatogram of the protein A purified material (FIG. 12A). However, as shown for v4248 high product purity fractions can be and were collected from the SEC purification step and the heterodimer purity typically improved to 80 to 95%, as estimated by the post-protein A post SEC SDS-PAGE (FIG. 12B). The purity was also confirmed by ultra performance liquid chromatography-size exclusion chromatography (UPLC-SEC) and mass spectroscopy (results not shown).

These results demonstrate that the exemplary bsAbs, and afucosylated versions of these bsAbs, can be expressed and purified using standard procedures employed for the IgG platform.

Example 10: Large Scale Production (Up to 25 L) of Exemplary bsAb

The exemplary bsAb v4248 was expressed in up to 25 L of transient CHO cell cultures to assess the production scalability and the large scale manufacturability. Expression and purification of the antibody was performed using the methods described above.

In a typical 25 L production, the yield of the exemplary bsAb v4248 after protein A and SEC purification was 10.8 mg/L, and the heterodimer purity was 94%. There was no loss in titre or difference in heterodimer purity compared to smaller scale expressions (50 ml or less).

The production data of the exemplary v4248 demonstrated the successful scalability and the application to large scale manufacturing amenable to typical IgG platform purification methods.

Example 11: Conjugation of Anti-HER2-HER3 bsAb to a Toxic Drug Payload to Generate an ADC Exemplary bsAb v4248 was conjugated as an antibody-drug conjugate (ADC) using a one-step procedure.

Conjugation was performed as follows. The starting protein sample was first buffer exchanged into 50 mM potassium phosphate pH 6.5, 50 mM NaCl and 2 mM EDTA using a PD-10 column, and adjusted to 10 µg/ml. A 10 mM solution of SMCC-DM1 dissolved in dimethylacetamide (DMA) was then added to 7.5 molar equivalents of the protein sample. DMA was further added to a final concentration of 10% v/v and the sample was mixed briefly. The reaction solution was incubated at 25° C. overnight with mixing. The reaction was monitored by determining the proportion of unconjugated protein sample by (hydrophobic interaction chromatography-high performance liquid chromatography) HIC-HPLC, and SMCC-DM1 was added in small increments until the amount of unconjugated sample was less than 5%. The product was then buffer exchanged into 20 mM sodium succinate pH 5.0 using a PD-10 column, and the protein concentration and drug-to-antibody ratio (DAR) were determined based on the absorbance at 252 and 280 nm. The buffer was adjusted to a final composition of 20 mM sodium succinate, 6% w/v trehalose and 0.02% w/v polysorbate 20, pH 5.0. High performance liquid chromatography-size exclusion chromatography (HPLC-SEC) was performed to identify any high molecular weight aggregate, which was purified out by SEC if it constituted more than 5% of the total protein content.

Figure 13:
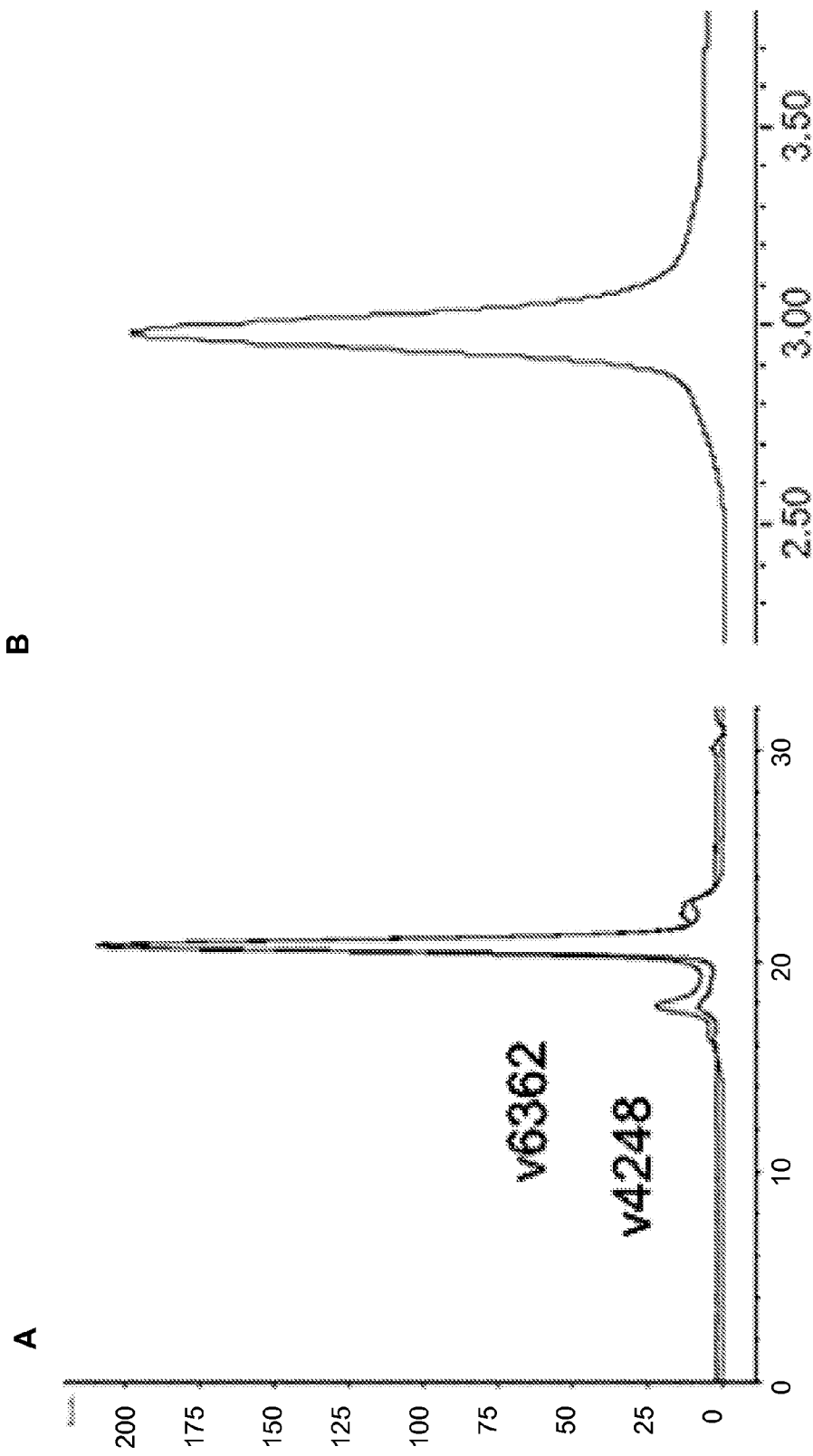
FIG. 13 shows the SEC profiles of exemplary molecules at different stages of the ADC conjugation.

FIG. 13 shows the SEC profiles of exemplary bsAbs at different stages of ADC conjugation. FIG. 13A shows the SEC profiles of v4248 and v6362 before and after conjugation to DM1. FIG. 13B shows UPLC-SEC of v6362 purified by SEC.

The exemplary bsAb v4248 was conjugated to SMCC-DM1 successfully, both at a small and large scale using 2 to 150 mg of starting protein. The initial total protein recovery, after the conjugation reaction and workup, was typically between 50 and 70%. Although v6362 typically contained 10-20% of high molecular weight (HMW) contaminants, a subsequent SEC purification successfully removed the impurities to recover a bsADCs sample of approximately 94% purity. The DAR of v6362 a typical conjugation is between 3.5 and 4.2, which is comparable to the DAR of 3.5 reported for a similar ADC such as Trastuzumab-DM1.

These results demonstrate that the exemplary bsAb can be successfully derivatized into an ADC using a one-step DM1 conjugation procedure. Subsequent purification of the ADC was also successful using a standard purification method. The process is also amenable to scale up.

Example 12: Stability of Anti-HER2-HER3 bsAb and bsADC

Differential scanning calorimetry (DSC) was performed to assess the stability of the antibody variants based on the melting temperature.

In brief, the DSC analysis was performed in the MicroCal™ VP-Capillary DSC (GE Healthcare) using 0.4 ml of purified protein adjusted to a concentration of 0.2 to 0.4 µg/ml in PBS. At the start of each DSC run, 5 buffer blank injections were performed to stabilize the baseline, and a buffer injection was placed before each sample injection for referencing. Each sample was scanned from 20 to 100° C. at a 60° C./hr rate, with low feedback, 8 sec filter, 5 min preTstat, and 70 psi nitrogen pressure. The sample thermograms were referenced and analyzed using Origin 7 software.

Figure 14:
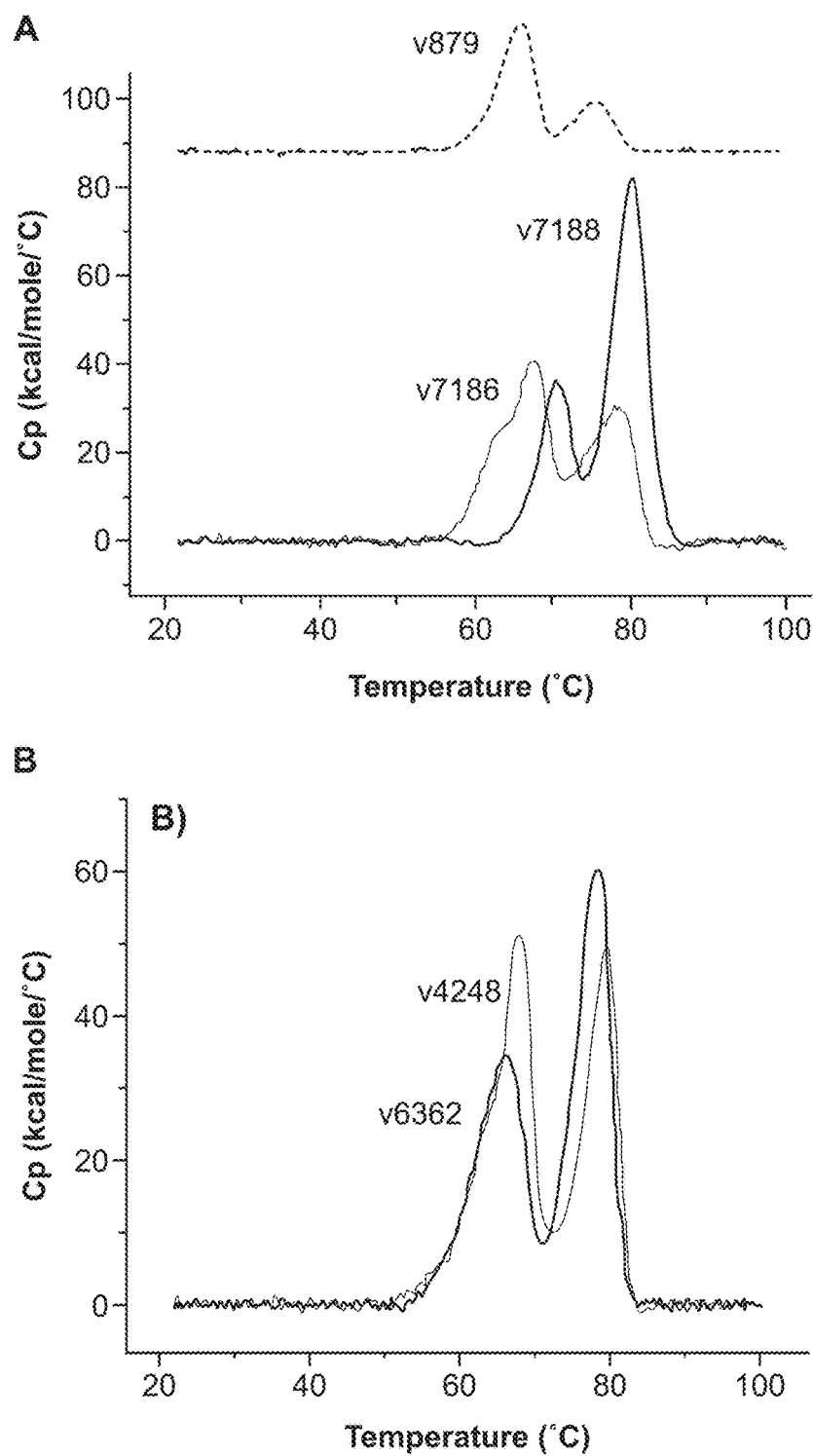
FIG. 14 depicts DSC thermograms of exemplary molecules and controls.

Thermograms for exemplary variants v7186, 4248, and 6362 are shown in FIG. 14A and FIG. 14B. The thermograms for v7186 and its corresponding one-armed antibody (OAA) controls v7188 and v879, were used to identify the melting temperatures ($T_m$) of constituent domains with peaks at 64, 67 and 78° C., likely corresponding to the CH2, scFv and Fab domains respectively. The melting of the CH3 domain is presumed to be buried within the first peak in the 60-70° C. region because of the mutations present in the particular heterodimeric Fc of v7186.

A comparison of the thermograms of bsAb v4248 and its corresponding bsADC v6362 shows that conjugation of the bsAb did not result in any significant stability loss. The $T_m$s appear to have decreased only slightly, from 68 and 80° C. in v4248 to 66 and 78° C. in v6362.

Overall, these results demonstrate that combining the individual antigen-binding domains onto a bi-specific antibody format does not significantly impact their inherent stability. In addition, antibodies in this bi-specific format can be conjugated to a toxin without significant impact on stability.

Example 13: Exemplary bsAb Binds Human FcγRs by SPR

The binding affinity of exemplary antibodies to several human FcγRs was measured by surface plasmon resonance (SPR) using the ProteOn™ XPR36 system from Bio-Rad, in order to demonstrate the FcγR binding capabilities of regular and afucosylated bsAbs.

HER2 (in 10 mM HEPES pH 6.8) was immobilized on CM5 chip through amine coupling until 3000 RU was reached. Exemplary HER2-binding antibody variants were subsequently captured on the HER2 surface at 300 RU. Running buffer and the surfactant was maintained at pH 6.8. Purified analyte FcγRs were diluted in its running buffer and injected at a flow rate of 20-30 μl/min for 2 minutes, followed by dissociation for another 4 minutes. Five two-fold serial dilutions of each analyte beginning at 20 nM were analyzed in triplicate. Sensograms were fit globally to a 1:1 Langmuir binding model. All experiments were conducted at room temperature. The results are shown in FIG. 15.

Among the antibody-FcγR binding pairs tested, there was no major difference (within approximately 2-fold) between the dissociation constants ($K_D$) of the exemplary bsAbs and that of the monospecific controls. For example, the FcγR 3aF $K_D$ of v4248 and v506 were $3.2 \times 10^{-7}$ and $6.7 \times 10^{-7}$, respectively. The observed ca. two-fold increase in binding affinity in FcγR 3aV when compared to 3aF is consistent with literature data. The $K_D$ of other FcγRs were also similar to values reported in the literature.

For the afucosylated v4248, the same binding affinity relationships were observed. Moreover, when compared with the regular, non-afucosylated, bsAb v4248, the binding affinity to FcγR 3aF and 3aV was improved by approximately 10-fold, which is expected based on literature data.

Together, these results demonstrate that bsAb v4248 exhibit FcγR binding affinities similar to an antibody that bears a WT IgG1 Fc. The bsAb is therefore expected to be equally competent in mediating effector mediated cytotoxic function compared to that of a regular antibody. Additionally, the afucosylated bsAb v7186 shows the expected increase in FcγR 3 aF and 3 aV binding affinity, and is anticipated to translate into an enhancement in effector mediated function based.

Example 14: Exemplary bsAb Exhibited Higher Bmax than Monospecific Bivalent Antibody in Human Tumor Cells Expressing Different Levels of Target Antigens The binding of the exemplary bsAb v4248 to different human tumor cell lines expressing varying levels of HER2 and HER3 was assessed by flow cytometry, and compared with the parental monospecific bivalent antibody control v506. The origin and receptor expression levels of the tested cell lines, BT-474, SKOV3, JIMT1, MDA-MB-231 and MCF7, are described in Table A1.

Cells were washed with PBS and resuspended in DMEM at $1 \times 10^5$ cells/100 μl. The cell suspension (100 μl) was added to microcentrifuge tubes, followed by 10 μl of the antibody variants in a range of final concentrations. The tubes were then incubated for 2 hr at 4° C. on a rotator. The tubes were centrifuged for 2 min 2000 RPM at room temperature and the cell pellets washed with 500 μl media. Each cell pellet was resuspended in 100 μl of fluorophore-labeled secondary antibody diluted in media to 2 μg/sample. The samples were then incubated for 1 hr at 4° C. on a rotator. After incubation, the cells were centrifuged for 2 min at 2000 rpm, supernatant removed and cell pellet washed in media. The cells were resuspended in 500 μl media, filtered (to remove large cell clumps) into a tube containing 5 μl propidium iodide (PI), and analyzed on a BD™ LSR II flow cytometer according to the manufacturer's instructions.

Binding parameters maximal binding (Bmax) representing the number of antibody molecules bound per cell, and $K_D$, the dissociation constant representing the half-saturation antibody concentration, were generated by curve fitting of the data using GraphPad Prism. Table 3 summarizes the binding of exemplary bsAb of v4248 to several human tumor cell lines expressing different levels of HER2 and HER3.

TABLE 3

Binding of v4248 to various cell lines

|  | BT-474 | SKOV3 | JIMT1 | MDA-MB-231 |
|---|---|---|---|---|
| v506 | | | | |
| Bmax | 34000 | 28700 | 6262 | 2930 |
| KD | 5.3 | 4.5 | 2.4 | 3.2 |
| v4248 | | | | |
| Bmax | 104000 | 39600 | 8390 | 5960 |
| KD | 36 | 14 | 13 | 24 |
| Bmax fold difference | 3.06 | 1.38 | 1.34 | 2.03 |

Bmax was reported as arbitrary unit median fluorescence intensity (MFI), which may vary with different instrument settings. KD is the apparent dissociation constant in nM.

Figure 16:
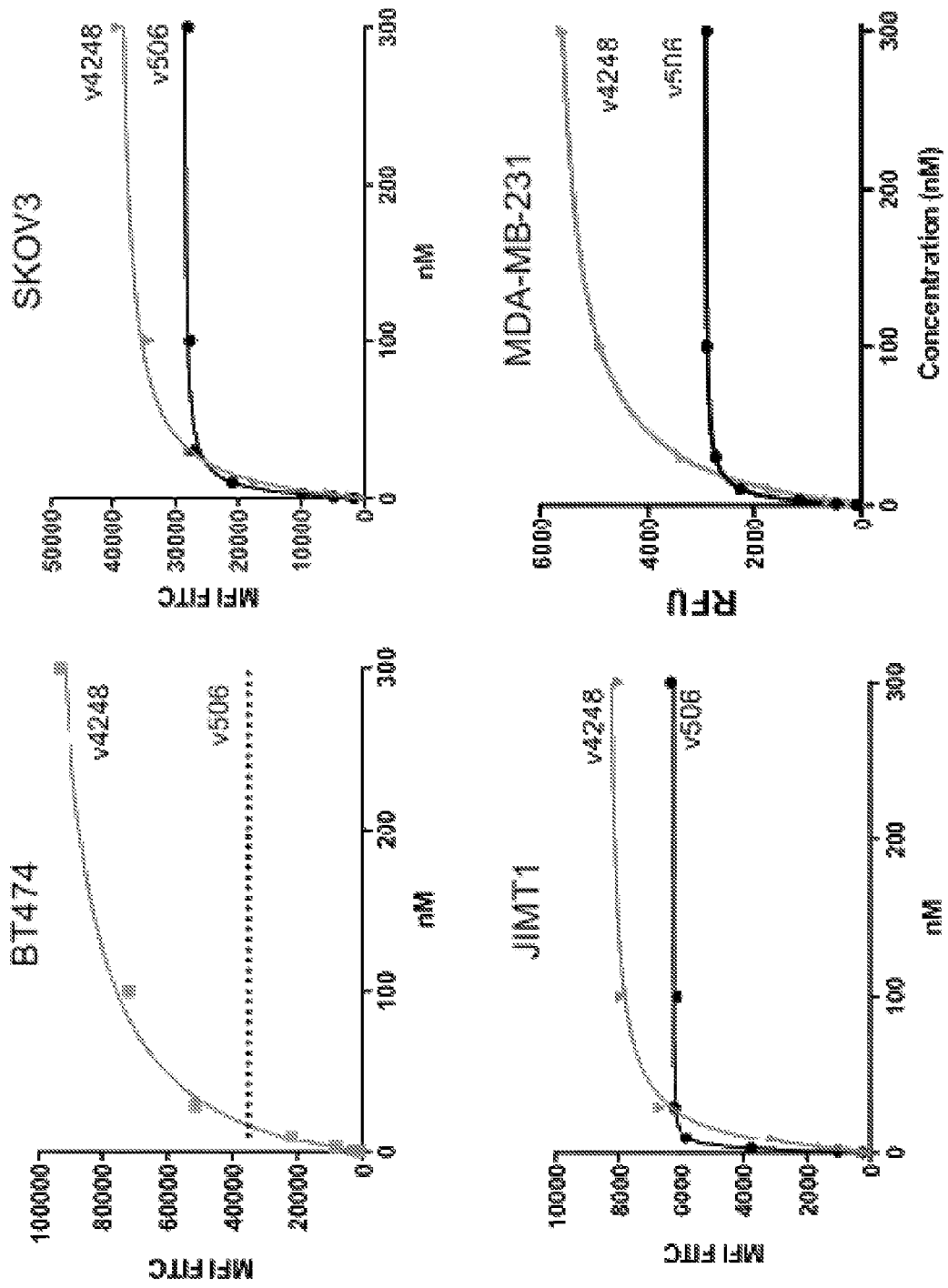
FIG. 16 depicts representative binding curves for v4248 in the cell lines BT-474, SKOV3, JIMT1 and MDA-MB-231.

FIG. 16 depicts representative FACS binding curves of exemplary bsAb v4248 in several human cancer cell lines expressing different levels of HER2 and HER3.

The exemplary bsAb v4248 showed increased Bmax in BT-474 cells compared to the monospecific bivalent control v506. Additionally, this increased cellular decoration property is consistently observed across different human tumor cells expressing different levels of HER2 and HER3, although the Bmax fold difference shows some variability. For example, in the low HER2 expressing MDA-MB-231, v4248 demonstrated significantly higher Bmax when compared to the monospecific bivalent antibody v506 which shares the same anti-HER2 binding domain. The increased Bmax between the bsAb v4248 and v506 was also observed in JIMT1 and SKOV3.

In summary, the exemplary bsAb v4248 showed higher cellular decoration compared to a monospecific bivalent antibody control in a number of human tumour cell lines expressing varying levels of HER2 and HER3 target receptors. A higher level of cell binding is expected to better potentiate effector mediated killing of target cells.

Example 15: bsADC Show Similar Human Cancer Cell Binding to Parental bsAb

The ability of bsADC v6362 to bind to cells was assessed in order to determine if there was any impact of conjugation on target antigen binding. The experiment was carried out as described in Example 14.

Figure 17:
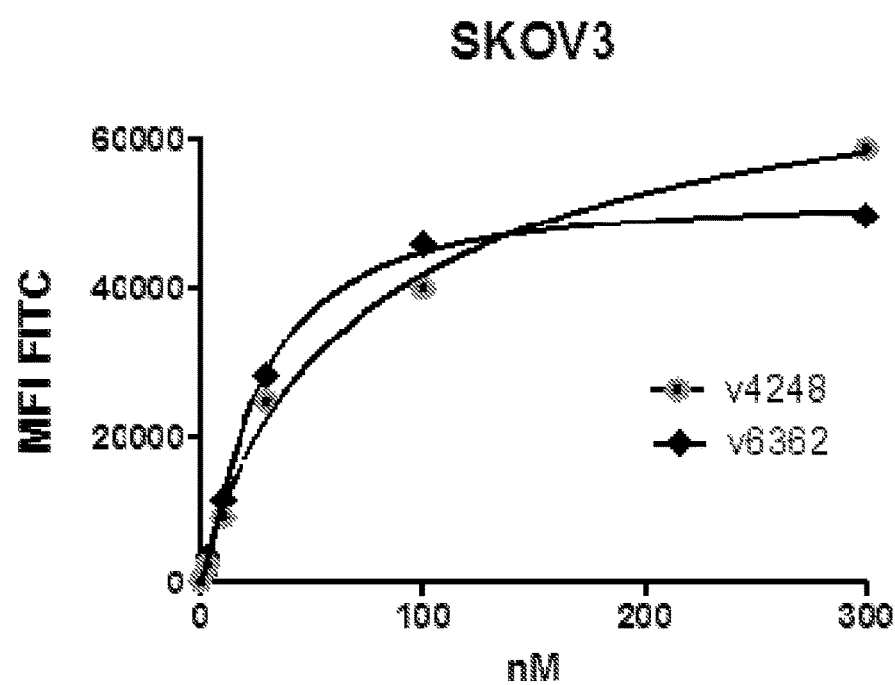
FIG. 17 depicts FACS binding curves of v4248 and v6362 in SKOV3 cells.

FIG. 17 depicts the binding of bsAb v4248 and its corresponding bsADC v6362 to the human ovarian cancer cell SKOV3.

In SKOV3 cells, v4248 and v6362 had a similar Bmax, but the ADC had higher apparent affinity. This result demonstrates that conjugation of the bsAb does not result in any adverse impact on its antigen binding capabilities, and the bsADC is expected to be equally capable of binding target human tumour cells compared to the originating bsAb.

Example 16: Exemplary Anti-HER2-HER3 bsAb Displayed Increased ADCC of Human Tumour Cells Over Anti-HER2 Monospecific Bivalent Antibodies The ability of bsAbs 4248 and 7186 to mediate ADCC compared against monospecific bivalent anti-HER2 control antibodies in human tumour cell lines SK-BR-3, JIMT1, SKOV3 and MDA-MB-231 was measured, as described below. The control antibody Herceptin™ was purchased from Roche.

Target cells (5,000 to 10,000 cells, in 50 µl) were seeded to each well of a 96-well plate, and the following day antibody was added to final concentrations ranging from 3 pM to 300 nM, distributed evenly on the logarithmic scale. After a 30 min incubation the effector cells were added at different E:T ratios. For human PBMC effector cells, the final E:T ratio was 25:1. For effector NK92 cells expressing the human FcRγ3a (158V/V), the E:T ratio was 5:1 or 1:1. The plate was then gently mixed by cross shaking and further incubated at 37° C./5% $CO_2$ for 6 hr.

The percentage of cells lysed was determined by measuring the amount of LDH released into the supernatant using the LDH kit and Flexstation 3. The absorbance values at 492 nm were all background-subtracted with those at 650 nm. The calculation of the results was as shown below and the dose response curve parameters were fitted in Graphpad Prism:

% cell lysis=100%×(ODsample−ODnonspecific)/(ODmax−ODmin)

where: $OD_{sample}$ corresponds to the background subtracted value of the sample; $OD_{nonspecific}$ corresponds to the readout in the LDH assay when the target cells were incubated with the effector cells, without other treatment; $OD_{max}$ corresponds to the maximum amount of target cell lysed. This readout was generated by adding 1% Triton X-100 to the target cells, incubated with antibody but without effector cells; $OD_{min}$ corresponds to the minimum amount of target cell lysed, in which the target cells were incubated in the assay buffer without effector cells and antibody.

The results of this assay are shown in FIGS. 18A-D.

Figure 18:
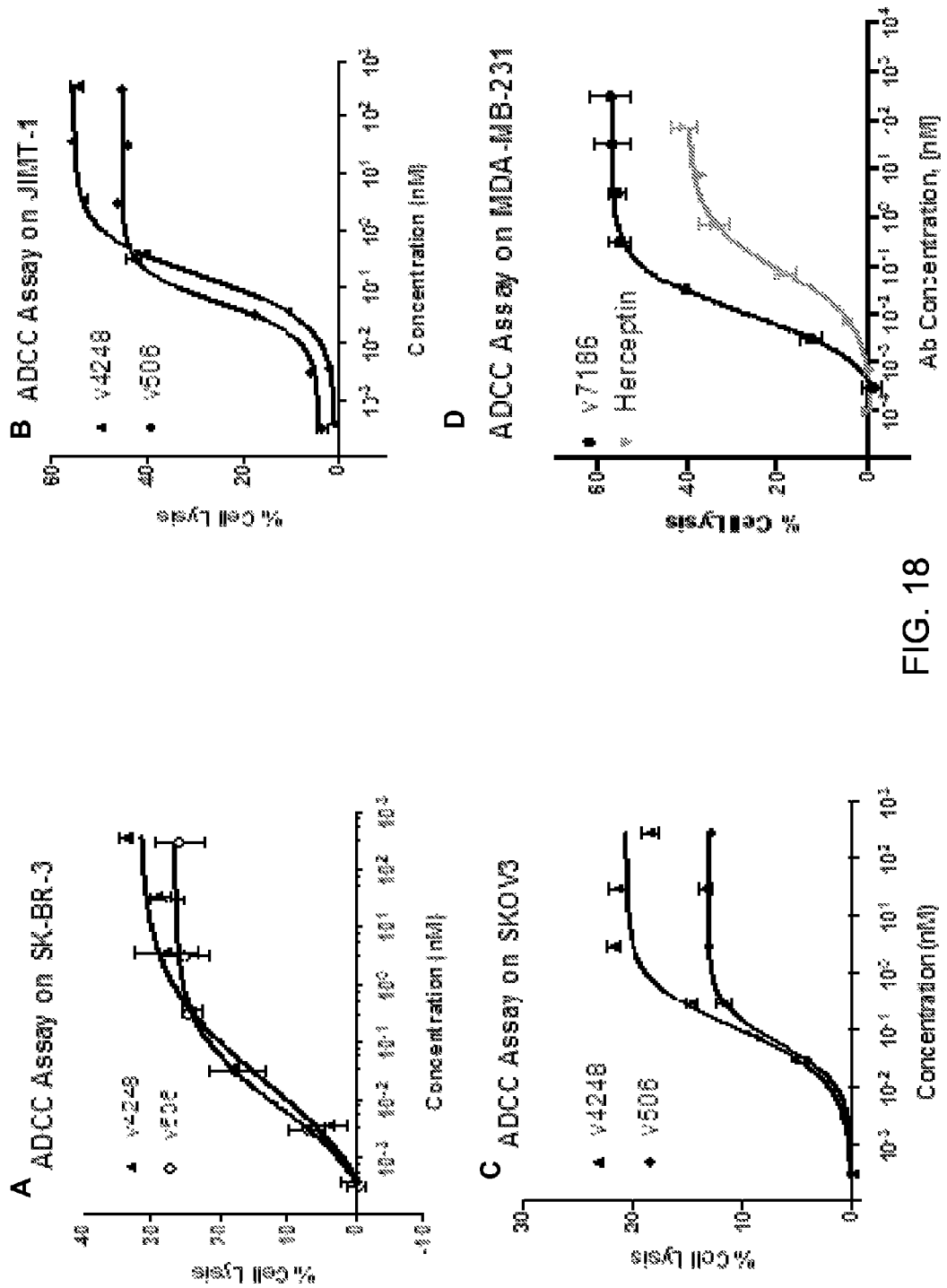
FIG. 18 depicts the ability of exemplary bsAbs to mediate ADCC in SK-BR-3 cells (FIG. 18A), JIMT1 cells (FIG. 18B), SKOV3 cells (FIG. 18C), and MDA-MD-231 cells (FIG. 18D).

As shown in FIG. 18A, in SK-BR-3 cells (HER2 3+), v4248 showed a similar efficacy and potency compared to the control antibody v506

FIG. 18B shows the ability of v4248 to mediate ADCC in JIMT1 (HER2 mid) cells, compared to the control antibody v506. The results demonstrated that in medium HER2 expressing cells, bsAb v4248 could mediate higher ADCC efficacy than the monospecific bivalent anti-HER2 control. The potencies between the bsAb and control are similar.

As shown in FIG. 18C, in SKOV3 cells, the exemplary bsAb v4248 showed a similar potency (based on the EC50 representing the antibody concentration that mediates half maximal % cell lysis), but a considerably higher max % cell lysis (approximately 1.6 fold) compared to the monospecific bivalent anti-HER2 control, v506.

To investigate the effects of afucosylation, the fully afucosylated bsAb v7186 showed a 1.5 fold higher max % cell lysis than Herceptin™ in MDA-MB-231, as shown in FIG. 18D, demonstrating that the exemplary bsAb can be produced as an afucosylated antibody to further enhance its ADCC efficacy and potency (as seen by the 9 fold improvement in EC50) on target cancer cells.

In summary, the results demonstrate that bsAb show an increase maximum level of ADCC cell lysis over that of a parental monospecific bivalent antibodies. This increase is consistent with the increase in cell binding (i.e. Bmax or cellular decoration). Moreover, the bsAbs can be produced in the afucosylated form to further increase the efficacy and potency of effector mediated function such as ADCC. The data demonstrates that bsAbs' are capable of mediating enhanced efficacy in killing target tumour cells.

Example 17: Exemplary Anti-HER2-HER3 bsAbs Inhibit In Vitro HER2 3+ Human Breast Tumor Cell Growth The ability of the exemplary anti-HER2-HER3 bsAbs to inhibit the growth of HER2 3+ human breast cancer cell line BT-474 was assessed as below. The addition of exogenous heregulin was tested to determine the ability of these bsAbs to neutralize the growth stimulatory effects of heregulin.

Each well of a 96-well plate was seeded with 4000 cells. Antibodies were added to final concentrations of up to 300 nM, in the absence or presence of 5 nM heregulin (with 1 hr pre-incubation of antibodies). The experiment was performed in triplicate. The final assay volume of the growth medium was 200 µL, and the 96-well plate was incubated 37° C. for 6 days. Media was removed from the plate, and 50 µL PBS was added to each well. The cell viability was then detected by Sulforhodamine B following the manufacturers' instructions. The absorbance was read by a plate reader and the percentage of cell growth relative to the untreated control was calculated by:

% cell growth=100%×(RLUsample)/(RLUuntreated)

Figure 19:
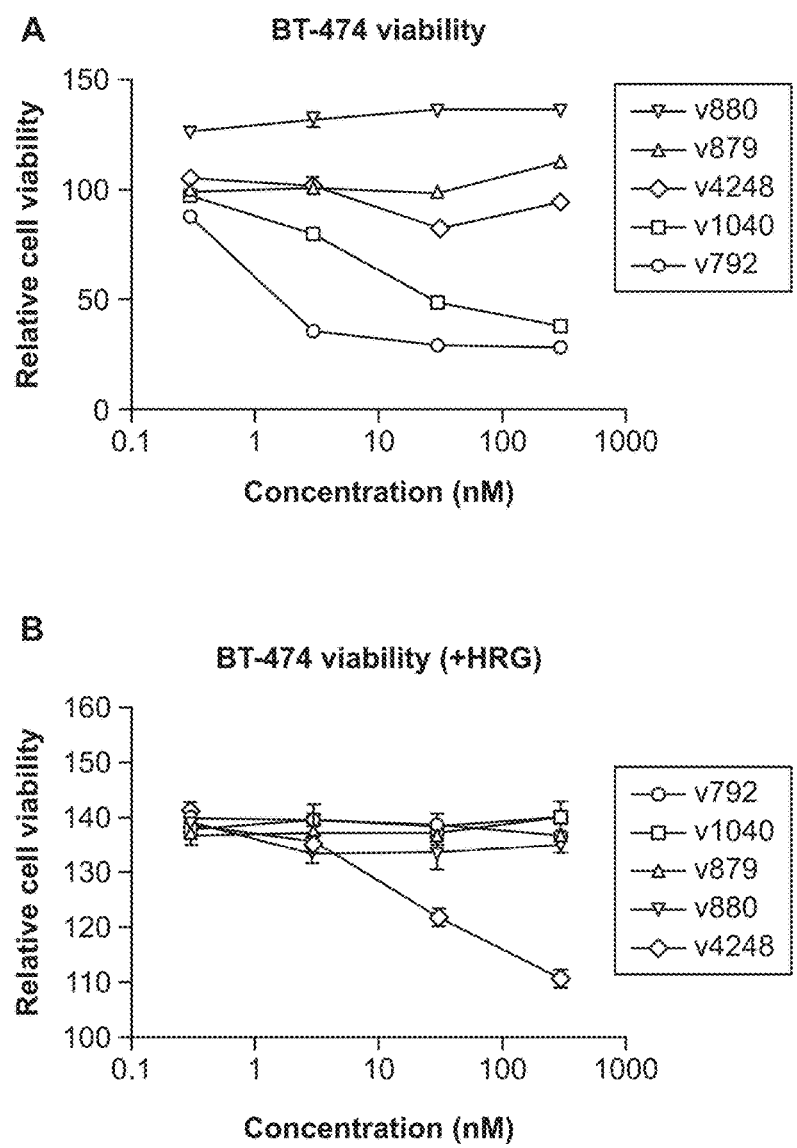
FIG. 19 shows the effects of exemplary bsAbs and controls on the viability of human breast cancer cells BT-474 relative to the untreated cells.

FIG. 19 shows the effects of exemplary bsAbs and controls on the viability of human breast cancer cells BT-474 relative to the untreated cells, in the absence (A) and presence (B) of heregulin.

Since HER2 and HER3 form a cognate receptor pair responsible for cell stimulation, there is a possibility for the bsAbs to crosslink these receptors in an undesired manner, leading to the activation of growth promoting signaling cascade.

Indeed, the exemplary bsAbs showed very different effects on BT-474 cell viability. For v880, a 36% increase in cell viability was observed, which sharply contrasts with MM-111 which reportedly inhibits cancer cell growth. Since they share the same HER2 and HER3 binding domains, the growth stimulation of v880 likely results from its unique way of crosslinking HER2 and HER3 on the cell surface. In comparison, v4248 which shares the same HER3 binding domain as v880, showed slight growth inhibition of approximately 5-17%. This is also very different from its corresponding monospecific anti-HER2 controls (v506 and v1040) which significantly inhibited BT-474 cell growth. These results highlight that anti-HER2-HER3 bsAbs exhibit distinct growth inhibition profiles.

The ability for bsAbs to neutralize the heregulin stimulated cell growth was also investigated. In the untreated control, heregulin stimulated BT-474 growth by approximately 38%. When the BT-474 cells were treated with antibodies, different dose response profiles were also observed. The bsAb v880 did not neutralize heregulin stimulated cell growth, as with the other monospecific control antibodies. In contrast, v4248 significantly neutralized the stimulatory effects of heregulin down to 11%. Similarly to the case described above, the ability of bsAbs to neutralize heregulin is not obvious based on its composition.

In summary, exemplary anti-HER2-HER3 bsAbs have different growth inhibition/stimulation effects on cancer cell growth.

Example 18: Exemplary bsAbs Showed Higher Internalization Vs. Controls and Changed the Level of Surface Receptors Displayed in Human Cancer Cell Lines An internalization assay was performed to determine the level of bsAb uptake in different cancer cell lines. Changes in the level of cell surface binding were also assessed, which may relate to the up- or down-regulation of target receptors induced by incubating the antibodies with the human tumour cells BT-474, JIMT1 and SKOV3.

The experiment was based on the methods reported by Schmidt, M. et al., Kinetics of anti-carcinoembryonic antigen antibody internalization: effects of affinity, bivalency, and stability. Cancer Immunol Immunother (2008) 57:1879-1890, which involved directly labeling the bsAb using the AlexaFluor® 488 Protein Labeling Kit (Invitrogen, cat. no. A10235), following the manufacturer's instructions.

In brief, 12-well plates were seeded with $1\times10^5$ cells/well and incubated overnight at 37° C./5% $CO_2$. The following day, the labeled antibodies were added to the desired final concentration (e.g. 200 nM) in DMEM+10% FBS and the plates were incubated for 24 hours at 37° C./5% $CO_2$. In the dark, media was aspirated and wells were washed twice with 500 µL PBS. To harvest cells, cell dissociation solution (Sigma) was added (250 µL) at 37° C. Cells were pelleted and resuspended in 100 µL DMEM+10% FBS without or with anti-Alexa Fluor 488, rabbit IgG fraction (Molecular Probes, A11094, lot 1214711) at 50 µg/mL, and incubated on ice for 30 min. Prior to analysis, 300 µL of the cell suspension was filtered, and 4 µl propidium iodide was added. Samples were analyzed using the LSRII flow cytometer. In some cases, a parallel cell binding experiment was performed at 4° C., in which internalization is not expected to occur at any significant rate in order to approximate $t_0$.

For each bsAb, the MFI of cells was measured by FACS. Internalization was determined by comparing the bound the labeled antibody incubated at either 4° C. or 37° C., being either quenched (Q) or unquenched (U) by the anti-Alexa Fluor 488 antibody. The initial receptor level ($S_i$), final receptor level ($S_f$) and amount of antibody internalized (I) were calculated as follows:

$$\text{quenching efficiency} = QE = 1 - (Q4/U4)$$

$$\text{initial surface receptor level} = Si = U4$$

$$\text{final surface receptor level} = Sf = (U37 - Q37)/QE$$

$$\text{antibody internalization/accumulation} = I = U37 - Sf$$

Figure 20:
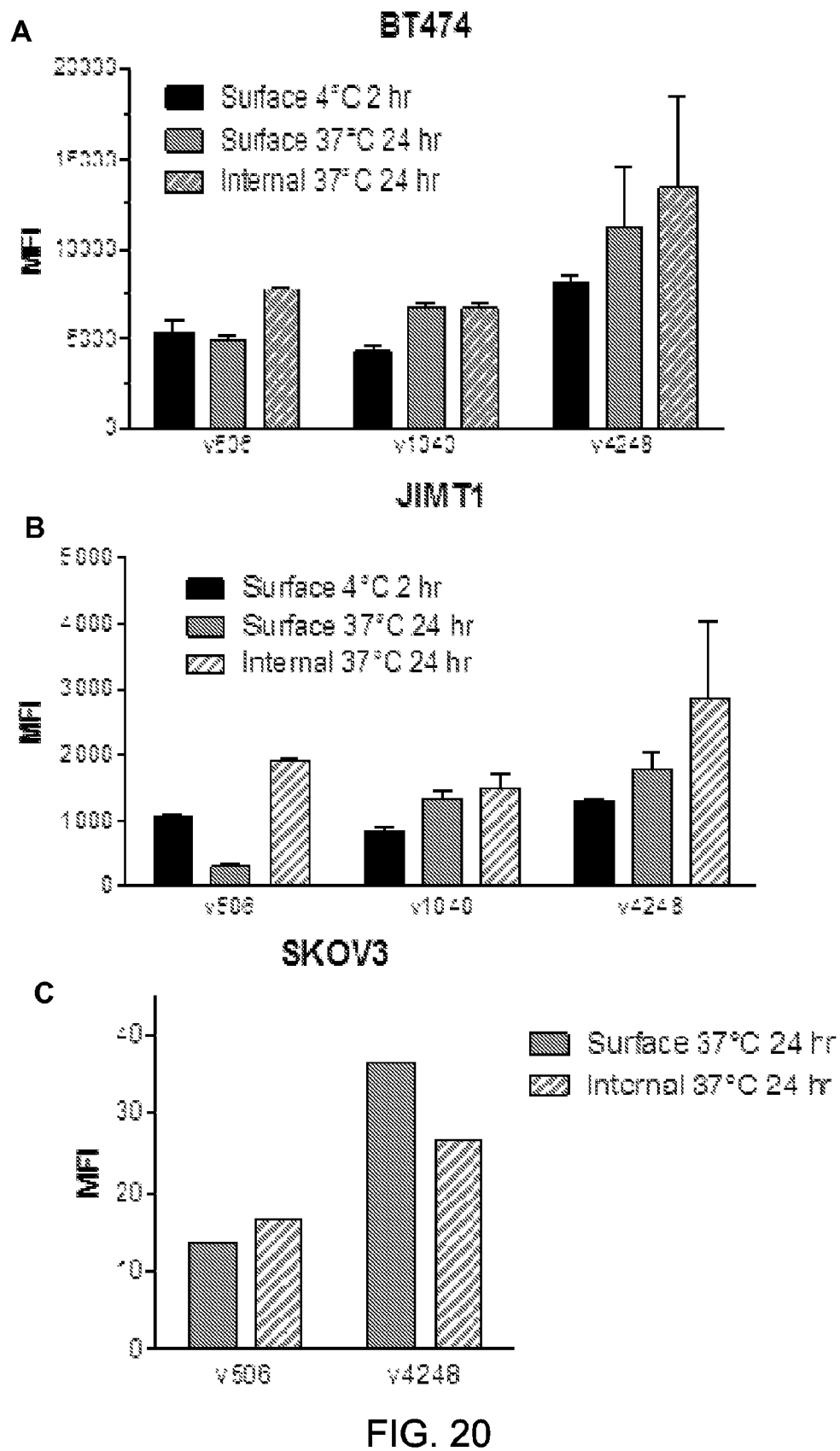
FIG. 20 depicts the ability of exemplary bsAbs to internalize and bind to the surface of JIMT1, SKOV3 and BT-474 cells.

The results are shown in FIG. 20 A) BT-474; B) JIMT1; and C) SKOV3.

In the tested human cancer cell lines, the exemplary bsAb v4248 showed increased internalization compared to its corresponding monospecific bivalent anti-HER2 control antibody v506. In addition, v4248 showed a considerably higher cellular surface decoration at the 37° C. 24 hr time point. In BT-474 and JIMT1, the higher cellular decoration is contributed by an increase in decoration, as well as a decrease in decoration of v506, over the 24 hr incubation period.

In summary, many exemplary bsAb antibodies displayed significantly higher internalization compared to the control, potentially implicating an increased potency and/or efficacy of the bsAb as an antibody-drug conjugate (ADC). An increase in cellular decoration over time may also implicate higher efficacy in targeting cancer cells for killing or inhibition via different mechanisms of action such as ADCC. These results provide a means to select a bsADC, which would require higher levels of internalization than the monospecific comparators, as well as favourable growth inhibition and growth factor neutralization properties.

Example 19: Cellular Staining and Localization of Exemplary bsAb v4248 in Trastuzumab Resistant Human Breast Cancer Cell Line Confocal microscopy was performed to visualize internalization of an exemplary bsAb in JIMT1 cells expressing the target receptors, providing details of antibody localization within target tumour cells.

The target cells were incubated with 200 nM antibody in serum-free DMEM, 37° C.+5% $CO_2$ for a defined duration. The cells were gently washed twice with warm sterile PBS (500 µl/well), and fixed with 250 µl of 10% formalin/PBS solution for 10 min at room temperature. The fixed cells were washed three times with PBS (500 µl/well), permeabilized with 250 µl/well of PBS containing 0.2% Triton X-100 for 5 min, and washed three times with 500 µl/well PBS. Cells were blocked with 500 µl/well of PBS+5% goat serum for 1 hr at room temperature. Blocking buffer was removed, and 300 µl/well of secondary antibody (Alexa Fluor 488-conjugated AffiniPure Fab Fragment Goat anti-Human IgG (H+L); Jackson ImmunoResearch Laboratories, Inc.; 109-547-003) was added and incubated for 1 hr at room temperature. The cells were washed three times with 500 µl/well of PBS and the coverslips containing fixed cells were then mounted on a slide using Prolong gold anti-fade with DAPI (Life Technologies; #P36931). 60× single images were acquired using Olympus FV1000 Confocal microscope.

Figure 21:
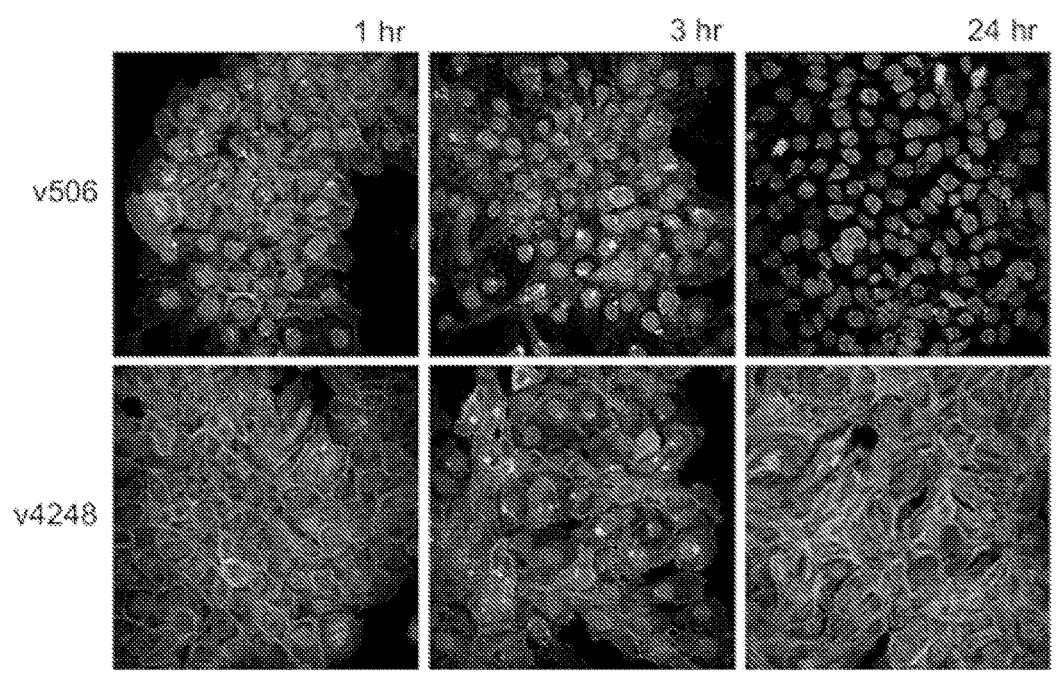
FIG. 21 depicts internalization of exemplary bsAb v4248 in JIMT1 cells, visualized by confocal microscopy.

The results are shown in FIG. 21.

The exemplary bsAb v4248 showed significant binding to JIMT1 at all tested incubation times (1, 3 and 24 hr). Antibody signal was present on the cell surface membrane and there was also diffuse cytoplasmic presence. Punctuation was also observed, and appeared most prominent at the 3 hr time point. In contrast, the monospecific bivalent anti-HER2 antibody control v506 showed a relatively lower membranous signal, but punctation and diffuse cytoplasmic presence was also prominent at the early 1 hr and 3 hr time points. Little signal was detected after 24 hr of incubation.

These results are largely consistent with the alternate detection method described in Example 18 in which there was an increase in surface and internal localization of the antibody in the cell. The exemplary molecules demonstrated cellular internalization into cancer cells in multiple alternative assays.

Example 20: Exemplary bsADC v6362 Inhibited Growth of Human Tumor Cancer Cell

An in vitro growth inhibition assay was performed using the bsADC v6362 to determine its potency and efficacy in killing or inhibiting growth of the cancer cell lines SKOV3, JIMT1, and MDA-MB-231. The cells were treated, and cell viability measurements were made in the same manner as for the growth inhibition assay described in Example 17.

Figure 22:
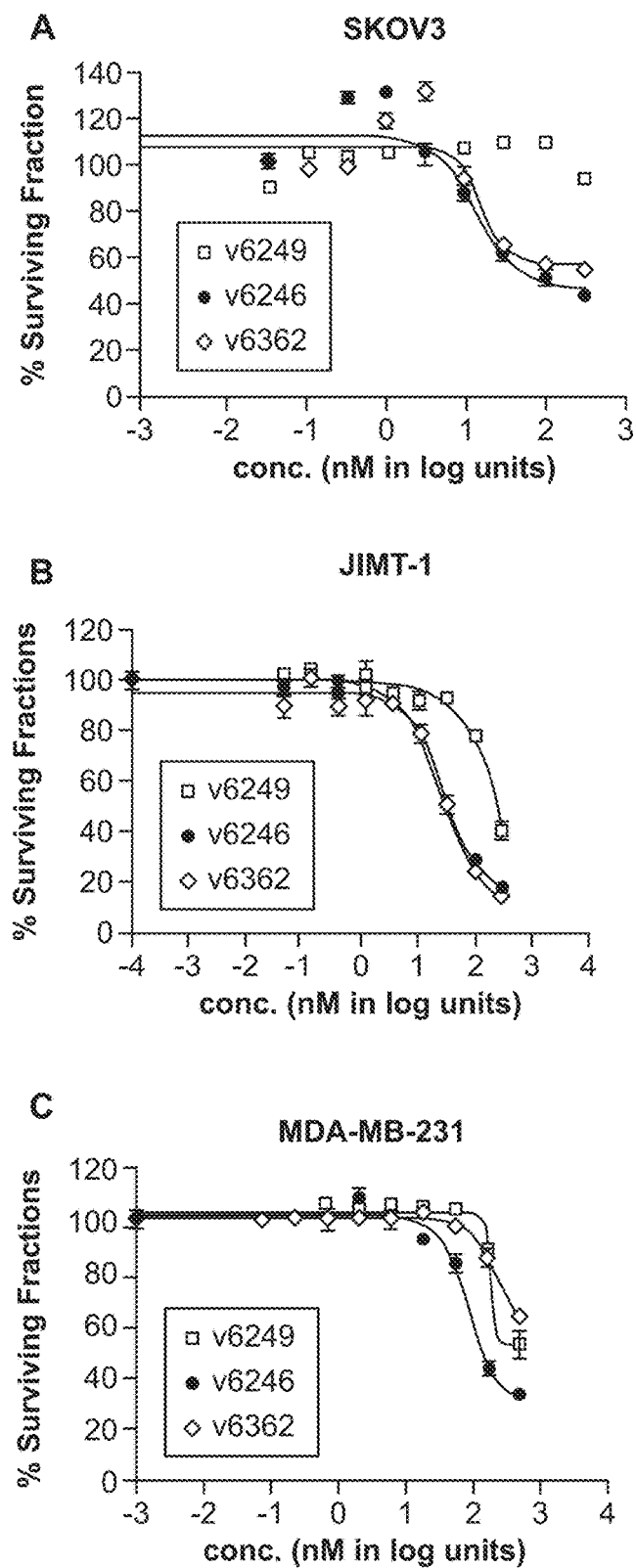
FIG. 22 depicts growth inhibition by exemplary the bsADCs v6362 and controls, in SKOV3 cells (FIG. 22A), JIMT1 cells (FIG. 22B), and MDA-MB-231 cells (FIG. 22C).

The results are shown in FIG. 22A (SKOV3 cells), FIG. 22B (JIMT1 cells) and FIG. 22C (MDA-MB-231 cells).

In SKOV3 and JIMT1 cells, bsADC v6362 appeared indistinguishable from monospecific bivalent control ADC v6246, and displayed a significantly improved potency compared to nonspecific control ADC v6249. In MDA-MB-231 cells, both bsADCs v6362 and ADC v6246 showed similarly low potency being rather similar to the nonspecific control ADC v6249.

These results confirmed that v6362 is active and is consistent with the fact that the bsAb is being internalized. Additionally, the similarity between v6362 and v6246 is in agreement with the assay condition which is performed in the absence of heregulin leading to receptor heterodimerization. The bsADC v6362 is expected to differentiate from v6246 showing enhanced potency in the presence of exogenous heregulin.

Example 21: Growth Inhibition of HER2 3+ Human Breast Cancer Cells by bsADC is not Reduced when the Cells are Stimulated by Exogenous Growth Factors Under the stimulation of exogenous growth factors some human cancer cells may become more resistant to the treatment with ADCs, as with BT-474 cells when stimulated exogenously in vitro by heregulin (Lewis Phillips et al, Clin Cancer Res 2014 20; 456). The growth inhibition property of exemplary bsADC v6362 in HER2 3+ human breast cancer cell BT-474 was assessed in the presence and absence of growth factors.

The growth inhibition assay was performed as described in Example 17. In brief, the cells were incubated with varying concentrations of bsADC for 5 days, under the absence of growth factors or presence of 10 nM EGF or 15 nM heregulin.

Figure 23:
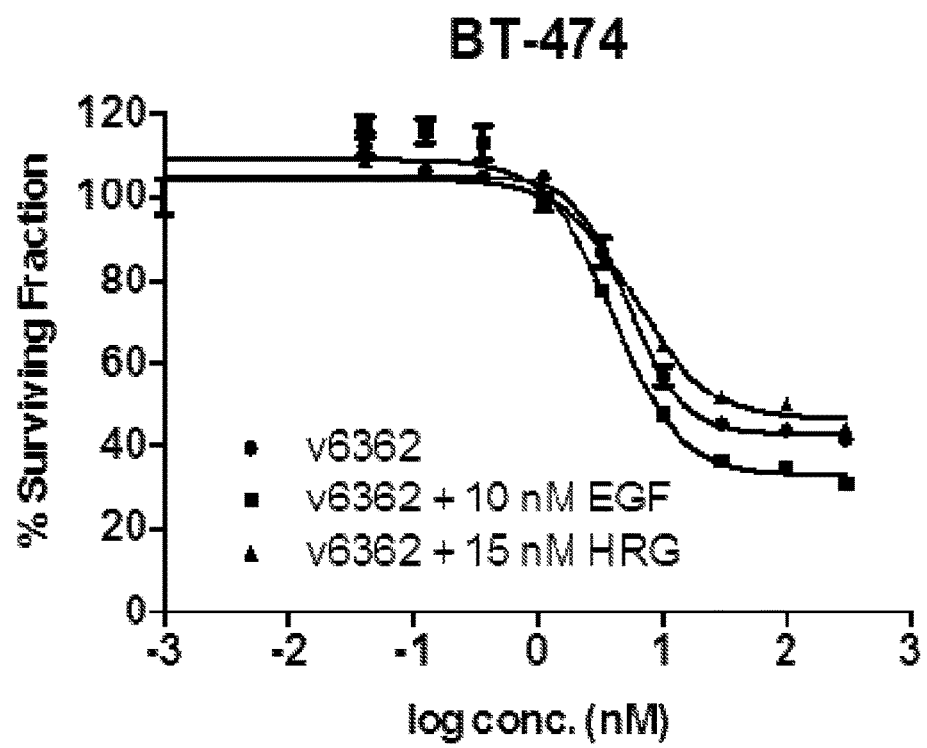
FIG. 23 depicts the ability of bsADCs to inhibit growth of HER2 3+ cells in the presence of exogenous growth factors.

FIG. 23 shows the dose response of exemplary bsADC in the absence of exogenous growth factors or presence of EGF or heregulin.

In BT-474, the growth inhibition potency and efficacy of bsADC v6362 was not reduced by the addition of EGF or heregulin. This is consistent with the ability for the corresponding unconjugated bsAb v4248 to neutralize heregulin's growth stimulatory effects in BT-474.

These results demonstrate that the growth inhibition potency and efficacy of the exemplary bsAb are not affected by exogenous growth factor stimulation.

Example 22: Exemplary bsAb and bsADC Neutralized Heregulin Stimulated Growth of HER2 3+ Human Gastric Cancer Cell In Vitro The ability of the exemplary anti-HER2-HER3 bsAb and bsADC to neutralize the growth stimulation of exogenous heregulin on a HER2 3+ human gastric cell line was assessed as below.

The growth inhibition assay was performed similarly to that described above. NCI-N87 cells were plated at 5000 cells/well on a 96-well plate. Cells were first incubated in serum free media containing 1% BSA for 6 hours, antibodies were then added at final concentrations of 100 nM, incubated for 15 minutes, before 5 nM heregulin was added. The experiment was performed in triplicate. The 96-well plate was incubated 37° C. for 5 days. Cell viability was assessed by using PrestoBlue following the manufacturers' instructions.

Figure 24:
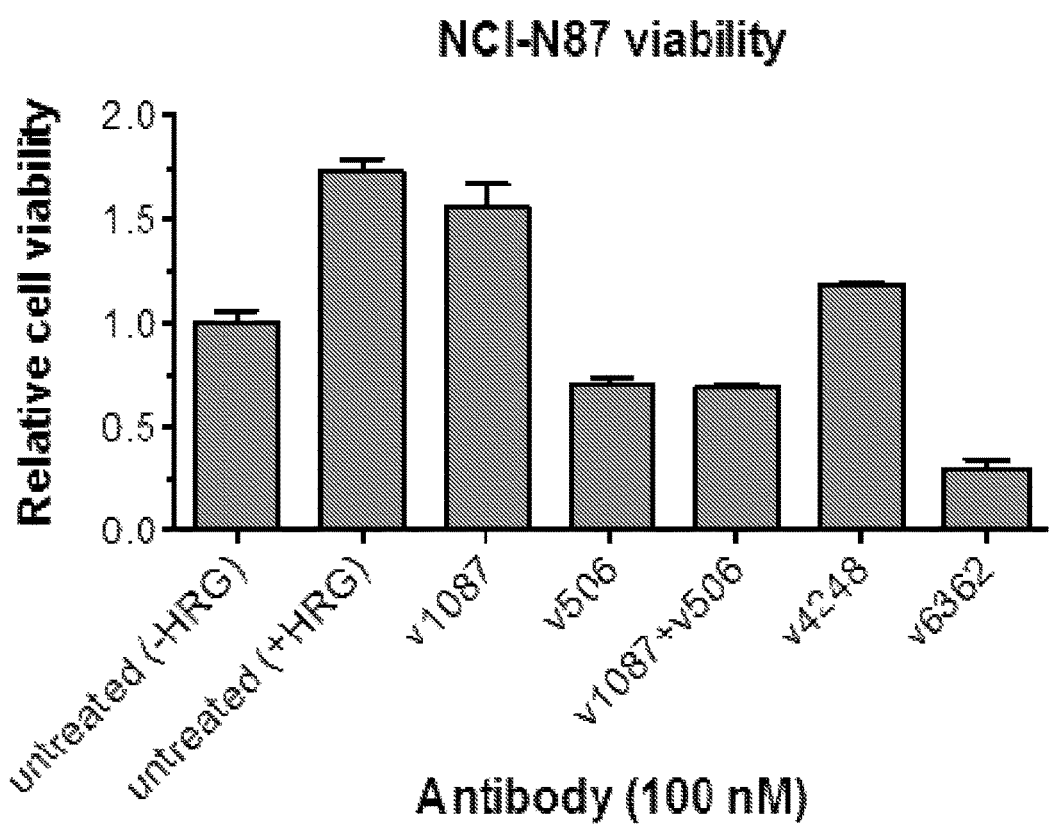
FIG. 24 depicts the ability of bsADCs to inhibit growth of the HER2 3+ gastric cancer cell line NCI-N87.

FIG. 24 shows the growth inhibition properties of exemplary bsAb v4248 and bsADC v6362 in a HER2 3+ gastric cancer cell line NCI-N87 in the presence of 5 nM heregulin.

NCI-N87 cells showed 73% increase in cell viability when stimulated by 5 nM heregulin. This growth stimulation effect was neutralized by an anti-HER2-HER3 control bsAb v1087, suppressing the heregulin stimulation effect to a 56% increase in cell viability. The monospecific anti-HER2 control v506 alone inhibited cell viability by 29%, which when combined with v1087 did not show further growth inhibition effects. In comparison, the exemplary bsAb v4248 also neutralized the growth stimulation effects of heregulin, reducing the cell viability stimulation to 19%. Moreover, the corresponding bsADC v6362 further inhibited cell viability by 70% compared to the untreated heregulin-free control, or 83% compared to the untreated heregulin-stimulated control.

These results demonstrate that the exemplary bsAb and bsADC are capable of neutralizing the growth stimulatory effects of heregulin, inhibiting growth of a different human cancer cell line such as the HER2 3+ gastric cancer cells NCI-N87. The heregulin neutralization effect was considerably different from the control anti-HER2-HER3 bsAb, presumably because of a different binding geometry and epitope.

Example 23: In Vitro Human Cardiomyocyte Toxicity Assays of bsAbs

Clinically, trastuzumab treatment is associated with cardiac dysfunction in 2-7% of cases. The risk of cardiomyopathy is increased when the treatment is combined with anthracycline chemotherapy such as doxorubicin, which by itself is also cardiotoxic. A growth inhibition assay was therefore performed on cardiomyocytes to identify potentially worse toxicity effects caused by bsAbs, which also target HER2.

The assay was performed in iCell™ (CellularDynamics) a manner similar to that of the already described growth inhibition assay. In brief, the cells were seeded into 96-well plates at 20,000 cells/well and maintained for 48 hr. The cell medium was then replaced with maintenance media and maintained for 72 hr. The cells were treated with 100 nM of exemplary variants, with or without 1 μM doxorubicin for 72 hr. Cell viability was assessed using AlamarBlue or Sulforhodamine B following the manufacturers' instructions.

Figure 25:
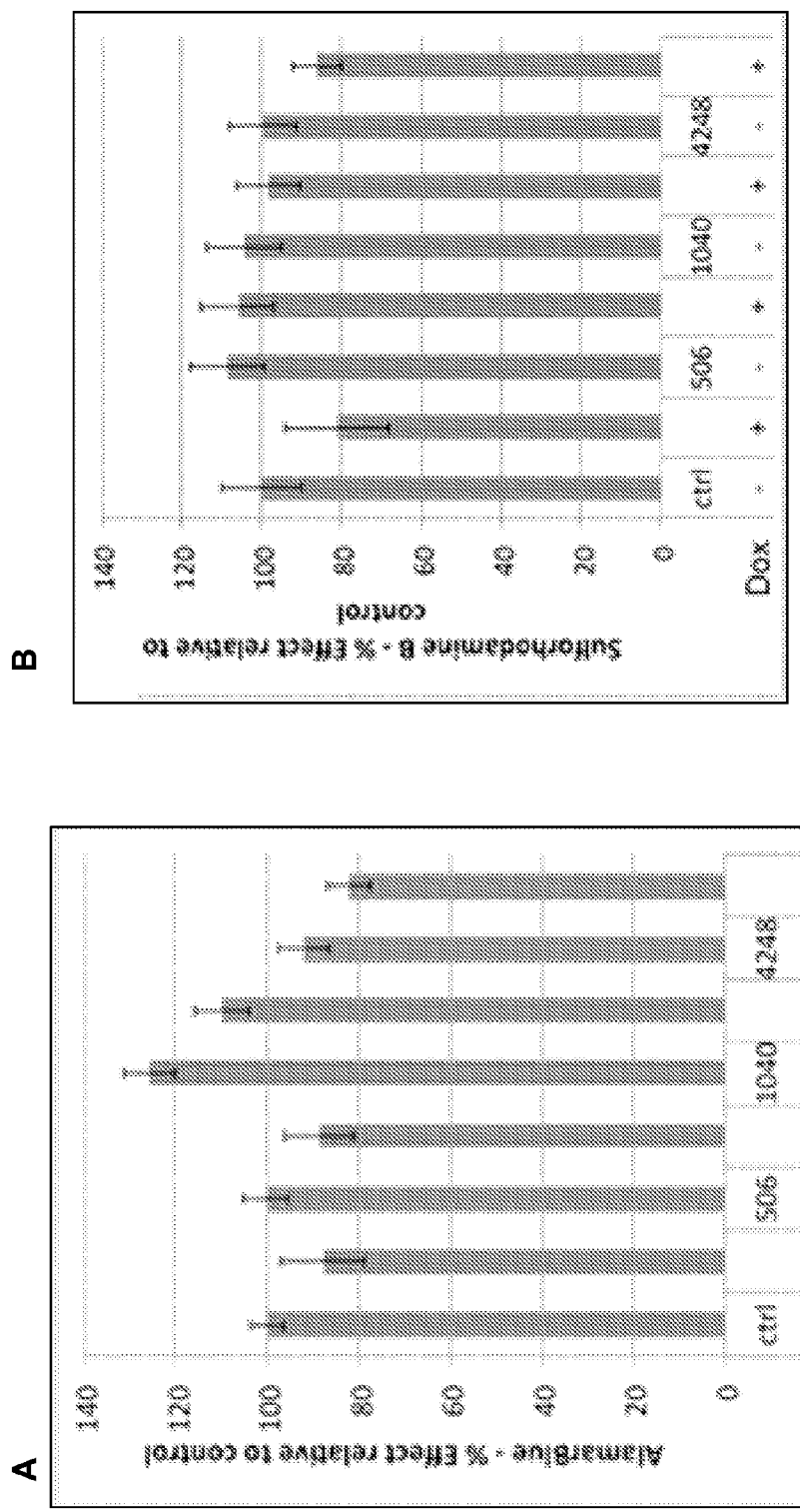
FIG. 25 depicts cardiomyocyte toxicity assay results, in which iCells™ were either untreated (ctrl) or treated with 100 nM of antibody, in the presence and absence of 1 μM doxorubicin. The growth effects were measured by both AlamarBlue™ (FIG. 25A) and Sulforhodamine B (FIG. 25B).

The results are shown in FIG. 25.

In the absence of doxorubicin, the exemplary bsAbs v4248 had no significant impact on the viability of iCells™, as with the monospecific control antibodies. Note that the apparent increase in iCell™ viability in the AlamarBlue™ assay for v1040 was not observed in other repeats (data not shown). In the presence of 1 μM doxorubicin, there was generally a small reduction in iCell™ viability, which was seemed to be more apparent in the AlamarBlue™ detection method (approximately 10 to 15%) than in the Sulforhodamine B method. However, the iCell™ viability upon bsAb treatment, +/−doxorubicin, was not significantly different from those of the monospecific control antibodies.

The exemplary bsAb v4248 showed similar profile as the controls v506 and v1040. These results demonstrate that the tested bsAbs show a toxicity profile comparable to parental monospecific bivalent and monovalent antibodies.

Example 24: Anti-Tumor Activity of an Anti-her2 and Anti-her3 Bi-Specific Antibody Drug Conjugate (bsADC) in a Trastuzumab Resistant Inflammatory Breast Cancer (T226) Human Patient-Derived Xenograft Model This in vivo experiment was aimed at determining the tumour growth inhibition efficacy of the bsADCs compared to monospecific antibody controls. The trastuzumab and chemotherapy resistant T226 xenograft model was derived from a HER2$^{3+}$, HER3$^+$, HRG$^+$, EGFR$^+$ primary breast cancer with an inflammatory phenotype and was used to assess the anti-tumour efficacy of an exemplary anti-HER2-HER3 bsADC.

Female athymic nude mice were inoculated with the tumor via the insertion of a 20 mm$^3$ tumour fragment subcutaneously. Tumours were monitored until they reached an average volume of 100 mm$^3$; animals were then randomized into 4 treatment groups: IgG control (n=14), v506; n=13, v6246; n=16, v6362; n=16. Dosing for each group is as follows:

A) IgG control (v6908) was dosed intravenously with a loading dose of 15 mg/kg on study day 1 and maintenance doses of 10 mg/kg administered on study days 4, 8, 11, 15, 18, 22, and 25

B) v506 was dosed intravenously with a loading dose of 15 mg/kg on study day 1 and maintenance doses of 10 mg/kg administered on study days 4, 8, 11, 15, 18, 22, and 25

C) v6246 was dosed intravenously with 5 mg/kg on study days 1 and 15

D) v6362 was dosed intravenously with 5 mg/kg on study days 1 and 15.

Animals were weighed twice weekly during the experimental period. Tumor volume was evaluated by measuring tumour diameters, with a calliper, biweekly during the treatment period and once a week during the follow-up period. The formula TV (mm$^3$)=[length (mm)×width (mm)$^2$]/2 was used, where the length and the width are the longest and the shortest diameters of the tumour, respectively.

Figure 26:
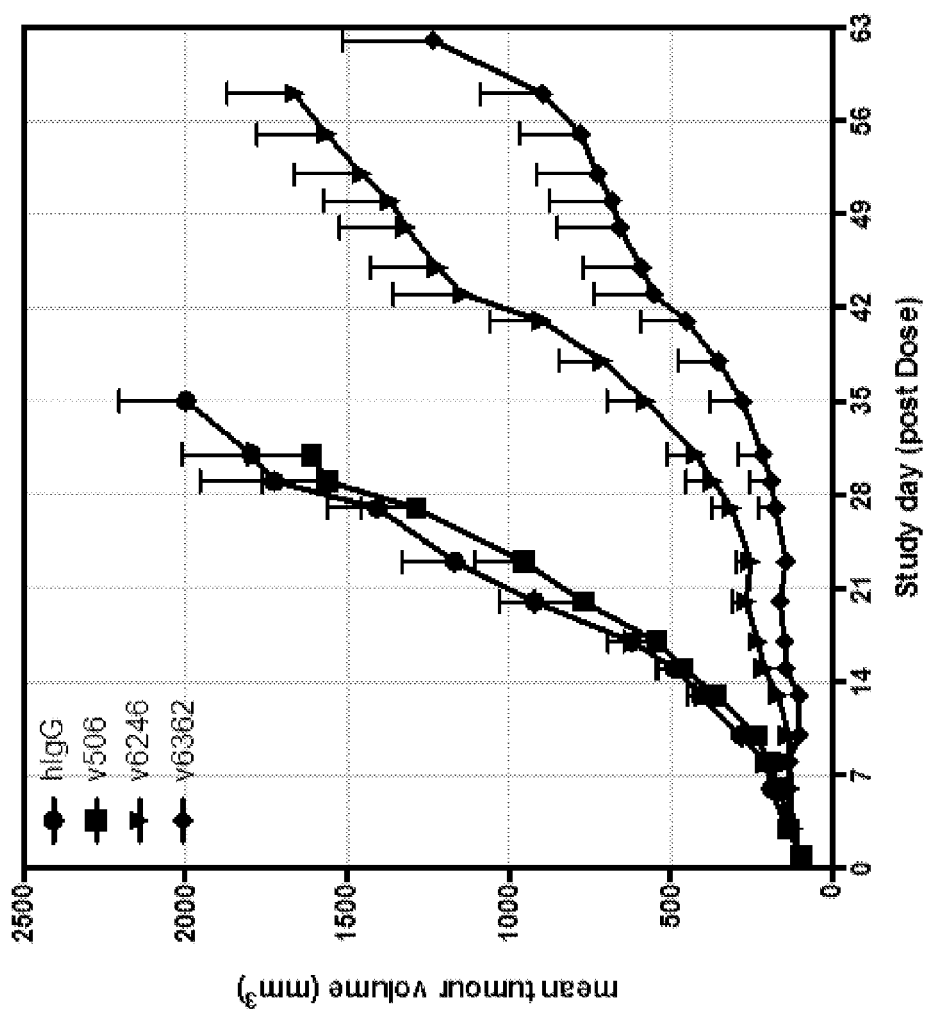
FIG. 26 depicts inhibition of tumour growth by v6362 in T226 PDX model.
Figure 27:
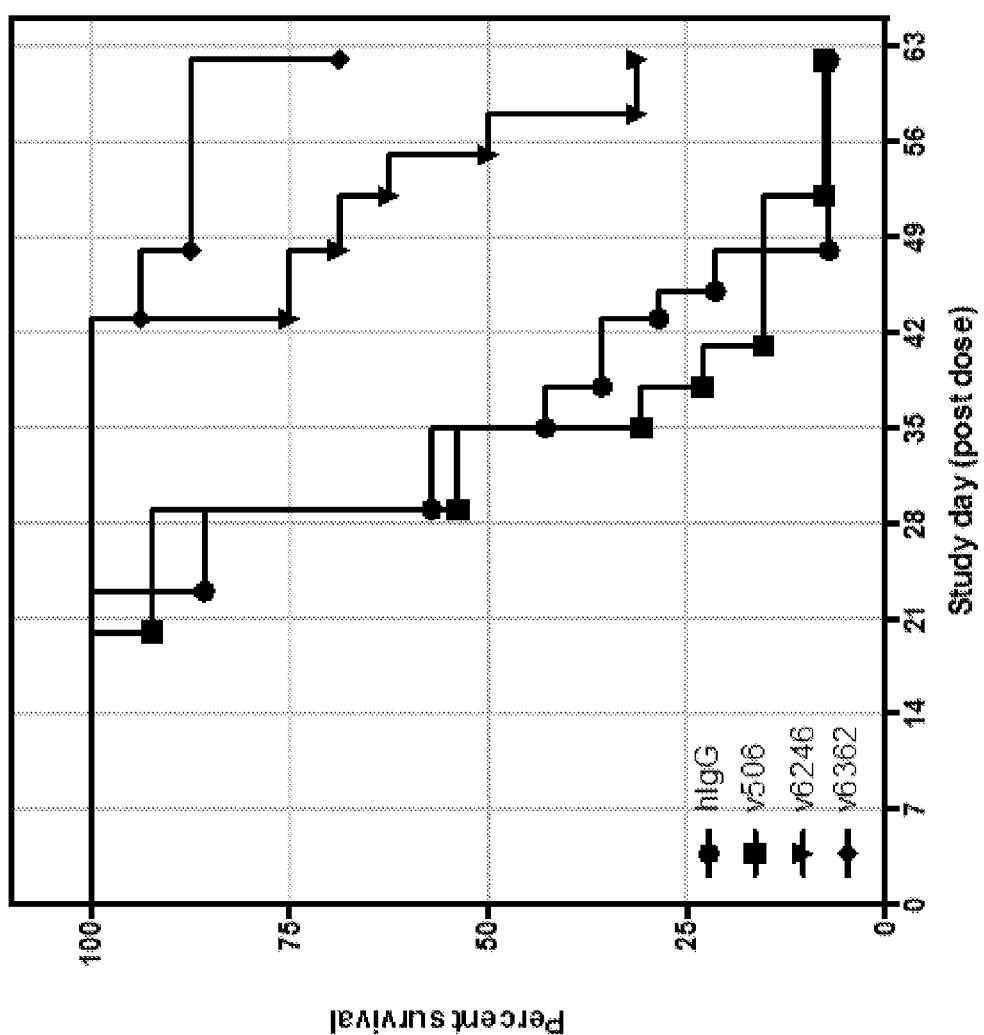
FIG. 27 shows a survival plot of the mice in the T226 PDX model.

The results of this study are shown in FIGS. 26 & 27. FIG. 26 shows the inhibition of tumour growth by exemplary bsAb in T226 PDX model. FIG. 27 shows a survival plot of the mice in the T226 PDX model, using a tumour volume of 2000 mm$^3$ as surrogate termination endpoint.

v6362 and v6246 demonstrated superior tumour growth inhibition compared to v506 and IgG control. v6362 induced superior tumour growth inhibition compared to the monospecific anti-HER2 v6246 (FIG. 26 and Table 4) in the trastuzumab resistant T226 human breast cancer xenograft model.

v6362 and v6246 prolonged survival compared to v506 and IgG control. The exemplary v6362 induced superior survival compared to v6246. In addition, v6362 was associated with an increase in the number of tumours showing complete responses (more than a 10% decrease below baseline), 6 and 1 respectively (FIG. 27 and Table 6). Tumour volume of greater than 2,000 mm$^3$ was the surrogate survival endpoint.

No significant decrease in body weight relative to baseline was observed following dosing with v6246 or v6362.

In summary, this study demonstrated the bsADCs superior tumour growth inhibition efficacy in a xenograft model, compared to a related monospecific bivalent antibody drug conjugate. The administration of bsADCs can also lead to better survival based on the tumour volume endpoint cutoff as surrogate measurement. The anti-tumour efficacy of the bsADCs in the T226 suggests a potential clinical utility in the treatment of inflammatory breast cancer and/or HER2+, HER3+, HRG+, EGFR+ cancers.

TABLE 4

Day 31 statistics of tumour growth inhibition in the T226 PDX model

| Day 31 Final day of trastuzumab reporting | IgG (n = 14) | v506 (n = 13) | v6246 (n = 16) | v6362 (n = 16) |
|---|---|---|---|---|
| Mean TV (mm3) (% change from Baseline) | 1797 (+1728%) | 1611 (+1573) | 422 (+332%) | 216 (+122%) |
| % TGI (vs. hIgG) | 0% | 11% | 77% | 88% |
| Complete response (>10% baseline regression) | 0/13 | 0/14 | 1/16 | 6/16 |
| Mean serum concentration (μg/ml) (day 7) | na | 128 | 15.26 | 39.5 |

TV: Tumour volume

TABLE 5

Day 58 statistics of tumour growth inhibition in the T226 PDX model:

| Day 58 Final day of T-DM1 reporting | V6246 | V6362 |
|---|---|---|
| Mean TV (mm3) (% change from Baseline) | 1679 (1616%) | 897 (+1167%) |
| % TGI (vs. v6246) | 0% | 47% |
| Median Survival (days) | 56.5 | undefined |

TV: Tumour volume

Example 25: Anti-Tumor Activity of an Anti-her2 and Anti-her3 Bi-Specific Antibody Drug Conjugate (bsADC) in the T226 PDX Model with Acquired HER2 Antibody Resistance This in vivo experiment was aimed at determining the tumour growth inhibition efficacy of the bsADCs in a model of acquired anti-HER2 resistance. The trastuzumab and chemotherapy resistant T226 xenograft model was derived from a HER2$^{3+}$, HER3$^+$, HRG$^+$, EGFR primary breast cancer with an inflammatory phenotype and was used to assess the anti-tumour efficacy of an exemplary anti-HER2-HER3 bsADC.

Female athymic nude mice were inoculated with the tumor via the insertion of a 20 mm$^3$ tumour fragment subcutaneously. Tumours were monitored until they reached an average volume of 100 mm$^3$; animals were then randomized into 3 treatment groups: IgG control (n=14), v506; n=13, and an anti-HER2 mAb acquired resistance group. Dosing for each group is as follows:

A) IgG control (v6908) was dosed intravenously with a loading dose of 15 mg/kg on study day 1 and maintenance doses of 10 mg/kg administered on study days 4, 8, 11, 15, 18, 22, and 25

B) v506 was dosed intravenously with a loading dose of 15 mg/kg on study day 1 and maintenance doses of 10 mg/kg administered on study days 4, 8, 11, 15, 18, 22, and 25

C) The HER2 converted group was dosed intravenously with an anti-HER2 therapy with a 15 mg/kg loading dose on day 1 and maintenance doses of 10 mg/kg on days 4, 8, 11, and 15. When the tumours failed to respond to therapy the animals received a 10 mg/kg dose of v6362 on days 20, 34, 41, 48, and 55 and received a 5 mg/kg dose on study day 27.

Animals were weighed twice weekly during the experimental period. Tumor volume was evaluated by measuring tumour diameters, with a calliper, biweekly during the treatment period and once a week during the follow-up period. The formula TV (mm$^3$)=[length (mm)×width (mm)$^2$]/2 was used, where the length and the width are the longest and the shortest diameters of the tumour, respectively.

Figure 28:
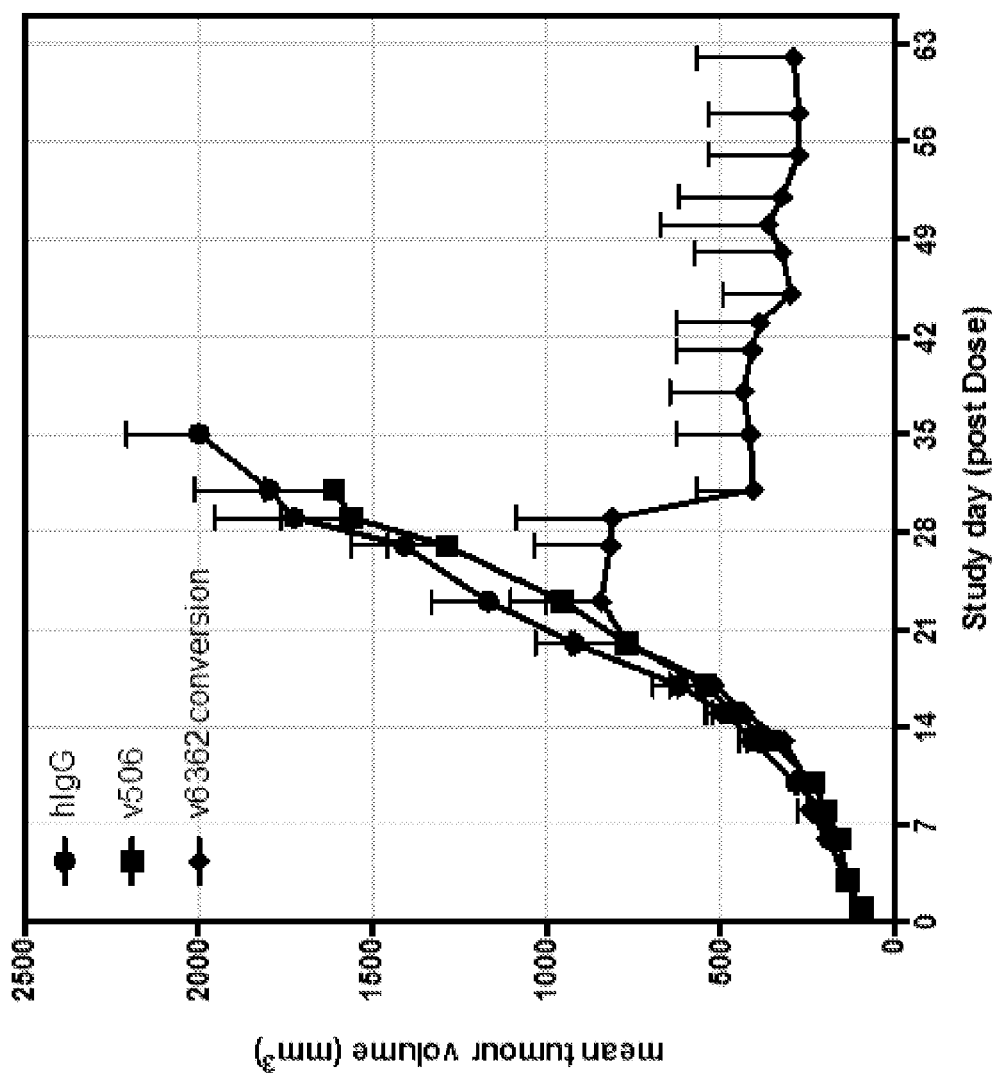
FIG. 28 depicts regression of tumour growth by v6362 in T226 PDX model, converted from an animal group that was not responsive to an initial anti-HER2 treatment.

The results of this study are shown in FIG. 28. FIG. 28 shows the regression of tumour growth by exemplary bsAb in T226 PDX model, converted from an animal group that was not responsive to an initial anti-HER2 treatment.

v6362 demonstrated tumor regression when dosed in animals not responding to an anti-HER2 therapy (dose conversion). On study day 62 the group receiving v6362 regressed the tumour volume from the day of conversion by 62% while animals receiving IgG control or v506 rapidly progressed and were terminated by day 35 (FIG. 28).

In summary, this study demonstrated the ability of bsADCs to cause tumour regression when the tumour failed to respond to earlier treatment(s) and were significantly advanced in growth. The anti-tumour efficacy of the bsADCs in the T226 suggests a potential clinical utility in the treatment of advanced inflammatory breast cancer and/or HER2+, HER3+, HRG+, EGFR+ cancers that are non-responsive to conventional anti-HER2 antibodies.

Example 26: Anti-Tumor Activity of an Anti-her2 and Anti-her3 Bi-Specific Antibody Drug Conjugate (bsADC) in an Invasive Ductal Breast Carcinoma (HBCx-13b) Patient-Derived Xenograft Model This in vivo experiment was aimed at determining the tumour growth inhibition efficacy of the bsADCs compared to monospecific antibody controls. The trastuzumab and chemotherapy resistant HBCx-13b xenograft model was derived from a HER2$^{3+}$, HER3+, HRG+ metastatic lesion of an invasive ductal carcinoma of the breast and was used to assess the anti-tumour efficacy of v6362.

Female athymic nude mice were inoculated with the tumour via the insertion of a 20 mm$^3$ tumor fragment subcutaneously. Tumours were monitored until they reached an average volume of 100 mm$^3$; animals were then randomized into 3 treatment groups: v506; n=7, v6246; n=7, and v6362; n=6. Dosing for each group was as follows:

A) v506 was dosed intravenously with a loading dose of 15 mg/kg on study day 1 and maintenance doses of 10 mg/kg administered on study days 4, 8, 11, 15, 18, 22, and 25

B) v6246 was dosed intravenously with a loading dose of 10 mg/kg on study day 1 and a maintenance dose of 5 mg/kg on study day 22

C) v6362 was dosed intravenously with a loading dose of 10 mg/kg on study day 1 and a maintenance dose of 5 mg/kg on study day 22.

Animals were weighed twice weekly during the experimental period. Tumor volume was evaluated by measuring tumour diameters, with a calliper, biweekly during the treatment period and once a week during the follow-up period. The formula TV (mm$^3$)=[length (mm)×width (mm)$^2$]/2 was used, where the length and the width are the longest and the shortest diameters of the tumour, respectively.

Figure 29:
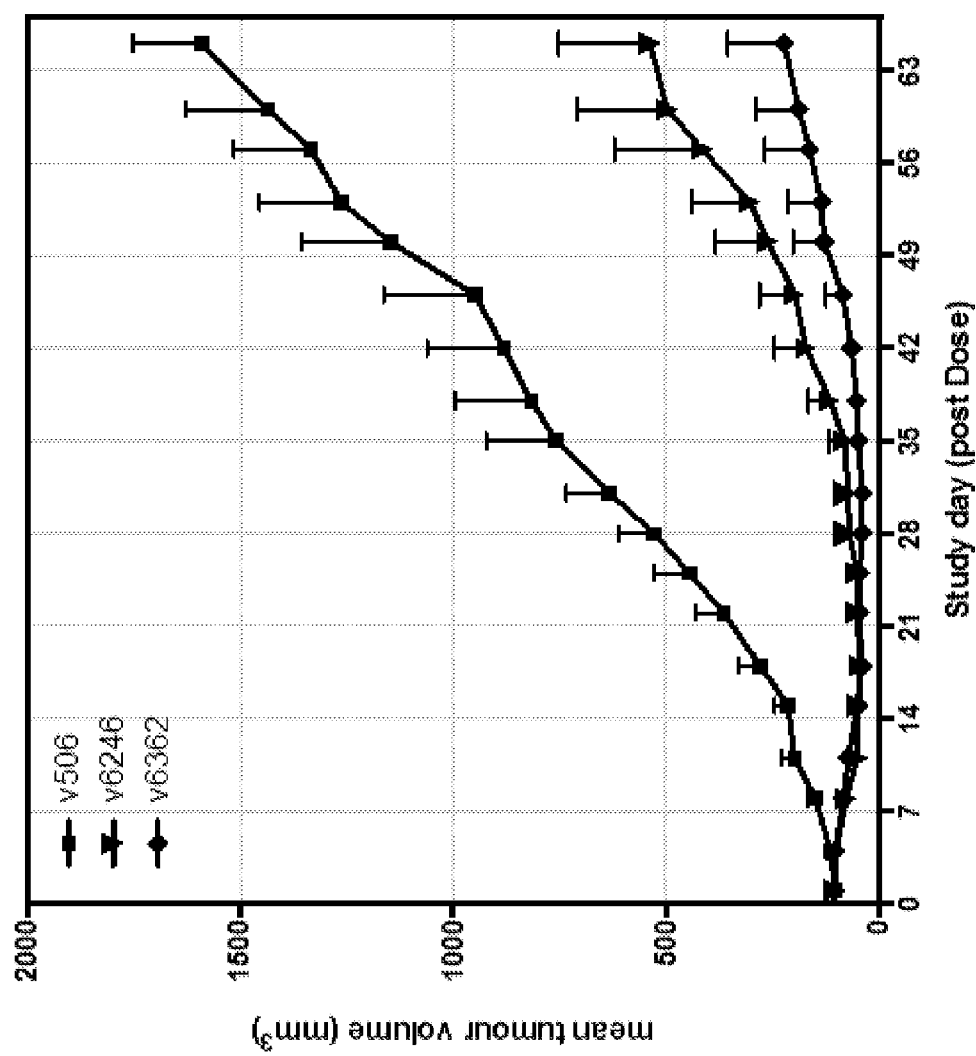
FIG. 29 depicts inhibition of tumour growth by exemplary bsAbs in HBCx-13b xenograft model.

The results are shown in FIG. 29.

v6362 and v6246 demonstrated superior tumour growth inhibition compared to v506. v6362 induced superior tumour growth inhibition compared to anti-v6246. In addition, v6362 was associated with an increase in the number of tumours showing complete responses (more than a 10% decrease below baseline), 4 and 2 respectively, at study termination (FIG. 29 and Table 7).

No significant decrease in body weight relative to baseline was observed following dosing with v6246 or v6362.

In summary, this study demonstrated the bsADCs superior tumour growth inhibition efficacy in a xenograft model, compared to a related monospecific bivalent antibody drug conjugate. The anti-tumour efficacy of the bsADCs in the HBCx-13b suggests a potential clinical utility in the treatment of metastatic invasive ductal breast cancers and/or HER2$^{3+}$, HER3+, HRG+ cancers.

TABLE 6

Statistics of tumour regression in the T226 PDX anti-HER2 acquired resistance model

|  | aHER2 - Day 1 | aHER2 - Day 20 | v6362 - Day 62 |
|---|---|---|---|
| Mean TV (mm3) | 96 | 768 | 290 |
| % Change from Day 1 baseline | +0% | +697% | +202% |
| % Change from Day 20 baseline | na | +0% | −62% |

TV: Tumour volume

TABLE 7

Statistics of tumour growth inhibition in the HBCx-13b PDX model:

| Day 65 | v506 (n = 7) | v6246 (n = 7) | v6362 (n = 6) |
|---|---|---|---|
| Mean TV (mm3) (% change from Baseline) | 1591 (+1449%) | 538 (+419%) | 224 (+112%) |
| % TGI | 0% | 77% | 86% |
| Complete response (>10% baseline regression) | 0 | 2/7 | 4/6 |

TV: Tumour volume

Example 27: Anti-Tumor Activity of an Anti-her2 and Anti-her3 Bispecific Antibody Drug Conjugate (bsADC) in a Breast Carcinoma with Cachexia (HBCx-5) Patient-Derived Xenograft Model This in vivo experiment was aimed at determining the tumour growth inhibition efficacy of the bsADCs compared to monospecific antibody controls. The trastuzumab and chemotherapy resistant HBCx-5 xenograft model was derived from a HER2$^{3+}$, HER3$^+$ breast carcinoma with cachexia and was used to assess the anti-tumour efficacy of v6362.

Female athymic nude mice were inoculated with the tumour via the insertion of a 20 mm$^3$ tumor fragment subcutaneously. Tumours were monitored until they reached an average volume of 100 mm$^3$; animals were then randomized into 3 treatment groups: IgG control, n=4; v506, n=5; and v6362; n=7. Dosing for each group was as follows:

IgG control was dosed intravenously with a loading dose of 15 mg/kg on study day 1 and maintenance doses of 10 mg/kg administered on study days 4, 8, 11, 15, 18, 22, and 25 v506 was dosed intravenously with a loading dose of 15 mg/kg on study day 1 and maintenance doses of 10 mg/kg administered on study days 4, 8, 11, 15, 18, 22, and 25 v6362 was dosed intravenously with 10 mg/kg on study days 1 and 10 mg/kg (½ IV and ½ IP) on study days 15, 22, 29, 36

Animals were weighed twice weekly during the experimental period. Tumor volume was evaluated by measuring tumour diameters, with a calliper, biweekly during the treatment period and once a week during the follow-up period. The formula TV (mm$^3$)=[length (mm)×width (mm)$^2$]/2 was used, where the length and the width are the longest and the shortest diameters of the tumour, respectively.

Figure 30:
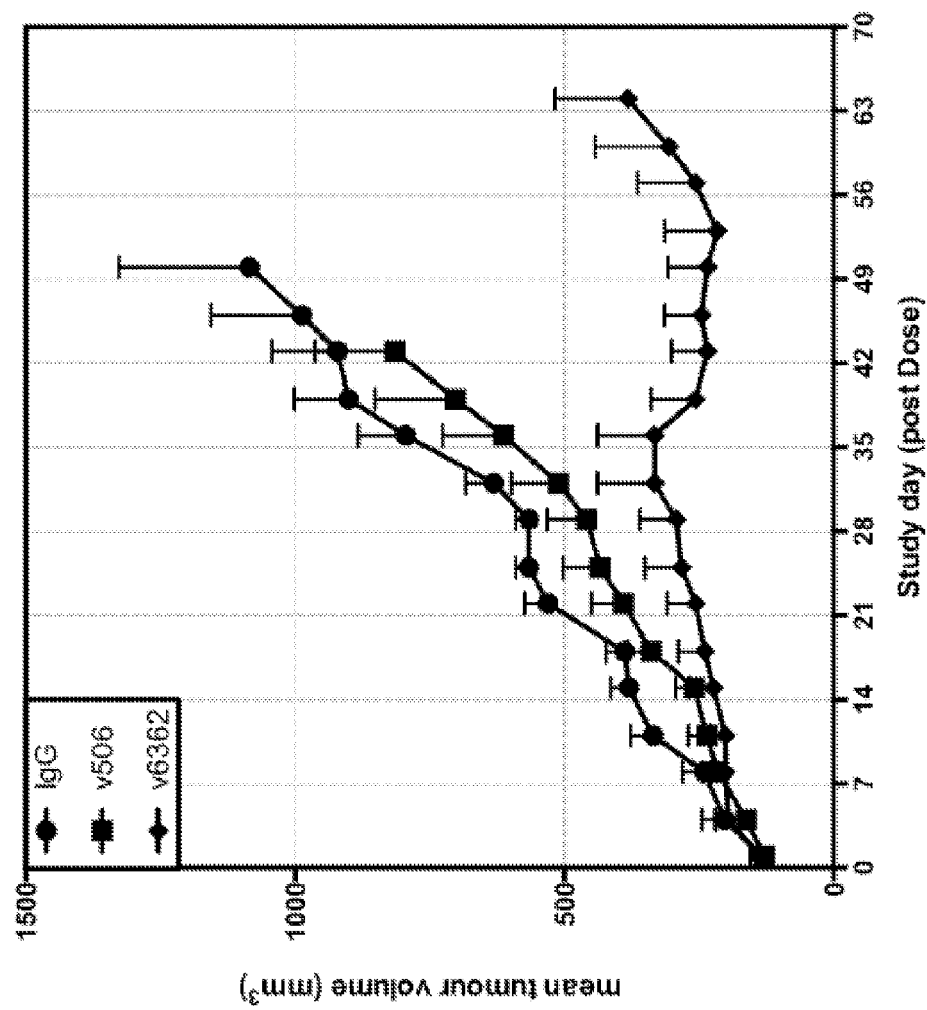
FIG. 30 depicts the anti-tumor activity of v6362 in a breast carcinoma with cachexia (HBCx-5) patient-derived xenograft model.

The results are shown in FIG. 30 and Table 8.

v6362 demonstrated superior tumour growth inhibition compared to IgG control and v506. In addition, v6362 was associated with an increase in the number of tumours showing responses (tumour volume less than 50% of control) compared to v506, 1 and 6 respectively, on study day 43 (FIG. 30 and Table 8).

No significant change in body weight relative to baseline was observed following dosing with v6362.

In summary, this study demonstrated the bsADCs superior tumour growth inhibition efficacy in a xenograft model compared to the standard of care. The anti-tumour efficacy of the bsADCs in the HBCx-5 suggests a potential clinical utility in the treatment of HER2$^{3+}$ and HER3+ breast carcinomas with cachexia.

TABLE 8 anti-tumor activity in HBCx-5 model

| Day 43 | IgG | v6246 | v6362 |
|---|---|---|---|
| Mean TV (mm3) (% change from Baseline) | 922 (+585%) | 815 (+531%) | 235 (+73%) |
| % TGI | 0% | 12% | 74% |
| Responders (TV <50% of control) | 0/4 | 1/5 | 6/7 |
| Body Weight - % Change from baseline | 0% | +1% | +4% |

TV: Tumour volume

Example 28: Anti-Tumor Activity of an Anti-her2 and Anti-her3 Bispecific Antibody Drug Conjugate (bsADC) in the HBCx-13b PDX Model with Acquired HER2 Antibody Resistance This in vivo experiment was aimed at determining the tumour growth inhibition efficacy of the bsADCs in a model with acquired resistance to v6246. The trastuzumab and chemotherapy resistant HBCx-13b xenograft model was derived from a HER2$^{3+}$, HER3$^+$ metastatic lesion of an invasive ductal carcinoma of the breast and was used to assess the anti-tumour efficacy of v6362.

Female athymic nude mice were inoculated with the tumour via the insertion of a 20 mm$^3$ tumor fragment subcutaneously. Tumours were monitored until they reached an average volume of 100 mm$^3$; animals were then randomized into 2 treatment groups IgG control, n=8; and v6246, n=10 which was then converted into v6362. Dosing for each group was as follows:

IgG control was dosed intravenously with a dose of 10 mg/kg at 2 qwk over 4 weeks v6246 was dosed intravenously with a dose of 1 mg/kg on study day 1 and 15.

The v6246 group was then converted into v6362 with 10 mg/kg dose on study day 29 and 43

Animals were weighed twice weekly during the experimental period. Tumor volume was evaluated by measuring tumour diameters, with a calliper, biweekly during the treatment period and once a week during the follow-up period. The formula TV (mm$^3$)=[length (mm)×width (mm)$^2$]/2 was used, where the length and the width are the longest and the shortest diameters of the tumour, respectively.

Figure 31:
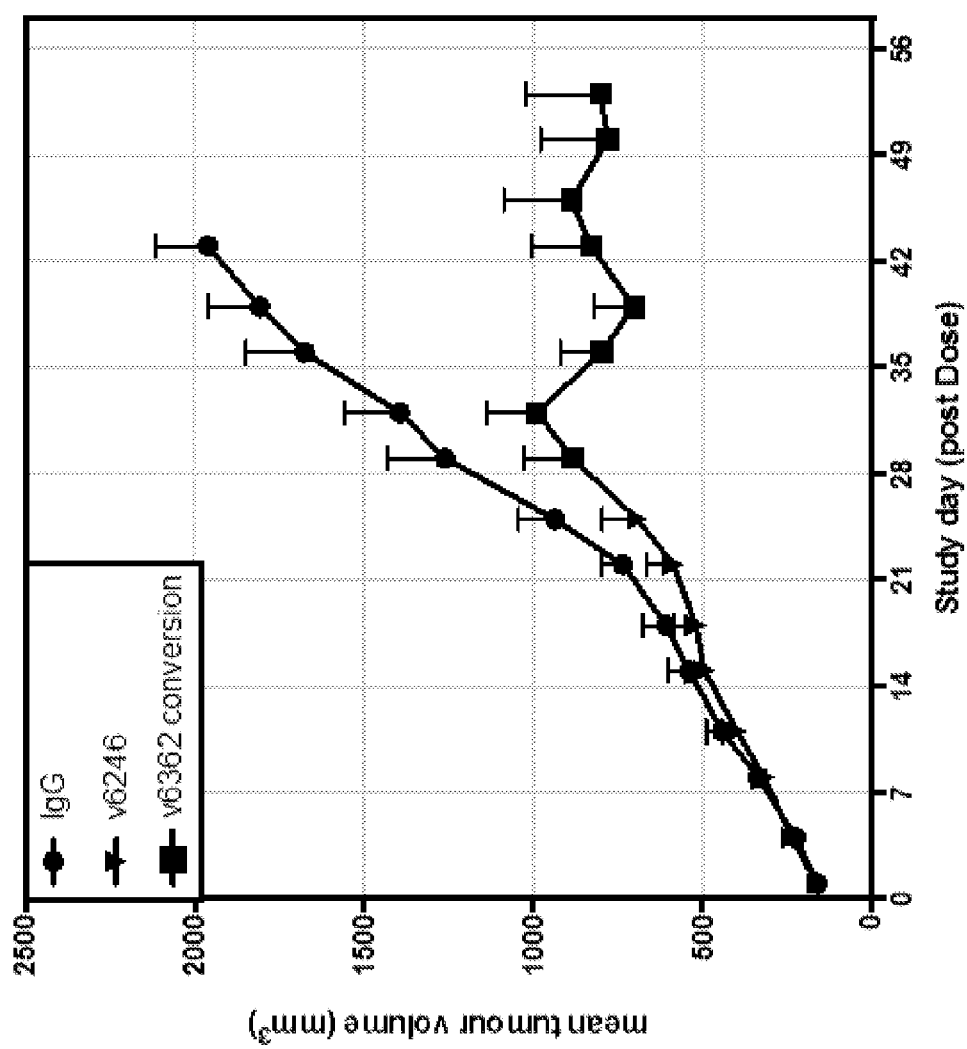
FIG. 31 depicts the anti-tumor activity of v6362 in the HBCx-13b PDX model with acquired HER2 antibody resistance.

The results are shown in FIG. 31 and Table 9 v6362 demonstrated tumor regression when dosed in animals not responding to v6246 therapy (dose conversion). On study day 53 the group receiving v6362 regressed the tumour volume from the day of conversion by 9% while animals receiving IgG control rapidly progressed and were terminated by day 43 (FIG. 31 and table 9).

In summary, this study demonstrated the ability of bsADCs to cause tumour regression when the tumour failed to respond to earlier treatment(s) and were significantly advanced in growth. The anti-tumour efficacy of the bsADCs in the HBCx-13b model suggests a potential clinical utility in the treatment of metastatic invasive ductal breast cancers that are non-responsive v6246.

TABLE 9 anti tumor activity in HBCx-13b model

|  | V6246 Day 1 | V6246 Day 29 | V6362 Day 53 |
|---|---|---|---|
| Mean TV (mm3) | 162 | 884 | 800 |
| % Change from Day 1 baseline | +0% | +445% | +393% |
| % Change from Day 29 baseline | na | +0% | −9% |

TV: Tumour volume

Example 29: Superior Platelet Counts of an Anti-HER2 and Anti-HER3 Bispecific Antibody Drug Conjugate (bsADC) Compared to T-DM1

This in vivo experiment was aimed at determining the effect of v6362 on circulating platelet counts in animals bearing MDA-MB-231 subcutaneous tumours.

The trastuzumab and chemotherapy resistant MDA-MB-231 xenograft model was derived from a triple negative breast cancer line (HER2$^{0+}$, ER$^-$, PR$^-$)

Female athymic nude mice were inoculated with a suspension of MDA-MB-231 cells subcutaneously on the right flank. Tumors were monitored until they reached an average volume of 115 mm$^3$; animals were then randomized into 3 treatment groups: IgG control, n=12; v6246, n=12; and v6362, n=12. Dosing for each group was as follows:

IgG control was dosed intravenously with a loading dose of 15 mg/kg on study day 1 and maintenance doses of 10 mg/kg administered on study days 4, 8, 11, 15 v6246 was dosed intravenously at 10 mg/kg on study day 1, 8, and 15 v6363 was dosed intravenously at 10 mg/kg on study days 1, 8 and 15

For platelet quantitation 0.25 ml blood was obtained from all animals on day 17 into K$_2$EDTA tubes. The blood was maintained at 4 centigrade prior to a standard clinical hematology profile.

Figure 32:
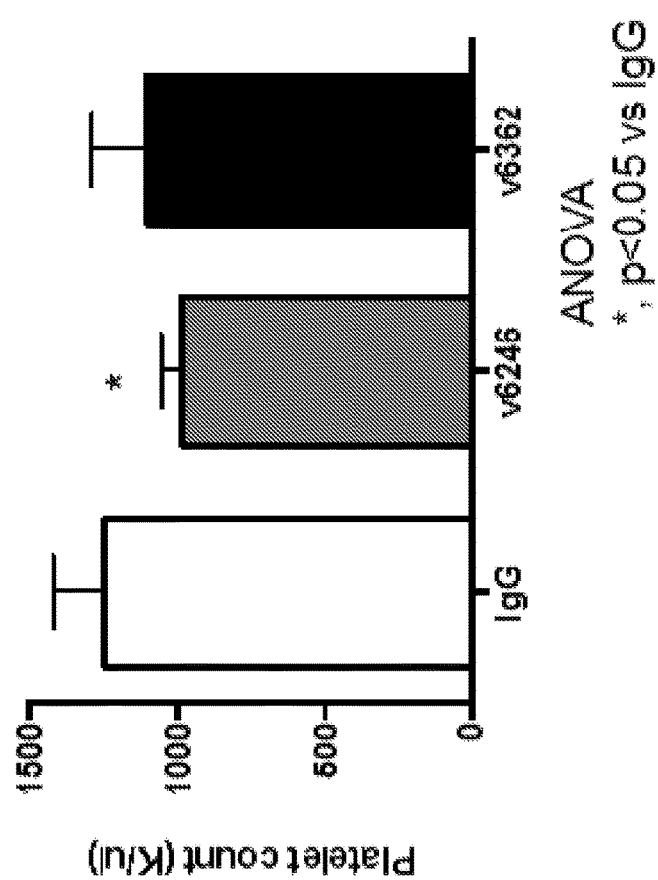
FIG. 32 compares the effect of v6362 to that of v6246 on platelet counts in vivo.
Figure 33:
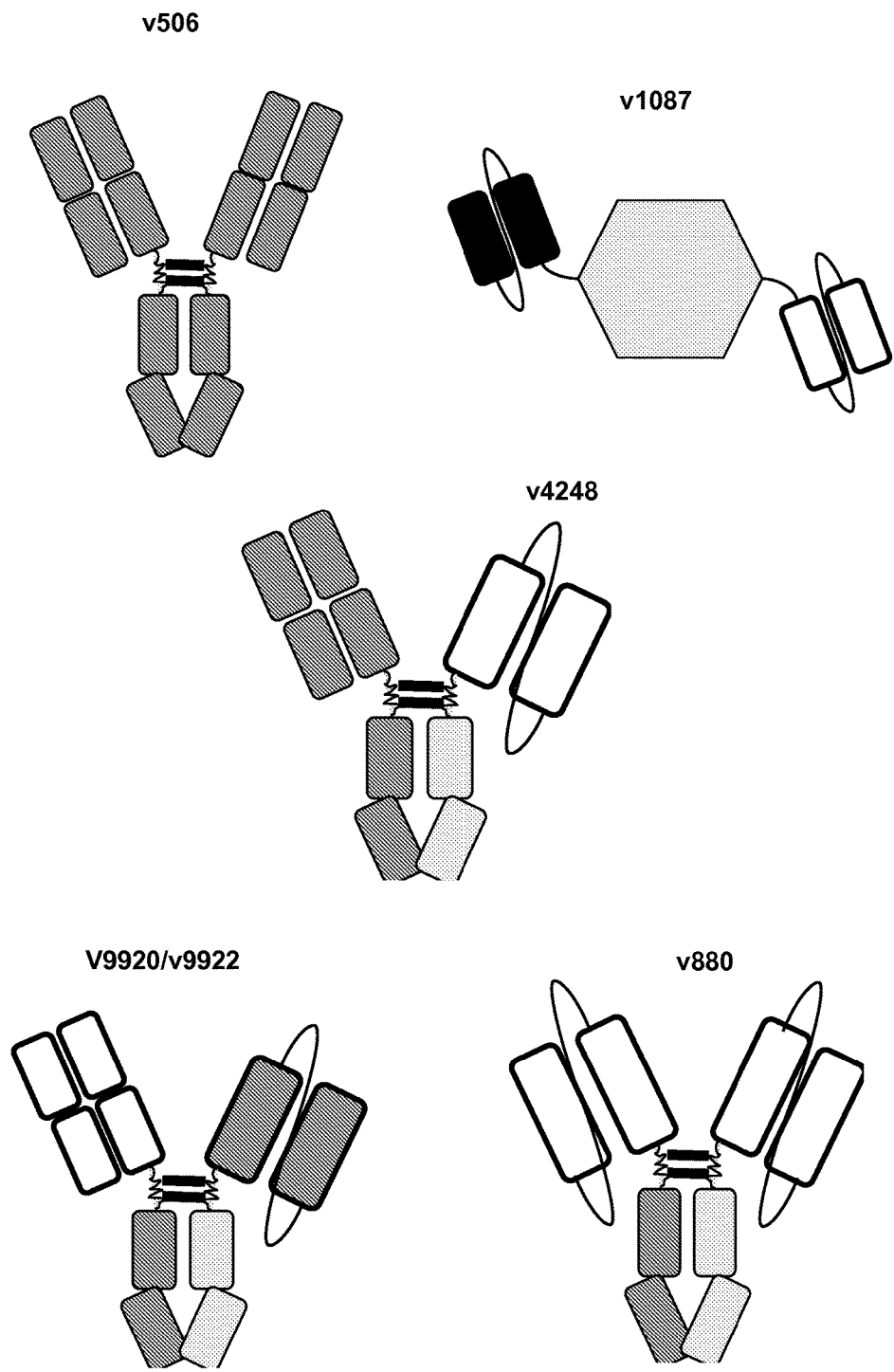
FIG. 33 provides a schematic representation of selected molecules described herein.

The results are shown in FIG. 32 and Table 10.

v6362 demonstrated no significant reduction in circulating platelet counts while v6246 demonstrated a significant reduction (FIG. 32). Mean serum concentration of v6246 and v6362 was equivalent on study day 7 (Table 10).

TABLE 10 effect of v6362 and v6246 on circulating platelet counts in animals bearing MDA-MB-231 subcutaneous tumours

|  |  | v6246 | v6362 |
|---|---|---|---|
| Drug exposure (day 7) | Mean serum concentration (µg/ml) | 15 | 14 |

In summary, this study demonstrated that v6362 may have reduced platelet toxicity compared to v6246.

The invention claimed is:

1. An isolated bi-specific antigen binding construct comprising:
   a first antigen-binding polypeptide construct which monovalently and specifically binds to an extracellular domain 4 (ECD4) of HER2 (human epidermal growth factor receptor 2), the first antigen-binding polypeptide construct comprising three variable heavy chain CDRs comprising the sequences set forth in SEQ ID NOs:49, 50, and 51, and three variable light chain CDRs comprising the sequences set forth in SEQ ID NOs:52, 53, and 54;
   a second antigen-binding polypeptide construct which monovalently and specifically binds to an extracellular domain (ECD) of HER3 (human epidermal growth factor receptor 3), the antigen-binding polypeptide construct comprising three variable heavy chain CDRs comprising the sequences set forth in SEQ ID NOs: 58, 59, and 60, and three variable light chain CDRs comprising the sequences DVS and as set forth in SEQ ID NOs:62 and 63; and
   an Fc comprising a first Fc polypeptide comprising a first CH3 domain and a second Fc polypeptide comprising a second CH3 domain, the first Fc polypeptide linked to the C-terminus of the first antigen-binding polypeptide construct with or without a linker and the second Fc polypeptide linked to the C-terminus of the second antigen-binding polypeptide construct with or without a linker;
   wherein the first antigen-binding polypeptide construct is a Fab format and the second antigen-binding polypeptide construct is an scFv format; and
   wherein the isolated bi-specific antigen binding construct has a geometry that allows the first antigen-binding polypeptide construct and the second antigen-binding polypeptide construct to each bind its respective extracellular domain and exhibit greater inhibition of heregulin-stimulated growth of BT-474 cells in vitro as compared to a control, wherein the control is v880 as described in FIG. 10.

2. The isolated bi-specific antigen binding construct of claim 1, wherein
   i. the first antigen-binding polypeptide construct is a Fab format comprising a first VH comprising the amino acid sequence set forth in SEQ ID NO:55 and a first VL comprising the amino acid sequence set forth in SEQ ID NO:56; and
   ii. the second antigen binding polypeptide construct in an scFv format comprising a second VH comprising the amino acid sequence set forth in SEQ ID NO:57 and a second VL comprising the amino acid sequence set forth in SEQ ID NO:61.

3. The isolated bi-specific antigen binding construct of claim 1, wherein the antigen-binding polypeptide construct in the scFv format is stabilized by addition of a disulphide bond between the VH and VL sequences, or by decreasing the surface hydrophobicity of the scFv.

4. The isolated bi-specific antigen binding construct of claim 1, wherein the Fc is derived from the Fc of an IgG1, IgG2, IgG3, IgG4, IgA or IgE antibody, or of an IgG subclass including IgG1, IgG2, IgG3, or IgG4, or a combination thereof.

5. The isolated bi-specific antigen binding construct of claim 1, wherein at least one CH3 domain comprises at least one amino acid modification that promotes the formation of a heterodimeric Fc with stability comparable to a wild-type homodimeric Fc.

6. The isolated bi-specific antigen binding construct of claim 5, wherein the dimerized CH3 domains of the heterodimeric Fc have a melting temperature (Tm) as measured by differential scanning calorimetry (DSC) of about 68, 69, 70, 71, 72, 73, 74, 75, 76, 77, 77.5, 78, 79, 80, 81, 82, 83, 84, or 85° C. or higher, and/or wherein the heterodimeric Fc is formed with a purity greater than about 75, 76, 77, 78, 79, 80, 81, 82, 83, 84, 85, 86, 87, 88, 89, 90, 91, 92, 93, 94, 95, 96, 97, 98, or 99% when produced; or wherein the heterodimeric Fc is formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed or when expressed via a single cell.

7. The isolated bi-specific antigen binding construct of claim 1, wherein the bi-specific antigen binding construct
   i. inhibits active HER2-HER3 heterodimer signaling by 50-100%;
   ii. inhibits EGFR-HER3 heterodimer signaling by at least 50%;
   iii. blocks heregulin-stimulated signaling of HER3 by up to 100%;
   iv. inhibits the growth of cancer cells in the presence or absence of growth factor;
   v. inhibits the growth of cancer cells in the presence of heregulin;
   vi. is internalized by cancer cells expressing HER2 and/or HER3;
   vii. exhibits increased internalization compared to the reference bivalent monospecific antibody in cancer cells co-expressing HER2 and HER3;
   viii. mediates increased ADCC towards HER2 and/or HER3 expressing cancer cells compared to the reference antibody;
   ix. mediates increased ADCC towards HER2 and/or HER3 expressing breast cancer cells, ovarian cancer cells, and gastric cancer cells;
   x. mediates increased ADCC towards HER2 and/or HER3 expressing breast cancer cells selected from high HER2 expressing cells, medium HER2 expressing cells, low HER2 expressing cells, triple negative breast cancer cells, estrogen receptor-positive breast cancer cells, and trastuzumab-resistant breast cancer cells; and/or
   xi. mediates increased ADCC towards HER2 and/or HER3 expressing cancer cells comprising a mutation known to cause cancer.

8. The isolated bi-specific antigen binding construct of claim 1, wherein the bi-specific antigen binding construct is afucosylated.

9. The isolated bi-specific antigen binding construct of claim 1, wherein the bi-specific antigen-binding construct is conjugated to a detectable label or a drug.

10. The isolated bi-specific antigen binding construct of claim 9, wherein the detectable label is a radioactive compound, a fluorescent compound, an enzyme, a substrate, an epitope tag, or a toxin.

11. The isolated bi-specific antigen binding construct of claim 9, wherein the drug is a toxin, a chemotherapeutic agent, an immune modulator, or a radioisotope.

12. The isolated bi-specific antigen binding construct of claim 9, wherein the drug is selected from a maytansine, auristatin, calicheamicin, or derivative thereof.

13. The isolated bi-specific antigen binding construct of claim 9, wherein the drug is a maytansine selected from DM1 and DM4.

14. The isolated bi-specific antigen binding construct of claim 13, wherein the drug is conjugated to the isolated bi-specific antigen binding construct with an SMCC linker (DM1), or an SPDB linker (DM4).

15. A pharmaceutical composition comprising the isolated bi-specific antigen binding construct of claim 1 and a pharmaceutical carrier.

16. The pharmaceutical composition of claim 15, wherein the carrier comprises a buffer, an antioxidant, a low molecular weight molecule, a drug, a protein, an amino acid, a carbohydrate, a lipid, a chelating agent, a stabilizer, or an excipient.

17. A method of inhibiting growth of a cancer cell expressing HER2 and HER3, or of inducing antibody-dependent cellular cytotoxicity (ADCC) in a cancer cell, or of inhibiting dimerization of HER2 and HER3 in a cancer cell, comprising contacting the cancer cell with an effective amount of the isolated bi-specific antigen binding construct of claim 1.

18. A method of inhibiting growth and/or proliferation of one or more tumor cells in a mammal, or a method of treating a tumor in a mammal, comprising administering an effective amount of the isolated bispecific antigen-binding construct of claim 1 to the mammal, wherein
  a) the one or more tumor cells express HER2 and HER3;
  b) the tumor is characterized by HER2 and/or HER3 overexpression;
  c) the tumor expresses low levels of HER2 and/or HER3; or
  d) the tumor co-expresses HER2 and HER3.

19. The isolated bi-specific antigen-binding construct of claim 1, comprising a polypeptide having the sequence set forth in SEQ ID NO:6, a polypeptide having the sequence set forth in SEQ ID NO:2, and a polypeptide having the sequence set forth in SEQ ID NO:16.

20. The isolated bi-specific antigen-binding construct of claim 19, conjugated to a detectable label or drug.

\* \* \* \* \*

SEQUENCE LISTING

```
<160> NUMBER OF SEQ ID NOS: 83

<210> SEQ ID NO 1
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gacatccaga tgacccagtc tccatcctcc ctgtctgcat ctgtaggaga cagagtcacc      60
atcacttgcc gggcaagtca ggacgttaac accgctgtag cttggtatca gcagaaacca     120
gggaaagccc ctaagctcct gatctattct gcatcctttt tgtacagtgg ggtcccatca     180
aggttcagtg gcagtcgatc tgggacagat ttcactctca ccatcagcag tctgcaacct     240
gaagattttg caacttacta ctgtcaacag cattacacta cccacccac tttcggccaa      300 gggaccaaag tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccaa     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
```

```
                    35                  40                  45
Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                     85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 3
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gaggtgcagc tggtggaaag cggaggagga ctggtgcagc caggaggatc tctgcgactg      60
agttgcgccg cttcaggatt caacatcaag gacacctaca ttcactgggt gcgacaggct     120
ccaggaaaag gactggagtg ggtggctcga atctatccca ctaatggata cacccggtat     180
gccgactccg tgaagggag gtttactatt agcgccgata tccaaaaaa cactgcttac     240 ctgcagatga acagcctgcg agccgaagat accgctgtgt actattgcag tcgatgggga     300
ggagacggat tctacgctat ggattattgg ggacagggga ccctggtgac agtgagctcc     360
gcctctacca agggcccag tgtgtttccc ctggctcctt ctagtaaatc cacctctgga     420
gggacagccg ctctgggatg tctggtgaag gactatttcc ccgagcctgt gaccgtgagt     480
tggaactcag gcgccctgac aagcggagtg cacactttc ctgctgtgct gcagtcaagc     540
gggctgtact ccctgtcctc tgtggtgaca gtgccaagtt caagcctggg cacacagact     600
tatatctgca acgtgaatca taagccctca atacaaaag tggacaagaa agtggagccc     660
aagagctgtg ataagaccca cacctgccct ccctgtccag ctccagaact gctgggagga     720
cctagcgtgt tcctgtttcc ccctaagcca aaagacactc tgatgatttc caggactccc     780
gaggtgacct gcgtggtggt ggacgtgtct cacgaggacc ccgaagtgaa gttcaactgg     840
tacgtggatg gcgtggaagt gcataatgct aagacaaaac caagagagga acagtacaac     900
tccacttatc gcgtcgtgag cgtgctgacc gtgctgcacc aggactggct gaacgggaag     960
gagtataagt gcaaagtcag taataaggcc ctgcctgctc aatcgaaaa aaccatctct    1020
```

```
aaggccaaag gccagccaag ggagcccag gtgtacacac tgccacccag cagagacgaa    1080
ctgaccaaga accaggtgtc cctgacatgt ctggtgaaag cttctatcc tagtgatatt    1140 gctgtggagt gggaatcaaa tggacagcca gagaacaatt acaagaccac acctccagtg    1200
ctggacagcg atggcagctt cttcctgtat tccaagctga cagtggataa atctcgatgg    1260
cagcagggga acgtgtttag ttgttcagtg atgcatgaag ccctgcacaa tcattacact    1320
cagaagagcc tgtccctgtc tcccggcaaa                                    1350

<210> SEQ ID NO 4
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg

```
                290                     295                     300
Val Val Ser Val Leu Thr Val Leu His Gln Asp Trp Leu Asn Gly Lys
305                     310                     315                     320

Glu Tyr Lys Cys Lys Val Ser Asn Lys Ala Leu Pro Ala Pro Ile Glu
                325                     330                     335

Lys Thr Ile Ser Lys Ala Lys Gly Gln Pro Arg Glu Pro Gln Val Tyr
                340                     345                     350

Thr Leu Pro Pro Ser Arg Asp Glu Leu Thr Lys Asn Gln Val Ser Leu
            355                     360                     365

Thr Cys Leu Val Lys Gly Phe Tyr Pro Ser Asp Ile Ala Val Glu Trp
        370                     375                     380

Glu Ser Asn Gly Gln Pro Glu Asn Asn Tyr Lys Thr Thr Pro Pro Val
385                     390                     395                     400

Leu Asp Ser Asp Gly Ser Phe Phe Leu Tyr Ser Lys Leu Thr Val Asp
                405                     410                     415

Lys Ser Arg Trp Gln Gln Gly Asn Val Phe Ser Cys Ser Val Met His
                420                     425                     430

Glu Ala Leu His Asn His Tyr Thr Gln Lys Ser Leu Ser Leu Ser Pro
            435                     440                     445

Gly Lys
    450

<210> SEQ ID NO 5
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gaggtgcagc tggtggaaag cggaggagga ctggtgcagc caggaggatc tctgcgactg     60
agttgcgccg cttcaggatt caacatcaag gacacctaca ttcactgggt gcgacaggct    120
ccaggaaaag gactggagtg ggtggctcga atctatccca ctaatggata caccgtat     180 gccgactccg tgaagggag gtttactatt agcgccgata tccaaaaa cactgcttac      240 ctgcagatga acagcctgcg agccgaagat accgctgtgt actattgcag tcgatgggga    300
ggagacggat tctacgctat ggattattgg ggacagggga ccctggtgac agtgagctcc    360
gcctctacca agggcccag tgtgtttccc ctggctcctt ctagtaaatc cacctctgga    420
gggacagccg ctctgggatg tctggtgaag gactatttcc ccgagcctgt gaccgtgagt    480
tggaactcag gcgccctgac aagcggagtg cacactttc ctgctgtgct gcagtcaagc    540
gggctgtact ccctgtcctc tgtggtgaca gtgccaagtt caagcctggg cacacagact    600
tatatctgca acgtgaatca taagccctca aatacaaaag tggacaagaa agtggagccc    660
aagagctgtg ataagccca cacctgccct ccctgtccag ctccagaact gctgggagga    720
cctagcgtgt tcctgtttcc ccctaagcca aaagacactc tgatgatttc caggactccc    780
gaggtgacct gcgtggtggt ggacgtgtct cacgaggacc ccgaagtgaa gttcaactgg    840
tacgtggatg gcgtggaagt gcataatgct aagacaaaac caagagagga acagtacaac    900
tccacttatc gcgtcgtgag cgtgctgacc gtgctgcacc aggactggct gaacgggaag    960
gagtataagt gcaaagtcag taataaggcc ctgcctgctc aatcgaaaaa aaccatctct   1020
aaggccaaag gccagccaag ggagcccag gtgtacgtgt accacccag cagagacgaa    1080
```

```
ctgaccaaga accaggtgtc cctgacatgt ctggtgaaag gcttctatcc tagtgatatt    1140
gctgtggagt gggaatcaaa tggacagcca gagaacaatt acaagaccac acctccagtg    1200
ctggacagcg atggcagctt cgccctggtg tccaagctga cagtggataa atctcgatgg    1260
cagcagggga acgtgtttag ttgttcagtg atgcatgaag ccctgcacaa tcattacact    1320
cagaagagcc tgtccctgtc tcccggcaaa                                     1350
```

<210> SEQ ID NO 6
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
                305                 310                 315                 320
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Val Tyr Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 7
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaggtgcagc tggtggaaag cggaggagga ctggtgcagc caggaggatc tctgcgactg      60
agttgcgccg cttcaggatt caacatcaag gacacctaca ttcactgggt gcgacaggct    120
ccaggaaaag gactggagtg ggtggctcga atctatccca ctaatggata cacccggtat    180
gccgactccg tgaaggggag gtttactatt agcgccgata catccaaaaa cactgcttac    240
ctgcagatga acagcctgcg agccgaagat accgctgtgt actattgcag tcgatgggga    300
ggagacggat tctacgctat ggattattgg ggacagggga ccctggtgac agtgagctcc    360
gcctctacca agggcccag tgtgtttccc ctggctcctt ctagtaaatc cacctctgga    420
gggacagccg ctctgggatg tctggtgaag gactatttcc ccgagcctgt gaccgtgagt    480
tggaactcag gcgccctgac aagcggagtg cacacttttc ctgctgtgct gcagtcaagc    540
gggctgtact ccctgtcctc tgtggtgaca gtgccaagtt caagcctggg cacacagact    600
tatatctgca acgtgaatca taagccctca aatacaaaag tggacaagaa agtggagccc    660
aagagctgtg ataagaccca cacctgccct ccctgtccag ctccagaact gctgggagga    720
cctagcgtgt tcctgtttcc ccctaagcca aaagacactc tgatgatttc aggactccc    780 gaggtgacct gcgtggtggt ggacgtgtct cacgaggacc ccgaagtgaa gttcaactgg    840
tacgtggatg gcgtggaagt gcataatgct aagacaaaac caagagagga acagtacaac    900
tccacttatc gcgtcgtgag cgtgctgacc gtgctgcacc aggactggct gaacgggaag    960
gagtataagt gcaaagtcag taataaggcc ctgcctgctc caatcgaaaa aaccatctct   1020
aaggccaaag ccagccaag ggagccccag gtgtacgtgc tgccacccag cagagacgaa   1080
ctgaccaaga accaggtgtc cctgctgtgt ctggtgaaag gcttctatcc tagtgatatt   1140
gctgtggagt gggaatcaaa tggacagcca gagaacaatt acctgacctg gcctccagtg   1200
```

```
ctggacagcg atggcagctt cttcctgtat tccaagctga cagtggataa atctcgatgg    1260
cagcagggga acgtgtttag ttgttcagtg atgcatgaag ccctgcacaa tcattacact    1320
cagaagagcc tgtccctgtc tcccggcaaa                                     1350
```

<210> SEQ ID NO 8
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
                    325                 330                 335
Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
            355                 360                 365

Leu Cys Leu Val Lys Gly Phe Tyr Pro Ser Asp Ile Ala Val Glu Trp
            370                 375                 380

Glu Ser Asn Gly Gln Pro Glu Asn Asn Tyr Leu Thr Trp Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 9
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaacctaaat ctagcgacaa gactcacacc tgcccacctt gtccagcacc agaactgctg      60
ggaggaccaa gcgtgttcct gtttccaccc aagcccaaag atactctgat gatcagccga     120
acacccgagg tcacttgcgt ggtcgtggac gtgtcccacg aggaccccga agtcaagttc     180
aactggtacg tggacggcgt cgaagtgcat aatgctaaga caaaaccacg ggaggaacag     240
tacaactcta cttatagagt cgtgagtgtc ctgaccgtgc tgcatcagga ttggctgaac     300
ggcaaagagt ataagtgcaa agtgtctaat aaggccctgc ctgctccaat cgagaaaaca     360
attagtaagg ctaaagggca gcccagggaa cctcaggtgt acacttatcc tccaagtcgc     420
gacgagctga ccaagaacca ggtctcactg acatgtctgg tgaaaggatt ttacccttcc     480
gatattgcag tggagtggga atctaatggc cagccagaga caattataa gaccacaccc     540 cctgtgctgg acagcgatgg gtccttcgca ctggtctcaa agctgaccgt ggacaaaagc     600
agatggcagc agggaaacgt ctttagctgt tccgtgatgc acgaagccct gcacaatcat     660
tacacacaga gtctctgag tctgtcacct ggcaaa                                 696

<210> SEQ ID NO 10
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
```

```
                35                  40                  45
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Tyr Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Ala Leu Val
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 11
<211> LENGTH: 1446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
caggtccagc tgcaggaatc tggaggagga ctggtgaagc caggagggtc tctgagactg    60
agttgcgccg cttcaggctt cacctttagc tcctactgga tgagctgggt gcggcaggca   120
cctggcaaag gactggagtg ggtggccaac atcaatagac gggagtgc ttcatactat    180 gtcgatagcg tgaagggaag gttcactatt agtcgcgacg atgcaaaaaa ctcactgtac   240
ctgcagatga atagcctgag ggccgaagac accgctgtct actattgcgc ccgggacaga   300
ggagtgggct attttgatct gtggggcgc ggaaccctgg tcacagtgtc tagtgcttcc   360
accgagggcg gggatcagg cggaggaggc agcggaggag agggagcca gtccgctctg   420 acacagcctg catctgtgag tggctcacca gggcagagca tcactatttc ctgtactggc   480
acctcaagcg atgtcggagg ctacaacttc gtgagctggt atcagcagca cccagggaag   540
gcacccaaac tgatgatcta cgacgtctcc gatcgaccaa gtggagtgtc agaccggttt   600
agcggcagca gtctggcaa tacagcctct ctgatcatta gtggactgca ggcagacgat   660
gaggccgatt actattgctc ctcttatgc agttcaagca ctcacgtgat ttttggggga   720
ggcactaaag tcaccgtgct gggcgcagcc gaacccaagt cctctgacaa acacatact   780 tgcccacctt gtccagctcc agagctgctg gaggaccaa gcgtgttcct gtttccaccc   840
aagcctaaag atactctgat gatcagccga acacctgaag tcacttgtgt ggtcgtggac   900
```

```
gtgtcccacg aggaccccga agtcaagttt aactggtacg tggacggcgt cgaggtgcat    960
aatgccaaga caaaacctag agaggaacag tacaactcca cttatagggt cgtgtctgtc   1020
ctgaccgtgc tgcaccagga ttggctgaac ggaaaggagt ataagtgcaa agtgtctaat   1080
aaggctctgc ctgcaccaat cgagaaaacc attagcaagg ctaaagggca gccccgcgaa   1140
cctcaggtgt acacactgcc tccatctcga gacgagctga ccaagaacca ggtcagcctg   1200
acatgtctgg tgaaaggctt ctatccaagt gatattgcag tggagtggga atccaatggg   1260
cagcccgaaa acaattacaa gaccacaccc cctgtgctgg acagcgatgg ctccttcttt   1320
ctgtattcca agctgaccgt ggacaaatct cgctggcagc aggggaacgt ctttagttgt   1380
tcagtgatgc atgaggccct gcacaatcat tacacacaga gagcctgtc cctgtctccc    1440 ggcaaa                                                              1446
```

<210> SEQ ID NO 12
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gln Val Gln Leu Gln Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
        195                 200                 205

Ala Ser Leu Ile Ile Ser Gly Leu Gln Ala Asp Asp Glu Ala Asp Tyr
    210                 215                 220

Tyr Cys Ser Ser Tyr Gly Ser Ser Ser Thr His Val Ile Phe Gly Gly
225                 230                 235                 240

Gly Thr Lys Val Thr Val Leu Gly Ala Ala Glu Pro Lys Ser Ser Asp
                245                 250                 255
```

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys

<210> SEQ ID NO 13
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
caggtccagc tggtgcagag cggggcagag gtcaagaaac ccggagaaag tctgaagatc      60
tcatgcaaag ggagtggata ctcattcacc agctattgga ttgcctgggt gaggcagatg     120
cctggcaagg ggctggaata catgggcctg atctatccag ggacagcgat acaaaatac     180 tcccctctt tccagggcca ggtcacaatt tccgtggaca agagtgtctc aactgcctat     240
ctgcagtgga gctccctgaa acctagcgat tccgcagtgt acttttgtgc caggcacgac     300
gtcgggtatt gcacagatcg cacttgtgct aagtggccag agtggctggg agtgtgggga     360
cagggaaccc tggtcacagt gtctagtgga ggaggaggct caagcggagg aggctctgga     420
ggaggagggt ctcagagtgt gctgactcag ccaccttcag tcagcgcagc tcctggacag     480
aaggtgacca tctcctgctc tggcagctct agtaacattg caacaattac gtgagctgg     540 tatcagcagc tgcctggcac cgccccaaag ctgctgatct acgaccacac aaatcggccc     600
gctggggtgc ctgatagatt cagtgggtca aaaagcggaa cctccgcttc tctggcaatt     660
agcggctttc gctccgagga cgaagctgat tactattgtg catcttggga ctacacactg     720

```
agtggctggg tgttcggagg cgggactaag ctgaccgtgc tgggggcagc cgaaccaaag    780
tcaagcgata aaactcatac ctgcccacca tgtcctgcac cagagctgct gggaggacct    840
tccgtgttcc tgtttcctcc aaagccaaaa gacaccctga tgatcagccg aacaccagaa    900
gtgacttgcg tggtcgtgga cgtctcccac gaggacccccg aagtgaagtt taactggtac    960
gtggatggcg tcgaggtgca taatgccaag accaaacccc gagaggaaca gtacaactca   1020
acttatcggg tcgtgagcgt cctgaccgtg ctgcaccagg actggctgaa cgggaaagag   1080
tataagtgca aagtgtctaa taaggccctg cccgctccta tcgagaaaac aattagcaag   1140
gcaaaaggcc agccaagaga acccccaggtg tacacttatc ccccttctag ggacgagctg   1200
accaagaacc aggtgagcct gacatgtctg gtcaaaggat tttaccccag tgatattgct   1260
gtggagtggg aatccaatgg ccagcctgaa aacaattata agaccacacc acccgtgctg   1320
gactccgatg gatctttcgc tctggtgtcc aagctgactg tcgataaatc tcggtggcag   1380
cagggcaacg tgtttagttg ttcagtcatg catgaggcac tgcacaatca ttacacacag   1440
aagagcctgt ccctgtctcc cggcaaa                                        1467
```

<210> SEQ ID NO 14
<211> LENGTH: 489
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 14

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Thr Asp Arg Thr Cys Ala Lys Trp
            100                 105                 110

Pro Glu Trp Leu Gly Val Trp Gly Gln Gly Thr Leu Val Thr Val Ser
        115                 120                 125

Ser Gly Gly Gly Gly Ser Ser Gly Gly Gly Ser Gly Gly Gly Gly Ser
    130                 135                 140

Gln Ser Val Leu Thr Gln Pro Pro Ser Val Ser Ala Ala Pro Gly Gln
145                 150                 155                 160

Lys Val Thr Ile Ser Cys Ser Gly Ser Ser Ser Asn Ile Gly Asn Asn
                165                 170                 175

Tyr Val Ser Trp Tyr Gln Gln Leu Pro Gly Thr Ala Pro Lys Leu Leu
            180                 185                 190

Ile Tyr Asp His Thr Asn Arg Pro Ala Gly Val Pro Asp Arg Phe Ser
        195                 200                 205

Gly Ser Lys Ser Gly Thr Ser Ala Ser Leu Ala Ile Ser Gly Phe Arg
    210                 215                 220
```

Ser Glu Asp Glu Ala Asp Tyr Tyr Cys Ala Ser Trp Asp Tyr Thr Leu
225                 230                 235                 240

Ser Gly Trp Val Phe Gly Gly Gly Thr Lys Leu Thr Val Leu Gly Ala
            245                 250                 255

Ala Glu Pro Lys Ser Ser Asp Lys Thr His Thr Cys Pro Pro Cys Pro
        260                 265                 270

Ala Pro Glu Leu Leu Gly Gly Pro Ser Val Phe Leu Phe Pro Pro Lys
    275                 280                 285

Pro Lys Asp Thr Leu Met Ile Ser Arg Thr Pro Glu Val Thr Cys Val
290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
        340                 345                 350

Gln Asp Trp Leu Asn Gly Lys Glu Tyr Lys Cys Lys Val Ser Asn Lys
    355                 360                 365

Ala Leu Pro Ala Pro Ile Glu Lys Thr Ile Ser Lys Ala Lys Gly Gln
370                 375                 380

Pro Arg Glu Pro Gln Val Tyr Thr Tyr Pro Pro Ser Arg Asp Glu Leu
385                 390                 395                 400

Thr Lys Asn Gln Val Ser Leu Thr Cys Leu Val Lys Gly Phe Tyr Pro
            405                 410                 415

Ser Asp Ile Ala Val Glu Trp Glu Ser Asn Gly Gln Pro Glu Asn Asn
        420                 425                 430

Tyr Lys Thr Thr Pro Pro Val Leu Asp Ser Asp Gly Ser Phe Ala Leu
    435                 440                 445

Val Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 15
<211> LENGTH: 1446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
caggtccagc tgcaggaatc tggaggagga ctggtgaagc caggagggtc tctgagactg      60
agttgcgccg cttcaggctt cacctttagc tcctactgga tgagctgggt gcggcaggca     120
cctggcaaag gactggagtg ggtggccaac atcaatagcg acgggagtgc ttcatactat     180
gtcgatagcg tgaagggaag gttcaccatt agtcgcgacg atgcaaaaaa ctcactgtac     240
ctgcagatga atagcctgag ggccgaagac acagctgtct actattgcgc ccgggacaga     300
ggagtgggct attttgatct gtggggcgc ggaacactgg tcactgtgtc tagtgcttcc     360
acaggaggcg ggggatcagg cggaggaggc agcggaggag gaggagcca gtccgctctg     420 actcagcctg catctgtgag tggctcacca gggcagagca tcaccatttc ctgtaccggc     480
acatcaagcg atgtcggagg ctacaacttc gtgagctggt atcagcagca cccagggaag     540

```
gcacccaaac tgatgatcta cgacgtctcc gatcgaccaa gtggagtgtc agaccggttt     600
agcggcagca agtctggcaa tactgcctct ctgatcatta gtggactgca ggcagacgat     660
gaggccgatt actattgctc ctcttatggc agttcaagca cccacgtgat tttcggggga     720
ggcaccaagg tcacagtgct gggcgcagcc gaacccaagt cctctgacaa aactcatacc     780
tgcccacctt gtccagctcc agagctgctg ggaggaccaa gcgtgttcct gtttccaccc     840
aagcctaaag atacactgat gatcagccga actcctgaag tcacctgtgt ggtcgtggac     900
gtgtcccacg aggaccccga agtcaagttt aactggtacg tggacggcgt cgaggtgcat     960
aatgccaaga ctaaacctag agaggaacag tacaactcca catatagggt cgtgtctgtc    1020
ctgactgtgc tgcaccagga ttggctgaac ggaaaggagt ataagtgcaa agtgtctaat    1080
aaggctctgc ctgcaccaat cgagaaaacc attagcaagg ctaaagggca gccccgcgaa    1140
cctcaggtgt acaccctgcc tccatctcga gacgagctga caaagaacca ggtcagcctg    1200
ctgtgtctgg tgaaaggctt ctatccaagt gatattgcag tggagtggga atccaatggg    1260
cagcccgaaa acaattacat gacatggccc cctgtgctgg acagcgatgg ctccttcttt    1320
ctgtattcca agctgactgt ggacaaatct cgctggcagc aggggaacgt ctttagttgt    1380
tcagtgatgc atgaggccct gcacaatcat acacccagag agagcctgtc cctgtctccc    1440
ggcaaa                                                               1446
```

<210> SEQ ID NO 16
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190
```

```
Pro Ser Gly Val Ser Asp Arg Phe Ser Gly Ser Lys Ser Gly Asn Thr
    195                 200                 205
Ala Ser Leu Ile Ile Ser Gly Leu Gln Ala Asp Asp Glu Ala Asp Tyr
210                 215                 220
Tyr Cys Ser Ser Tyr Gly Ser Ser Thr His Val Ile Phe Gly Gly Gly
225                 230                 235                 240
Gly Thr Lys Val Thr Val Leu Gly Ala Ala Glu Pro Lys Ser Ser Asp
                245                 250                 255
Lys Thr His Thr Cys Pro Pro Cys Pro Ala Pro Glu Leu Leu Gly Gly
                260                 265                 270
Pro Ser Val Phe Leu Phe Pro Pro Lys Pro Lys Asp Thr Leu Met Ile
            275                 280                 285
Ser Arg Thr Pro Glu Val Thr Cys Val Val Val Asp Val Ser His Glu
290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
                325                 330                 335
Val Val Ser Val Leu Thr Val Leu His Gln Asp Trp Leu Asn Gly Lys
            340                 345                 350
Glu Tyr Lys Cys Lys Val Ser Asn Lys Ala Leu Pro Ala Pro Ile Glu
        355                 360                 365
Lys Thr Ile Ser Lys Ala Lys Gly Gln Pro Arg Glu Pro Gln Val Tyr
    370                 375                 380
Thr Leu Pro Pro Ser Arg Asp Glu Leu Thr Lys Asn Gln Val Ser Leu
385                 390                 395                 400
Leu Cys Leu Val Lys Gly Phe Tyr Pro Ser Asp Ile Ala Val Glu Trp
                405                 410                 415
Glu Ser Asn Gly Gln Pro Glu Asn Asn Tyr Met Thr Trp Pro Pro Val
            420                 425                 430
Leu Asp Ser Asp Gly Ser Phe Phe Leu Tyr Ser Lys Leu Thr Val Asp
        435                 440                 445
Lys Ser Arg Trp Gln Gln Gly Asn Val Phe Ser Cys Ser Val Met His
    450                 455                 460
Glu Ala Leu His Asn His Tyr Thr Gln Lys Ser Leu Ser Leu Ser Pro
465                 470                 475                 480
Gly Lys

<210> SEQ ID NO 17
<211> LENGTH: 3285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
caggtgcagc tgcaggagtc cggaggagga ctggtgaagc aggagggtc cctgagactg      60 tcttgcgccg ctagtggctt cacctttagc tcctactgga tgtcttgggt gaggcaggca     120
cctggcaagg gactggagtg ggtggcaaac atcaatcgcg acggatcagc cagctactat     180
gtggatagcg tcaagggcag gtttacaatt agtcgcgacg atgctaaaaa ctcactgtac     240
ctgcagatga atagcctgcg ggcagaggat actgccgtgt actattgcgc cagagacagg     300
ggagtcggct atttcgatct gtgggggaga ggaactctgg tgaccgtctc tagtgctagc     360
```

```
accggaggcg ggggatctgg cggaggaggc agtggaggag agggtccca gtctgctctg    420
acacagccag caagtgtgtc aggcagcccc gggcagtcaa tcactattag ctgtactggc    480
acctcaagcg acgtgggagg ctacaacttt gtcagctggt atcagcagca ccctggaaaa    540
gccccaaagc tgatgatcta cgacgtgagc gatcgacctt ccggcgtctc tgatcggttc    600
tccgggtcta agagtggaaa tactgcctcc ctgatcattt ctgggctgca ggctgacgat    660
gaggcagact actattgctc ctcttatgga agttcaagca cccatgtgat cttcggggga    720
ggcacaaaag tgactgtcct gggcgcagcc tcagatgctc acaaaagcga ggtggcacat    780
cggttcaagg acctggggga ggaaaacttt aaagccctgg tgctgattgc attcgcccag    840
tacctgcagc agagcccatt tgaggaccac gtgaagctgg tcaacgaggt gaccgagttc    900
gccaaaacat gcgtggccga cgagtccgct gaaaattgtg ataagtctct gcatactctg    960
tttggagata aactgtgcac cgtggccaca ctgcgagaga cctacggcga aatggcagac   1020
tgctgtgcca agcaggagcc agaaagaaac gagtgcttcc tgcagcacaa agacgataac   1080
ccaaatctgc cacgactggt gcgaccagaa gtggacgtca tgtgtactgc tttccacgat   1140
aatgaggaaa cctttctgaa gaaatacctg tatgagatcg cccggagaca tccctacttt   1200
tatgcacctg aactgctgtt cttttgccaa agatacaagg ctgcattcac cgagtgctgt   1260
caggccgctg ataaagcagc ctgcctgctg ccaaagctgg acgagctgcg agatgaaggc   1320
aaggcctcct ctgctaaaca gagactgaag tgtgccagcc tgcagaaatt cggcgagagg   1380
gcttttaagg cttgggcagt ggcacgactg tcccagagat tccctaaggc agagtttgcc   1440
gaagtctcta aactggtgac tgacctgacc aaggtgcaca ccgagtgctg tcatggcgac   1500
ctgctggaat cgccgacga tcgcgctgat ctggcaaagt acatctgtga aaaccaggac   1560
agcattagtt caaagctgaa agagtgctgt gaaaaacccc tgctggagaa gagccactgc   1620
atcgcagagt ggaaaacga cgaaatgccc gccgatctgc ctagtctggc tgcagacttc   1680
gtggagtcaa aagatgtctg taagaattac gctgaagcaa aggatgtgtt cctgggcatg   1740
tttctgtacg agtatgctag cgccaccca gactactccg tggtcctgct gctgaggctg   1800
gccaagacct atgagaccac actggaaaaa tgctgtgccg ctgcagatcc ccatgagtgc   1860
tatgccaaag tgttcgacga gttcaagcca ctggtcgagg aaccccagaa cctgattaag   1920
cagaattgtg agctgtttga acagctgggc gagtacaaat tccagaacgc cctgctggtg   1980
cgctatacaa agaaagtccc tcaggtgagc acaccaactc tggtggaagt ctccaggaat   2040
ctgggaaagg tcggctctaa atgctgtaag caccccgagg ccaaacgcat gccttgcgct   2100
gaagattacc tgtccgtggt cctgaaccag ctgtgtgtgc tgcatgagaa gacccccagtc   2160
tctgaccggg tgacaaaatg ctgtactgaa gtctggtga tcgacgcc ctgctttagc   2220
gccctggagg tggatgaaac atatgtccct aaggagttcc aggctgaaac cttcacattt   2280
cacgcagaca tctgtactct gtccgagaaa gaaagacaga ttaagaaaca gaccgccctg   2340
gtcgagctgg tgaagcataa acccaaggcc acaaaagaac agctgaaggc tgtgatggac   2400
gatttcgccg cttttgtcga gaatgctgt aaggctgacg ataaggaaac ttgctttgca   2460
gaggaaggga agaaactggt ggcagcatcc caggctgcac tgggactggc agctgcactg   2520
caggtccagc tggtgcagtc tggcgccgag gtgaagaaac tggggaaag tctgaaaatc   2580
tcctgtaagg gcagtgggta ctcattcacc agctattgga ttgcctgggt gaggcagatg   2640
ccaggaaagg gcctggagta catgggactg atctatcctg cgacagcga tacaaaatac   2700
```

```
tcaccaagct tcagggcca ggtcacaatt agcgtggata agtccgtctc tactgcctat    2760
ctgcagtgga gctccctgaa acctagtgac tcagccgtgt acttctgcgc tcgccacgac    2820
gtcggctatt gcacagatcg aacttgtgcc aagtggccag agtggctggg agtgtgggga    2880
cagggaaccc tggtgacagt ctctagtggg ggaggcgggt caagcggagg agggtccgga    2940
ggaggaggaa gccagtccgt gctgacccag ccccttctg tcagtgccgc tcctggccag    3000
aaggtgacaa tctcatgcag cgggtcctct agtaacattg gaaacaatta cgtgagctgg    3060
tatcagcagc tgccagggac cgctcccaag ctgctgatct acgatcatac aaatagacct    3120
gcaggagtgc cagacaggtt ttccggctct aaaagtggga cctcagccag cctggctatt    3180
agcggcttcc ggtccgagga cgaagcagat tactattgtg cctcctggga ctatacactg    3240
tctggctggg tgttcggcgg gggaactaag ctgaccgtcc tgggg    3285
```

<210> SEQ ID NO 18
<211> LENGTH: 1095
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Gly Gly Gly Ser Gly Gly
        115                 120                 125

Gly Gly Ser Gly Gly Gly Ser Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
        195                 200                 205

Ala Ser Leu Ile Ile Ser Gly Leu Gln Ala Asp Asp Glu Ala Asp Tyr
    210                 215                 220

Tyr Cys Ser Ser Tyr Gly Ser Ser Ser Thr His Val Ile Phe Gly Gly
225                 230                 235                 240

Gly Thr Lys Val Thr Val Leu Gly Ala Ala Ser Asp Ala His Lys Ser
                245                 250                 255
```

```
Glu Val Ala His Arg Phe Lys Asp Leu Gly Glu Asn Phe Lys Ala
                260                 265                 270

Leu Val Leu Ile Ala Phe Ala Gln Tyr Leu Gln Gln Ser Pro Phe Glu
    275                 280                 285

Asp His Val Lys Leu Val Asn Glu Val Thr Glu Phe Ala Lys Thr Cys
290                 295                 300

Val Ala Asp Glu Ser Ala Glu Asn Cys Asp Lys Ser Leu His Thr Leu
305                 310                 315                 320

Phe Gly Asp Lys Leu Cys Thr Val Ala Thr Leu Arg Glu Thr Tyr Gly
                325                 330                 335

Glu Met Ala Asp Cys Cys Ala Lys Gln Glu Pro Glu Arg Asn Glu Cys
            340                 345                 350

Phe Leu Gln His Lys Asp Asp Asn Pro Asn Leu Pro Arg Leu Val Arg
        355                 360                 365

Pro Glu Val Asp Val Met Cys Thr Ala Phe His Asp Asn Glu Glu Thr
    370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
                405                 410                 415

Thr Glu Cys Cys Gln Ala Ala Asp Lys Ala Ala Cys Leu Leu Pro Lys
            420                 425                 430

Leu Asp Glu Leu Arg Asp Glu Gly Lys Ala Ser Ser Ala Lys Gln Arg
        435                 440                 445

Leu Lys Cys Ala Ser Leu Gln Lys Phe Gly Glu Arg Ala Phe Lys Ala
    450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
                485                 490                 495

Cys His Gly Asp Leu Leu Glu Cys Ala Asp Asp Arg Ala Asp Leu Ala
            500                 505                 510

Lys Tyr Ile Cys Glu Asn Gln Asp Ser Ile Ser Ser Lys Leu Lys Glu
        515                 520                 525

Cys Cys Glu Lys Pro Leu Leu Glu Lys Ser His Cys Ile Ala Glu Val
    530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
                565                 570                 575

Phe Leu Gly Met Phe Leu Tyr Glu Tyr Ala Arg Arg His Pro Asp Tyr
            580                 585                 590

Ser Val Val Leu Leu Leu Arg Leu Ala Lys Thr Tyr Glu Thr Thr Leu
        595                 600                 605

Glu Lys Cys Cys Ala Ala Ala Asp Pro His Glu Cys Tyr Ala Lys Val
    610                 615                 620

Phe Asp Glu Phe Lys Pro Leu Val Glu Glu Pro Gln Asn Leu Ile Lys
625                 630                 635                 640

Gln Asn Cys Glu Leu Phe Glu Gln Leu Gly Glu Tyr Lys Phe Gln Asn
                645                 650                 655

Ala Leu Leu Val Arg Tyr Thr Lys Lys Val Pro Gln Val Ser Thr Pro
            660                 665                 670

Thr Leu Val Glu Val Ser Arg Asn Leu Gly Lys Val Gly Ser Lys Cys
```

-continued

```
            675                 680                 685
Cys Lys His Pro Glu Ala Lys Arg Met Pro Cys Ala Glu Asp Tyr Leu
    690                 695                 700
Ser Val Val Leu Asn Gln Leu Cys Val Leu His Glu Lys Thr Pro Val
705                 710                 715                 720
Ser Asp Arg Val Thr Lys Cys Cys Thr Glu Ser Leu Val Asn Arg Arg
                725                 730                 735
Pro Cys Phe Ser Ala Leu Glu Val Asp Glu Thr Tyr Val Pro Lys Glu
                740                 745                 750
Phe Gln Ala Glu Thr Phe Thr Phe His Ala Asp Ile Cys Thr Leu Ser
                755                 760                 765
Glu Lys Glu Arg Gln Ile Lys Lys Gln Thr Ala Leu Val Glu Leu Val
770                 775                 780
Lys His Lys Pro Lys Ala Thr Lys Glu Gln Leu Lys Ala Val Met Asp
785                 790                 795                 800
Asp Phe Ala Ala Phe Val Glu Lys Cys Cys Lys Ala Asp Asp Lys Glu
                805                 810                 815
Thr Cys Phe Ala Glu Glu Gly Lys Lys Leu Val Ala Ala Ser Gln Ala
                820                 825                 830
Ala Leu Gly Leu Ala Ala Leu Gln Val Gln Leu Val Gln Ser Gly
                835                 840                 845
Ala Glu Val Lys Lys Pro Gly Glu Ser Leu Lys Ile Ser Cys Lys Gly
850                 855                 860
Ser Gly Tyr Ser Phe Thr Ser Tyr Trp Ile Ala Trp Val Arg Gln Met
865                 870                 875                 880
Pro Gly Lys Gly Leu Glu Tyr Met Gly Leu Ile Tyr Pro Gly Asp Ser
                885                 890                 895
Asp Thr Lys Tyr Ser Pro Ser Phe Gln Gly Gln Val Thr Ile Ser Val
                900                 905                 910
Asp Lys Ser Val Ser Thr Ala Tyr Leu Gln Trp Ser Ser Leu Lys Pro
            915                 920                 925
Ser Asp Ser Ala Val Tyr Phe Cys Ala Arg His Asp Val Gly Tyr Cys
930                 935                 940
Thr Asp Arg Thr Cys Ala Lys Trp Pro Glu Trp Leu Gly Val Trp Gly
945                 950                 955                 960
Gln Gly Thr Leu Val Thr Val Ser Ser Gly Gly Gly Gly Ser Ser Gly
                965                 970                 975
Gly Gly Ser Gly Gly Gly Ser Gln Ser Val Leu Thr Gln Pro Pro
            980                 985                 990
Ser Val Ser Ala Ala Pro Gly Gln Lys Val Thr Ile Ser Cys Ser Gly
            995                1000                1005
Ser Ser Ser Asn Ile Gly Asn Asn Tyr Val Ser Trp Tyr Gln Gln
            1010                1015                1020
Leu Pro Gly Thr Ala Pro Lys Leu Leu Ile Tyr Asp His Thr Asn
            1025                1030                1035
Arg Pro Ala Gly Val Pro Asp Arg Phe Ser Gly Ser Lys Ser Gly
            1040                1045                1050
Thr Ser Ala Ser Leu Ala Ile Ser Gly Phe Arg Ser Glu Asp Glu
            1055                1060                1065
Ala Asp Tyr Tyr Cys Ala Ser Trp Asp Tyr Thr Leu Ser Gly Trp
            1070                1075                1080
Val Phe Gly Gly Gly Thr Lys Leu Thr Val Leu Gly
            1085                1090                1095
```

<210> SEQ ID NO 19
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gatattcaga tgacccagtc cccaagctcc ctgagtgcct cagtgggcga ccgagtcacc      60
atcacatgca aggcttccca ggatgtgtct attggagtcg catggtacca gcagaagcca     120
ggcaaagcac ccaagctgct gatctatagc gcctcctacc ggtataccgg cgtgccctct     180
agattctctg gcagtgggtc aggaacagac tttactctga ccatctctag tctgcagcct     240
gaggatttcg ctacctacta ttgccagcag tactatatct acccatatac ctttggccag     300
gggacaaaag tggagatcaa gaggactgtg gccgctccct ccgtcttcat ttttcccccct    360
tctgacgaac agctgaaaag tggcacagcc agcgtggtct gtctgctgaa caatttctac     420
cctcgcgaag ccaaagtgca gtggaaggtc gataacgctc tgcagagcgg caacagccag     480
gagtctgtga ctgaacagga cagtaaagat tcaacctata gcctgtcaag cacactgact     540
ctgagcaagg cagactacga gaagcacaaa gtgtatgcct gcgaagtcac acatcagggg     600
ctgtcctctc ctgtgactaa gagctttaac agaggagagt gt                        642
```

<210> SEQ ID NO 20
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

180                 185                 190
Ala Cys Glu Val Thr His Gln Gly Leu Ser Ser Pro Val Thr Lys Ser
         195                 200                 205

Phe Asn Arg Gly Glu Cys
     210

<210> SEQ ID NO 21
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gaagtgcagc tggtcgaatc tggaggagga ctggtgcagc caggagggtc cctgcgcctg      60
tcttgcgccg ctagtggctt cacttttacc gactacacca tggattgggt gcgacaggca     120
cctggaaagg gcctggagtg ggtcgccgat gtgaacccaa atagcggagg ctccatctac     180
aaccagcggt tcaagggccg gttcacccty tcagtggacc ggagcaaaaa caccctgtat     240
ctgcagatga atagcctgcg agccgaagat actgctgtgt actattgcgc ccggaatctg     300
gggccctcct tctactttga ctattggggg cagggaactc tggtcaccgt gagctccgcc     360
tccaccaagg gccttctgt gttcccactg gctccctcta gtaaatccac atctggggga     420
actgcagccc tgggctgtct ggtgaaggac tacttcccag agcccgtcac agtgtcttgg     480
aacagtggcg ctctgacttc tggggtccac acctttcctg cagtgctgca gtcaagcggg     540
ctgtacagcc tgtcctctgt ggtcaccgtg ccaagttcaa gcctgggaac acagacttat     600
atctgcaacg tgaatcacaa gccatccaat acaaaagtcg acaagaaagt ggaacccaag     660
tcttgtgata aacccatac atgccccct tgtcctgcac cagagctgct gggaggacca     720
agcgtgttcc tgtttccacc caagcctaaa gatacactga tgattagtag gaccccagaa     780
gtcacatgcg tggtcgtgga cgtgagccac gaggaccccg aagtcaagtt taactggtac     840
gtggacggcg tcgaggtgca taatgccaag actaaaccca gggaggaaca gtacaacagt     900
acctatcgcg tcgtgtcagt cctgacagtg ctgcatcagg attggctgaa cgggaaagag     960
tataagtgca agtgagcaa taaggctctg cccgcaccta tcgagaaaac aatttccaag    1020
gcaaaaggac agcctagaga accacaggtg tacgtgctgc ctccatcaag ggatgagctg    1080
acaaagaacc aggtcagcct gctgtgtctg gtgaaaggat tctatccctc tgacattgct    1140
gtggagtggg aaagtaatgg ccagcctgag aacaattacc tgacctggcc ccctgtgctg    1200
gactcagatg gcagcttctt tctgtatagc aagctgaccg tcgacaaatc ccggtggcag    1260
caggggaatg tgtttagttg ttcagtcatg cacgaggcac tgcacaacca ttacacccag    1320
aagtcactgt cactgtcacc aggg                                           1344

<210> SEQ ID NO 22
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Thr Asp Tyr
             20                  25                  30

Thr Met Asp Trp Val Arg Gln Ala Pro Gly Lys Gly Leu Glu Trp Val
         35                  40                  45

Ala Asp Val Asn Pro Asn Ser Gly Gly Ser Ile Tyr Asn Gln Arg Phe
     50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Leu Pro Pro Ser Arg Asp Glu Leu Thr Lys Asn Gln Val Ser Leu Leu
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Leu Thr Trp Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
```

<210> SEQ ID NO 23
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
gaagtgcagc tggtcgaatc tggaggagga ctggtgcagc caggagggtc cctgcgcctg      60
tcttgcgccg ctagtggctt cacttttacc gactacacca tggattgggt gcgacaggca     120
cctggaaagg gcctggagtg ggtcgccgat gtgaacccaa atagcggagg ctccatctac     180
aaccagcggt tcaagggccg gttcaccctg tcagtggacc ggagcaaaaa caccctgtat     240
ctgcagatga atagcctgcg agccgaagat actgctgtgt actattgcgc ccggaatctg     300
gggccctcct tctactttga ctattggggg cagggaactc tggtcaccgt gagctccgcc     360
tccaccaagg gaccttctgt gttcccactg gctccctcta gtaaatccac atctggggga     420
actgcagccc tgggctgtct ggtgaaggac tacttcccag agcccgtcac agtgtcttgg     480
aacagtggcg ctctgacttc tggggtccac acctttcctg cagtgctgca gtcaagcggg     540
ctgtacagcc tgtcctctgt ggtcaccgtg ccaagttcaa gcctgggaac acagacttat     600
atctgcaacg tgaatcacaa gccatccaat acaaaagtcg acaagaaagt ggaacccaag     660
tcttgtgata aaacccatac atgccccccct tgtcctgcac cagagctgct gggaggacca     720
agcgtgttcc tgtttccacc caagcctaaa gatacactga tgattagtag gaccccagaa     780
gtcacatgcg tggtcgtgga cgtgagccac gaggacccecg aagtcaagtt taactgtgac     840
gtggacggcg tcgaggtgca taatgccaag actaaaccca gggaggaaca gtacaacagt     900
acctatcgcg tcgtgtcagt cctgacagtg ctgcatcagg attggctgaa cgggaaagag     960
tataagtgca aagtgagcaa taaggctctg cccgcaccta tcgagaaaac aatttccaag    1020
gcaaaaggac agcctagaga accacaggtg tacgtgtatc ctccatcaag ggatgagctg    1080
acaaagaacc aggtcagcct gacttgtctg gtgaaaggat tctatccctc tgacattgct    1140
gtggagtggg aaagtaatgg ccagcctgag aacaattaca agaccacacc cctgtgctg    1200
gactcagatg gcagcttcgc gctggtgagc aagctgaccg tcgacaaatc ccggtggcag    1260
caggggaatg tgtttagttg ttcagtcatg cacgaggcac tgcacaacca ttacacccag    1320
aagtcactgt cactgtcacc aggg                                           1344
```

<210> SEQ ID NO 24
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45
```

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Tyr Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Ala Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 25
<211> LENGTH: 1350
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 25

```
gaagtccagc tggtcgaaag cggaggagga ctggtgcagc caggagggtc tctgcgactg      60
agttgcgccg cttcaggctt caacatcaag gacacctaca ttcactgggt gcgccaggct     120
cctggaaaag gcctggagtg ggtggcacga atctatccaa ctaatggata cacccggtat     180
gcagacagcg tgaagggccg gttcaccatt agcgcagata catccaaaaa cactgcctac     240
ctgcagatga acagcctgcg agccgaagat actgctgtgt actattgcag tcggtgggga     300
ggcgacggct tctacgctat ggattattgg gggcagggaa ccctggtcac agtgagctcc     360
gcatctacaa aggggcctag tgtgtttcca ctggcccoct ctagtaaatc cacctctggg     420
ggaacagcag ccctgggatg tctggtgaag gactatttcc cagagcccgt cactgtgagt     480
tggaactcag gcgccctgac atccggggtc atacttttc ctgctgtgct gcagtcaagc     540
ggcctgtact ctctgtcctc tgtggtcacc gtgccaagtt caagcctggg gactcagacc     600
tatatctgca acgtgaatca caagccaagc aatacaaaag tcgacaagaa agtggaaccc     660
aagagctgtg ataaaacaca tacttgcccc ccttgtcctg caccagagct gctgggagga     720
ccatccgtgt tcctgtttcc acccaagcct aaagacaccc tgatgatttc aggactcca      780
gaagtcacct gcgtggtcgt ggacgtgtct cacgaggacc ccgaagtcaa gttcaactgg     840
tacgtggatg gcgtcgaggt gcataatgcc aagacaaaac ccaggagga acagtacaac      900
tcaacttatc gcgtcgtgag cgtcctgacc gtgctgcacc aggactggct gaacggcaag     960
gagtataagt gcaaagtgag caataaggct ctgcccgcac ctatcgagaa aaccattagc    1020
aaggccaaag ggcagcctag agaaccacag gtctacgtgt atcctccaag cagggacgag    1080
ctgaccaaga accaggtctc cctgacatgt ctggtgaaag gttttacccc cagtgatatc    1140
gctgtggagt gggaatcaaa tggacagcct gaaaacaatt ataagaccac accccctgtg    1200
ctggacagcg atggcagctt cgctctggtc tccaagctga ctgtggataa atctcggtgg    1260
cagcagggca acgtctttag ttgttcagtg atgcatgagg cactgcacaa tcattacacc    1320
cagaagagcc tgtccctgtc tcccggcaaa                                     1350
```

<210> SEQ ID NO 26
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 27
<211> LENGTH: 696
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 27

```
gaacctaaaa gcagcgacaa gacccacaca tgccccccctt gtccagctcc agaactgctg    60
ggaggaccaa gcgtgttcct gtttccaccc aagcccaaag atacactgat gatcagccga   120
actcccgagg tcacctgcgt ggtcgtggac gtgtcccacg aggaccccga agtcaagttc   180
aactggtacg tggacggcgt cgaagtgcat aatgcaaaga ctaaaccacg ggaggaacag   240
tacaactcta catatagagt cgtgagtgtc ctgactgtgc tgcatcagga ttggctgaac   300
ggcaaagagt ataagtgcaa agtgtctaat aaggccctgc ctgctccaat cgagaaaact   360
attagtaagg caaaagggca gcccagggaa cctcaggtct acgtgctgcc tccaagtcgc   420
gacgagctga ccaagaacca ggtctcactg ctgtgtctgg tgaaaggatt ctatccttcc   480
gatattgccg tggagtggga atctaatggc cagccagaga caattacct gacctggccc    540
cctgtgctgg acagcgatgg gtccttcttt ctgtattcaa agctgacagt ggacaaaagc   600
agatggcagc agggaaacgt ctttagctgt tccgtgatgc acgaagccct gcacaatcat   660
tacacccaga gtctctgag tctgtcacct ggcaaa                               696
```

<210> SEQ ID NO 28
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Glu Pro Lys Ser Ser Asp Lys Thr His Thr Cys Pro Pro Cys Pro Ala
1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Val Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
```

Ser Leu Ser Leu Ser Pro Gly Lys
225                 230

<210> SEQ ID NO 29
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gatattcaga tgacccagtc ccctagctcc ctgtccgctt ctgtgggcga cagggtcact     60
atcacctgcc gcgcatctca ggatgtgaac accgcagtcg cctggtacca gcagaagcct    120
gggaaagctc caaagctgct gatctacagt gcatcattcc tgtattcagg agtgcccagc    180
cggtttagcg gcagcagatc tggcaccgac ttcacactga ctatctctag tctgcagcct    240
gaggattttg ccacatacta ttgccagcag cactatacca caccccctac tttcggccag    300
gggaccaaag tggagatcaa gcgaactgtg gccgctccaa gtgtcttcat ttttccaccc    360
agcgacgaac agctgaaatc cggcacagct tctgtggtct gtctgctgaa caacttctac    420
cccagagagg ccaaagtgca gtggaaggtc gataacgctc tgcagagtgg caacagccag    480
gagagcgtga cagaacagga ctccaaagat tctacttata gtctgtcaag caccctgaca    540
ctgagcaagg cagactacga aaagcataaa gtgtatgcct gtgaggtgac ccatcagggg    600
ctgtcttctc ccgtgaccaa gtctttcaac cgaggcgaat gt                       642

<210> SEQ ID NO 30
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gacatccaga tgacacagtc ccccagctcc ctgagtgcat cagtgggcga cagggtcaca      60
attacttgcc gcgcttccca ggatgtgaac accgctgtcg catggtacca gcagaagcct    120
ggaaaagcac caaagctgct gatctacagc gcctccttcc tgtattccgg cgtgccctct    180
cggttttctg gaagtagatc aggcacagac ttcaccctga caatttctag tctgcagcct    240
gaggattttg ccacttacta ttgccagcag cactatacca cccccctac attcggccag     300 gggactaaag tggagatcaa gcgaaccgtg gccgctcctt ccgtcttcat ttttccaccc    360
tctgacgaac agctgaaaag tggacagcc tcagtggtct gtctgctgaa caattttac     420 ccaagagaag ctaaagtgca gtggaaggtc gataacgcac tgcagagcgg caattcccag    480
gagtctgtga ccgaacagga cagtaaagat tcaacatata gcctgtcaag cactctgacc    540
ctgtctaagg ccgattacga aagcacaaa gtgtatgctt gcgaagtcac tcatcagggc    600
ctgtcctctc ccgtgaccaa gagcttcaat cgggggagt gt                        642

<210> SEQ ID NO 32
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 33
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gaagtccagc tggtcgaaag cggaggagga ctggtgcagc caggagggtc tctgcgactg      60
agttgcgccg cttcaggctt caacatcaag gacacctaca ttcactgggt gcgccaggct     120
cctggaaaag gcctggagtg ggtggcacga atctatccaa ctaatggata cacccggtat     180
gcagacagcg tgaagggccg gttcaccatt agcgcagata catccaaaaa cactgcctac     240
ctgcagatga acagcctgcg agccgaagat actgctgtgt actattgcag tcggtgggga     300
ggcgacggct tctacgctat ggattattgg ggcagggaa ccctggtcac agtgagctcc      360
gcatctacaa aggggcctag tgtgtttcca ctggcccct ctagtaaatc cacctctggg      420
ggaacagcag ccctgggatg tctggtgaag gactatttcc cagagcccgt cactgtgagt     480
tggaactcag gcgccctgac atccggggtc catacttttc ctgctgtgct gcagtcaagc     540
ggcctgtact ctctgtcctc tgtggtcacc gtgccaagtt caagcctggg gactcagacc     600
tatatctgca acgtgaatca caagccaagc aatacaaaag tcgacaagaa agtggaaccc     660
aagagctgtg ataaaacaca tacttgcccc ccttgtcctg caccagagct gctgggagga     720
ccatccgtgt tcctgtttcc acccaagcct aaagacaccc tgatgatttc caggactcca     780
gaagtcacct gcgtggtcgt ggacgtgtct cacgaggacc ccgaagtcaa gttcaactgg     840
tacgtggatg gcgtcgaggt gcataatgcc aagacaaaac ccagggagga acagtacaac     900
tcaacttatc gcgtcgtgag cgtcctgacc gtgctgcacc aggactggct gaacggcaaa     960
gagtataagt gcaaagtgag caataaggct ctgcccgcac tatcgagaa aaccattagc    1020
aaggccaaag gcagcctag agaaccacag gtctacgtgt atcctccaag cagggacgag    1080
ctgaccaaga accaggtctc cctgacatgt ctggtgaaag gtttttaccc cagtgatatc    1140
gctgtggagt gggaatcaaa tggacagcct gaaaacaatt ataagaccac ccccctgtg    1200
ctggacagcg atggcagctt cgctctggtc tccaagctga ctgtggataa atctcggtgg    1260
cagcagggca acgtctttag ttgttcagtg atgcatgagg cactgcacaa tcattacacc    1320
cagaagagcc tgtccctgtc tcccggc                                        1347

<210> SEQ ID NO 34
<211> LENGTH: 449
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380
```

| Glu | Ser | Asn | Gly | Gln | Pro | Glu | Asn | Asn | Tyr | Lys | Thr | Thr | Pro | Pro | Val |
| --- | --- | --- | --- | --- | --- | --- | --- | --- | --- | --- | --- | --- | --- | --- | --- |
| 385 | | | | 390 | | | | | 395 | | | | | 400 | |

| Leu | Asp | Ser | Asp | Gly | Ser | Phe | Ala | Leu | Val | Ser | Lys | Leu | Thr | Val | Asp |
| --- | --- | --- | --- | --- | --- | --- | --- | --- | --- | --- | --- | --- | --- | --- | --- |
| | | | 405 | | | | | 410 | | | | | 415 | | |

| Lys | Ser | Arg | Trp | Gln | Gln | Gly | Asn | Val | Phe | Ser | Cys | Ser | Val | Met | His |
| --- | --- | --- | --- | --- | --- | --- | --- | --- | --- | --- | --- | --- | --- | --- | --- |
| | | 420 | | | | | 425 | | | | | 430 | | | |

| Glu | Ala | Leu | His | Asn | His | Tyr | Thr | Gln | Lys | Ser | Leu | Ser | Leu | Ser | Pro |
| --- | --- | --- | --- | --- | --- | --- | --- | --- | --- | --- | --- | --- | --- | --- | --- |
| | | | 435 | | | | 440 | | | | | 445 | | | |

Gly

<210> SEQ ID NO 35
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gacattcaga tgacacagag ccccagctcc ctgagtgctt cagtcggcga cagggtgact    60
atcacctgcc gcgcatccca ggatgtcaac accgctgtgg catggtacca gcagaagcct   120
ggaaaagccc caaagctgct gatctacagc gcttccttcc tgtattctgg cgtgccaagt   180
cggttttctg gaagtagatc aggcactgac ttcacactga ctatctctag tctgcagccc   240
gaagattttg ccacctacta ttgccagcag cactatacca caccccctac attcggacag   300
ggcactaaag tggagattaa gggcgggtca ggcggaggga gcggaggagg gtccggagga   360
gggtctggag gagggagtgg agaggtccag ctggtggaat ctggaggagg actggtgcag   420
cctggaggct cactgcgact gagctgtgcc gcttccggct ttaacatcaa agacacatac   480
attcattggg tcaggcaggc caccgggaag ggactggaat gggtggcccg catctatccc   540
acaaatgggt acactcgata tgccgacagc gtgaaaggac ggtttaccat ttctgctgat   600
accagtaaga cacagcata cctgcagatg aacagcctgc gcgcagagga tacagccgtg   660
tactattgca gtcgatgggg gggagacggc ttctacgcca tggattattg gggccagggg   720
actctggtca ccgtgtcaag cgcagccgaa cctaaatcct ctgacaagac ccacacatgc   780
ccaccctgtc ctgctccaga gctgctggga ggaccatccg tgttcctgtt cctcccaaag   840
cctaaagata cactgatgat tagccgcact cccgaagtca cctgtgtggt cgtggacgtg   900
tcccacgagg accccgaagt caagttcaac tggtacgtgg acggcgtcga ggtgcataat   960
gccaagacta aaccaagaga ggaacagtac aattcaacct atagggtcgt gagcgtcctg  1020
acagtgctgc atcaggattg gctgaacggc aaggagtata agtgcaaagt gtctaacaag  1080
gccctgcccg ctcctatcga aagactatt agcaaggcaa aagggcagcc acgggaaccc  1140
caggtctacg tgctgccccc tagcagagac gagctgacca aaaaccaggt ctccctgctg  1200
tgtctggtga agggcttta tcctagtgat atcgctgtgg agtgggaatc aaatgggcag  1260
ccagaaaaca attacctgac atggccaccc gtgctggaca gcgatgggtc cttctttctg  1320
tattccaaac tgactgtgga caagtctaga tggcagcagg gaaacgtctt cagctgttcc  1380
gtgatgcacg aggccctgca caatcattac acccagaagt ctctgagtct gtcacccggc  1440
```

<210> SEQ ID NO 36
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Ser Gly Gly Ser Gly Gly Glu
        115                 120                 125

Val Gln Leu Val Glu Ser Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ala Glu Pro Lys Ser Ser Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Val
    370                 375                 380

Leu Pro Pro Ser Arg Asp Glu Leu Thr Lys Asn Gln Val Ser Leu Leu

```
                   385                 390                 395                 400
Cys Leu Val Lys Gly Phe Tyr Pro Ser Asp Ile Ala Val Glu Trp Glu
                405                 410                 415

Ser Asn Gly Gln Pro Glu Asn Asn Tyr Leu Thr Trp Pro Pro Val Leu
            420                 425                 430

Asp Ser Asp Gly Ser Phe Phe Leu Tyr Ser Lys Leu Thr Val Asp Lys
            435                 440                 445

Ser Arg Trp Gln Gln Gly Asn Val Phe Ser Cys Ser Val Met His Glu
        450                 455                 460

Ala Leu His Asn His Tyr Thr Gln Lys Ser Leu Ser Leu Ser Pro Gly
465                 470                 475                 480

<210> SEQ ID NO 37
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gacattcaga tgacacagag ccccagctcc ctgagtgctt cagtcggcga cagggtgact      60
atcacctgcc gcgcatccca ggatgtcaac accgctgtgg catggtacca gcagaagcct    120
ggaaaagccc caaagctgct gatctacagc gcttccttcc tgtattctgg cgtgccaagt    180
cggttttctg gaagtagatc aggcactgac ttcacactga ctatctctag tctgcagccc    240
gaagattttg ccacctacta ttgccagcag cactatacca cccccctac attcggatgc     300 ggcactaaag tggagattaa gggcgggtca ggcggaggga gcggaggagg gtccggagga    360
gggtctggag gagggagtgg agaggtccag ctggtggaat ctggaggagg actggtgcag    420
cctggaggct cactgcgact gagctgtgcc gcttccggct taacatcaa agacacatac     480 attcattggg tcaggcaggc caccgggaag tgcctggaat gggtggcccg catctatccc    540
acaaatgggt acactcgata tgccgacagc gtgaaggac ggtttaccat ttctgctgat     600
accagtaaga cacagcata cctgcagatg aacagcctgc gcgcagagga tacagccgtg     660
tactattgca gtcgatgggg gggagacggc ttctacgcca tggattattg gggccagggg    720
actctggtca ccgtgtcaag cgcagccgaa cctaaatcct ctgacaagac ccacacatgc    780
ccaccctgtc ctgctccaga gctgctggga ggaccatccg tgttcctgtt cctccaaag    840 cctaaagata cactgatgat tagccgcact cccgaagtca cctgtgtggt cgtggacgtg    900
tcccacgagg accccgaagt caagttcaac tggtacgtgg acggcgtcga ggtgcataat    960
gccaagacta aaccaagaga ggaacagtac aattcaacct ataggtcgt gagcgtcctg   1020 acagtgctgc atcaggattg gctgaacggc aaggagtata gtgcaaagt gtctaacaag   1080 gccctgcccg ctcctatcga gaagactatt agcaaggcaa aagggcagcc acggaaccc    1140 caggtctacg tgctgccccc tagcagagac gagctgacca aaaaccaggt ctccctgctg   1200
tgtctggtga agggcttta tcctagtgat atcgctgtgg agtgggaatc aaatgggcag   1260
ccagaaaaca attacctgac atggccaccc gtgctggaca gcgatgggtc cttctttctg   1320
tattccaaac tgactgtgga caagtctaga tggcagcagg gaaacgtctt cagctgttcc   1380
gtgatgcacg aggccctgca caatcattac acccagaagt ctctgagtct gtcacccggc   1440

<210> SEQ ID NO 38
<211> LENGTH: 480
```

<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Ser Gly Gly
            100                 105                 110

Gly Ser Gly Gly Gly Ser Gly Gly Gly Ser Gly Gly Gly Ser Gly Glu
        115                 120                 125

Val Gln Leu Val Glu Ser Gly Gly Gly Leu Val Gln Pro Gly Gly Ser
130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ala Glu Pro Lys Ser Ser Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Val
    370                 375                 380

```
Leu Pro Pro Ser Arg Asp Glu Leu Thr Lys Asn Gln Val Ser Leu Leu
385                 390                 395                 400

Cys Leu Val Lys Gly Phe Tyr Pro Ser Asp Ile Ala Val Glu Trp Glu
            405                 410                 415

Ser Asn Gly Gln Pro Glu Asn Asn Tyr Leu Thr Trp Pro Pro Val Leu
        420                 425                 430

Asp Ser Asp Gly Ser Phe Phe Leu Tyr Ser Lys Leu Thr Val Asp Lys
    435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

<210> SEQ ID NO 39
<211> LENGTH: 1443
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
caggtccagc tgcaggagag cggaggaggg ctggtcaaac ccggaggatc actgagactg      60
tcatgtgctg cttcaggatt cacttttagc tcctactgga tgtcttgggt gagacaggct     120
cctggcaagt gcctggagtg ggtggccaac atcaataggg acggctccgc ttcttactat     180
gtggatagcg tcaaggggag gttcactatt cccgcgacg atgcaaaaaa ctctctgtac      240
ctgcagatga atagcctgcg cgccgaagac accgctgtgt actattgtgc ccgggacaga     300
ggagtcggct attttgatct gtggggcga ggaactctgg tgaccgtctc tagtgccagc      360
accggaggag gaggctctgg aggaggaggg agtggaggcg ggggaagtca gtcagctctg     420
acccagccag caagcgtgtc cggatctccc ggccagagta tcacaatttc atgcaccggc     480
acatcaagcg atgtgggcgg gtacaacttc gtcagctggt atcagcagca ccccgggaag     540
gcacctaaac tgatgatcta cgacgtgtcc gatcgaccct ccggcgtctc tgaccggttt     600
agtgggtcaa agagcggaaa taccgccagc ctgatcattt ccggactgca ggcagacgat     660
gaggccgatt actattgctc ctcttatggc agttcaagca cacatgtgat tttcggctgt     720
gggactaaag tcaccgtgct gggagctgcc gaaccaaaaa gtagtgacaa acccataccc     780
tgccccccct gccggcgcc agaactgctg gaggaccaa gcgtgttcct gtttccaccc      840
aagcctaaag acaccctgat gatttcccgg actcctgagg tcacctgcgt ggtcgtggac     900
gtgtctcacg aggaccccga agtcaagttc aactggtacg tggatggcgt cgaagtgcat     960
aatgccaaga ccaaaccccg ggaggaacag tacaactcta cctatagagt cgtgagtgtc    1020
ctgacagtgc tgcaccagga ctggctgaat gggaaggagt ataagtgtaa agtgagcaac    1080
aaagccctgc ccgccccaat cgaaaaaaca atctctaaag caaaggaca gcctcgcgaa     1140 ccacaggtct acgtgctgcc ccctagccgc gacgaactga ctaaaaatca ggtctctctg    1200
ctgtgtctgg tcaaaggatt ctacccttcc gacatcgccg tggagtggga agtaacggc     1260 cagcccgaga acaattacct gacctggccc cctgtgctgg actctgatgg gagtttcttt    1320
ctgtattcaa agctgacagt cgataaaagc cggtggcagc agggcaatgt gttcagctgc    1380
tccgtcatgc acgaagcact gcacaaccat tacactcaga gtccctgtc cctgtcacct     1440 ggc                                                                 1443
```

<210> SEQ ID NO 40
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Cys Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Gly Gly Gly Ser Gly Gly
        115                 120                 125

Gly Gly Ser Gly Gly Gly Ser Gln Ser Ala Leu Thr Gln Pro Ala
130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
        195                 200                 205

Ala Ser Leu Ile Ile Ser Gly Leu Gln Ala Asp Asp Glu Ala Asp Tyr
    210                 215                 220

Tyr Cys Ser Ser Tyr Gly Ser Ser Thr His Val Ile Phe Gly Cys
225                 230                 235                 240

Gly Thr Lys Val Thr Val Leu Gly Ala Ala Glu Pro Lys Ser Ser Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu

```
              355                 360                 365
Lys Thr Ile Ser Lys Ala Lys Gly Gln Pro Arg Glu Pro Gln Val Tyr
370                 375                 380

Val Leu Pro Pro Ser Arg Asp Glu Leu Thr Lys Asn Gln Val Ser Leu
385                 390                 395                 400

Leu Cys Leu Val Lys Gly Phe Tyr Pro Ser Asp Ile Ala Val Glu Trp
                405                 410                 415

Glu Ser Asn Gly Gln Pro Glu Asn Asn Tyr Leu Thr Trp Pro Pro Val
                420                 425                 430

Leu Asp Ser Asp Gly Ser Phe Phe Leu Tyr Ser Lys Leu Thr Val Asp
                435                 440                 445

Lys Ser Arg Trp Gln Gln Gly Asn Val Phe Ser Cys Ser Val Met His
                450                 455                 460

Glu Ala Leu His Asn His Tyr Thr Gln Lys Ser Leu Ser Leu Ser Pro
465                 470                 475                 480

Gly

<210> SEQ ID NO 41
<211> LENGTH: 1443
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caggtccagc tgcaggagag cggaggaggg ctggtcaaac cggaggatc actgagactg      60 tcatgtgctg cttcaggatt cactttagc tcctactgga tgtcttgggt gagacaggct    120
cctggcaagt gcctggagtg ggtggccaac atcaataggg acggctccgc ttcttactat    180
gtggatagcg tcaaggggag gttcactatt tcccgcgacg atgcaaaaaa ctctctgtac    240
ctgcagatga atagcctgcg cgccgaagac accgctgtgt actattgtgc ccgggacaga    300
ggagtcggct attttgatct gtggggcga ggaactctgg tgaccgtctc tagtgccagc    360
accggaggag gaggctctgg aggaggaggg agtggaggcg ggggaagtca gtcagctctg    420
acccagccag caagcgtgtc cggatctccc ggccagagta tcacaatttc atgcaccggc    480
acatcaagcg atgtgggcgg gtacaacttc gtcagctggt atcagcagca ccccgggaag    540
gcacctaaac tgatgatcta cgacgtgtcc gatcgaccct ccggcgtctc tgaccggttt    600
agtgggtcaa agagcggaaa taccgccagc ctgaccattt ccggactgca ggcagacgat    660
gaggccgatt actattgctc ctcttatggc agttcaagca cacatgtgat tttcggctgt    720
gggactaaag tcaccgtgct gggagctgcc gaaccaaaaa gtagtgacaa acccataccc    780
tgccccccct gcccggcgcc agaactgctg ggaggaccaa gcgtgttcct gtttccaccc    840
aagcctaaag acaccctgat gatttcccgg actcctgagg tcacctgcgt ggtcgtggac    900
gtgtctcacg aggaccccga agtcaagttc aactggtacg tggatggcgt cgaagtgcat    960
aatgccaaga ccaaacccg ggaggaacag tacaactcta cctatagagt cgtgagtgtc   1020
ctgacagtgc tgcaccagga ctggctgaat gggaaggagt ataagtgtaa agtgagcaac   1080
aaagccctgc ccgccccaat cgaaaaaaca atctctaaag caaaggaca gcctcgcgaa   1140 ccacaggtct acgtgctgcc cctagccgc gacgaactga ctaaaaatca ggtctctctg   1200
ctgtgtctgg tcaaaggatt ctaccttcc gacatcgccg tggagtggga agtaacggc   1260 cagcccgaga acaattacct gacctggccc cctgtgctgg actctgatgg gagttctctt   1320
```

-continued

```
ctgtattcaa agctgacagt cgataaaagc cggtggcagc agggcaatgt gttcagctgc    1380
tccgtcatgc acgaagcact gcacaaccat tacactcaga agtccctgtc cctgtcacct    1440
ggc                                                                  1443
```

<210> SEQ ID NO 42
<211> LENGTH: 481
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Cys Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Val Gly Gly Tyr Asn Phe Val Ser Trp Tyr Gln Gln
                165                 170                 175

His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
        195                 200                 205

Ala Ser Leu Thr Ile Ser Gly Leu Gln Ala Asp Asp Glu Ala Asp Tyr
    210                 215                 220

Tyr Cys Ser Ser Tyr Gly Ser Ser Thr His Val Ile Phe Gly Cys
225                 230                 235                 240

Gly Thr Lys Val Thr Val Leu Gly Ala Ala Glu Pro Lys Ser Ser Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
```

```
            325                 330                 335
Val Val Ser Val Leu Thr Val Leu His Gln Asp Trp Leu Asn Gly Lys
        340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Val Leu Pro Pro Ser Arg Asp Glu Leu Thr Lys Asn Gln Val Ser Leu
385                 390                 395                 400

Leu Cys Leu Val Lys Gly Phe Tyr Pro Ser Asp Ile Ala Val Glu Trp
                405                 410                 415

Glu Ser Asn Gly Gln Pro Glu Asn Asn Tyr Leu Thr Trp Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly
```

```
<210> SEQ ID NO 43
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
cagagcgcac tgactcagcc tgcttccgtg tccggctccc ctgggcagag tattacaatc      60
tcatgcactg gcacctcatc cgacgtgggc gggtacaact tgtcagctg gtatcagcag     120 cacccaggca aggcccccaa actgatgatc tacgacgtgt ccgatcggcc ttccggggtc     180
tctgacagat ctctccggatc taagagtggc aataccgcca gcctgatcat ttccgggctg     240
caggcagacg atgaggccga ttactattgc agctcctatg gatctagttc aacacatgtg     300
atcttcggag cgggaccaa ggtgacagtc ctggggcagc ctaaagcggc gccctctgtg      360
actctgtttc ccctagctc cgaggaactg caggctaaca aggcaactct ggtgtgtctg     420
attagcgact ctacccagg agctgtgacc gtcgcctgga aggctgattc tagtcccgtg     480
aaagcaggcg tcgagaccac aactcctagt aagcagtcaa caacaagta cgcagcctca     540 agctatctgt ctctgacacc cgaacagtgg aaaagtcaca ggtcatatag ctgccaggtg     600
actcacgagg gctcaactgt ggagaaaacc gtcgcaccaa ccgaatgttc c              651
```

```
<210> SEQ ID NO 44
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
```

```
                    20                  25                  30
Asn Phe Val Ser Trp Tyr Gln Gln His Pro Gly Lys Ala Pro Lys Leu
                35                  40                  45
Met Ile Tyr Asp Val Ser Asp Arg Pro Ser Gly Val Ser Asp Arg Phe
            50                  55                  60
Ser Gly Ser Lys Ser Gly Asn Thr Ala Ser Leu Ile Ile Ser Gly Leu
65                  70                  75                  80
Gln Ala Asp Asp Glu Ala Asp Tyr Tyr Cys Ser Ser Tyr Gly Ser Ser
                85                  90                  95
Ser Thr His Val Ile Phe Gly Gly Thr Lys Val Thr Val Leu Gly
                100                 105                 110
Gln Pro Lys Ala Ala Pro Ser Val Thr Leu Phe Pro Pro Ser Ser Glu
            115                 120                 125
Glu Leu Gln Ala Asn Lys Ala Thr Leu Val Cys Leu Ile Ser Asp Phe
        130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215

<210> SEQ ID NO 45
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
cagagcgcac tgactcagcc tgcatccgtg tccgggtccc ctgggcagag cattactatt      60
tcatgtactg gaacttcttc agacgtgggc gggtacaact tcgtgtcctg gtatcagcag     120 cacccggca aggcacctaa actgatgatc tacgacgtga gcgatcgacc aagcgggtc       180 tccgacagat tttctggaag taaatcaggc aataccgcct ctctgatcat tagtgggctg     240
caggccgacg atgaggctga ttactattgc agctcctatg gatctagtag cacccatgtc     300
attttcggag gcggaacaaa ggtcaccgtc ctgagaaccg tggcggcgcc cagtgtcttc     360
atttttcccc ctagcgacga acagctgaag tctgggacag ccagtgtggt ctgtctgctg     420
aacaacttct accctcgcga ggctaaagtg cagtggaagg tcgataacgc actgcagtcc     480
ggaaattctc aggagagtgt gactgaacag gactcaaaag atagcaccta ttccctgtca     540
agcacactga ctctgagcaa ggccgactac gagaagcata agtgtatgc ttgtgaagtc      600 acccaccagg ggctgagttc accagtcaca aaatcattca acagagggga gtgc           654

<210> SEQ ID NO 46
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 46

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Phe Val Ser Trp Tyr Gln Gln His Pro Gly Lys Ala Pro Lys Leu
        35                  40                  45
Met Ile Tyr Asp Val Ser Asp Arg Pro Ser Gly Val Ser Asp Arg Phe
    50                  55                  60
Ser Gly Ser Lys Ser Gly Asn Thr Ala Ser Leu Ile Ile Ser Gly Leu
65                  70                  75                  80
Gln Ala Asp Asp Glu Ala Asp Tyr Tyr Cys Ser Ser Tyr Gly Ser Ser
                85                  90                  95
Ser Thr His Val Ile Phe Gly Gly Gly Thr Lys Val Thr Val Leu Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 47
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
caggtccagc tgcaggaatc tggcggagga ctggtcaaac ctggaggctc tctgagactg      60
tcatgtgctg ctagtggctt actttcagc tcctactgga tgtcttgggt gcgacaggcc     120
cccggcaagg gactggagtg ggtcgcaaac atcaatagag acggatctgc cagttactat     180
gtggatagcg tcaagggccg gttcaccatt tcaagagacg atgctaaaaa cagcctgtat     240
ctgcagatga acagcctgag ggccgaagac acagctgtgt actattgcgc acgcgatcgc     300
ggcgtgggat atttcgatct gtggggccgc ggaaccctgg tgaccgtctc atctgctagc     360
actaagggc cttccgtgtt tccactggct ccctctagta aatccacctc tggaggcaca     420
gctgcactgg gatgtctggt gaaggattac ttccctgaac cagtcacagt gagttggaac     480
tcagggctc tgacaagtgg agtccatact tttcccgcag tgctgcagtc aagcggactg     540
tactccctgt cctctgtggt caccgtgcct agttcaagcc tgggcaccca gacatatatc     600
tgcaacgtga atcacaagcc atcaaataca aagtcgaca agaaagtgga gcccaagagc     660
tgtgataaaa ctcatacctg cccaccttgt ccggcgccag aactgctggg aggaccaagc     720
```

-continued

```
gtgttcctgt ttccacccaa gcctaaagac accctgatga tttcccggac tcctgaggtc    780
acctgcgtgg tcgtggacgt gtctcacgag accccgaag tcaagttcaa ctggtacgtg     840
gatggcgtcg aagtgcataa tgccaagacc aaaccccggg aggaacagta caactctacc    900
tatagagtcg tgagtgtcct gacagtgctg caccaggact ggctgaatgg aaggagtat     960 aagtgtaaag tgagcaacaa agccctgccc gccccaatcg aaaaaacaat ctctaaagca   1020
aaaggacagc ctcgcgaacc acaggtctac gtctaccccc catcaagaga tgaactgaca   1080
aaaaatcagg tctctctgac atgcctggtc aaaggattct accccttccga catcgccgtg   1140 gagtgggaaa gtaacggcca gcccgagaac aattacaaga ccacacccccc tgtcctggac   1200 tctgatggga gtttcgctct ggtgtcaaag ctgaccgtcg ataaaagccg gtggcagcag   1260
ggcaatgtgt ttagctgctc cgtcatgcac gaagccctgc acaatcacta cacacagaag   1320
tccctgagcc tgagccctgg c                                              1341
```

<210> SEQ ID NO 48
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Val Tyr
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Ala Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Asn Ile Lys Asp Thr
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Pro Thr Asn Gly
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Gly Gly Asp Gly Phe Tyr Ala Met Asp Tyr
```

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Arg Ala Ser Gln Asp Val Asn Thr Ala Val Ala
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Ser Ala Ser Phe Leu Tyr Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Gln Gln His Tyr Thr Thr Pro Pro Thr
1               5

<210> SEQ ID NO 55
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

```
<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser
        115

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Phe Thr Phe Ser Ser Tyr Trp
```

```
<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Asn Arg Asp Gly Ser Ala Ser
1               5

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Arg Asp Arg Gly Val Gly Tyr Phe Asp Leu
1               5                   10

<210> SEQ ID NO 61
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Val Thr Val Leu
            100                 105                 110

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Ser Asp Val Gly Gly Tyr Asn Phe
1               5

<210> SEQ ID NO 63
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Ser Tyr Gly Ser Ser Ser Thr His Val Ile
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Tyr Trp Met Ser
1               5

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asn Ile Asn Arg Asp Gly Ser Ala Ser Tyr Tyr Val Asp Ser Val Lys
1               5                   10                  15

Gly

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Arg Gly Val Gly Tyr Phe Asp Leu
1               5

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Gly Thr Ser Ser Asp Val Gly Gly Tyr Asn Phe Val Ser
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68
```

Asp Val Ser Asp Arg Pro Ser
1               5

<210> SEQ ID NO 69
<211> LENGTH: 217
<212> TYPE: PRT
<213> ORGANISM: Homo sapiens

<400> SEQUENCE: 69

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 70
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Ser Gly Gly Ser Gly Ser Ser
    210                 215                 220

Ala Asp Asp Ala Lys Lys Asp Ala Ala Lys Lys Asp Asp Ala Lys Lys
225                 230                 235                 240

Asp Asp Ala Lys Lys Asp Gly Gly Ser Gly Gly Ser Gly Glu
            245                 250                 255

Val Gln Leu Val Glu Ser Gly Gly Gly Leu Val Gln Pro Gly Gly Ser
            260                 265                 270

Leu Arg Leu Ser Cys Ala Ala Ser Gly Phe Asn Ile Lys Asp Thr Tyr
        275                 280                 285

Ile His Trp Val Arg Gln Ala Pro Gly Lys Gly Leu Glu Trp Val Ala
    290                 295                 300

Arg Ile Tyr Pro Thr Asn Gly Tyr Thr Arg Tyr Ala Asp Ser Val Lys
305                 310                 315                 320

Gly Arg Phe Thr Ile Ser Ala Asp Thr Ser Lys Asn Thr Ala Tyr Leu
            325                 330                 335

Gln Met Asn Ser Leu Arg Ala Glu Asp Thr Ala Val Tyr Tyr Cys Ser
        340                 345                 350

Arg Trp Gly Gly Asp Gly Phe Tyr Ala Met Asp Tyr Trp Gly Gln Gly
        355                 360                 365

Thr Leu Val Thr Val Ser Ser Ala Ser Thr Lys Gly Pro Ser Val Phe
370                 375                 380

Pro Leu Ala Pro Ser Ser Lys Ser Thr Ser Gly Gly Thr Ala Ala Leu
385                 390                 395                 400

Gly Cys Leu Val Lys Asp Tyr Phe Pro Glu Pro Val Thr Val Ser Trp
            405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
        435                 440                 445

Ser Ser Leu Gly Thr Gln Thr Tyr Ile Cys Asn Val Asn His Lys Pro
    450                 455                 460

Ser Asn Thr Lys Val Asp Lys Lys Val Glu Pro Lys Ser Cys Asp Lys
465                 470                 475                 480

Thr His Thr Cys Pro Pro Cys Pro Ala Pro Glu Leu Leu Gly Gly Pro
            485                 490                 495
```

```
Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser His Glu Asp
            515                 520                 525

Pro Glu Val Lys Phe Asn Trp Tyr Val Asp Gly Val Glu Val His Asn
        530                 535                 540

Ala Lys Thr Lys Pro Arg Glu Glu Gln Tyr Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Val
            595                 600                 605

Tyr Pro Pro Ser Arg Asp Glu Leu Thr Lys Asn Gln Val Ser Leu Thr
        610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Ala Leu Val Ser Lys Leu Thr Val Asp Lys
            660                 665                 670

Ser Arg Trp Gln Gln Gly Asn Val Phe Ser Cys Ser Val Met His Glu
            675                 680                 685

Ala Leu His Asn His Tyr Thr Gln Lys Ser Leu Ser Leu Ser Pro Gly
        690                 695                 700

<210> SEQ ID NO 71
<211> LENGTH: 697
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Gly Gly Ser Gly Gly Gly Ser Glu
    210                 215                 220

Gly Gly Gly Ser Glu Gly Gly Ser Glu Gly Gly Ser Glu Gly
225                 230                 235                 240

Gly Gly Ser Gly Gly Ser Gly Glu Val Gln Leu Val Glu Ser Gly
            245                 250                 255

Gly Gly Leu Val Gln Pro Gly Gly Ser Leu Arg Leu Ser Cys Ala Ala
            260                 265                 270

Ser Gly Phe Asn Ile Lys Asp Thr Tyr Ile His Trp Val Arg Gln Ala
        275                 280                 285

Pro Gly Lys Gly Leu Glu Trp Val Ala Arg Ile Tyr Pro Thr Asn Gly
    290                 295                 300

Tyr Thr Arg Tyr Ala Asp Ser Val Lys Gly Arg Phe Thr Ile Ser Ala
305                 310                 315                 320

Asp Thr Ser Lys Asn Thr Ala Tyr Leu Gln Met Asn Ser Leu Arg Ala
                325                 330                 335

Glu Asp Thr Ala Val Tyr Tyr Cys Ser Arg Trp Gly Gly Asp Gly Phe
            340                 345                 350

Tyr Ala Met Asp Tyr Trp Gly Gln Gly Thr Leu Val Thr Val Ser Ser
        355                 360                 365

Ala Ser Thr Lys Gly Pro Ser Val Phe Pro Leu Ala Pro Ser Ser Lys
    370                 375                 380

Ser Thr Ser Gly Gly Thr Ala Ala Leu Gly Cys Leu Val Lys Asp Tyr
385                 390                 395                 400

Phe Pro Glu Pro Val Thr Val Ser Trp Asn Ser Gly Ala Leu Thr Ser
                405                 410                 415

Gly Val His Thr Phe Pro Ala Val Leu Gln Ser Ser Gly Leu Tyr Ser
            420                 425                 430

Leu Ser Ser Val Val Thr Val Pro Ser Ser Ser Leu Gly Thr Gln Thr
        435                 440                 445

Tyr Ile Cys Asn Val Asn His Lys Pro Ser Asn Thr Lys Val Asp Lys
    450                 455                 460

Lys Val Glu Pro Lys Ser Cys Asp Lys Thr His Thr Cys Pro Pro Cys
465                 470                 475                 480

Pro Ala Pro Glu Leu Leu Gly Gly Pro Ser Val Phe Leu Phe Pro Pro
                485                 490                 495

Lys Pro Lys Asp Thr Leu Met Ile Ser Arg Thr Pro Glu Val Thr Cys
            500                 505                 510

Val Val Val Asp Val Ser His Glu Asp Pro Glu Val Lys Phe Asn Trp
        515                 520                 525

Tyr Val Asp Gly Val Glu Val His Asn Ala Lys Thr Lys Pro Arg Glu
    530                 535                 540

Glu Gln Tyr Asn Ser Thr Tyr Arg Val Val Ser Val Leu Thr Val Leu
545                 550                 555                 560

His Gln Asp Trp Leu Asn Gly Lys Glu Tyr Lys Cys Lys Val Ser Asn
                565                 570                 575

```
Lys Ala Leu Pro Ala Pro Ile Glu Lys Thr Ile Ser Lys Ala Lys Gly
                580                 585                 590

Gln Pro Arg Glu Pro Gln Val Tyr Val Tyr Pro Pro Ser Arg Asp Glu
            595                 600                 605

Leu Thr Lys Asn Gln Val Ser Leu Thr Cys Leu Val Lys Gly Phe Tyr
        610                 615                 620

Pro Ser Asp Ile Ala Val Glu Trp Glu Ser Asn Gly Gln Pro Glu Asn
625                 630                 635                 640

Asn Tyr Lys Thr Thr Pro Pro Val Leu Asp Ser Asp Gly Ser Phe Ala
                645                 650                 655

Leu Val Ser Lys Leu Thr Val Asp Lys Ser Arg Trp Gln Gln Gly Asn
            660                 665                 670

Val Phe Ser Cys Ser Val Met His Glu Ala Leu His Asn His Tyr Thr
        675                 680                 685

Gln Lys Ser Leu Ser Leu Ser Pro Gly
    690                 695

<210> SEQ ID NO 72
<211> LENGTH: 705
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Val Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser Gly Gly Ser Gly Gly Gly Ser
    210                 215                 220

Gly Ser Ser Ala Asp Asp Ala Lys Lys Asp Ala Ala Lys Lys Asp Asp
225                 230                 235                 240
```

```
Ala Lys Lys Asp Asp Ala Lys Lys Asp Gly Gly Ser Gly Gly Gly
                245                 250                 255

Ser Gly Gln Val Gln Leu Gln Glu Ser Gly Gly Gly Leu Val Lys Pro
                260                 265                 270

Gly Gly Ser Leu Arg Leu Ser Cys Ala Ala Ser Gly Phe Thr Phe Ser
            275                 280                 285

Ser Tyr Trp Met Ser Trp Val Arg Gln Ala Pro Gly Lys Gly Leu Glu
        290                 295                 300

Trp Val Ala Asn Ile Asn Arg Asp Gly Ser Ala Ser Tyr Tyr Val Asp
305                 310                 315                 320

Ser Val Lys Gly Arg Phe Thr Ile Ser Arg Asp Asp Ala Lys Asn Ser
                325                 330                 335

Leu Tyr Leu Gln Met Asn Ser Leu Arg Ala Glu Asp Thr Ala Val Tyr
                340                 345                 350

Tyr Cys Ala Arg Asp Arg Gly Val Gly Tyr Phe Asp Leu Trp Gly Arg
            355                 360                 365

Gly Thr Leu Val Thr Val Ser Ser Ala Ser Thr Lys Gly Pro Ser Val
        370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
                420                 425                 430

Leu Gln Ser Ser Gly Leu Tyr Ser Leu Ser Ser Val Val Thr Val Pro
            435                 440                 445

Ser Ser Ser Leu Gly Thr Gln Thr Tyr Ile Cys Asn Val Asn His Lys
        450                 455                 460

Pro Ser Asn Thr Lys Val Asp Lys Lys Val Glu Pro Lys Ser Cys Asp
465                 470                 475                 480

Lys Thr His Thr Cys Pro Pro Cys Pro Ala Pro Glu Leu Leu Gly Gly
                485                 490                 495

Pro Ser Val Phe Leu Phe Pro Pro Lys Pro Lys Asp Thr Leu Met Ile
                500                 505                 510

Ser Arg Thr Pro Glu Val Thr Cys Val Val Val Asp Val Ser His Glu
            515                 520                 525

Asp Pro Glu Val Lys Phe Asn Trp Tyr Val Asp Gly Val Glu Val His
        530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
                580                 585                 590

Lys Thr Ile Ser Lys Ala Lys Gly Gln Pro Arg Glu Pro Gln Val Tyr
            595                 600                 605

Val Leu Pro Pro Ser Arg Asp Glu Leu Thr Lys Asn Gln Val Ser Leu
        610                 615                 620

Leu Cys Leu Val Lys Gly Phe Tyr Pro Ser Asp Ile Ala Val Glu Trp
625                 630                 635                 640

Glu Ser Asn Gly Gln Pro Glu Asn Asn Tyr Leu Thr Trp Pro Pro Val
                645                 650                 655
```

```
Leu Asp Ser Asp Gly Ser Phe Phe Leu Tyr Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn His Tyr Thr Gln Lys Ser Leu Ser Leu Ser Pro
    690                 695                 700

Gly
705

<210> SEQ ID NO 73
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Val Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser Ser Gly Gly Ser Gly Gly Gly
    210                 215                 220

Gly Ser Glu Gly Gly Gly Ser Glu Gly Gly Gly Ser Glu Gly Gly Gly
225                 230                 235                 240

Ser Glu Gly Gly Gly Ser Gly Gly Ser Gly Gln Val Gln Leu Gln
                245                 250                 255

Glu Ser Gly Gly Gly Leu Val Lys Pro Gly Gly Ser Leu Arg Leu Ser
            260                 265                 270

Cys Ala Ala Ser Gly Phe Thr Phe Ser Ser Tyr Trp Met Ser Trp Val
        275                 280                 285

Arg Gln Ala Pro Gly Lys Gly Leu Glu Trp Val Ala Asn Ile Asn Arg
    290                 295                 300
```

Asp Gly Ser Ala Ser Tyr Tyr Val Asp Ser Val Lys Gly Arg Phe Thr
305                 310                 315                 320

Ile Ser Arg Asp Asp Ala Lys Asn Ser Leu Tyr Leu Gln Met Asn Ser
            325                 330                 335

Leu Arg Ala Glu Asp Thr Ala Val Tyr Tyr Cys Ala Arg Asp Arg Gly
                340                 345                 350

Val Gly Tyr Phe Asp Leu Trp Gly Arg Gly Thr Leu Val Thr Val Ser
            355                 360                 365

Ser Ala Ser Thr Lys Gly Pro Ser Val Phe Pro Leu Ala Pro Ser Ser
370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
            435                 440                 445

Thr Tyr Ile Cys Asn Val Asn His Lys Pro Ser Asn Thr Lys Val Asp
    450                 455                 460

Lys Lys Val Glu Pro Lys Ser Cys Asp Lys Thr His Thr Cys Pro Pro
465                 470                 475                 480

Cys Pro Ala Pro Glu Leu Leu Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
            515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Val Leu Pro Pro Ser Arg Asp
            595                 600                 605

Glu Leu Thr Lys Asn Gln Val Ser Leu Leu Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Leu Thr Trp Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
            675                 680                 685

Thr Gln Lys Ser Leu Ser Leu Ser Pro Gly
    690                 695

<210> SEQ ID NO 74
<211> LENGTH: 2112

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74

```
gatattcaga tgacccagag cccttcttcc ctgtccgctt ccgtgggaga tcgcgtgact    60
attacttgtc gagcctctca ggatgtgaac accgccgtgg cttggtacca gcagaagcct   120
ggaaaagctc caaagctgct gatctacagt gcatcattcc tgtattcagg agtcccaagc   180
cggtttagcg gcagccggtc tggcacagac ttcactctga ccattagctc cctgcagccc   240
gaggattttg ccacttacta ttgccagcag cactatacca cacccctac attcgggcag    300
ggaactaaag tggagatcaa gcgcaccgtg gccgctcctt ctgtcttcat tttccaccc    360
agtgacgaac agctgaagtc cggcacagcc tctgtggtct gtctgctgaa caatttttac   420
ccacgagaag ccaaagtgca gtggaaggtc gataacgctc tgcagagtgg caacagccag   480
gagagcgtga ccgaacagga ctccaaagat tctacatata gtctgtctag tacactgact   540
ctgagcaagg cagactacga gaagcacaaa gtgtatgctt gcgaagtcac tcatcagggc   600
ctgtcaagcc ccgtgaccaa gtccttcaat aggggagagt gtggagggag tggaggaggg   660
tcaggcagct ctgcagacga tgccaagaaa gacgcagcca agaaagatga cgccaagaaa   720
gacgatgcta agaaagatgg aggagggagc ggaggagggt ccgagaggt gcagctggtc    780
gaaagcggag aggactggt gcagcctgga ggctctctgc ggctgagttg cgctgcatca    840
ggcttcaaca tcaaagacac ctacattcat tgggtgagac aggcccccgg caagggactg   900
gagtgggtcg ccaggatcta tcctaccaat ggctacacaa gatatgccga cagcgtgaaa   960
gggcgcttca ctattagcgc agatacttcc aagaacaccg cctacctgca gatgaacagc  1020
ctgcgagctg aagatacagc agtgtactat tgtagccggt ggggcggcga tggattctac  1080
gcaatggact actggggaca gggaaccctg gtcaccgtct caagcgctag cactaagggg  1140
ccttccgtgt ttccactggc tccctctagt aaatccacct ctggaggcac agctgcactg  1200
ggatgtctgg tgaaggatta cttccctgaa ccagtcacag tgagttggaa ctcaggggct  1260
ctgacaagtg gagtccatac ttttcccgca gtgctgcagt caagcggact gtactccctg  1320
tcctctgtgg tcaccgtgcc tagttcaagc ctgggcaccc agacatatat ctgcaacgtg  1380
aatcacaagc catcaaatac aaaagtcgac aagaaagtgg agcccaagag ctgtgataaa  1440
actcatacct gcccaccttg tccggcgcca gaactgctgg gaggaccaag cgtgttcctg  1500
tttccaccca gcctaaaga cacctgatg atttcccgga ctcctgaggt cacctgcgtg   1560
gtcgtggacg tgtctcacga ggaccccgaa gtcaagttca ctggtacgt ggatggcgtc    1620
gaagtgcata atgccaagac caaaccccgg gaggaacagt acaactctac ctatagagtc  1680
gtgagtgtcc tgacagtgct gcaccaggac tggctgaatg gcaaggagta taagtgtaaa  1740
gtgagcaaca aagccctgcc cgccccaatc gaaaaaacaa tctctaaagc aaaaggacag  1800
cctcgcgaac acaggtcta cgtctacccc ccatcaagag atgaactgac aaaaaatcag   1860
gtctctctga catgcctggt caaaggattc taccttccg acatcgccgt ggagtgggaa   1920
agtaacggcc agcccgagaa caattacaag accacacccc ctgtcctgga ctctgatggg  1980
agtttcgctc tggtgtcaaa gctgaccgtc gataaaagcc ggtggcagca gggcaatgtg  2040
tttagctgct ccgtcatgca cgaagccctg cacaatcact acacacagaa gtccctgagc  2100
ctgagccctg gc                                                       2112
```

<210> SEQ ID NO 75
<211> LENGTH: 2091
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

| | | | | | |
|---|---|---|---|---|---|
| gatattcaga | tgactcagag | cccctcaagc | ctgtccgcct | ccgtgggaga | tagagtgact | 60 |
| attacttgta | gagcctcaca | ggatgtcaac | accgctgtgg | catggtacca | gcagaagcct | 120 |
| ggcaaagctc | caaagctgct | gatctactcc | gcatctttcc | tgtattctgg | ggtcccaagt | 180 |
| cggtttagtg | gctcaagaag | cgggacagac | ttcactctga | ccattagctc | cctgcagccc | 240 |
| gaggattttg | ccacttacta | ttgccagcag | cactatacca | cccccctac | attcggacag | 300 |
| ggcactaaag | tggagatcaa | gcgcaccgtg | gccgctcctt | ctgtcttcat | ttttccaccc | 360 |
| agcgacgaac | agctgaaatc | aggcacagcc | agcgtggtct | gtctgctgaa | caattttac | 420 |
| ccacgagaag | ccaaagtgca | gtggaaggtc | gataacgctc | tgcagtccgg | caattctcag | 480 |
| gagagtgtga | ccgaacagga | ctcaaaagat | agcacatatt | ccctgtctag | tacactgact | 540 |
| ctgtctaagg | cagactacga | gaagcacaaa | gtgtatgcct | gcgaagtcac | tcatcagggg | 600 |
| ctgtcaagcc | ccgtgaccaa | gagcttcaat | aggggagagt | gttccggagg | aggatctgga | 660 |
| ggaggaagtg | agggaggagg | cagcgaaggc | gggggatctg | agggaggcgg | aagtgagggc | 720 |
| ggaggatcag | gcggaggaag | cggagaggtg | cagctggtcg | aatccggagg | aggactggtg | 780 |
| cagcctggag | ggtccctgcg | actgtcttgc | gcagccagtg | gctttaacat | caaagacacc | 840 |
| tacattcatt | gggtgagaca | ggctcccggg | aagggactgg | agtgggtcgc | aaggatctat | 900 |
| cctaccaatg | gatacacaag | atatgccgac | agcgtgaaag | gccgcttcac | tatttcagca | 960 |
| gatactagca | gaaccaccgc | ctacctgcag | atgaatagcc | tgcgagccga | agatacagct | 1020 |
| gtgtactatt | gttcccggtg | gggcggagat | ggattctacg | caatggatta | ttggggacag | 1080 |
| ggaaccctgg | tcaccgtctc | aagcgctagc | actaaggggc | cttccgtgtt | tccactggct | 1140 |
| ccctctagta | atccaccctc | tggaggcaca | gctgcactgg | gatgtctggt | gaaggattac | 1200 |
| ttccctgaac | cagtcacagt | gagttggaac | tcagggggctc | tgacaagtgg | agtccatact | 1260 |
| tttcccgcag | tgctgcagtc | aagcggactg | tactccctgt | cctctgtggt | caccgtgcct | 1320 |
| agttcaagcc | tgggcaccca | gacatatatc | tgcaacgtga | atcacaagcc | atcaaataca | 1380 |
| aaagtcgaca | agaaagtgga | gcccaagagc | tgtgataaaa | ctcatacctg | cccaccttgt | 1440 |
| ccggcgccag | aactgctggg | aggaccaagc | gtgttcctgt | tccacccaa | gcctaaagac | 1500 |
| accctgatga | tttcccggac | tcctgaggtc | acctgcgtgg | tcgtggacgt | gtctcacgag | 1560 |
| gaccccgaag | tcaagttcaa | ctggtacgtg | gatggcgtcg | aagtgcataa | tgccaagacc | 1620 |
| aaaccccggg | aggaacagta | caactctacc | tatagagtcg | tgagtgtcct | gacagtgctg | 1680 |
| caccaggact | ggctgaatgg | gaaggagtat | aagtgtaaag | tgagcaacaa | agccctgccc | 1740 |
| gccccaatcg | aaaaaacaat | ctctaaagca | aaggacagc | ctcgcgaacc | acaggtctac | 1800 |
| gtctacccc | catcaagaga | tgaactgaca | aaaaatcagg | tctctctgac | atgcctggtc | 1860 |
| aaaggattct | acccttccga | catcgccgtg | gagtgggaaa | gtaacggcca | gcccgagaac | 1920 |
| aattacaaga | ccacaccccc | tgtcctggac | tctgatggga | gtttcgctct | ggtgtcaaag | 1980 |
| ctgaccgtcg | ataaaagccg | gtggcagcag | ggcaatgtgt | ttagctgctc | cgtcatgcac | 2040 |

```
gaagccctgc acaatcacta cacacagaag tccctgagcc tgagccctgg c          2091
```

```
<210> SEQ ID NO 76
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
cagagcgcac tgactcagcc cgcctccgtg tctgggtccc ctgggcagag cattactatt    60
tcatgtactg gaacaagctc cgatgtcggc gggtacaact tgtgagctg gtatcagcag   120 cacccaggaa aggcccccaa actgatgatc tacgacgtgt ccgataggcc ctctggcgtc   180
agtgaccgct tcagcggcag caagtctggc aataccgcca gtctgatcat ttcaggcctg   240
caggcagacg atgaggccga ttactattgc agctcctatg gtctagttc aactcatgtg    300 atcttcggag gcgggaccaa ggtgacagtc ctgggccagc ctaaagccgc tccaagcgtg   360
acactgtttc cccctagctc cgaggaactg caggcaaaca aggccactct ggtgtgtctg   420
atttccgact tctaccctgg ggctgtgacc gtcgcttgga aggcagattc tagtcccgtg   480
aaagcaggag tcgagaccac aactccttca aagcagagca acaacaagta cgcagcctca   540
agctatctga gtctgacacc agaacagtgg aagagccacc gcagttactc atgccaagtg   600
actcatgagg gctctactgt ggaaaaaacc gtcgcccca cagaatgttc cggaggctct    660
ggaggaggca gcgggtcctc tgccgacgat gctaagaaag acgctgcaaa gaaagacgat   720
gccaagaaag acgatgctaa gaaagatgga ggaggcagcg gaggaggctc cggacaggtg   780
cagctgcagg agtctggagg aggactggtc aagcctggag gatctctgcg actgagttgc   840
gccgcttcag gcttcacctt tagttcatac tggatgagct gggtgagaca ggccccaggc   900
aaagggctgg aatgggtcgc aaacatcaat agggacggga gcgcctccta ctatgtggat   960
agcgtcaagg gacggtttac cattagcaga gacgatgcca aaaactccct gtatctgcag  1020
atgaacagcc tgcagctgaa ggacacagca gtgtactatt gtgctcggga tagaggcgtc  1080
ggatatttcg atctgtgggg acgaggaacc ctggtcaccg tctcaagcgc tagcactaag  1140
gggccttccg tgtttccact ggctccctct agtaaatcca cctctggagg cacagctgca  1200
ctgggatgtc tggtgaagga ttacttccct gaaccagtca cagtgagttg gaactcaggg  1260
gctctgacaa gtggagtcca tacttttccc gcagtgctgc agtcaagcgg actgtactcc  1320
ctgtcctctg tggtcaccgt gcctagttca agcctgggca cccagacata tatctgcaac  1380
gtgaatcaca gccatcaaa tacaaaagtc gacaagaaag tggagcccaa gagctgtgat  1440
aaaactcata cctgcccacc ttgtccggcg ccagaactgc tgggaggacc aagcgtgttc  1500
ctgtttccac ccaagcctaa agacaccctg atgatttccc ggactcctga ggtcacctgc  1560
gtggtcgtgg acgtgtctca cgaggacccc gaagtcaagt tcaactggta cgtggatggc  1620
gtcgaagtgc ataatgccaa gaccaaaccc cgggaggaac agtacaactc tacctataga  1680
gtcgtgagtg tcctgacagt gctgcaccag gactggctga atgggaagga gtataagtgt  1740
aaagtgagca acaaagccct gccgccccca atcgaaaaaa caatctctaa agcaaaagga  1800
cagcctcgcg aaccacaggt ctacgtgctg cccctagcc gcgacgaact gactaaaaat  1860
caggtctctc tgctgtgtct ggtcaaagga ttctacccct tccgacatcg cgtggagtgg  1920
gaaagtaacg gccagcccga gaacaattac ctgacctggc cccctgtgct ggactctgat  1980
```

```
gggagtttct ttctgtattc aaagctgaca gtcgataaaa gccggtggca gcagggcaat    2040
gtgttcagct gctccgtcat gcacgaagca ctgcacaacc attacactca gaagtccctg    2100
tccctgtcac ctggc                                                     2115
```

<210> SEQ ID NO 77
<211> LENGTH: 2094
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
cagagcgcac tgactcagcc tgcttccgtg tccgggagcc ctgggcagag cattacaatc      60
tcatgcactg gaacctcatc cgatgtcggc gggtacaact ttgtgagttg gtatcagcag     120
cacccaggca aggcacccaa actgatgatc tacgacgtgt ctgataggcc ctctggggtc     180
agtgaccgct tcagcggctc caagtctggg aataccgctt ccctgatcat ttctgggctg     240
caggctgacg atgaggcaga ttactattgc agctcctatg gatctagttc aactcatgtg     300
atcttcggag gcgggaccaa ggtgacagtc ctgggccagc ctaaagccgc tccatccgtg     360
acactgtttc cccctagctc cgaggaactg caggccaaca aggctactct ggtgtgtctg     420
attagcgact ctaccctggg cgctgtgacc gtcgcatgga aggccgattc tagtcccgtg     480
aaagcaggcg tcgagaccac aactccttca aagcagagca caacaagta cgcagcctca     540 agctatctgt ccctgacacc agaacagtgg aagtctcacc gcagttactc atgccaagtg     600
actcatgagg gcagcactgt ggaaaaaacc gtcgccccca cagagtgttc ctctggagga     660
gggagtggag gagggtcaga gggaggcggg agcgaaggag gcgggtccga gggaggcggg     720
tctgaaggag gagggagcgg aggagggtcc ggacaggtgc agctgcagga gtccggagga     780
ggactggtca gcctggagg ctctctgcga ctgagttgcg ctgcatcagg cttcaccttt     840
agttcatact ggatgagctg ggtgagacag gccccaggga aaggactgga atgggtcgca     900
aacatcaata gggacggaag cgcctcctac tatgtggatt ccgtcaaggg ccggtttacc     960
attagtagag acgatgccaa aaactcactg tatctgcaga tgaatagcct gcgagccgaa    1020
gacacagctg tgtactattg tgctcgggat agaggcgtcg gctatttcga tctgtgggga    1080
cgaggaaccc tggtcaccgt ctcaagcgct agcactaagg ggccttccgt gtttccactg    1140
gctccctcta gtaaatccac ctctggaggc acagctgcac tgggatgtct ggtgaaggat    1200
tacttccctg aaccagtcac agtgagttgg aactcagggg ctctgacaag tggagtccat    1260
acttttcccg cagtgctgca gtcaagcgga ctgtactccc tgtcctctgt ggtcaccgtg    1320
cctagttcaa gcctgggcac ccagacatat atctgcaacg tgaatcacaa gccatcaaat    1380
acaaaagtcg acaagaaagt ggagcccaag agctgtgata aaactcatac ctgcccacct    1440
tgtccggcgc cagaactgct gggaggacca agcgtgttcc tgtttccacc caagcctaaa    1500
gacaccctga tgatttcccg gactcctgag gtcacctgcg tggtcgtgga cgtgtctcac    1560
gaggaccccg aagtcaagtt caactggtac gtggatggcg tcgaagtgca taatgccaag    1620
accaaacccc gggaggaaca gtacaactct acctatagag tcgtgagtgt cctgacagtg    1680
ctgcaccagg actggctgaa tgggaaggag tataagtgta agtgagcaa caaagccctg    1740 cccgccccaa tcgaaaaaac aatctctaaa gcaaaggac agcctcgcga accacaggtc    1800
tacgtgctgc cccctagccg cgacgaactg actaaaaatc aggtctctct gctgtgtctg    1860
```

```
gtcaaaggat tctacccttc cgacatcgcc gtggagtggg aaagtaacgg ccagcccgag    1920
aacaattacc tgacctggcc ccctgtgctg gactctgatg ggagtttctt tctgtattca    1980
aagctgacag tcgataaaag ccggtggcag cagggcaatg tgttcagctg ctccgtcatg    2040
cacgaagcac tgcacaacca ttacactcag aagtccctgt ccctgtcacc tggc          2094
```

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 79
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
agaaccgtgg cggcgcccag tgtcttcatt tttccccta gcgacgaaca gctgaagtct    60
gggacagcca gtgtggtctg tctgctgaac aacttctacc ctcgcgaggc taaagtgcag    120
tggaaggtcg ataacgcact gcagtccgga aattctcagg agagtgtgac tgaacaggac    180
tcaaaagata gcacctattc cctgtcaagc acactgactc tgagcaaggc cgactacgag    240
aagcataaag tgtatgcttg tgaagtcacc caccagggc tgagttcacc agtcacaaaa    300
tcattcaaca gaggggagtg c                                              321
```

<210> SEQ ID NO 80
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp

```
            20                  25                  30
Phe Tyr Pro Gly Ala Val Thr Val Ala Trp Lys Ala Asp Ser Ser Pro
            35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 81
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
gggcagccta aagcggcgcc ctctgtgact ctgtttcccc ctagctccga ggaactgcag    60
gctaacaagg caactctggt gtgtctgatt agcgacttct acccaggagc tgtgaccgtc   120
gcctggaagg ctgattctag tcccgtgaaa gcaggcgtcg agaccacaac tcctagtaag   180
cagtcaaaca acaagtacgc agcctcaagc tatctgtctc tgacacccga acagtggaaa   240
agtcacaggt catatagctg ccaggtgact cacgagggct caactgtgga gaaaaccgtc   300
gcaccaaccg aatgttcc                                                318
```

<210> SEQ ID NO 82
<211> LENGTH: 17
<212> TYPE: PRT
<213> ORGANISM: Unknown
<220> FEATURE:
<223> OTHER INFORMATION: Description of Unknown:
      Stanniocalcin signal sequence

<400> SEQUENCE: 82

```
Met Leu Gln Asn Ser Ala Val Leu Leu Leu Leu Val Ile Ser Ala Ser
1               5                   10                  15

Ala
```

<210> SEQ ID NO 83
<211> LENGTH: 22
<212> TYPE: PRT
<213> ORGANISM: Unknown
<220> FEATURE:
<223> OTHER INFORMATION: Description of Unknown:
      consensus signal sequence

<400> SEQUENCE: 83

```
Met Pro Thr Trp Ala Trp Trp Leu Phe Leu Val Leu Leu Leu Ala Leu
1               5                   10                  15

Trp Ala Pro Ala Arg Gly
            20
```